US006197495B1

(12) United States Patent
Qiu et al.

(10) Patent No.: US 6,197,495 B1
(45) Date of Patent: Mar. 6, 2001

(54) **METHODS USING THE *STAPHYLOCOCCUS AUREUS* GLYCYL TRNA SYNTHETASE CRYSTALLINE STRUCTURE**

(75) Inventors: Xiayang Qiu, Audubon, PA (US); Neal Frederick Osborne, Rusper; Christine Mary Richardson, Buntingford, both of (GB); Cheryl A. Janson, Bryn Mawr, PA (US)

(73) Assignees: SmithKline Beecham Corporation, Philadelphia, PA (US); SmithKline Beecham plc, Middlesex (GB)

( * ) Notice: Subject to any disclaimer, the term of this patent is extended or adjusted under 35 U.S.C. 154(b) by 0 days.

(21) Appl. No.: 09/076,432

(22) Filed: May 10, 1998

Related U.S. Application Data

(63) Continuation of application No. 08/792,295, filed on Jan. 31, 1997.

(51) Int. Cl.[7] .............................. C12Q 1/70; C12N 9/00; A61K 38/00

(52) U.S. Cl. ................................ 435/4; 435/183; 514/12; 702/19; 702/22

(58) Field of Search .......................... 435/183, 4; 514/12; 702/19, 22

(56) References Cited

PUBLICATIONS

Niyomporng et al., "Biosynthesis of the Peptidoglycan of Bacterial Cell Walls", *J. Biol. Chem., vol. 243, No. 4*, pp. 773–778 ,(1968).

Niyomporn, et al., "Glycyl–tRNA Synthetase (*Staphylococcus aureus*)", *Meth. Enzymol., vol. 17*, pp. 966–970, (1971).

Belrhali, et al., "Crystal Structures at 2.5 Angstrom Resolution of Seryl–tRNA Synthetase Complexed with two Analogs of Seryl Adenylate", *Science*, vol. 263(5152), pp. 1432–1436, (1994).

Ueda, et al., "X–ray Crystallographic Conformational Study of 5'–O–[N–(L–alanyl)–sulfamoyl]adenosine, A Substrate Analog for Alanyl–tRNA Synthetase.", *Biochim. Biophys. Acta*, vol. 1080(2), pp. 126–134, (1991).

Logan, et al., "Crystal Structure of Glycyl–tRNA Synthetase from Thermus Thermophilus", *EMBO J.*, vol. 17(17), pp. 4156–4167, (1995).

*Primary Examiner*—Lisa J. Hobbs
(74) *Attorney, Agent, or Firm*—Edward R. Gimmi; William T. King; Charles M. Kinzig

(57) ABSTRACT

A novel Staphylococcus glycyl tRNA synthetase crystalline structure is identified. Also disclosed are methods of identifying inhibitors of these synthetases and/or active sites, and inhibitors identified by these methods.

4 Claims, 135 Drawing Sheets

FIGURE 1A

CRYST1 81.490 123.070 127.480 90.00 90.00 90.00 P212121

| | Atom | | Residue AA | No. | X | Y | Z |
|---|---|---|---|---|---|---|---|
| ATOM | 1 | CB | MET | 1 | 26.350 | -12.380 | 34.911 |
| ATOM | 2 | CG | MET | 1 | 24.811 | -12.477 | 34.478 |
| ATOM | 3 | SD | MET | 1 | 23.347 | -11.804 | 35.520 |
| ATOM | 4 | CE | MET | 1 | 21.876 | -12.705 | 34.649 |
| ATOM | 5 | C | MET | 1 | 26.118 | -14.451 | 36.395 |
| ATOM | 6 | O | MET | 1 | 26.546 | -15.494 | 35.876 |
| ATOM | 7 | N | MET | 1 | 28.315 | -13.256 | 36.258 |
| ATOM | 8 | CA | MET | 1 | 26.817 | -13.111 | 36.214 |
| ATOM | 9 | N | ALA | 2 | 25.034 | -14.389 | 37.149 |
| ATOM | 10 | CA | ALA | 2 | 24.247 | -15.561 | 37.439 |
| ATOM | 11 | CB | ALA | 2 | 23.187 | -15.245 | 38.486 |
| ATOM | 12 | C | ALA | 2 | 23.607 | -16.202 | 36.224 |
| ATOM | 13 | O | ALA | 2 | 22.791 | -15.594 | 35.498 |
| ATOM | 14 | N | LYS | 3 | 24.002 | -17.452 | 36.030 |
| ATOM | 15 | CA | LYS | 3 | 23.489 | -18.270 | 34.951 |
| ATOM | 16 | CB | LYS | 3 | 24.354 | -19.536 | 34.808 |
| ATOM | 17 | CG | LYS | 3 | 25.391 | -19.766 | 35.943 |
| ATOM | 18 | CD | LYS | 3 | 24.770 | -20.353 | 37.203 |
| ATOM | 19 | CE | LYS | 3 | 24.117 | -21.724 | 36.938 |
| ATOM | 20 | NZ | LYS | 3 | 25.025 | -22.916 | 36.909 |
| ATOM | 21 | C | LYS | 3 | 22.027 | -18.617 | 35.291 |
| ATOM | 22 | O | LYS | 3 | 21.081 | -17.944 | 34.832 |
| ATOM | 23 | N | ASP | 4 | 21.862 | -19.612 | 36.159 |
| ATOM | 24 | CA | ASP | 4 | 20.556 | -20.075 | 36.589 |
| ATOM | 25 | CB | ASP | 4 | 20.728 | -21.507 | 37.118 |
| ATOM | 26 | CG | ASP | 4 | 19.521 | -22.413 | 36.846 |
| ATOM | 27 | OD1 | ASP | 4 | 18.386 | -21.911 | 36.666 |
| ATOM | 28 | OD2 | ASP | 4 | 19.699 | -23.658 | 36.831 |
| ATOM | 29 | C | ASP | 4 | 20.101 | -19.140 | 37.713 |
| ATOM | 30 | O | ASP | 4 | 20.924 | -18.423 | 38.267 |
| ATOM | 31 | N | MET | 5 | 18.796 | -19.036 | 37.961 |
| ATOM | 32 | CA | MET | 5 | 18.316 | -18.246 | 39.102 |
| ATOM | 33 | CB | MET | 5 | 16.894 | -17.692 | 38.923 |
| ATOM | 34 | CG | MET | 5 | 16.331 | -16.937 | 40.192 |
| ATOM | 35 | SD | MET | 5 | 16.671 | -15.076 | 40.424 |
| ATOM | 36 | CE | MET | 5 | 18.427 | -15.020 | 40.792 |
| ATOM | 37 | C | MET | 5 | 18.299 | -19.266 | 40.229 |
| ATOM | 38 | O | MET | 5 | 18.686 | -18.964 | 41.342 |
| ATOM | 39 | N | ASP | 6 | 17.901 | -20.494 | 39.898 |
| ATOM | 40 | CA | ASP | 6 | 17.840 | -21.624 | 40.845 |
| ATOM | 41 | CB | ASP | 6 | 17.325 | -22.908 | 40.162 |
| ATOM | 42 | CG | ASP | 6 | 15.983 | -22.708 | 39.428 |
| ATOM | 43 | OD1 | ASP | 6 | 15.734 | -23.447 | 38.440 |
| ATOM | 44 | OD2 | ASP | 6 | 15.179 | -21.822 | 39.825 |
| ATOM | 45 | C | ASP | 6 | 19.188 | -21.939 | 41.477 |
| ATOM | 46 | O | ASP | 6 | 19.256 | -22.359 | 42.619 |

FIGURE 1B

| | Atom | | Residue AA | Residue No. | X | Y | Z |
|---|---|---|---|---|---|---|---|
| ATOM | 47 | N | THR | 7 | 20.260 | -21.803 | 40.714 |
| ATOM | 48 | CA | THR | 7 | 21.565 | -22.060 | 41.269 |
| ATOM | 49 | CB | THR | 7 | 22.663 | -21.995 | 40.227 |
| ATOM | 50 | OG1 | THR | 7 | 22.642 | -23.198 | 39.458 |
| ATOM | 51 | CG2 | THR | 7 | 24.019 | -21.856 | 40.870 |
| ATOM | 52 | C | THR | 7 | 21.798 | -20.993 | 42.295 |
| ATOM | 53 | O | THR | 7 | 22.185 | -21.299 | 43.413 |
| ATOM | 54 | N | ILE | 8 | 21.500 | -19.749 | 41.943 |
| ATOM | 55 | CA | ILE | 8 | 21.696 | -18.639 | 42.866 |
| ATOM | 56 | CB | ILE | 8 | 21.549 | -17.273 | 42.140 |
| ATOM | 57 | CG2 | ILE | 8 | 20.921 | -16.219 | 43.062 |
| ATOM | 58 | CG1 | ILE | 8 | 22.919 | -16.817 | 41.620 |
| ATOM | 59 | CD1 | ILE | 8 | 23.573 | -17.809 | 40.738 |
| ATOM | 60 | C | ILE | 8 | 20.885 | -18.713 | 44.177 |
| ATOM | 61 | O | ILE | 8 | 21.457 | -18.595 | 45.248 |
| ATOM | 62 | N | VAL | 9 | 19.573 | -18.904 | 44.112 |
| ATOM | 63 | CA | VAL | 9 | 18.793 | -19.020 | 45.334 |
| ATOM | 64 | CB | VAL | 9 | 17.321 | -19.355 | 45.049 |
| ATOM | 65 | CG1 | VAL | 9 | 16.688 | -20.054 | 46.220 |
| ATOM | 66 | CG2 | VAL | 9 | 16.570 | -18.094 | 44.777 |
| ATOM | 67 | C | VAL | 9 | 19.418 | -20.121 | 46.179 |
| ATOM | 68 | O | VAL | 9 | 19.635 | -19.953 | 47.371 |
| ATOM | 69 | N | SER | 10 | 19.786 | -21.217 | 45.543 |
| ATOM | 70 | CA | SER | 10 | 20.378 | -22.318 | 46.263 |
| ATOM | 71 | CB | SER | 10 | 20.691 | -23.455 | 45.305 |
| ATOM | 72 | OG | SER | 10 | 21.227 | -24.561 | 46.002 |
| ATOM | 73 | C | SER | 10 | 21.625 | -21.906 | 47.035 |
| ATOM | 74 | O | SER | 10 | 21.703 | -22.107 | 48.245 |
| ATOM | 75 | N | LEU | 11 | 22.609 | -21.335 | 46.358 |
| ATOM | 76 | CA | LEU | 11 | 23.799 | -20.914 | 47.068 |
| ATOM | 77 | CB | LEU | 11 | 24.862 | -20.386 | 46.126 |
| ATOM | 78 | CG | LEU | 11 | 26.081 | -19.873 | 46.870 |
| ATOM | 79 | CD1 | LEU | 11 | 27.237 | -20.847 | 46.751 |
| ATOM | 80 | CD2 | LEU | 11 | 26.450 | -18.536 | 46.332 |
| ATOM | 81 | C | LEU | 11 | 23.426 | -19.840 | 48.083 |
| ATOM | 82 | O | LEU | 11 | 24.173 | -19.592 | 49.001 |
| ATOM | 83 | N | ALA | 12 | 22.276 | -19.193 | 47.936 |
| ATOM | 84 | CA | ALA | 12 | 21.890 | -18.190 | 48.913 |
| ATOM | 85 | CB | ALA | 12 | 20.821 | -17.273 | 48.373 |
| ATOM | 86 | C | ALA | 12 | 21.402 | -18.919 | 50.152 |
| ATOM | 87 | O | ALA | 12 | 22.089 | -18.916 | 51.172 |
| ATOM | 88 | N | LYS | 13 | 20.255 | -19.587 | 50.054 |
| ATOM | 89 | CA | LYS | 13 | 19.678 | -20.322 | 51.175 |
| ATOM | 90 | CB | LYS | 13 | 18.550 | -21.230 | 50.674 |
| ATOM | 91 | CG | LYS | 13 | 18.195 | -22.440 | 51.579 |
| ATOM | 92 | CD | LYS | 13 | 17.663 | -22.031 | 53.001 |
| ATOM | 93 | CE | LYS | 13 | 17.204 | -23.232 | 53.925 |
| ATOM | 94 | NZ | LYS | 13 | 16.360 | -22.851 | 55.146 |

FIGURE 1C

| | Atom | | Residue AA | No. | X | Y | Z |
|---|---|---|---|---|---|---|---|
| ATOM | 95 | C | LYS | 13 | 20.715 | -21.120 | 51.948 |
| ATOM | 96 | O | LYS | 13 | 21.181 | -20.719 | 52.994 |
| ATOM | 97 | N | HIS | 14 | 21.156 | -22.208 | 51.375 |
| ATOM | 98 | CA | HIS | 14 | 22.114 | -23.042 | 52.041 |
| ATOM | 99 | CB | HIS | 14 | 22.538 | -24.157 | 51.100 |
| ATOM | 100 | CG | HIS | 14 | 23.990 | -24.505 | 51.204 |
| ATOM | 101 | CD2 | HIS | 14 | 24.619 | -25.594 | 51.705 |
| ATOM | 102 | ND1 | HIS | 14 | 24.984 | -23.651 | 50.775 |
| ATOM | 103 | CE1 | HIS | 14 | 26.164 | -24.200 | 51.002 |
| ATOM | 104 | NE2 | HIS | 14 | 25.969 | -25.380 | 51.567 |
| ATOM | 105 | C | HIS | 14 | 23.365 | -22.400 | 52.607 |
| ATOM | 106 | O | HIS | 14 | 23.961 | -22.940 | 53.523 |
| ATOM | 107 | N | ARG | 15 | 23.847 | -21.332 | 52.001 |
| ATOM | 108 | CA | ARG | 15 | 25.083 | -20.732 | 52.476 |
| ATOM | 109 | CB | ARG | 15 | 25.868 | -20.210 | 51.281 |
| ATOM | 110 | CG | ARG | 15 | 27.246 | -19.755 | 51.556 |
| ATOM | 111 | CD | ARG | 15 | 27.815 | -20.598 | 52.606 |
| ATOM | 112 | NE | ARG | 15 | 27.934 | -21.979 | 52.186 |
| ATOM | 113 | CZ | ARG | 15 | 29.072 | -22.505 | 51.742 |
| ATOM | 114 | NH1 | ARG | 15 | 30.158 | -21.736 | 51.650 |
| ATOM | 115 | NH2 | ARG | 15 | 29.167 | -23.814 | 51.509 |
| ATOM | 116 | C | ARG | 15 | 24.864 | -19.672 | 53.550 |
| ATOM | 117 | O | ARG | 15 | 25.800 | -19.110 | 54.107 |
| ATOM | 118 | N | GLY | 16 | 23.612 | -19.457 | 53.892 |
| ATOM | 119 | CA | GLY | 16 | 23.331 | -18.494 | 54.914 |
| ATOM | 120 | C | GLY | 16 | 23.402 | -17.119 | 54.343 |
| ATOM | 121 | O | GLY | 16 | 24.202 | -16.306 | 54.757 |
| ATOM | 122 | N | PHE | 17 | 22.609 | -16.881 | 53.322 |
| ATOM | 123 | CA | PHE | 17 | 22.555 | -15.568 | 52.729 |
| ATOM | 124 | CB | PHE | 17 | 22.958 | -15.571 | 51.247 |
| ATOM | 125 | CG | PHE | 17 | 24.379 | -15.114 | 50.971 |
| ATOM | 126 | CD1 | PHE | 17 | 25.416 | -16.024 | 50.928 |
| ATOM | 127 | CD2 | PHE | 17 | 24.648 | -13.801 | 50.639 |
| ATOM | 128 | CE1 | PHE | 17 | 26.686 | -15.638 | 50.549 |
| ATOM | 129 | CE2 | PHE | 17 | 25.916 | -13.410 | 50.259 |
| ATOM | 130 | CZ | PHE | 17 | 26.932 | -14.330 | 50.213 |
| ATOM | 131 | C | PHE | 17 | 21.106 | -15.210 | 52.888 |
| ATOM | 132 | O | PHE | 17 | 20.815 | -14.133 | 53.325 |
| ATOM | 133 | N | VAL | 18 | 20.193 | -16.121 | 52.573 |
| ATOM | 134 | CA | VAL | 18 | 18.759 | -15.853 | 52.719 |
| ATOM | 135 | CB | VAL | 18 | 18.139 | -15.144 | 51.447 |
| ATOM | 136 | CG1 | VAL | 18 | 16.727 | -14.687 | 51.706 |
| ATOM | 137 | CG2 | VAL | 18 | 18.922 | -13.930 | 51.076 |
| ATOM | 138 | C | VAL | 18 | 18.031 | -17.178 | 52.993 |
| ATOM | 139 | O | VAL | 18 | 18.306 | -18.173 | 52.333 |
| ATOM | 140 | N | PHE | 19 | 17.178 | -17.201 | 54.019 |
| ATOM | 141 | CA | PHE | 19 | 16.400 | -18.381 | 54.385 |
| ATOM | 142 | CB | PHE | 19 | 16.522 | -18.726 | 55.874 |

FIGURE 1D

| | Atom | | Residue AA | No. | X | Y | Z |
|---|---|---|---|---|---|---|---|
| ATOM | 143 | CG | PHE | 19 | 17.925 | -18.879 | 56.371 |
| ATOM | 144 | CD1 | PHE | 19 | 18.727 | -19.903 | 55.905 |
| ATOM | 145 | CD2 | PHE | 19 | 18.454 | -17.987 | 57.313 |
| ATOM | 146 | CE1 | PHE | 19 | 20.044 | -20.036 | 56.370 |
| ATOM | 147 | CE2 | PHE | 19 | 19.769 | -18.112 | 57.780 |
| ATOM | 148 | CZ | PHE | 19 | 20.560 | -19.126 | 57.314 |
| ATOM | 149 | C | PHE | 19 | 14.963 | -17.980 | 54.166 |
| ATOM | 150 | O | PHE | 19 | 14.613 | -16.820 | 54.312 |
| ATOM | 151 | N | PRO | 20 | 14.096 | -18.933 | 53.854 |
| ATOM | 152 | CD | PRO | 20 | 14.351 | -20.360 | 53.647 |
| ATOM | 153 | CA | PRO | 20 | 12.688 | -18.616 | 53.636 |
| ATOM | 154 | CB | PRO | 20 | 12.157 | -19.884 | 52.993 |
| ATOM | 155 | CG | PRO | 20 | 12.966 | -20.921 | 53.627 |
| ATOM | 156 | C | PRO | 20 | 11.945 | -18.286 | 54.946 |
| ATOM | 157 | O | PRO | 20 | 12.056 | -19.012 | 55.967 |
| ATOM | 158 | N | GLY | 21 | 11.173 | -17.195 | 54.901 |
| ATOM | 159 | CA | GLY | 21 | 10.395 | -16.728 | 56.054 |
| ATOM | 160 | C | GLY | 21 | 9.426 | -17.743 | 56.632 |
| ATOM | 161 | O | GLY | 21 | 8.875 | -18.560 | 55.891 |
| ATOM | 162 | N | SER | 22 | 9.212 | -17.681 | 57.949 |
| ATOM | 163 | CA | SER | 22 | 8.332 | -18.625 | 58.653 |
| ATOM | 164 | CB | SER | 22 | 6.865 | -18.230 | 58.524 |
| ATOM | 165 | OG | SER | 22 | 6.634 | -16.942 | 59.028 |
| ATOM | 166 | C | SER | 22 | 8.515 | -20.037 | 58.103 |
| ATOM | 167 | O | SER | 22 | 7.577 | -20.839 | 58.134 |
| ATOM | 168 | N | ASP | 23 | 9.735 | -20.343 | 57.662 |
| ATOM | 169 | CA | ASP | 23 | 10.027 | -21.631 | 57.086 |
| ATOM | 170 | CB | ASP | 23 | 11.538 | -21.811 | 56.903 |
| ATOM | 171 | CG | ASP | 23 | 11.894 | -23.096 | 56.102 |
| ATOM | 172 | OD1 | ASP | 23 | 10.954 | -23.716 | 55.556 |
| ATOM | 173 | OD2 | ASP | 23 | 13.097 | -23.487 | 56.015 |
| ATOM | 174 | C | ASP | 23 | 9.439 | -22.821 | 57.836 |
| ATOM | 175 | O | ASP | 23 | 8.398 | -23.314 | 57.460 |
| ATOM | 176 | N | ILE | 24 | 10.081 | -23.229 | 58.929 |
| ATOM | 177 | CA | ILE | 24 | 9.682 | -24.396 | 59.735 |
| ATOM | 178 | CB | ILE | 24 | 10.444 | -24.472 | 61.115 |
| ATOM | 179 | CG2 | ILE | 24 | 11.963 | -24.390 | 60.922 |
| ATOM | 180 | CG1 | ILE | 24 | 9.990 | -23.347 | 62.047 |
| ATOM | 181 | CD1 | ILE | 24 | 10.372 | -23.563 | 63.462 |
| ATOM | 182 | C | ILE | 24 | 8.190 | -24.610 | 60.006 |
| ATOM | 183 | O | ILE | 24 | 7.766 | -25.743 | 60.221 |
| ATOM | 184 | N | TYR | 25 | 7.402 | -23.544 | 60.068 |
| ATOM | 185 | CA | TYR | 25 | 5.981 | -23.714 | 60.301 |
| ATOM | 186 | CB | TYR | 25 | 5.379 | -22.480 | 60.949 |
| ATOM | 187 | CG | TYR | 25 | 5.544 | -22.499 | 62.434 |
| ATOM | 188 | CD1 | TYR | 25 | 6.799 | -22.700 | 63.006 |
| ATOM | 189 | CE1 | TYR | 25 | 6.962 | -22.794 | 64.391 |
| ATOM | 190 | CD2 | TYR | 25 | 4.445 | -22.380 | 63.281 |

FIGURE 1E

| | Atom | | Residue AA | No. | X | Y | Z |
|---|---|---|---|---|---|---|---|
| ATOM | 191 | CE2 | TYR | 25 | 4.600 | -22.471 | 64.691 |
| ATOM | 192 | CZ | TYR | 25 | 5.864 | -22.686 | 65.232 |
| ATOM | 193 | OH | TYR | 25 | 6.045 | -22.851 | 66.582 |
| ATOM | 194 | C | TYR | 25 | 5.299 | -24.014 | 58.984 |
| ATOM | 195 | O | TYR | 25 | 4.448 | -24.900 | 58.901 |
| ATOM | 196 | N | GLY | 26 | 5.716 | -23.307 | 57.940 |
| ATOM | 197 | CA | GLY | 26 | 5.140 | -23.506 | 56.623 |
| ATOM | 198 | C | GLY | 26 | 5.567 | -22.393 | 55.691 |
| ATOM | 199 | O | GLY | 26 | 5.667 | -22.592 | 54.484 |
| ATOM | 200 | N | GLY | 27 | 5.830 | -21.219 | 56.250 |
| ATOM | 201 | CA | GLY | 27 | 6.234 | -20.099 | 55.426 |
| ATOM | 202 | C | GLY | 27 | 5.149 | -19.048 | 55.222 |
| ATOM | 203 | O | GLY | 27 | 4.103 | -19.032 | 55.904 |
| ATOM | 204 | N | LEU | 28 | 5.440 | -18.122 | 54.318 |
| ATOM | 205 | CA | LEU | 28 | 4.527 | -17.049 | 54.000 |
| ATOM | 206 | CB | LEU | 28 | 4.649 | -15.907 | 54.997 |
| ATOM | 207 | CG | LEU | 28 | 3.573 | -14.853 | 54.798 |
| ATOM | 208 | CD1 | LEU | 28 | 2.225 | -15.479 | 55.117 |
| ATOM | 209 | CD2 | LEU | 28 | 3.825 | -13.645 | 55.672 |
| ATOM | 210 | C | LEU | 28 | 4.941 | -16.566 | 52.637 |
| ATOM | 211 | O | LEU | 28 | 6.138 | -16.434 | 52.352 |
| ATOM | 212 | N | SER | 29 | 3.943 | -16.336 | 51.791 |
| ATOM | 213 | CA | SER | 29 | 4.132 | -15.884 | 50.419 |
| ATOM | 214 | CB | SER | 29 | 2.822 | -15.310 | 49.884 |
| ATOM | 215 | OG | SER | 29 | 2.174 | -14.539 | 50.873 |
| ATOM | 216 | C | SER | 29 | 5.260 | -14.893 | 50.195 |
| ATOM | 217 | O | SER | 29 | 5.212 | -13.759 | 50.697 |
| ATOM | 218 | N | ASN | 30 | 6.278 | -15.374 | 49.472 |
| ATOM | 219 | CA | ASN | 30 | 7.472 | -14.608 | 49.084 |
| ATOM | 220 | CB | ASN | 30 | 7.240 | -13.845 | 47.764 |
| ATOM | 221 | CG | ASN | 30 | 8.408 | -13.978 | 46.762 |
| ATOM | 222 | OD1 | ASN | 30 | 9.582 | -13.744 | 47.077 |
| ATOM | 223 | ND2 | ASN | 30 | 8.068 | -14.354 | 45.544 |
| ATOM | 224 | C | ASN | 30 | 7.885 | -13.610 | 50.141 |
| ATOM | 225 | O | ASN | 30 | 7.792 | -12.382 | 49.935 |
| ATOM | 226 | N | THR | 31 | 8.282 | -14.138 | 51.289 |
| ATOM | 227 | CA | THR | 31 | 8.724 | -13.305 | 52.397 |
| ATOM | 228 | CB | THR | 31 | 7.581 | -13.166 | 53.499 |
| ATOM | 229 | OG1 | THR | 31 | 6.866 | -14.407 | 53.620 |
| ATOM | 230 | CG2 | THR | 31 | 6.546 | -12.046 | 53.105 |
| ATOM | 231 | C | THR | 31 | 10.004 | -14.010 | 52.837 |
| ATOM | 232 | O | THR | 31 | 10.014 | -15.229 | 52.967 |
| ATOM | 233 | N | TRP | 32 | 11.100 | -13.261 | 52.941 |
| ATOM | 234 | CA | TRP | 32 | 12.420 | -13.826 | 53.260 |
| ATOM | 235 | CB | TRP | 32 | 13.374 | -13.621 | 52.049 |
| ATOM | 236 | CG | TRP | 32 | 12.858 | -14.222 | 50.781 |
| ATOM | 237 | CD2 | TRP | 32 | 13.242 | -15.480 | 50.224 |
| ATOM | 238 | CE2 | TRP | 32 | 12.297 | -15.808 | 49.244 |

FIGURE 1F

| | Atom | | Residue AA | No. | X | Y | Z |
|---|---|---|---|---|---|---|---|
| ATOM | 239 | CE3 | TRP | 32 | 14.284 | -16.378 | 50.480 |
| ATOM | 240 | CD1 | TRP | 32 | 11.758 | -13.824 | 50.089 |
| ATOM | 241 | NE1 | TRP | 32 | 11.403 | -14.776 | 49.178 |
| ATOM | 242 | CZ2 | TRP | 32 | 12.353 | -16.998 | 48.526 |
| ATOM | 243 | CZ3 | TRP | 32 | 14.342 | -17.564 | 49.763 |
| ATOM | 244 | CH2 | TRP | 32 | 13.382 | -17.862 | 48.802 |
| ATOM | 245 | C | TRP | 32 | 13.129 | -13.325 | 54.514 |
| ATOM | 246 | O | TRP | 32 | 13.014 | -12.162 | 54.909 |
| ATOM | 247 | N | ASP | 33 | 13.896 | -14.212 | 55.120 |
| ATOM | 248 | CA | ASP | 33 | 14.655 | -13.846 | 56.294 |
| ATOM | 249 | CB | ASP | 33 | 14.490 | -14.902 | 57.419 |
| ATOM | 250 | CG | ASP | 33 | 13.100 | -14.879 | 58.095 |
| ATOM | 251 | OD1 | ASP | 33 | 12.677 | -15.927 | 58.596 |
| ATOM | 252 | OD2 | ASP | 33 | 12.426 | -13.841 | 58.177 |
| ATOM | 253 | C | ASP | 33 | 16.115 | -13.759 | 55.833 |
| ATOM | 254 | O | ASP | 33 | 16.592 | -14.639 | 55.129 |
| ATOM | 255 | N | TYR | 34 | 16.779 | -12.653 | 56.134 |
| ATOM | 256 | CA | TYR | 34 | 18.173 | -12.491 | 55.782 |
| ATOM | 257 | CB | TYR | 34 | 18.556 | -11.025 | 55.693 |
| ATOM | 258 | CG | TYR | 34 | 18.090 | -10.383 | 54.406 |
| ATOM | 259 | CD1 | TYR | 34 | 16.730 | -10.343 | 54.078 |
| ATOM | 260 | CE1 | TYR | 34 | 16.298 | -9.794 | 52.868 |
| ATOM | 261 | CD2 | TYR | 34 | 19.008 | -9.852 | 53.488 |
| ATOM | 262 | CE2 | TYR | 34 | 18.581 | -9.306 | 52.274 |
| ATOM | 263 | CZ | TYR | 34 | 17.228 | -9.283 | 51.973 |
| ATOM | 264 | OH | TYR | 34 | 16.793 | -8.777 | 50.771 |
| ATOM | 265 | C | TYR | 34 | 19.039 | -13.173 | 56.799 |
| ATOM | 266 | O | TYR | 34 | 19.142 | -12.739 | 57.906 |
| ATOM | 267 | N | GLY | 35 | 19.663 | -14.257 | 56.397 |
| ATOM | 268 | CA | GLY | 35 | 20.514 | -15.015 | 57.277 |
| ATOM | 269 | C | GLY | 35 | 21.759 | -14.243 | 57.594 |
| ATOM | 270 | O | GLY | 35 | 21.944 | -13.150 | 57.080 |
| ATOM | 271 | N | PRO | 36 | 22.679 | -14.857 | 58.352 |
| ATOM | 272 | CD | PRO | 36 | 22.544 | -16.305 | 58.584 |
| ATOM | 273 | CA | PRO | 36 | 23.979 | -14.389 | 58.847 |
| ATOM | 274 | CB | PRO | 36 | 24.696 | -15.686 | 59.173 |
| ATOM | 275 | CG | PRO | 36 | 23.589 | -16.541 | 59.627 |
| ATOM | 276 | C | PRO | 36 | 24.776 | -13.572 | 57.858 |
| ATOM | 277 | O | PRO | 36 | 25.316 | -12.515 | 58.190 |
| ATOM | 278 | N | LEU | 37 | 24.885 | -14.088 | 56.645 |
| ATOM | 279 | CA | LEU | 37 | 25.609 | -13.401 | 55.612 |
| ATOM | 280 | CB | LEU | 37 | 26.161 | -14.416 | 54.643 |
| ATOM | 281 | CG | LEU | 37 | 27.296 | -15.166 | 55.304 |
| ATOM | 282 | CD1 | LEU | 37 | 27.910 | -16.256 | 54.414 |
| ATOM | 283 | CD2 | LEU | 37 | 28.307 | -14.112 | 55.634 |
| ATOM | 284 | C | LEU | 37 | 24.739 | -12.363 | 54.916 |
| ATOM | 285 | O | LEU | 37 | 25.207 | -11.263 | 54.611 |
| ATOM | 286 | N | GLY | 38 | 23.457 | -12.677 | 54.747 |

FIGURE 1G

| | Atom | | Residue AA | No. | X | Y | Z |
|---|---|---|---|---|---|---|---|
| ATOM | 287 | CA | GLY | 38 | 22.541 | -11.756 | 54.096 |
| ATOM | 288 | C | GLY | 38 | 22.460 | -10.375 | 54.712 |
| ATOM | 289 | O | GLY | 38 | 22.414 | -9.374 | 54.013 |
| ATOM | 290 | N | VAL | 39 | 22.384 | -10.317 | 56.030 |
| ATOM | 291 | CA | VAL | 39 | 22.326 | -9.038 | 56.717 |
| ATOM | 292 | CB | VAL | 39 | 22.351 | -9.176 | 58.228 |
| ATOM | 293 | CG1 | VAL | 39 | 20.981 | -9.035 | 58.780 |
| ATOM | 294 | CG2 | VAL | 39 | 23.018 | -10.479 | 58.633 |
| ATOM | 295 | C | VAL | 39 | 23.542 | -8.214 | 56.389 |
| ATOM | 296 | O | VAL | 39 | 23.435 | -7.082 | 55.942 |
| ATOM | 297 | N | GLU | 40 | 24.710 | -8.786 | 56.621 |
| ATOM | 298 | CA | GLU | 40 | 25.927 | -8.047 | 56.388 |
| ATOM | 299 | CB | GLU | 40 | 27.155 | -8.941 | 56.634 |
| ATOM | 300 | CG | GLU | 40 | 28.157 | -8.438 | 57.729 |
| ATOM | 301 | CD | GLU | 40 | 27.575 | -8.403 | 59.130 |
| ATOM | 302 | OE1 | GLU | 40 | 26.981 | -9.419 | 59.589 |
| ATOM | 303 | OE2 | GLU | 40 | 27.737 | -7.338 | 59.764 |
| ATOM | 304 | C | GLU | 40 | 25.892 | -7.423 | 54.999 |
| ATOM | 305 | O | GLU | 40 | 25.870 | -6.199 | 54.882 |
| ATOM | 306 | N | LEU | 41 | 25.720 | -8.249 | 53.970 |
| ATOM | 307 | CA | LEU | 41 | 25.670 | -7.749 | 52.585 |
| ATOM | 308 | CB | LEU | 41 | 25.342 | -8.867 | 51.592 |
| ATOM | 309 | CG | LEU | 41 | 25.321 | -8.483 | 50.136 |
| ATOM | 310 | CD1 | LEU | 41 | 26.712 | -8.450 | 49.640 |
| ATOM | 311 | CD2 | LEU | 41 | 24.549 | -9.491 | 49.384 |
| ATOM | 312 | C | LEU | 41 | 24.628 | -6.655 | 52.450 |
| ATOM | 313 | O | LEU | 41 | 24.960 | -5.554 | 52.039 |
| ATOM | 314 | N | LYS | 42 | 23.391 | -6.931 | 52.863 |
| ATOM | 315 | CA | LYS | 42 | 22.329 | -5.948 | 52.751 |
| ATOM | 316 | CB | LYS | 42 | 21.015 | -6.493 | 53.267 |
| ATOM | 317 | CG | LYS | 42 | 19.843 | -5.583 | 53.001 |
| ATOM | 318 | CD | LYS | 42 | 18.600 | -6.227 | 53.529 |
| ATOM | 319 | CE | LYS | 42 | 17.370 | -5.407 | 53.309 |
| ATOM | 320 | NZ | LYS | 42 | 16.185 | -6.037 | 54.010 |
| ATOM | 321 | C | LYS | 42 | 22.690 | -4.693 | 53.491 |
| ATOM | 322 | O | LYS | 42 | 22.268 | -3.613 | 53.113 |
| ATOM | 323 | N | ASN | 43 | 23.527 | -4.828 | 54.512 |
| ATOM | 324 | CA | ASN | 43 | 23.952 | -3.685 | 55.305 |
| ATOM | 325 | CB | ASN | 43 | 24.139 | -4.060 | 56.761 |
| ATOM | 326 | CG | ASN | 43 | 22.882 | -3.835 | 57.551 |
| ATOM | 327 | OD1 | ASN | 43 | 22.251 | -4.778 | 58.037 |
| ATOM | 328 | ND2 | ASN | 43 | 22.459 | -2.575 | 57.622 |
| ATOM | 329 | C | ASN | 43 | 25.146 | -2.943 | 54.757 |
| ATOM | 330 | O | ASN | 43 | 25.280 | -1.745 | 54.992 |
| ATOM | 331 | N | ASN | 44 | 26.012 | -3.646 | 54.031 |
| ATOM | 332 | CA | ASN | 44 | 27.149 | -3.009 | 53.385 |
| ATOM | 333 | CB | ASN | 44 | 28.123 | -4.056 | 52.875 |
| ATOM | 334 | CG | ASN | 44 | 28.853 | -4.765 | 53.986 |

FIGURE 1H

| | Atom | | Residue AA | No. | X | Y | Z |
|---|---|---|---|---|---|---|---|
| ATOM | 335 | OD1 | ASN | 44 | 28.318 | -5.648 | 54.638 |
| ATOM | 336 | ND2 | ASN | 44 | 30.100 | -4.397 | 54.190 |
| ATOM | 337 | C | ASN | 44 | 26.542 | -2.221 | 52.199 |
| ATOM | 338 | O | ASN | 44 | 27.041 | -1.173 | 51.797 |
| ATOM | 339 | N | VAL | 45 | 25.456 | -2.745 | 51.642 |
| ATOM | 340 | CA | VAL | 45 | 24.747 | -2.100 | 50.560 |
| ATOM | 341 | CB | VAL | 45 | 23.605 | -2.990 | 50.066 |
| ATOM | 342 | CG1 | VAL | 45 | 22.660 | -2.220 | 49.192 |
| ATOM | 343 | CG2 | VAL | 45 | 24.144 | -4.142 | 49.325 |
| ATOM | 344 | C | VAL | 45 | 24.133 | -0.878 | 51.194 |
| ATOM | 345 | O | VAL | 45 | 24.420 | 0.249 | 50.796 |
| ATOM | 346 | N | LYS | 46 | 23.368 | -1.138 | 52.260 |
| ATOM | 347 | CA | LYS | 46 | 22.631 | -0.137 | 53.038 |
| ATOM | 348 | CB | LYS | 46 | 21.782 | -0.828 | 54.104 |
| ATOM | 349 | CG | LYS | 46 | 20.396 | -0.228 | 54.280 |
| ATOM | 350 | CD | LYS | 46 | 19.305 | -1.261 | 54.686 |
| ATOM | 351 | CE | LYS | 46 | 19.424 | -1.791 | 56.132 |
| ATOM | 352 | NZ | LYS | 46 | 18.507 | -2.934 | 56.442 |
| ATOM | 353 | C | LYS | 46 | 23.476 | 0.956 | 53.668 |
| ATOM | 354 | O | LYS | 46 | 22.975 | 2.023 | 53.988 |
| ATOM | 355 | N | ALA | 47 | 24.772 | 0.720 | 53.788 |
| ATOM | 356 | CA | ALA | 47 | 25.646 | 1.716 | 54.378 |
| ATOM | 357 | CB | ALA | 47 | 26.625 | 1.062 | 55.318 |
| ATOM | 358 | C | ALA | 47 | 26.382 | 2.562 | 53.375 |
| ATOM | 359 | O | ALA | 47 | 26.532 | 3.753 | 53.591 |
| ATOM | 360 | N | ALA | 48 | 26.845 | 1.954 | 52.284 |
| ATOM | 361 | CA | ALA | 48 | 27.577 | 2.671 | 51.234 |
| ATOM | 362 | CB | ALA | 48 | 28.007 | 1.732 | 50.185 |
| ATOM | 363 | C | ALA | 48 | 26.686 | 3.723 | 50.643 |
| ATOM | 364 | O | ALA | 48 | 27.129 | 4.763 | 50.217 |
| ATOM | 365 | N | TRP | 49 | 25.406 | 3.428 | 50.648 |
| ATOM | 366 | CA | TRP | 49 | 24.405 | 4.333 | 50.166 |
| ATOM | 367 | CB | TRP | 49 | 23.063 | 3.659 | 50.250 |
| ATOM | 368 | CG | TRP | 49 | 22.062 | 4.385 | 49.517 |
| ATOM | 369 | CD2 | TRP | 49 | 21.258 | 5.458 | 49.997 |
| ATOM | 370 | CE2 | TRP | 49 | 20.429 | 5.860 | 48.932 |
| ATOM | 371 | CE3 | TRP | 49 | 21.150 | 6.115 | 51.218 |
| ATOM | 372 | CD1 | TRP | 49 | 21.710 | 4.185 | 48.228 |
| ATOM | 373 | NE1 | TRP | 49 | 20.728 | 5.065 | 47.862 |
| ATOM | 374 | CZ2 | TRP | 49 | 19.502 | 6.887 | 49.052 |
| ATOM | 375 | CZ3 | TRP | 49 | 20.223 | 7.137 | 51.335 |
| ATOM | 376 | CH2 | TRP | 49 | 19.412 | 7.511 | 50.259 |
| ATOM | 377 | C | TRP | 49 | 24.368 | 5.564 | 51.036 |
| ATOM | 378 | O | TRP | 49 | 24.502 | 6.656 | 50.568 |
| ATOM | 379 | N | TRP | 50 | 24.107 | 5.376 | 52.312 |
| ATOM | 380 | CA | TRP | 50 | 24.058 | 6.482 | 53.258 |
| ATOM | 381 | CB | TRP | 50 | 23.893 | 5.950 | 54.718 |
| ATOM | 382 | CG | TRP | 50 | 23.295 | 6.983 | 55.719 |

FIGURE 1I

| | Atom | | Residue AA | No. | X | Y | Z |
|---|---|---|---|---|---|---|---|
| ATOM | 383 | CD2 | TRP | 50 | 21.900 | 7.182 | 56.026 |
| ATOM | 384 | CE2 | TRP | 50 | 21.798 | 8.374 | 56.766 |
| ATOM | 385 | CE3 | TRP | 50 | 20.728 | 6.478 | 55.717 |
| ATOM | 386 | CD1 | TRP | 50 | 23.958 | 8.023 | 56.328 |
| ATOM | 387 | NE1 | TRP | 50 | 23.062 | 8.864 | 56.944 |
| ATOM | 388 | CZ2 | TRP | 50 | 20.584 | 8.878 | 57.186 |
| ATOM | 389 | CZ3 | TRP | 50 | 19.523 | 6.981 | 56.133 |
| ATOM | 390 | CH2 | TRP | 50 | 19.457 | 8.170 | 56.857 |
| ATOM | 391 | C | TRP | 50 | 25.349 | 7.289 | 53.146 |
| ATOM | 392 | O | TRP | 50 | 25.341 | 8.514 | 53.020 |
| ATOM | 393 | N | GLN | 51 | 26.453 | 6.565 | 53.178 |
| ATOM | 394 | CA | GLN | 51 | 27.789 | 7.120 | 53.107 |
| ATOM | 395 | CB | GLN | 51 | 28.767 | 5.999 | 52.753 |
| ATOM | 396 | CG | GLN | 51 | 30.017 | 5.934 | 53.599 |
| ATOM | 397 | CD | GLN | 51 | 30.966 | 7.076 | 53.304 |
| ATOM | 398 | OE1 | GLN | 51 | 31.789 | 6.988 | 52.384 |
| ATOM | 399 | NE2 | GLN | 51 | 30.871 | 8.154 | 54.094 |
| ATOM | 400 | C | GLN | 51 | 27.868 | 8.201 | 52.061 |
| ATOM | 401 | O | GLN | 51 | 27.957 | 9.380 | 52.385 |
| ATOM | 402 | N | LYS | 52 | 27.710 | 7.790 | 50.813 |
| ATOM | 403 | CA | LYS | 52 | 27.787 | 8.682 | 49.678 |
| ATOM | 404 | CB | LYS | 52 | 28.082 | 7.855 | 48.430 |
| ATOM | 405 | CG | LYS | 52 | 29.264 | 6.882 | 48.547 |
| ATOM | 406 | CD | LYS | 52 | 30.571 | 7.611 | 48.753 |
| ATOM | 407 | CE | LYS | 52 | 31.775 | 6.684 | 48.554 |
| ATOM | 408 | NZ | LYS | 52 | 33.122 | 7.263 | 48.979 |
| ATOM | 409 | C | LYS | 52 | 26.559 | 9.582 | 49.444 |
| ATOM | 410 | O | LYS | 52 | 26.686 | 10.779 | 49.268 |
| ATOM | 411 | N | PHE | 53 | 25.365 | 9.026 | 49.485 |
| ATOM | 412 | CA | PHE | 53 | 24.170 | 9.815 | 49.228 |
| ATOM | 413 | CB | PHE | 53 | 22.956 | 8.915 | 48.980 |
| ATOM | 414 | CG | PHE | 53 | 22.735 | 8.598 | 47.536 |
| ATOM | 415 | CD1 | PHE | 53 | 23.262 | 7.438 | 46.955 |
| ATOM | 416 | CD2 | PHE | 53 | 22.039 | 9.477 | 46.729 |
| ATOM | 417 | CE1 | PHE | 53 | 23.097 | 7.166 | 45.580 |
| ATOM | 418 | CE2 | PHE | 53 | 21.863 | 9.210 | 45.343 |
| ATOM | 419 | CZ | PHE | 53 | 22.394 | 8.056 | 44.779 |
| ATOM | 420 | C | PHE | 53 | 23.792 | 10.848 | 50.241 |
| ATOM | 421 | O | PHE | 53 | 22.996 | 11.719 | 49.928 |
| ATOM | 422 | N | ILE | 54 | 24.328 | 10.765 | 51.455 |
| ATOM | 423 | CA | ILE | 54 | 23.948 | 11.717 | 52.499 |
| ATOM | 424 | CB | ILE | 54 | 23.057 | 11.068 | 53.537 |
| ATOM | 425 | CG2 | ILE | 54 | 22.448 | 12.129 | 54.395 |
| ATOM | 426 | CG1 | ILE | 54 | 21.987 | 10.196 | 52.885 |
| ATOM | 427 | CD1 | ILE | 54 | 20.908 | 10.938 | 52.190 |
| ATOM | 428 | C | ILE | 54 | 25.096 | 12.277 | 53.295 |
| ATOM | 429 | O | ILE | 54 | 25.168 | 13.476 | 53.572 |
| ATOM | 430 | N | THR | 55 | 25.953 | 11.378 | 53.737 |

FIGURE 1J

| | Atom | | Residue AA | No. | X | Y | Z |
|---|---|---|---|---|---|---|---|
| ATOM | 431 | CA | THR | 55 | 27.055 | 11.801 | 54.550 |
| ATOM | 432 | CB | THR | 55 | 27.824 | 10.601 | 55.221 |
| ATOM | 433 | OG1 | THR | 55 | 26.985 | 9.953 | 56.205 |
| ATOM | 434 | CG2 | THR | 55 | 29.082 | 11.094 | 55.939 |
| ATOM | 435 | C | THR | 55 | 27.948 | 12.740 | 53.784 |
| ATOM | 436 | O | THR | 55 | 28.197 | 13.840 | 54.239 |
| ATOM | 437 | N | GLN | 56 | 28.351 | 12.373 | 52.583 |
| ATOM | 438 | CA | GLN | 56 | 29.228 | 13.256 | 51.824 |
| ATOM | 439 | CB | GLN | 56 | 30.174 | 12.429 | 50.972 |
| ATOM | 440 | CG | GLN | 56 | 31.130 | 11.609 | 51.808 |
| ATOM | 441 | CD | GLN | 56 | 31.537 | 10.306 | 51.140 |
| ATOM | 442 | OE1 | GLN | 56 | 30.731 | 9.368 | 51.040 |
| ATOM | 443 | NE2 | GLN | 56 | 32.793 | 10.238 | 50.675 |
| ATOM | 444 | C | GLN | 56 | 28.576 | 14.382 | 51.000 |
| ATOM | 445 | O | GLN | 56 | 29.151 | 15.465 | 50.882 |
| ATOM | 446 | N | SER | 57 | 27.389 | 14.150 | 50.449 |
| ATOM | 447 | CA | SER | 57 | 26.709 | 15.170 | 49.650 |
| ATOM | 448 | CB | SER | 57 | 25.711 | 14.497 | 48.716 |
| ATOM | 449 | OG | SER | 57 | 24.838 | 13.677 | 49.478 |
| ATOM | 450 | C | SER | 57 | 25.971 | 16.216 | 50.501 |
| ATOM | 451 | O | SER | 57 | 24.784 | 16.037 | 50.830 |
| ATOM | 452 | N | PRO | 58 | 26.602 | 17.388 | 50.724 |
| ATOM | 453 | CD | PRO | 58 | 27.830 | 17.822 | 50.047 |
| ATOM | 454 | CA | PRO | 58 | 26.064 | 18.500 | 51.516 |
| ATOM | 455 | CB | PRO | 58 | 27.001 | 19.649 | 51.145 |
| ATOM | 456 | CG | PRO | 58 | 28.262 | 18.973 | 50.899 |
| ATOM | 457 | C | PRO | 58 | 24.610 | 18.850 | 51.204 |
| ATOM | 458 | O | PRO | 58 | 23.921 | 19.487 | 51.987 |
| ATOM | 459 | N | PHE | 59 | 24.147 | 18.427 | 50.046 |
| ATOM | 460 | CA | PHE | 59 | 22.790 | 18.712 | 49.648 |
| ATOM | 461 | CB | PHE | 59 | 22.512 | 18.125 | 48.261 |
| ATOM | 462 | CG | PHE | 59 | 23.365 | 18.695 | 47.166 |
| ATOM | 463 | CD1 | PHE | 59 | 23.265 | 20.049 | 46.817 |
| ATOM | 464 | CD2 | PHE | 59 | 24.271 | 17.877 | 46.471 |
| ATOM | 465 | CE1 | PHE | 59 | 24.065 | 20.598 | 45.786 |
| ATOM | 466 | CE2 | PHE | 59 | 25.083 | 18.408 | 45.432 |
| ATOM | 467 | CZ | PHE | 59 | 24.979 | 19.772 | 45.090 |
| ATOM | 468 | C | PHE | 59 | 21.777 | 18.100 | 50.573 |
| ATOM | 469 | O | PHE | 59 | 20.842 | 18.748 | 51.010 |
| ATOM | 470 | N | ASN | 60 | 21.990 | 16.837 | 50.883 |
| ATOM | 471 | CA | ASN | 60 | 21.014 | 16.103 | 51.657 |
| ATOM | 472 | CB | ASN | 60 | 20.626 | 14.834 | 50.891 |
| ATOM | 473 | CG | ASN | 60 | 21.203 | 14.797 | 49.504 |
| ATOM | 474 | OD1 | ASN | 60 | 20.471 | 14.831 | 48.535 |
| ATOM | 475 | ND2 | ASN | 60 | 22.520 | 14.756 | 49.401 |
| ATOM | 476 | C | ASN | 60 | 21.263 | 15.748 | 53.125 |
| ATOM | 477 | O | ASN | 60 | 22.412 | 15.705 | 53.612 |
| ATOM | 478 | N | VAL | 61 | 20.137 | 15.448 | 53.786 |

FIGURE 1K

| | Atom | | Residue AA | No. | X | Y | Z |
|---|---|---|---|---|---|---|---|
| ATOM | 479 | CA | VAL | 61 | 20.050 | 15.062 | 55.191 |
| ATOM | 480 | CB | VAL | 61 | 19.325 | 16.133 | 56.042 |
| ATOM | 481 | CG1 | VAL | 61 | 20.133 | 17.428 | 56.083 |
| ATOM | 482 | CG2 | VAL | 61 | 17.917 | 16.393 | 55.489 |
| ATOM | 483 | C | VAL | 61 | 19.188 | 13.819 | 55.219 |
| ATOM | 484 | O | VAL | 61 | 18.393 | 13.581 | 54.308 |
| ATOM | 485 | N | GLY | 62 | 19.333 | 13.031 | 56.270 |
| ATOM | 486 | CA | GLY | 62 | 18.548 | 11.823 | 56.356 |
| ATOM | 487 | C | GLY | 62 | 17.512 | 11.965 | 57.433 |
| ATOM | 488 | O | GLY | 62 | 17.489 | 12.969 | 58.127 |
| ATOM | 489 | N | ILE | 63 | 16.575 | 11.033 | 57.463 |
| ATOM | 490 | CA | ILE | 63 | 15.550 | 10.995 | 58.466 |
| ATOM | 491 | CB | ILE | 63 | 14.349 | 11.946 | 58.174 |
| ATOM | 492 | CG2 | ILE | 63 | 14.787 | 13.200 | 57.537 |
| ATOM | 493 | CG1 | ILE | 63 | 13.332 | 11.325 | 57.258 |
| ATOM | 494 | CD1 | ILE | 63 | 11.997 | 12.008 | 57.376 |
| ATOM | 495 | C | ILE | 63 | 15.108 | 9.534 | 58.638 |
| ATOM | 496 | O | ILE | 63 | 15.733 | 8.612 | 58.103 |
| ATOM | 497 | N | ASP | 64 | 14.122 | 9.315 | 59.499 |
| ATOM | 498 | CA | ASP | 64 | 13.569 | 7.982 | 59.756 |
| ATOM | 499 | CB | ASP | 64 | 14.337 | 7.254 | 60.873 |
| ATOM | 500 | CG | ASP | 64 | 13.965 | 5.755 | 60.993 |
| ATOM | 501 | OD1 | ASP | 64 | 12.750 | 5.425 | 61.080 |
| ATOM | 502 | OD2 | ASP | 64 | 14.902 | 4.909 | 61.015 |
| ATOM | 503 | C | ASP | 64 | 12.127 | 8.201 | 60.177 |
| ATOM | 504 | O | ASP | 64 | 11.844 | 8.551 | 61.306 |
| ATOM | 505 | N | ALA | 65 | 11.224 | 8.061 | 59.231 |
| ATOM | 506 | CA | ALA | 65 | 9.829 | 8.260 | 59.502 |
| ATOM | 507 | CB | ALA | 65 | 9.116 | 8.703 | 58.245 |
| ATOM | 508 | C | ALA | 65 | 9.226 | 6.987 | 60.042 |
| ATOM | 509 | O | ALA | 65 | 9.854 | 5.921 | 60.011 |
| ATOM | 510 | N | ALA | 66 | 7.961 | 7.099 | 60.435 |
| ATOM | 511 | CA | ALA | 66 | 7.210 | 6.011 | 61.034 |
| ATOM | 512 | CB | ALA | 66 | 6.237 | 6.590 | 62.041 |
| ATOM | 513 | C | ALA | 66 | 6.460 | 5.143 | 60.057 |
| ATOM | 514 | O | ALA | 66 | 5.709 | 5.649 | 59.259 |
| ATOM | 515 | N | ILE | 67 | 6.623 | 3.835 | 60.135 |
| ATOM | 516 | CA | ILE | 67 | 5.884 | 2.985 | 59.239 |
| ATOM | 517 | CB | ILE | 67 | 6.176 | 1.565 | 59.503 |
| ATOM | 518 | CG2 | ILE | 67 | 5.240 | 0.684 | 58.732 |
| ATOM | 519 | CG1 | ILE | 67 | 7.606 | 1.271 | 59.113 |
| ATOM | 520 | CD1 | ILE | 67 | 7.961 | -0.169 | 59.370 |
| ATOM | 521 | C | ILE | 67 | 4.399 | 3.220 | 59.449 |
| ATOM | 522 | O | ILE | 67 | 3.589 | 3.012 | 58.548 |
| ATOM | 523 | N | LEU | 68 | 4.033 | 3.640 | 60.653 |
| ATOM | 524 | CA | LEU | 68 | 2.626 | 3.929 | 60.960 |
| ATOM | 525 | CB | LEU | 68 | 2.245 | 3.425 | 62.371 |
| ATOM | 526 | CG | LEU | 68 | 1.955 | 1.956 | 62.706 |

FIGURE 1L

| | Atom | | Residue AA | No. | X | Y | Z |
|---|---|---|---|---|---|---|---|
| ATOM | 527 | CD1 | LEU | 68 | 0.723 | 1.474 | 61.960 |
| ATOM | 528 | CD2 | LEU | 68 | 3.140 | 1.089 | 62.380 |
| ATOM | 529 | C | LEU | 68 | 2.355 | 5.445 | 60.866 |
| ATOM | 530 | O | LEU | 68 | 3.007 | 6.250 | 61.537 |
| ATOM | 531 | N | MET | 69 | 1.415 | 5.837 | 60.013 |
| ATOM | 532 | CA | MET | 69 | 1.076 | 7.247 | 59.897 |
| ATOM | 533 | CB | MET | 69 | 2.046 | 7.998 | 58.976 |
| ATOM | 534 | CG | MET | 69 | 2.394 | 7.364 | 57.607 |
| ATOM | 535 | SD | MET | 69 | 3.550 | 8.460 | 56.676 |
| ATOM | 536 | CE | MET | 69 | 5.227 | 7.677 | 56.906 |
| ATOM | 537 | C | MET | 69 | -0.376 | 7.550 | 59.548 |
| ATOM | 538 | O | MET | 69 | -1.117 | 6.698 | 59.012 |
| ATOM | 539 | N | ASN | 70 | -0.784 | 8.742 | 59.982 |
| ATOM | 540 | CA | ASN | 70 | -2.130 | 9.303 | 59.796 |
| ATOM | 541 | CB | ASN | 70 | -2.079 | 10.813 | 60.084 |
| ATOM | 542 | CG | ASN | 70 | -3.446 | 11.459 | 60.126 |
| ATOM | 543 | OD1 | ASN | 70 | -3.672 | 12.468 | 59.458 |
| ATOM | 544 | ND2 | ASN | 70 | -4.352 | 10.909 | 60.930 |
| ATOM | 545 | C | ASN | 70 | -2.683 | 9.034 | 58.393 |
| ATOM | 546 | O | ASN | 70 | -2.240 | 9.636 | 57.415 |
| ATOM | 547 | N | PRO | 71 | -3.724 | 8.186 | 58.303 |
| ATOM | 548 | CD | PRO | 71 | -4.508 | 7.660 | 59.438 |
| ATOM | 549 | CA | PRO | 71 | -4.352 | 7.823 | 57.032 |
| ATOM | 550 | CB | PRO | 71 | -5.636 | 7.108 | 57.461 |
| ATOM | 551 | CG | PRO | 71 | -5.301 | 6.534 | 58.788 |
| ATOM | 552 | C | PRO | 71 | -4.667 | 9.014 | 56.147 |
| ATOM | 553 | O | PRO | 71 | -4.613 | 8.874 | 54.925 |
| ATOM | 554 | N | ALA | 72 | -4.996 | 10.175 | 56.739 |
| ATOM | 555 | CA | ALA | 72 | -5.318 | 11.387 | 55.950 |
| ATOM | 556 | CB | ALA | 72 | -5.513 | 12.622 | 56.853 |
| ATOM | 557 | C | ALA | 72 | -4.254 | 11.655 | 54.870 |
| ATOM | 558 | O | ALA | 72 | -4.574 | 12.137 | 53.780 |
| ATOM | 559 | N | VAL | 73 | -3.004 | 11.295 | 55.158 |
| ATOM | 560 | CA | VAL | 73 | -1.921 | 11.451 | 54.205 |
| ATOM | 561 | CB | VAL | 73 | -0.613 | 10.960 | 54.778 |
| ATOM | 562 | CG1 | VAL | 73 | 0.309 | 10.493 | 53.664 |
| ATOM | 563 | CG2 | VAL | 73 | 0.035 | 12.069 | 55.581 |
| ATOM | 564 | C | VAL | 73 | -2.220 | 10.619 | 52.994 |
| ATOM | 565 | O | VAL | 73 | -2.253 | 11.119 | 51.893 |
| ATOM | 566 | N | TRP | 74 | -2.490 | 9.350 | 53.209 |
| ATOM | 567 | CA | TRP | 74 | -2.777 | 8.448 | 52.114 |
| ATOM | 568 | CB | TRP | 74 | -3.016 | 7.041 | 52.657 |
| ATOM | 569 | CG | TRP | 74 | -1.766 | 6.497 | 53.316 |
| ATOM | 570 | CD2 | TRP | 74 | -0.485 | 6.359 | 52.704 |
| ATOM | 571 | CE2 | TRP | 74 | 0.410 | 5.912 | 53.695 |
| ATOM | 572 | CE3 | TRP | 74 | -0.002 | 6.578 | 51.413 |
| ATOM | 573 | CD1 | TRP | 74 | -1.605 | 6.120 | 54.634 |
| ATOM | 574 | NE1 | TRP | 74 | -0.297 | 5.771 | 54.864 |

FIGURE 1M

| | Atom | | Residue AA | No. | X | Y | Z |
|---|---|---|---|---|---|---|---|
| ATOM | 575 | CZ2 | TRP | 74 | 1.767 | 5.684 | 53.426 |
| ATOM | 576 | CZ3 | TRP | 74 | 1.344 | 6.352 | 51.152 |
| ATOM | 577 | CH2 | TRP | 74 | 2.213 | 5.910 | 52.150 |
| ATOM | 578 | C | TRP | 74 | -3.873 | 8.890 | 51.145 |
| ATOM | 579 | O | TRP | 74 | -4.086 | 8.258 | 50.106 |
| ATOM | 580 | N | GLU | 75 | -4.561 | 9.977 | 51.476 |
| ATOM | 581 | CA | GLU | 75 | -5.594 | 10.516 | 50.603 |
| ATOM | 582 | CB | GLU | 75 | -6.708 | 11.126 | 51.407 |
| ATOM | 583 | CG | GLU | 75 | -7.369 | 10.156 | 52.327 |
| ATOM | 584 | CD | GLU | 75 | -8.386 | 10.851 | 53.197 |
| ATOM | 585 | OE1 | GLU | 75 | -7.981 | 11.819 | 53.903 |
| ATOM | 586 | OE2 | GLU | 75 | -9.590 | 10.467 | 53.157 |
| ATOM | 587 | C | GLU | 75 | -4.950 | 11.590 | 49.766 |
| ATOM | 588 | O | GLU | 75 | -5.175 | 11.656 | 48.572 |
| ATOM | 589 | N | ALA | 76 | -4.145 | 12.437 | 50.398 |
| ATOM | 590 | CA | ALA | 76 | -3.438 | 13.489 | 49.671 |
| ATOM | 591 | CB | ALA | 76 | -2.752 | 14.437 | 50.615 |
| ATOM | 592 | C | ALA | 76 | -2.398 | 12.829 | 48.778 |
| ATOM | 593 | O | ALA | 76 | -1.732 | 13.513 | 47.991 |
| ATOM | 594 | N | SER | 77 | -2.180 | 11.527 | 49.000 |
| ATOM | 595 | CA | SER | 77 | -1.247 | 10.741 | 48.189 |
| ATOM | 596 | CB | SER | 77 | -0.497 | 9.705 | 49.043 |
| ATOM | 597 | OG | SER | 77 | -1.305 | 8.578 | 49.336 |
| ATOM | 598 | C | SER | 77 | -2.042 | 10.042 | 47.070 |
| ATOM | 599 | O | SER | 77 | -1.475 | 9.643 | 46.042 |
| ATOM | 600 | N | GLY | 78 | -3.356 | 9.910 | 47.281 |
| ATOM | 601 | CA | GLY | 78 | -4.221 | 9.263 | 46.309 |
| ATOM | 602 | C | GLY | 78 | -4.087 | 7.750 | 46.354 |
| ATOM | 603 | O | GLY | 78 | -4.821 | 7.032 | 45.671 |
| ATOM | 604 | N | HIS | 79 | -3.141 | 7.252 | 47.152 |
| ATOM | 605 | CA | HIS | 79 | -2.938 | 5.808 | 47.299 |
| ATOM | 606 | CB | HIS | 79 | -1.827 | 5.515 | 48.309 |
| ATOM | 607 | CG | HIS | 79 | -0.463 | 5.491 | 47.709 |
| ATOM | 608 | CD2 | HIS | 79 | 0.639 | 4.776 | 48.038 |
| ATOM | 609 | ND1 | HIS | 79 | -0.105 | 6.282 | 46.636 |
| ATOM | 610 | CE1 | HIS | 79 | 1.163 | 6.058 | 46.331 |
| ATOM | 611 | NE2 | HIS | 79 | 1.639 | 5.150 | 47.166 |
| ATOM | 612 | C | HIS | 79 | -4.229 | 5.130 | 47.773 |
| ATOM | 613 | O | HIS | 79 | -4.436 | 3.934 | 47.550 |
| ATOM | 614 | N | LEU | 80 | -5.063 | 5.897 | 48.465 |
| ATOM | 615 | CA | LEU | 80 | -6.321 | 5.403 | 48.944 |
| ATOM | 616 | CB | LEU | 80 | -7.165 | 6.589 | 49.390 |
| ATOM | 617 | CG | LEU | 80 | -7.708 | 6.553 | 50.822 |
| ATOM | 618 | CD1 | LEU | 80 | -8.834 | 5.530 | 50.941 |
| ATOM | 619 | CD2 | LEU | 80 | -6.568 | 6.271 | 51.811 |
| ATOM | 620 | C | LEU | 80 | -7.019 | 4.668 | 47.794 |
| ATOM | 621 | O | LEU | 80 | -7.624 | 3.613 | 47.998 |
| ATOM | 622 | N | ASN | 81 | -6.879 | 5.207 | 46.579 |

FIGURE 1N

| Atom | | | Residue AA | No. | X | Y | Z |
|---|---|---|---|---|---|---|---|
| ATOM | 623 | CA | ASN | 81 | -7.492 | 4.640 | 45.360 |
| ATOM | 624 | CB | ASN | 81 | -8.777 | 5.431 | 44.972 |
| ATOM | 625 | CG | ASN | 81 | -8.722 | 6.943 | 45.344 |
| ATOM | 626 | OD1 | ASN | 81 | -7.917 | 7.730 | 44.807 |
| ATOM | 627 | ND2 | ASN | 81 | -9.613 | 7.344 | 46.249 |
| ATOM | 628 | C | ASN | 81 | -6.578 | 4.493 | 44.113 |
| ATOM | 629 | O | ASN | 81 | -6.494 | 3.431 | 43.506 |
| ATOM | 630 | N | ASN | 82 | -5.942 | 5.580 | 43.707 |
| ATOM | 631 | CA | ASN | 82 | -5.068 | 5.568 | 42.552 |
| ATOM | 632 | CB | ASN | 82 | -4.433 | 6.947 | 42.351 |
| ATOM | 633 | CG | ASN | 82 | -5.485 | 8.078 | 42.232 |
| ATOM | 634 | OD1 | ASN | 82 | -5.215 | 9.234 | 42.603 |
| ATOM | 635 | ND2 | ASN | 82 | -6.686 | 7.748 | 41.715 |
| ATOM | 636 | C | ASN | 82 | -3.996 | 4.498 | 42.698 |
| ATOM | 637 | O | ASN | 82 | -3.502 | 3.973 | 41.688 |
| ATOM | 638 | N | PHE | 83 | -3.594 | 4.201 | 43.943 |
| ATOM | 639 | CA | PHE | 83 | -2.591 | 3.132 | 44.163 |
| ATOM | 640 | CB | PHE | 83 | -2.036 | 3.070 | 45.607 |
| ATOM | 641 | CG | PHE | 83 | -1.194 | 1.824 | 45.882 |
| ATOM | 642 | CD1 | PHE | 83 | -1.806 | 0.613 | 46.273 |
| ATOM | 643 | CD2 | PHE | 83 | 0.193 | 1.834 | 45.654 |
| ATOM | 644 | CE1 | PHE | 83 | -1.056 | -0.551 | 46.413 |
| ATOM | 645 | CE2 | PHE | 83 | 0.952 | 0.665 | 45.798 |
| ATOM | 646 | CZ | PHE | 83 | 0.327 | -0.530 | 46.175 |
| ATOM | 647 | C | PHE | 83 | -3.330 | 1.826 | 43.851 |
| ATOM | 648 | O | PHE | 83 | -4.176 | 1.339 | 44.640 |
| ATOM | 649 | N | ASN | 84 | -2.946 | 1.217 | 42.740 |
| ATOM | 650 | CA | ASN | 84 | -3.626 | 0.017 | 42.332 |
| ATOM | 651 | CB | ASN | 84 | -4.925 | 0.438 | 41.633 |
| ATOM | 652 | CG | ASN | 84 | -6.162 | 0.142 | 42.452 |
| ATOM | 653 | OD1 | ASN | 84 | -6.967 | -0.687 | 42.064 |
| ATOM | 654 | ND2 | ASN | 84 | -6.354 | 0.857 | 43.548 |
| ATOM | 655 | C | ASN | 84 | -2.841 | -0.940 | 41.410 |
| ATOM | 656 | O | ASN | 84 | -1.686 | -0.686 | 40.950 |
| ATOM | 657 | N | ALA | 85 | -3.488 | -2.091 | 41.230 |
| ATOM | 658 | CA | ALA | 85 | -3.061 | -3.174 | 40.353 |
| ATOM | 659 | CB | ALA | 85 | -2.431 | -4.353 | 41.159 |
| ATOM | 660 | C | ALA | 85 | -4.465 | -3.530 | 39.809 |
| ATOM | 661 | O | ALA | 85 | -5.319 | -4.028 | 40.565 |
| ATOM | 662 | N | PRO | 86 | -4.808 | -2.982 | 38.622 |
| ATOM | 663 | CD | PRO | 86 | -4.138 | -1.832 | 37.973 |
| ATOM | 664 | CA | PRO | 86 | -6.109 | -3.244 | 37.990 |
| ATOM | 665 | CB | PRO | 86 | -6.079 | -2.334 | 36.737 |
| ATOM | 666 | CG | PRO | 86 | -5.301 | -1.135 | 37.230 |
| ATOM | 667 | C | PRO | 86 | -6.290 | -4.744 | 37.643 |
| ATOM | 668 | O | PRO | 86 | -5.261 | -5.408 | 37.279 |
| ATOM | 669 | OT | PRO | 86 | -7.457 | -5.236 | 37.815 |
| ATOM | 670 | CB | ALA | 150 | -9.259 | -1.337 | 39.891 |

FIGURE 1O

| | Atom | | Residue AA | No. | X | Y | Z |
|---|---|---|---|---|---|---|---|
| ATOM | 671 | C | ALA | 150 | -8.591 | -3.142 | 41.644 |
| ATOM | 672 | O | ALA | 150 | -9.636 | -3.252 | 42.345 |
| ATOM | 673 | N | ALA | 150 | -9.441 | -3.796 | 39.273 |
| ATOM | 674 | CA | ALA | 150 | -8.680 | -2.785 | 40.107 |
| ATOM | 675 | N | ALA | 151 | -7.356 | -3.292 | 42.155 |
| ATOM | 676 | CA | ALA | 151 | -7.122 | -3.646 | 43.556 |
| ATOM | 677 | CB | ALA | 151 | -6.622 | -5.100 | 43.644 |
| ATOM | 678 | C | ALA | 151 | -6.136 | -2.710 | 44.285 |
| ATOM | 679 | O | ALA | 151 | -5.024 | -2.462 | 43.786 |
| ATOM | 680 | N | ASN | 152 | -6.555 | -2.182 | 45.454 |
| ATOM | 681 | CA | ASN | 152 | -5.706 | -1.297 | 46.305 |
| ATOM | 682 | CB | ASN | 152 | -6.514 | -0.173 | 46.981 |
| ATOM | 683 | CG | ASN | 152 | -5.635 | 0.751 | 47.810 |
| ATOM | 684 | OD1 | ASN | 152 | -5.959 | 1.085 | 48.952 |
| ATOM | 685 | ND2 | ASN | 152 | -4.493 | 1.128 | 47.254 |
| ATOM | 686 | C | ASN | 152 | -4.947 | -2.156 | 47.354 |
| ATOM | 687 | O | ASN | 152 | -5.446 | -2.513 | 48.448 |
| ATOM | 688 | N | LEU | 153 | -3.712 | -2.451 | 46.973 |
| ATOM | 689 | CA | LEU | 153 | -2.785 | -3.304 | 47.705 |
| ATOM | 690 | CB | LEU | 153 | -1.719 | -3.766 | 46.681 |
| ATOM | 691 | CG | LEU | 153 | -1.890 | -3.530 | 45.152 |
| ATOM | 692 | CD1 | LEU | 153 | -0.510 | -3.491 | 44.449 |
| ATOM | 693 | CD2 | LEU | 153 | -2.832 | -4.590 | 44.526 |
| ATOM | 694 | C | LEU | 153 | -2.087 | -2.754 | 48.976 |
| ATOM | 695 | O | LEU | 153 | -1.036 | -3.258 | 49.356 |
| ATOM | 696 | N | MET | 154 | -2.621 | -1.718 | 49.617 |
| ATOM | 697 | CA | MET | 154 | -1.970 | -1.165 | 50.822 |
| ATOM | 698 | CB | MET | 154 | -2.513 | 0.226 | 51.150 |
| ATOM | 699 | CG | MET | 154 | -2.319 | 1.275 | 50.056 |
| ATOM | 700 | SD | MET | 154 | -3.018 | 2.859 | 50.539 |
| ATOM | 701 | CE | MET | 154 | -1.966 | 3.276 | 51.958 |
| ATOM | 702 | C | MET | 154 | -2.312 | -2.109 | 51.953 |
| ATOM | 703 | O | MET | 154 | -3.446 | -2.614 | 51.993 |
| ATOM | 704 | N | PHE | 155 | -1.377 | -2.357 | 52.872 |
| ATOM | 705 | CA | PHE | 155 | -1.674 | -3.301 | 53.967 |
| ATOM | 706 | CB | PHE | 155 | -0.390 | -3.952 | 54.475 |
| ATOM | 707 | CG | PHE | 155 | -0.278 | -5.410 | 54.136 |
| ATOM | 708 | CD1 | PHE | 155 | -1.360 | -6.269 | 54.346 |
| ATOM | 709 | CD2 | PHE | 155 | 0.914 | -5.935 | 53.644 |
| ATOM | 710 | CE1 | PHE | 155 | -1.246 | -7.634 | 54.074 |
| ATOM | 711 | CE2 | PHE | 155 | 1.038 | -7.301 | 53.367 |
| ATOM | 712 | CZ | PHE | 155 | -0.040 | -8.149 | 53.583 |
| ATOM | 713 | C | PHE | 155 | -2.587 | -2.796 | 55.118 |
| ATOM | 714 | O | PHE | 155 | -2.234 | -1.901 | 55.919 |
| ATOM | 715 | N | ALA | 156 | -3.746 | -3.431 | 55.229 |
| ATOM | 716 | CA | ALA | 156 | -4.754 | -3.024 | 56.201 |
| ATOM | 717 | CB | ALA | 156 | -6.131 | -3.500 | 55.713 |
| ATOM | 718 | C | ALA | 156 | -4.586 | -3.355 | 57.691 |

FIGURE 1P

| | Atom | | Residue AA | No. | X | Y | Z |
|---|---|---|---|---|---|---|---|
| ATOM | 719 | O | ALA | 156 | -4.446 | -4.528 | 58.060 |
| ATOM | 720 | N | THR | 157 | -4.655 | -2.331 | 58.544 |
| ATOM | 721 | CA | THR | 157 | -4.576 | -2.559 | 59.985 |
| ATOM | 722 | CB | THR | 157 | -3.161 | -2.315 | 60.576 |
| ATOM | 723 | OG1 | THR | 157 | -3.015 | -3.127 | 61.750 |
| ATOM | 724 | CG2 | THR | 157 | -2.965 | -0.849 | 61.002 |
| ATOM | 725 | C | THR | 157 | -5.609 | -1.753 | 60.785 |
| ATOM | 726 | O | THR | 157 | -6.201 | -0.782 | 60.276 |
| ATOM | 727 | N | ALA | 158 | -5.830 | -2.195 | 62.029 |
| ATOM | 728 | CA | ALA | 158 | -6.769 | -1.560 | 62.961 |
| ATOM | 729 | CB | ALA | 158 | -7.998 | -2.460 | 63.209 |
| ATOM | 730 | C | ALA | 158 | -6.041 | -1.283 | 64.271 |
| ATOM | 731 | O | ALA | 158 | -5.348 | -2.168 | 64.802 |
| ATOM | 732 | N | GLN | 159 | -6.209 | -0.055 | 64.773 |
| ATOM | 733 | CA | GLN | 159 | -5.572 | 0.386 | 66.009 |
| ATOM | 734 | CB | GLN | 159 | -4.699 | 1.594 | 65.713 |
| ATOM | 735 | CG | GLN | 159 | -3.917 | 2.123 | 66.912 |
| ATOM | 736 | CD | GLN | 159 | -3.217 | 3.446 | 66.583 |
| ATOM | 737 | OE1 | GLN | 159 | -2.010 | 3.633 | 66.841 |
| ATOM | 738 | NE2 | GLN | 159 | -3.975 | 4.371 | 65.971 |
| ATOM | 739 | C | GLN | 159 | -6.582 | 0.728 | 67.106 |
| ATOM | 740 | O | GLN | 159 | -7.052 | 1.870 | 67.189 |
| ATOM | 741 | N | GLY | 160 | -6.899 | -0.270 | 67.939 |
| ATOM | 742 | CA | GLY | 160 | -7.860 | -0.112 | 69.032 |
| ATOM | 743 | C | GLY | 160 | -8.879 | -1.268 | 69.132 |
| ATOM | 744 | O | GLY | 160 | -8.686 | -2.263 | 69.872 |
| ATOM | 745 | N | ALA | 161 | -9.992 | -1.112 | 68.409 |
| ATOM | 746 | CA | ALA | 161 | -11.069 | -2.115 | 68.343 |
| ATOM | 747 | CB | ALA | 161 | -11.548 | -2.514 | 69.770 |
| ATOM | 748 | C | ALA | 161 | -12.268 | -1.686 | 67.420 |
| ATOM | 749 | O | ALA | 161 | -12.526 | -2.435 | 66.435 |
| ATOM | 750 | OT | ALA | 161 | -12.912 | -0.607 | 67.623 |
| ATOM | 751 | CB | ALA | 164 | -15.791 | -0.318 | 63.377 |
| ATOM | 752 | C | ALA | 164 | -13.539 | -0.063 | 62.220 |
| ATOM | 753 | O | ALA | 164 | -12.340 | -0.348 | 61.945 |
| ATOM | 754 | N | ALA | 164 | -13.735 | -0.946 | 64.603 |
| ATOM | 755 | CA | ALA | 164 | -14.368 | -0.892 | 63.239 |
| ATOM | 756 | N | ALA | 165 | -14.204 | 0.928 | 61.627 |
| ATOM | 757 | CA | ALA | 165 | -13.566 | 1.841 | 60.681 |
| ATOM | 758 | CB | ALA | 165 | -14.528 | 2.161 | 59.486 |
| ATOM | 759 | C | ALA | 165 | -13.263 | 3.109 | 61.507 |
| ATOM | 760 | O | ALA | 165 | -14.156 | 3.586 | 62.236 |
| ATOM | 761 | N | THR | 166 | -11.995 | 3.555 | 61.451 |
| ATOM | 762 | CA | THR | 166 | -11.415 | 4.749 | 62.133 |
| ATOM | 763 | CB | THR | 166 | -12.276 | 5.348 | 63.292 |
| ATOM | 764 | OG1 | THR | 166 | -12.832 | 4.292 | 64.097 |
| ATOM | 765 | CG2 | THR | 166 | -13.364 | 6.322 | 62.755 |
| ATOM | 766 | C | THR | 166 | -10.075 | 4.320 | 62.723 |

FIGURE 1Q

| | Atom | | Residue AA | No. | X | Y | Z |
|---|---|---|---|---|---|---|---|
| ATOM | 767 | O | THR | 166 | -9.100 | 5.117 | 62.816 |
| ATOM | 768 | N | ASN | 167 | -10.096 | 3.066 | 63.194 |
| ATOM | 769 | CA | ASN | 167 | -8.925 | 2.363 | 63.754 |
| ATOM | 770 | CB | ASN | 167 | -9.349 | 1.045 | 64.460 |
| ATOM | 771 | CG | ASN | 167 | -10.650 | 1.196 | 65.306 |
| ATOM | 772 | OD1 | ASN | 167 | -11.764 | 1.178 | 64.763 |
| ATOM | 773 | ND2 | ASN | 167 | -10.504 | 1.358 | 66.618 |
| ATOM | 774 | C | ASN | 167 | -8.132 | 2.046 | 62.478 |
| ATOM | 775 | O | ASN | 167 | -6.896 | 1.920 | 62.501 |
| ATOM | 776 | N | ALA | 168 | -8.897 | 1.945 | 61.380 |
| ATOM | 777 | CA | ALA | 168 | -8.418 | 1.696 | 60.021 |
| ATOM | 778 | CB | ALA | 168 | -9.616 | 1.798 | 59.028 |
| ATOM | 779 | C | ALA | 168 | -7.271 | 2.633 | 59.587 |
| ATOM | 780 | O | ALA | 168 | -7.488 | 3.781 | 59.163 |
| ATOM | 781 | N | ILE | 169 | -6.050 | 2.155 | 59.777 |
| ATOM | 782 | CA | ILE | 169 | -4.854 | 2.890 | 59.390 |
| ATOM | 783 | CB | ILE | 169 | -4.118 | 3.465 | 60.612 |
| ATOM | 784 | CG2 | ILE | 169 | -5.110 | 4.230 | 61.493 |
| ATOM | 785 | CG1 | ILE | 169 | -3.444 | 2.346 | 61.407 |
| ATOM | 786 | CD1 | ILE | 169 | -2.450 | 2.854 | 62.410 |
| ATOM | 787 | C | ILE | 169 | -4.012 | 1.811 | 58.692 |
| ATOM | 788 | O | ILE | 169 | -4.293 | 0.611 | 58.860 |
| ATOM | 789 | N | PHE | 170 | -3.027 | 2.184 | 57.877 |
| ATOM | 790 | CA | PHE | 170 | -2.260 | 1.141 | 57.196 |
| ATOM | 791 | CB | PHE | 170 | -2.618 | 1.071 | 55.736 |
| ATOM | 792 | CG | PHE | 170 | -4.039 | 1.336 | 55.480 |
| ATOM | 793 | CD1 | PHE | 170 | -5.004 | 0.444 | 55.921 |
| ATOM | 794 | CD2 | PHE | 170 | -4.437 | 2.525 | 54.868 |
| ATOM | 795 | CE1 | PHE | 170 | -6.357 | 0.735 | 55.764 |
| ATOM | 796 | CE2 | PHE | 170 | -5.784 | 2.822 | 54.706 |
| ATOM | 797 | CZ | PHE | 170 | -6.747 | 1.925 | 55.156 |
| ATOM | 798 | C | PHE | 170 | -0.803 | 1.368 | 57.252 |
| ATOM | 799 | O | PHE | 170 | -0.319 | 2.397 | 57.769 |
| ATOM | 800 | N | LEU | 171 | -0.105 | 0.412 | 56.658 |
| ATOM | 801 | CA | LEU | 171 | 1.337 | 0.463 | 56.587 |
| ATOM | 802 | CB | LEU | 171 | 1.928 | -0.943 | 56.681 |
| ATOM | 803 | CG | LEU | 171 | 1.151 | -2.044 | 57.392 |
| ATOM | 804 | CD1 | LEU | 171 | 2.139 | -3.163 | 57.661 |
| ATOM | 805 | CD2 | LEU | 171 | 0.499 | -1.564 | 58.675 |
| ATOM | 806 | C | LEU | 171 | 1.707 | 1.130 | 55.253 |
| ATOM | 807 | O | LEU | 171 | 1.005 | 0.965 | 54.244 |
| ATOM | 808 | N | ARG | 172 | 2.796 | 1.896 | 55.274 |
| ATOM | 809 | CA | ARG | 172 | 3.307 | 2.617 | 54.110 |
| ATOM | 810 | CB | ARG | 172 | 4.472 | 3.541 | 54.524 |
| ATOM | 811 | CG | ARG | 172 | 5.796 | 2.853 | 54.938 |
| ATOM | 812 | CD | ARG | 172 | 6.824 | 3.914 | 55.311 |
| ATOM | 813 | NE | ARG | 172 | 8.011 | 3.399 | 56.007 |
| ATOM | 814 | CZ | ARG | 172 | 9.012 | 4.167 | 56.470 |

FIGURE 1R

| | Atom | | Residue AA | No. | X | Y | Z |
|---|---|---|---|---|---|---|---|
| ATOM | 815 | NH1 | ARG | 172 | 8.971 | 5.495 | 56.319 |
| ATOM | 816 | NH2 | ARG | 172 | 10.073 | 3.615 | 57.078 |
| ATOM | 817 | C | ARG | 172 | 3.772 | 1.747 | 52.950 |
| ATOM | 818 | O | ARG | 172 | 4.615 | 0.866 | 53.131 |
| ATOM | 819 | N | PRO | 173 | 3.197 | 1.950 | 51.751 |
| ATOM | 820 | CD | PRO | 173 | 1.946 | 2.643 | 51.435 |
| ATOM | 821 | CA | PRO | 173 | 3.616 | 1.158 | 50.600 |
| ATOM | 822 | CB | PRO | 173 | 2.377 | 1.190 | 49.705 |
| ATOM | 823 | CG | PRO | 173 | 1.285 | 1.650 | 50.579 |
| ATOM | 824 | C | PRO | 173 | 4.770 | 1.941 | 49.949 |
| ATOM | 825 | O | PRO | 173 | 5.507 | 1.442 | 49.097 |
| ATOM | 826 | N | GLU | 174 | 4.941 | 3.175 | 50.398 |
| ATOM | 827 | CA | GLU | 174 | 5.955 | 4.038 | 49.859 |
| ATOM | 828 | CB | GLU | 174 | 5.335 | 4.880 | 48.750 |
| ATOM | 829 | CG | GLU | 174 | 6.198 | 6.021 | 48.222 |
| ATOM | 830 | CD | GLU | 174 | 5.581 | 6.686 | 46.986 |
| ATOM | 831 | OE1 | GLU | 174 | 6.341 | 7.002 | 46.036 |
| ATOM | 832 | OE2 | GLU | 174 | 4.332 | 6.862 | 46.949 |
| ATOM | 833 | C | GLU | 174 | 6.562 | 4.919 | 50.930 |
| ATOM | 834 | O | GLU | 174 | 5.886 | 5.710 | 51.594 |
| ATOM | 835 | N | THR | 175 | 7.867 | 4.809 | 51.026 |
| ATOM | 836 | CA | THR | 175 | 8.681 | 5.539 | 51.970 |
| ATOM | 837 | CB | THR | 175 | 10.062 | 4.953 | 51.871 |
| ATOM | 838 | OG1 | THR | 175 | 9.955 | 3.542 | 52.095 |
| ATOM | 839 | CG2 | THR | 175 | 11.017 | 5.588 | 52.852 |
| ATOM | 840 | C | THR | 175 | 8.763 | 7.071 | 51.819 |
| ATOM | 841 | O | THR | 175 | 9.172 | 7.785 | 52.738 |
| ATOM | 842 | N | ALA | 176 | 8.323 | 7.579 | 50.677 |
| ATOM | 843 | CA | ALA | 176 | 8.401 | 9.011 | 50.388 |
| ATOM | 844 | CB | ALA | 176 | 8.128 | 9.238 | 48.939 |
| ATOM | 845 | C | ALA | 176 | 7.507 | 9.896 | 51.198 |
| ATOM | 846 | O | ALA | 176 | 7.902 | 10.976 | 51.618 |
| ATOM | 847 | N | GLN | 177 | 6.272 | 9.460 | 51.346 |
| ATOM | 848 | CA | GLN | 177 | 5.312 | 10.229 | 52.087 |
| ATOM | 849 | CB | GLN | 177 | 4.037 | 9.418 | 52.272 |
| ATOM | 850 | CG | GLN | 177 | 3.291 | 9.241 | 50.961 |
| ATOM | 851 | CD | GLN | 177 | 3.356 | 10.512 | 50.128 |
| ATOM | 852 | OE1 | GLN | 177 | 2.918 | 11.583 | 50.571 |
| ATOM | 853 | NE2 | GLN | 177 | 3.979 | 10.419 | 48.953 |
| ATOM | 854 | C | GLN | 177 | 5.889 | 10.686 | 53.404 |
| ATOM | 855 | O | GLN | 177 | 5.796 | 11.862 | 53.753 |
| ATOM | 856 | N | GLY | 178 | 6.584 | 9.773 | 54.069 |
| ATOM | 857 | CA | GLY | 178 | 7.212 | 10.088 | 55.338 |
| ATOM | 858 | C | GLY | 178 | 8.171 | 11.254 | 55.195 |
| ATOM | 859 | O | GLY | 178 | 8.404 | 11.988 | 56.149 |
| ATOM | 860 | N | ILE | 179 | 8.744 | 11.424 | 54.010 |
| ATOM | 861 | CA | ILE | 179 | 9.650 | 12.536 | 53.800 |
| ATOM | 862 | CB | ILE | 179 | 10.609 | 12.326 | 52.608 |

FIGURE 1S

| | Atom | | Residue AA | No. | X | Y | Z |
|---|---|---|---|---|---|---|---|
| ATOM | 863 | CG2 | ILE | 179 | 11.754 | 13.330 | 52.692 |
| ATOM | 864 | CG1 | ILE | 179 | 11.174 | 10.910 | 52.615 |
| ATOM | 865 | CD1 | ILE | 179 | 12.222 | 10.657 | 51.550 |
| ATOM | 866 | C | ILE | 179 | 8.839 | 13.791 | 53.532 |
| ATOM | 867 | O | ILE | 179 | 9.010 | 14.803 | 54.211 |
| ATOM | 868 | N | PHE | 180 | 7.911 | 13.710 | 52.585 |
| ATOM | 869 | CA | PHE | 180 | 7.108 | 14.875 | 52.216 |
| ATOM | 870 | CB | PHE | 180 | 6.062 | 14.494 | 51.184 |
| ATOM | 871 | CG | PHE | 180 | 6.653 | 14.170 | 49.878 |
| ATOM | 872 | CD1 | PHE | 180 | 6.156 | 13.139 | 49.108 |
| ATOM | 873 | CD2 | PHE | 180 | 7.779 | 14.860 | 49.440 |
| ATOM | 874 | CE1 | PHE | 180 | 6.787 | 12.788 | 47.894 |
| ATOM | 875 | CE2 | PHE | 180 | 8.411 | 14.521 | 48.244 |
| ATOM | 876 | CZ | PHE | 180 | 7.916 | 13.482 | 47.466 |
| ATOM | 877 | C | PHE | 180 | 6.474 | 15.597 | 53.370 |
| ATOM | 878 | O | PHE | 180 | 6.536 | 16.835 | 53.466 |
| ATOM | 879 | N | VAL | 181 | 5.859 | 14.814 | 54.242 |
| ATOM | 880 | CA | VAL | 181 | 5.215 | 15.363 | 55.420 |
| ATOM | 881 | CB | VAL | 181 | 4.461 | 14.261 | 56.210 |
| ATOM | 882 | CG1 | VAL | 181 | 3.239 | 13.833 | 55.442 |
| ATOM | 883 | CG2 | VAL | 181 | 5.364 | 13.047 | 56.447 |
| ATOM | 884 | C | VAL | 181 | 6.248 | 16.034 | 56.330 |
| ATOM | 885 | O | VAL | 181 | 5.918 | 16.952 | 57.093 |
| ATOM | 886 | N | ASN | 182 | 7.496 | 15.583 | 56.229 |
| ATOM | 887 | CA | ASN | 182 | 8.565 | 16.121 | 57.047 |
| ATOM | 888 | CB | ASN | 182 | 9.427 | 14.992 | 57.652 |
| ATOM | 889 | CG | ASN | 182 | 8.758 | 14.312 | 58.860 |
| ATOM | 890 | OD1 | ASN | 182 | 9.156 | 14.505 | 60.017 |
| ATOM | 891 | ND2 | ASN | 182 | 7.740 | 13.518 | 58.587 |
| ATOM | 892 | C | ASN | 182 | 9.427 | 17.086 | 56.277 |
| ATOM | 893 | O | ASN | 182 | 10.598 | 17.277 | 56.607 |
| ATOM | 894 | N | TYR | 183 | 8.851 | 17.722 | 55.268 |
| ATOM | 895 | CA | TYR | 183 | 9.627 | 18.671 | 54.477 |
| ATOM | 896 | CB | TYR | 183 | 8.911 | 19.044 | 53.144 |
| ATOM | 897 | CG | TYR | 183 | 9.484 | 20.289 | 52.430 |
| ATOM | 898 | CD1 | TYR | 183 | 8.692 | 21.428 | 52.219 |
| ATOM | 899 | CE1 | TYR | 183 | 9.223 | 22.602 | 51.646 |
| ATOM | 900 | CD2 | TYR | 183 | 10.839 | 20.352 | 52.032 |
| ATOM | 901 | CE2 | TYR | 183 | 11.382 | 21.532 | 51.451 |
| ATOM | 902 | CZ | TYR | 183 | 10.569 | 22.649 | 51.271 |
| ATOM | 903 | OH | TYR | 183 | 11.118 | 23.814 | 50.768 |
| ATOM | 904 | C | TYR | 183 | 9.927 | 19.920 | 55.285 |
| ATOM | 905 | O | TYR | 183 | 11.085 | 20.213 | 55.620 |
| ATOM | 906 | N | ALA | 184 | 8.863 | 20.642 | 55.604 |
| ATOM | 907 | CA | ALA | 184 | 8.981 | 21.884 | 56.336 |
| ATOM | 908 | CB | ALA | 184 | 7.597 | 22.407 | 56.705 |
| ATOM | 909 | C | ALA | 184 | 9.884 | 21.753 | 57.570 |
| ATOM | 910 | O | ALA | 184 | 10.780 | 22.585 | 57.797 |

FIGURE 1T

| | Atom | | Residue AA | No. | X | Y | Z |
|---|---|---|---|---|---|---|---|
| ATOM | 911 | N | ASN | 185 | 9.707 | 20.661 | 58.312 |
| ATOM | 912 | CA | ASN | 185 | 10.498 | 20.406 | 59.522 |
| ATOM | 913 | CB | ASN | 185 | 10.141 | 19.035 | 60.144 |
| ATOM | 914 | CG | ASN | 185 | 8.661 | 18.902 | 60.536 |
| ATOM | 915 | OD1 | ASN | 185 | 7.936 | 19.888 | 60.615 |
| ATOM | 916 | ND2 | ASN | 185 | 8.218 | 17.668 | 60.788 |
| ATOM | 917 | C | ASN | 185 | 12.012 | 20.460 | 59.254 |
| ATOM | 918 | O | ASN | 185 | 12.697 | 21.360 | 59.736 |
| ATOM | 919 | N | VAL | 186 | 12.514 | 19.514 | 58.455 |
| ATOM | 920 | CA | VAL | 186 | 13.938 | 19.428 | 58.130 |
| ATOM | 921 | CB | VAL | 186 | 14.208 | 18.429 | 57.009 |
| ATOM | 922 | CG1 | VAL | 186 | 15.686 | 18.432 | 56.670 |
| ATOM | 923 | CG2 | VAL | 186 | 13.734 | 17.047 | 57.408 |
| ATOM | 924 | C | VAL | 186 | 14.404 | 20.761 | 57.644 |
| ATOM | 925 | O | VAL | 186 | 15.520 | 21.193 | 57.919 |
| ATOM | 926 | N | GLN | 187 | 13.529 | 21.387 | 56.877 |
| ATOM | 927 | CA | GLN | 187 | 13.802 | 22.686 | 56.340 |
| ATOM | 928 | CB | GLN | 187 | 12.521 | 23.248 | 55.702 |
| ATOM | 929 | CG | GLN | 187 | 12.374 | 24.776 | 55.692 |
| ATOM | 930 | CD | GLN | 187 | 13.573 | 25.509 | 55.070 |
| ATOM | 931 | OE1 | GLN | 187 | 14.430 | 24.899 | 54.416 |
| ATOM | 932 | NE2 | GLN | 187 | 13.649 | 26.825 | 55.301 |
| ATOM | 933 | C | GLN | 187 | 14.310 | 23.566 | 57.473 |
| ATOM | 934 | O | GLN | 187 | 15.514 | 23.881 | 57.542 |
| ATOM | 935 | N | ALA | 188 | 13.402 | 23.846 | 58.409 |
| ATOM | 936 | CA | ALA | 188 | 13.678 | 24.704 | 59.554 |
| ATOM | 937 | CB | ALA | 188 | 12.389 | 24.980 | 60.304 |
| ATOM | 938 | C | ALA | 188 | 14.752 | 24.181 | 60.514 |
| ATOM | 939 | O | ALA | 188 | 15.821 | 24.814 | 60.672 |
| ATOM | 940 | N | SER | 189 | 14.468 | 23.031 | 61.140 |
| ATOM | 941 | CA | SER | 189 | 15.379 | 22.402 | 62.101 |
| ATOM | 942 | CB | SER | 189 | 14.836 | 21.038 | 62.519 |
| ATOM | 943 | OG | SER | 189 | 14.642 | 20.216 | 61.390 |
| ATOM | 944 | C | SER | 189 | 16.806 | 22.262 | 61.562 |
| ATOM | 945 | O | SER | 189 | 17.758 | 22.122 | 62.341 |
| ATOM | 946 | N | MET | 190 | 16.936 | 22.296 | 60.232 |
| ATOM | 947 | CA | MET | 190 | 18.229 | 22.187 | 59.575 |
| ATOM | 948 | CB | MET | 190 | 18.214 | 21.026 | 58.594 |
| ATOM | 949 | CG | MET | 190 | 17.992 | 19.714 | 59.275 |
| ATOM | 950 | SD | MET | 190 | 19.144 | 19.446 | 60.655 |
| ATOM | 951 | CE | MET | 190 | 20.815 | 19.750 | 59.914 |
| ATOM | 952 | C | MET | 190 | 18.697 | 23.468 | 58.883 |
| ATOM | 953 | O | MET | 190 | 19.888 | 23.575 | 58.517 |
| ATOM | 954 | N | ALA | 191 | 17.761 | 24.409 | 58.687 |
| ATOM | 955 | CA | ALA | 191 | 18.024 | 25.716 | 58.053 |
| ATOM | 956 | CB | ALA | 191 | 19.055 | 26.516 | 58.901 |
| ATOM | 957 | C | ALA | 191 | 18.493 | 25.603 | 56.588 |
| ATOM | 958 | O | ALA | 191 | 19.533 | 26.178 | 56.177 |

FIGURE 1U

| | Atom | | Residue AA | No. | X | Y | Z |
|---|---|---|---|---|---|---|---|
| ATOM | 959 | N | LYS | 192 | 17.664 | 24.948 | 55.785 |
| ATOM | 960 | CA | LYS | 192 | 18.024 | 24.702 | 54.403 |
| ATOM | 961 | CB | LYS | 192 | 17.410 | 23.372 | 53.953 |
| ATOM | 962 | CG | LYS | 192 | 17.860 | 22.145 | 54.741 |
| ATOM | 963 | CD | LYS | 192 | 19.175 | 21.541 | 54.224 |
| ATOM | 964 | CE | LYS | 192 | 20.365 | 22.496 | 54.321 |
| ATOM | 965 | NZ | LYS | 192 | 21.668 | 21.845 | 54.012 |
| ATOM | 966 | C | LYS | 192 | 17.746 | 25.762 | 53.347 |
| ATOM | 967 | O | LYS | 192 | 16.751 | 26.480 | 53.417 |
| ATOM | 968 | N | LYS | 193 | 18.660 | 25.863 | 52.384 |
| ATOM | 969 | CA | LYS | 193 | 18.493 | 26.759 | 51.246 |
| ATOM | 970 | CB | LYS | 193 | 19.819 | 27.416 | 50.854 |
| ATOM | 971 | CG | LYS | 193 | 20.350 | 28.415 | 51.904 |
| ATOM | 972 | CD | LYS | 193 | 19.270 | 29.448 | 52.337 |
| ATOM | 973 | CE | LYS | 193 | 19.493 | 29.995 | 53.791 |
| ATOM | 974 | NZ | LYS | 193 | 18.215 | 30.335 | 54.589 |
| ATOM | 975 | C | LYS | 193 | 18.037 | 25.741 | 50.212 |
| ATOM | 976 | O | LYS | 193 | 18.547 | 24.621 | 50.226 |
| ATOM | 977 | N | LEU | 194 | 17.150 | 26.129 | 49.291 |
| ATOM | 978 | CA | LEU | 194 | 16.572 | 25.180 | 48.334 |
| ATOM | 979 | CB | LEU | 194 | 15.740 | 25.839 | 47.260 |
| ATOM | 980 | CG | LEU | 194 | 14.288 | 25.380 | 47.517 |
| ATOM | 981 | CD1 | LEU | 194 | 13.330 | 25.989 | 46.517 |
| ATOM | 982 | CD2 | LEU | 194 | 14.145 | 23.865 | 47.484 |
| ATOM | 983 | C | LEU | 194 | 17.327 | 23.992 | 47.793 |
| ATOM | 984 | O | LEU | 194 | 16.748 | 22.911 | 47.688 |
| ATOM | 985 | N | PRO | 195 | 18.570 | 24.175 | 47.322 |
| ATOM | 986 | CD | PRO | 195 | 19.383 | 25.384 | 47.093 |
| ATOM | 987 | CA | PRO | 195 | 19.246 | 22.951 | 46.838 |
| ATOM | 988 | CB | PRO | 195 | 20.523 | 23.497 | 46.197 |
| ATOM | 989 | CG | PRO | 195 | 20.771 | 24.802 | 47.016 |
| ATOM | 990 | C | PRO | 195 | 19.550 | 22.026 | 48.067 |
| ATOM | 991 | O | PRO | 195 | 20.548 | 22.207 | 48.781 |
| ATOM | 992 | N | PHE | 196 | 18.642 | 21.100 | 48.357 |
| ATOM | 993 | CA | PHE | 196 | 18.833 | 20.206 | 49.477 |
| ATOM | 994 | CB | PHE | 196 | 18.543 | 20.946 | 50.782 |
| ATOM | 995 | CG | PHE | 196 | 17.093 | 20.973 | 51.169 |
| ATOM | 996 | CD1 | PHE | 196 | 16.507 | 19.879 | 50.931 |
| ATOM | 998 | CE1 | PHE | 196 | 15.187 | 19.903 | 52.164 |
| ATOM | 999 | CE2 | PHE | 196 | 14.980 | 22.133 | 51.309 |
| ATOM | 1000 | CZ | PHE | 196 | 14.417 | 21.030 | 51.925 |
| ATOM | 1001 | C | PHE | 196 | 17.938 | 18.981 | 49.339 |
| ATOM | 1002 | O | PHE | 196 | 16.794 | 19.101 | 48.894 |
| ATOM | 1003 | N | GLY | 197 | 18.453 | 17.816 | 49.742 |
| ATOM | 1004 | CA | GLY | 197 | 17.692 | 16.578 | 49.651 |
| ATOM | 1005 | C | GLY | 197 | 17.358 | 16.022 | 51.019 |
| ATOM | 1006 | O | GLY | 197 | 17.786 | 16.583 | 52.016 |

FIGURE 1V

| Atom | | | Residue AA | No. | X | Y | Z |
|---|---|---|---|---|---|---|---|
| ATOM | 1007 | N | ILE | 198 | 16.606 | 14.927 | 51.078 |
| ATOM | 1008 | CA | ILE | 198 | 16.225 | 14.303 | 52.356 |
| ATOM | 1009 | CB | ILE | 198 | 14.857 | 14.824 | 52.866 |
| ATOM | 1010 | CG2 | ILE | 198 | 14.576 | 14.286 | 54.243 |
| ATOM | 1011 | CG1 | ILE | 198 | 14.831 | 16.338 | 52.959 |
| ATOM | 1012 | CD1 | ILE | 198 | 13.487 | 16.856 | 53.414 |
| ATOM | 1013 | C | ILE | 198 | 16.090 | 12.767 | 52.226 |
| ATOM | 1014 | O | ILE | 198 | 14.975 | 12.240 | 52.060 |
| ATOM | 1015 | N | GLY | 199 | 17.199 | 12.041 | 52.343 |
| ATOM | 1016 | CA | GLY | 199 | 17.132 | 10.590 | 52.203 |
| ATOM | 1017 | C | GLY | 199 | 16.592 | 9.851 | 53.408 |
| ATOM | 1018 | O | GLY | 199 | 16.372 | 10.456 | 54.439 |
| ATOM | 1019 | N | GLN | 200 | 16.337 | 8.559 | 53.275 |
| ATOM | 1020 | CA | GLN | 200 | 15.856 | 7.775 | 54.396 |
| ATOM | 1021 | CB | GLN | 200 | 14.608 | 8.408 | 55.022 |
| ATOM | 1022 | CG | GLN | 200 | 13.341 | 8.367 | 54.181 |
| ATOM | 1023 | CD | GLN | 200 | 12.085 | 7.886 | 54.966 |
| ATOM | 1024 | OE1 | GLN | 200 | 10.978 | 8.413 | 54.792 |
| ATOM | 1025 | NE2 | GLN | 200 | 12.256 | 6.863 | 55.803 |
| ATOM | 1026 | C | GLN | 200 | 15.573 | 6.321 | 54.039 |
| ATOM | 1027 | O | GLN | 200 | 14.670 | 6.037 | 53.263 |
| ATOM | 1028 | N | ILE | 201 | 16.335 | 5.388 | 54.600 |
| ATOM | 1029 | CA | ILE | 201 | 16.114 | 3.962 | 54.330 |
| ATOM | 1030 | CB | ILE | 201 | 17.283 | 3.157 | 54.793 |
| ATOM | 1031 | CG2 | ILE | 201 | 17.009 | 1.685 | 54.662 |
| ATOM | 1032 | CG1 | ILE | 201 | 18.492 | 3.575 | 54.002 |
| ATOM | 1033 | CD1 | ILE | 201 | 19.711 | 2.913 | 54.456 |
| ATOM | 1034 | C | ILE | 201 | 14.904 | 3.481 | 55.100 |
| ATOM | 1035 | O | ILE | 201 | 14.591 | 4.007 | 56.166 |
| ATOM | 1036 | N | GLY | 202 | 14.226 | 2.460 | 54.615 |
| ATOM | 1037 | CA | GLY | 202 | 13.078 | 2.040 | 55.378 |
| ATOM | 1038 | C | GLY | 202 | 12.239 | 0.888 | 54.893 |
| ATOM | 1039 | O | GLY | 202 | 12.474 | 0.311 | 53.830 |
| ATOM | 1040 | N | LYS | 203 | 11.243 | 0.569 | 55.713 |
| ATOM | 1041 | CA | LYS | 203 | 10.331 | -0.509 | 55.437 |
| ATOM | 1042 | CB | LYS | 203 | 9.987 | -1.241 | 56.740 |
| ATOM | 1043 | CG | LYS | 203 | 10.196 | -2.740 | 56.698 |
| ATOM | 1044 | CD | LYS | 203 | 11.657 | -3.080 | 56.855 |
| ATOM | 1045 | CE | LYS | 203 | 12.006 | -4.469 | 56.326 |
| ATOM | 1046 | NZ | LYS | 203 | 11.232 | -5.556 | 56.899 |
| ATOM | 1047 | C | LYS | 203 | 9.064 | 0.017 | 54.733 |
| ATOM | 1048 | O | LYS | 203 | 8.487 | 1.039 | 55.129 |
| ATOM | 1049 | N | SER | 204 | 8.709 | -0.638 | 53.626 |
| ATOM | 1050 | CA | SER | 204 | 7.510 | -0.317 | 52.852 |
| ATOM | 1051 | CB | SER | 204 | 7.870 | 0.339 | 51.497 |
| ATOM | 1052 | OG | SER | 204 | 8.096 | 1.758 | 51.576 |
| ATOM | 1053 | C | SER | 204 | 6.851 | -1.687 | 52.670 |
| ATOM | 1054 | O | SER | 204 | 7.545 | -2.691 | 52.669 |

FIGURE 1W

| Atom | | | Residue AA | No. | X | Y | Z |
|---|---|---|---|---|---|---|---|
| ATOM | 1055 | N | PHE | 205 | 5.528 | -1.739 | 52.590 |
| ATOM | 1056 | CA | PHE | 205 | 4.830 | -3.015 | 52.460 |
| ATOM | 1057 | CB | PHE | 205 | 4.150 | -3.443 | 53.784 |
| ATOM | 1058 | CG | PHE | 205 | 5.052 | -3.437 | 55.008 |
| ATOM | 1059 | CD1 | PHE | 205 | 5.324 | -2.258 | 55.693 |
| ATOM | 1060 | CD2 | PHE | 205 | 5.596 | -4.611 | 55.490 |
| ATOM | 1061 | CE1 | PHE | 205 | 6.114 | -2.251 | 56.819 |
| ATOM | 1062 | CE2 | PHE | 205 | 6.388 | -4.599 | 56.618 |
| ATOM | 1063 | CZ | PHE | 205 | 6.647 | -3.417 | 57.282 |
| ATOM | 1064 | C | PHE | 205 | 3.748 | -2.957 | 51.384 |
| ATOM | 1065 | O | PHE | 205 | 2.905 | -2.067 | 51.374 |
| ATOM | 1066 | N | ARG | 206 | 3.716 | -3.980 | 50.545 |
| ATOM | 1067 | CA | ARG | 206 | 2.750 | -4.082 | 49.455 |
| ATOM | 1068 | CB | ARG | 206 | 3.479 | -4.007 | 48.122 |
| ATOM | 1069 | CG | ARG | 206 | 3.246 | -2.730 | 47.369 |
| ATOM | 1070 | CD | ARG | 206 | 4.122 | -1.569 | 47.856 |
| ATOM | 1071 | NE | ARG | 206 | 5.071 | -1.073 | 46.834 |
| ATOM | 1072 | CZ | ARG | 206 | 4.798 | -0.830 | 45.534 |
| ATOM | 1073 | NH1 | ARG | 206 | 3.575 | -1.030 | 45.015 |
| ATOM | 1074 | NH2 | ARG | 206 | 5.765 | -1.360 | 44.731 |
| ATOM | 1075 | C | ARG | 206 | 1.978 | -5.398 | 49.503 |
| ATOM | 1076 | O | ARG | 206 | 2.574 | -6.489 | 49.485 |
| ATOM | 1077 | N | ASN | 207 | 0.656 | -5.299 | 49.564 |
| ATOM | 1078 | CA | ASN | 207 | 0.206 | -6.481 | 49.585 |
| ATOM | 1079 | CB | ASN | 207 | -1.603 | -6.104 | 50.082 |
| ATOM | 1080 | CG | ASN | 207 | -2.454 | -7.317 | 50.461 |
| ATOM | 1081 | OD1 | ASN | 207 | -2.051 | -8.483 | 50.308 |
| ATOM | 1082 | ND2 | ASN | 207 | -3.647 | -7.036 | 50.980 |
| ATOM | 1083 | C | ASN | 207 | -0.276 | -6.966 | 48.134 |
| ATOM | 1084 | O | ASN | 207 | -1.221 | -6.643 | 47.401 |
| ATOM | 1085 | N | GLU | 208 | 0.743 | -7.731 | 47.731 |
| ATOM | 1086 | CA | GLU | 208 | 0.888 | -8.258 | 46.356 |
| ATOM | 1087 | CB | GLU | 208 | 2.298 | -8.843 | 46.164 |
| ATOM | 1088 | CG | GLU | 208 | 2.966 | -8.376 | 44.889 |
| ATOM | 1089 | CD | GLU | 208 | 2.847 | -6.871 | 44.637 |
| ATOM | 1090 | OE1 | GLU | 208 | 3.887 | -6.191 | 44.762 |
| ATOM | 1091 | OE2 | GLU | 208 | 1.741 | -6.362 | 44.299 |
| ATOM | 1092 | C | GLU | 208 | -0.174 | -9.223 | 45.783 |
| ATOM | 1093 | O | GLU | 208 | -1.329 | -9.263 | 46.256 |
| ATOM | 1094 | N | ILE | 209 | 0.196 | -9.936 | 44.712 |
| ATOM | 1095 | CA | ILE | 209 | -0.728 | -10.881 | 44.079 |
| ATOM | 1096 | CB | ILE | 209 | -1.254 | -10.373 | 42.687 |
| ATOM | 1097 | CG2 | ILE | 209 | -2.408 | -9.335 | 42.885 |
| ATOM | 1098 | CG1 | ILE | 209 | -0.097 | -9.886 | 41.782 |
| ATOM | 1099 | CD1 | ILE | 209 | 0.434 | -8.495 | 42.078 |
| ATOM | 1100 | C | ILE | 209 | -0.086 | -12.256 | 43.928 |
| ATOM | 1101 | O | ILE | 209 | -0.404 | -13.216 | 44.680 |
| ATOM | 1102 | N | THR | 210 | 0.860 | -12.320 | 42.992 |

FIGURE 1X

| Atom | | | Residue AA | No. | X | Y | Z |
|---|---|---|---|---|---|---|---|
| ATOM | 1103 | CA | THR | 210 | 1.601 | -13.541 | 42.709 |
| ATOM | 1104 | CB | THR | 210 | 1.236 | -14.054 | 41.280 |
| ATOM | 1105 | OG1 | THR | 210 | 1.976 | -15.244 | 40.986 |
| ATOM | 1106 | CG2 | THR | 210 | 1.473 | -12.960 | 40.209 |
| ATOM | 1107 | C | THR | 210 | 3.113 | -13.234 | 42.891 |
| ATOM | 1108 | O | THR | 210 | 3.912 | -13.364 | 41.942 |
| ATOM | 1109 | N | PRO | 211 | 3.515 | -12.825 | 44.132 |
| ATOM | 1110 | CD | PRO | 211 | 2.756 | -12.743 | 45.404 |
| ATOM | 1111 | CA | PRO | 211 | 4.915 | -12.503 | 44.388 |
| ATOM | 1112 | CB | PRO | 211 | 5.024 | -12.682 | 45.898 |
| ATOM | 1113 | CG | PRO | 211 | 3.755 | -12.095 | 46.353 |
| ATOM | 1114 | C | PRO | 211 | 5.938 | -13.271 | 43.558 |
| ATOM | 1115 | O | PRO | 211 | 6.085 | -14.506 | 43.654 |
| ATOM | 1116 | N | GLY | 212 | 6.490 | -12.508 | 42.617 |
| ATOM | 1117 | CA | GLY | 212 | 7.501 | -12.991 | 41.701 |
| ATOM | 1118 | C | GLY | 212 | 8.781 | -13.409 | 42.394 |
| ATOM | 1119 | O | GLY | 212 | 9.524 | -12.585 | 42.957 |
| ATOM | 1120 | N | ASN | 213 | 8.990 | -14.723 | 42.350 |
| ATOM | 1121 | CA | ASN | 213 | 10.124 | -15.434 | 42.945 |
| ATOM | 1122 | CB | ASN | 213 | 10.594 | -16.565 | 42.002 |
| ATOM | 1123 | CG | ASN | 213 | 10.700 | -16.119 | 40.514 |
| ATOM | 1124 | OD1 | ASN | 213 | 9.786 | -15.478 | 39.971 |
| ATOM | 1125 | ND2 | ASN | 213 | 11.823 | -16.465 | 39.858 |
| ATOM | 1126 | C | ASN | 213 | 11.305 | -14.613 | 43.517 |
| ATOM | 1127 | O | ASN | 213 | 11.668 | -13.565 | 42.996 |
| ATOM | 1128 | N | PHE | 214 | 11.831 | -15.082 | 44.648 |
| ATOM | 1129 | CA | PHE | 214 | 12.930 | -14.444 | 45.340 |
| ATOM | 1130 | CB | PHE | 214 | 14.247 | -14.698 | 44.622 |
| ATOM | 1131 | CG | PHE | 214 | 15.379 | -15.038 | 45.546 |
| ATOM | 1132 | CD1 | PHE | 214 | 16.688 | -14.759 | 45.203 |
| ATOM | 1133 | CD2 | PHE | 214 | 15.137 | -15.671 | 46.748 |
| ATOM | 1134 | CE1 | PHE | 214 | 17.725 | -15.107 | 46.037 |
| ATOM | 1135 | CE2 | PHE | 214 | 16.168 | -16.025 | 47.591 |
| ATOM | 1136 | CZ | PHE | 214 | 17.459 | -15.744 | 47.236 |
| ATOM | 1137 | C | PHE | 214 | 12.762 | -12.970 | 45.612 |
| ATOM | 1138 | O | PHE | 214 | 11.724 | -12.359 | 45.328 |
| ATOM | 1139 | N | ILE | 215 | 13.850 | -12.408 | 46.119 |
| ATOM | 1140 | CA | ILE | 215 | 13.943 | -11.009 | 46.497 |
| ATOM | 1141 | CB | ILE | 215 | 15.411 | -10.603 | 46.832 |
| ATOM | 1142 | CG2 | ILE | 215 | 15.430 | -9.446 | 47.791 |
| ATOM | 1143 | CG1 | ILE | 215 | 16.156 | -11.732 | 47.522 |
| ATOM | 1144 | CD1 | ILE | 215 | 17.555 | -11.356 | 47.885 |
| ATOM | 1145 | C | ILE | 215 | 13.369 | -9.985 | 45.494 |
| ATOM | 1146 | O | ILE | 215 | 13.156 | -8.815 | 45.865 |
| ATOM | 1147 | N | PHE | 216 | 13.129 | -10.373 | 44.238 |
| ATOM | 1148 | CA | PHE | 216 | 12.590 | -9.384 | 43.311 |
| ATOM | 1149 | CB | PHE | 216 | 12.766 | -9.728 | 41.810 |
| ATOM | 1150 | CG | PHE | 216 | 12.693 | -11.233 | 41.452 |

FIGURE 1Y

| | Atom | | Residue AA | No. | X | Y | Z |
|---|---|---|---|---|---|---|---|
| ATOM | 1151 | CD1 | PHE | 216 | 11.571 | -11.762 | 40.765 |
| ATOM | 1152 | CD2 | PHE | 216 | 13.816 | -12.076 | 41.622 |
| ATOM | 1153 | CE1 | PHE | 216 | 11.579 | -13.076 | 40.244 |
| ATOM | 1154 | CE2 | PHE | 216 | 13.827 | -13.408 | 41.095 |
| ATOM | 1155 | CZ | PHE | 216 | 12.713 | -13.890 | 40.409 |
| ATOM | 1156 | C | PHE | 216 | 11.174 | -8.954 | 43.655 |
| ATOM | 1157 | O | PHE | 216 | 10.867 | -7.753 | 43.624 |
| ATOM | 1158 | N | ARG | 217 | 10.311 | -9.898 | 44.010 |
| ATOM | 1159 | CA | ARG | 217 | 8.961 | -9.483 | 44.380 |
| ATOM | 1160 | CB | ARG | 217 | 7.932 | -9.752 | 43.273 |
| ATOM | 1161 | CG | ARG | 217 | 7.030 | -8.552 | 42.961 |
| ATOM | 1162 | CD | ARG | 217 | 5.864 | -8.929 | 42.050 |
| ATOM | 1163 | NE | ARG | 217 | 4.737 | -9.519 | 42.785 |
| ATOM | 1164 | CZ | ARG | 217 | 3.574 | -9.900 | 42.235 |
| ATOM | 1165 | NH1 | ARG | 217 | 3.363 | -9.770 | 40.927 |
| ATOM | 1166 | NH2 | ARG | 217 | 2.591 | -10.372 | 42.997 |
| ATOM | 1167 | C | ARG | 217 | 8.523 | -10.098 | 45.710 |
| ATOM | 1168 | O | ARG | 217 | 7.943 | -11.195 | 45.758 |
| ATOM | 1169 | N | THR | 218 | 8.772 | -9.337 | 46.778 |
| ATOM | 1170 | CA | THR | 218 | 8.472 | -9.725 | 48.149 |
| ATOM | 1171 | CB | THR | 218 | 9.711 | -9.500 | 49.071 |
| ATOM | 1172 | OG1 | THR | 218 | 10.388 | -8.300 | 48.671 |
| ATOM | 1173 | CG2 | THR | 218 | 10.689 | -10.687 | 49.019 |
| ATOM | 1174 | C | THR | 218 | 7.346 | -8.848 | 48.648 |
| ATOM | 1175 | O | THR | 218 | 7.290 | -7.657 | 48.326 |
| ATOM | 1176 | N | ARG | 219 | 6.473 | -9.430 | 49.461 |
| ATOM | 1177 | CA | ARG | 219 | 5.336 | -8.701 | 50.023 |
| ATOM | 1178 | CB | ARG | 219 | 4.425 | -9.658 | 50.798 |
| ATOM | 1179 | CG | ARG | 219 | 4.364 | -11.050 | 50.203 |
| ATOM | 1180 | CD | ARG | 219 | 3.026 | -11.722 | 50.457 |
| ATOM | 1181 | NE | ARG | 219 | 1.853 | -10.948 | 49.978 |
| ATOM | 1182 | CZ | ARG | 219 | 1.079 | -11.238 | 48.904 |
| ATOM | 1183 | NH1 | ARG | 219 | 1.309 | -12.292 | 48.103 |
| ATOM | 1184 | NH2 | ARG | 219 | -0.019 | -10.520 | 48.676 |
| ATOM | 1185 | C | ARG | 219 | 5.824 | -7.607 | 50.962 |
| ATOM | 1186 | O | ARG | 219 | 5.088 | -6.691 | 51.282 |
| ATOM | 1187 | N | GLU | 220 | 7.072 | -7.707 | 51.392 |
| ATOM | 1188 | CA | GLU | 220 | 7.645 | -6.746 | 52.314 |
| ATOM | 1189 | CB | GLU | 220 | 7.668 | -7.366 | 53.702 |
| ATOM | 1190 | CG | GLU | 220 | 8.390 | -6.579 | 54.764 |
| ATOM | 1191 | CD | GLU | 220 | 8.699 | -7.428 | 55.954 |
| ATOM | 1192 | OE1 | GLU | 220 | 9.880 | -7.505 | 56.326 |
| ATOM | 1193 | OE2 | GLU | 220 | 7.765 | -8.047 | 56.491 |
| ATOM | 1194 | C | GLU | 220 | 9.057 | -6.481 | 51.837 |
| ATOM | 1195 | O | GLU | 220 | 9.751 | -7.430 | 51.491 |
| ATOM | 1196 | N | PHE | 221 | 9.504 | -5.218 | 51.894 |
| ATOM | 1197 | CA | PHE | 221 | 10.836 | -4.815 | 51.400 |
| ATOM | 1198 | CB | PHE | 221 | 10.783 | -4.649 | 49.875 |

FIGURE 1Z

| | Atom | | Residue AA | No. | X | Y | Z |
|---|---|---|---|---|---|---|---|
| ATOM | 1199 | CG | PHE | 221 | 9.708 | -3.696 | 49.419 |
| ATOM | 1200 | CD1 | PHE | 221 | 9.956 | -2.330 | 49.346 |
| ATOM | 1201 | CD2 | PHE | 221 | 8.407 | -4.164 | 49.142 |
| ATOM | 1202 | CE1 | PHE | 221 | 8.926 | -1.445 | 49.012 |
| ATOM | 1203 | CE2 | PHE | 221 | 7.360 | -3.282 | 48.805 |
| ATOM | 1204 | CZ | PHE | 221 | 7.619 | -1.928 | 48.743 |
| ATOM | 1205 | C | PHE | 221 | 11.326 | -3.494 | 51.951 |
| ATOM | 1206 | O | PHE | 221 | 10.551 | -2.673 | 52.440 |
| ATOM | 1207 | N | GLU | 222 | 12.597 | -3.237 | 51.700 |
| ATOM | 1208 | CA | GLU | 222 | 13.231 | -2.009 | 52.125 |
| ATOM | 1209 | CB | GLU | 222 | 14.496 | -2.323 | 52.913 |
| ATOM | 1210 | CG | GLU | 222 | 14.301 | -2.519 | 54.371 |
| ATOM | 1211 | CD | GLU | 222 | 15.604 | -2.573 | 55.101 |
| ATOM | 1212 | OE1 | GLU | 222 | 16.104 | -1.520 | 55.524 |
| ATOM | 1213 | OE2 | GLU | 222 | 16.136 | -3.676 | 55.248 |
| ATOM | 1214 | C | GLU | 222 | 13.595 | -1.132 | 50.922 |
| ATOM | 1215 | O | GLU | 222 | 14.251 | -1.607 | 49.988 |
| ATOM | 1216 | N | GLN | 223 | 13.206 | 0.141 | 50.983 |
| ATOM | 1217 | CA | GLN | 223 | 13.480 | 1.112 | 49.938 |
| ATOM | 1218 | CB | GLN | 223 | 12.461 | 2.215 | 50.000 |
| ATOM | 1219 | CG | GLN | 223 | 11.053 | 1.686 | 50.096 |
| ATOM | 1220 | CD | GLN | 223 | 10.275 | 1.809 | 48.803 |
| ATOM | 1221 | OE1 | GLN | 223 | 10.824 | 1.639 | 47.716 |
| ATOM | 1222 | NE2 | GLN | 223 | 8.980 | 2.098 | 48.919 |
| ATOM | 1223 | C | GLN | 223 | 14.863 | 1.698 | 50.093 |
| ATOM | 1224 | O | GLN | 223 | 15.811 | 0.967 | 50.328 |
| ATOM | 1225 | N | MET | 224 | 14.990 | 3.003 | 49.922 |
| ATOM | 1226 | CA | MET | 224 | 16.271 | 3.663 | 50.050 |
| ATOM | 1227 | CB | MET | 224 | 17.370 | 2.824 | 49.450 |
| ATOM | 1228 | CG | MET | 224 | 18.506 | 2.649 | 50.353 |
| ATOM | 1229 | SD | MET | 224 | 19.018 | 1.020 | 50.206 |
| ATOM | 1230 | CE | MET | 224 | 20.692 | 1.255 | 49.950 |
| ATOM | 1231 | C | MET | 224 | 16.185 | 4.930 | 49.267 |
| ATOM | 1232 | O | MET | 224 | 17.081 | 5.242 | 48.507 |
| ATOM | 1233 | N | GLU | 225 | 15.128 | 5.689 | 49.512 |
| ATOM | 1234 | CA | GLU | 225 | 14.827 | 6.937 | 48.806 |
| ATOM | 1235 | CB | GLU | 225 | 13.335 | 7.143 | 48.845 |
| ATOM | 1236 | CG | GLU | 225 | 12.636 | 5.820 | 48.712 |
| ATOM | 1237 | CD | GLU | 225 | 11.176 | 5.961 | 48.533 |
| ATOM | 1238 | OE1 | GLU | 225 | 10.626 | 6.903 | 49.127 |
| ATOM | 1239 | OE2 | GLU | 225 | 10.582 | 5.139 | 47.798 |
| ATOM | 1240 | C | GLU | 225 | 15.517 | 8.213 | 49.247 |
| ATOM | 1241 | O | GLU | 225 | 16.087 | 8.285 | 50.326 |
| ATOM | 1242 | N | LEU | 226 | 15.447 | 9.225 | 48.394 |
| ATOM | 1243 | CA | LEU | 226 | 16.054 | 10.521 | 48.660 |
| ATOM | 1244 | CB | LEU | 226 | 17.509 | 10.555 | 48.197 |
| ATOM | 1245 | CG | LEU | 226 | 18.235 | 11.898 | 48.160 |
| ATOM | 1246 | CD1 | LEU | 226 | 19.699 | 11.670 | 48.286 |

FIGURE 1AA

| | Atom | | Residue AA | No. | X | Y | Z |
|---|---|---|---|---|---|---|---|
| ATOM | 1247 | CD2 | LEU | 226 | 17.964 | 12.641 | 46.880 |
| ATOM | 1248 | C | LEU | 226 | 15.291 | 11.466 | 47.808 |
| ATOM | 1249 | O | LEU | 226 | 15.174 | 11.231 | 46.630 |
| ATOM | 1250 | N | GLU | 227 | 14.742 | 12.513 | 48.394 |
| ATOM | 1251 | CA | GLU | 227 | 14.000 | 13.483 | 47.615 |
| ATOM | 1252 | CB | GLU | 227 | 12.660 | 13.794 | 48.251 |
| ATOM | 1253 | CG | GLU | 227 | 11.498 | 13.457 | 47.369 |
| ATOM | 1254 | CD | GLU | 227 | 11.245 | 11.977 | 47.307 |
| ATOM | 1255 | OE1 | GLU | 227 | 10.089 | 11.573 | 47.435 |
| ATOM | 1256 | OE2 | GLU | 227 | 12.197 | 11.202 | 47.142 |
| ATOM | 1257 | C | GLU | 227 | 14.822 | 14.729 | 47.564 |
| ATOM | 1258 | O | GLU | 227 | 15.109 | 15.318 | 48.606 |
| ATOM | 1259 | N | PHE | 228 | 15.244 | 15.103 | 46.359 |
| ATOM | 1260 | CA | PHE | 228 | 16.065 | 16.300 | 46.146 |
| ATOM | 1261 | CB | PHE | 228 | 17.058 | 16.061 | 45.000 |
| ATOM | 1262 | CG | PHE | 228 | 18.128 | 17.085 | 44.898 |
| ATOM | 1263 | CD1 | PHE | 228 | 17.895 | 18.296 | 44.284 |
| ATOM | 1264 | CD2 | PHE | 228 | 19.387 | 16.828 | 45.389 |
| ATOM | 1265 | CE1 | PHE | 228 | 18.911 | 19.232 | 44.162 |
| ATOM | 1266 | CE2 | PHE | 228 | 20.413 | 17.761 | 45.268 |
| ATOM | 1267 | CZ | PHE | 228 | 20.176 | 18.957 | 44.657 |
| ATOM | 1268 | C | PHE | 228 | 15.108 | 17.444 | 45.799 |
| ATOM | 1269 | O | PHE | 228 | 14.272 | 17.295 | 44.888 |
| ATOM | 1270 | N | PHE | 229 | 15.149 | 18.519 | 46.599 |
| ATOM | 1271 | CA | PHE | 229 | 14.303 | 19.689 | 46.363 |
| ATOM | 1272 | CB | PHE | 229 | 13.751 | 20.236 | 47.662 |
| ATOM | 1273 | CG | PHE | 229 | 12.793 | 19.311 | 48.281 |
| ATOM | 1274 | CD1 | PHE | 229 | 13.240 | 18.169 | 48.897 |
| ATOM | 1275 | CD2 | PHE | 229 | 11.443 | 19.469 | 48.084 |
| ATOM | 1276 | CE1 | PHE | 229 | 12.354 | 17.193 | 49.289 |
| ATOM | 1277 | CE2 | PHE | 229 | 10.550 | 18.491 | 48.477 |
| ATOM | 1278 | CZ | PHE | 229 | 11.003 | 17.354 | 49.074 |
| ATOM | 1279 | C | PHE | 229 | 15.104 | 20.664 | 45.530 |
| ATOM | 1280 | O | PHE | 229 | 16.285 | 20.968 | 45.823 |
| ATOM | 1281 | N | CYS | 230 | 14.444 | 21.105 | 44.460 |
| ATOM | 1282 | CA | CYS | 230 | 15.054 | 21.928 | 43.436 |
| ATOM | 1283 | CB | CYS | 230 | 15.089 | 21.104 | 42.153 |
| ATOM | 1284 | SG | CYS | 230 | 16.294 | 21.646 | 40.991 |
| ATOM | 1285 | C | CYS | 230 | 14.309 | 23.197 | 43.145 |
| ATOM | 1286 | O | CYS | 230 | 13.074 | 23.187 | 43.119 |
| ATOM | 1287 | N | LYS | 231 | 15.057 | 24.283 | 42.937 |
| ATOM | 1288 | CA | LYS | 231 | 14.452 | 25.558 | 42.581 |
| ATOM | 1289 | CB | LYS | 231 | 15.534 | 26.631 | 42.445 |
| ATOM | 1290 | CG | LYS | 231 | 15.016 | 28.025 | 42.003 |
| ATOM | 1291 | CD | LYS | 231 | 14.816 | 28.184 | 40.448 |
| ATOM | 1292 | CE | LYS | 231 | 16.157 | 28.234 | 39.633 |
| ATOM | 1293 | NZ | LYS | 231 | 16.027 | 28.079 | 38.130 |
| ATOM | 1294 | C | LYS | 231 | 13.816 | 25.234 | 41.215 |

FIGURE 1BB

| | Atom | | Residue AA | No. | X | Y | Z |
|---|---|---|---|---|---|---|---|
| ATOM | 1295 | O | LYS | 231 | 14.515 | 24.775 | 40.303 |
| ATOM | 1296 | N | PRO | 232 | 12.505 | 25.506 | 41.045 |
| ATOM | 1297 | CD | PRO | 232 | 11.797 | 26.323 | 42.045 |
| ATOM | 1298 | CA | PRO | 232 | 11.633 | 25.288 | 39.876 |
| ATOM | 1299 | CB | PRO | 232 | 10.518 | 26.304 | 40.095 |
| ATOM | 1300 | CG | PRO | 232 | 10.348 | 26.258 | 41.552 |
| ATOM | 1301 | C | PRO | 232 | 12.137 | 25.323 | 38.428 |
| ATOM | 1302 | O | PRO | 232 | 11.339 | 25.088 | 37.519 |
| ATOM | 1303 | N | GLY | 233 | 13.419 | 25.625 | 38.194 |
| ATOM | 1304 | CA | GLY | 233 | 13.933 | 25.674 | 36.832 |
| ATOM | 1305 | C | GLY | 233 | 14.897 | 24.556 | 36.506 |
| ATOM | 1306 | O | GLY | 233 | 14.862 | 23.975 | 35.431 |
| ATOM | 1307 | N | GLU | 234 | 15.671 | 24.159 | 37.491 |
| ATOM | 1308 | CA | GLU | 234 | 16.655 | 23.123 | 37.282 |
| ATOM | 1309 | CB | GLU | 234 | 17.792 | 23.356 | 38.247 |
| ATOM | 1310 | CG | GLU | 234 | 18.166 | 24.817 | 38.305 |
| ATOM | 1311 | CD | GLU | 234 | 18.391 | 25.329 | 39.738 |
| ATOM | 1312 | OE1 | GLU | 234 | 18.085 | 24.599 | 40.723 |
| ATOM | 1313 | OE2 | GLU | 234 | 18.880 | 26.480 | 39.881 |
| ATOM | 1314 | C | GLU | 234 | 16.188 | 21.663 | 37.346 |
| ATOM | 1315 | O | GLU | 234 | 17.020 | 20.743 | 37.325 |
| ATOM | 1316 | N | GLU | 235 | 14.876 | 21.436 | 37.376 |
| ATOM | 1317 | CA | GLU | 235 | 14.336 | 20.074 | 37.433 |
| ATOM | 1318 | CB | GLU | 235 | 12.833 | 20.031 | 37.058 |
| ATOM | 1319 | CG | GLU | 235 | 12.421 | 20.559 | 35.639 |
| ATOM | 1320 | CD | GLU | 235 | 12.479 | 22.105 | 35.479 |
| ATOM | 1321 | OE1 | GLU | 235 | 12.218 | 22.621 | 34.351 |
| ATOM | 1322 | OE2 | GLU | 235 | 12.772 | 22.796 | 36.486 |
| ATOM | 1323 | C | GLU | 235 | 15.155 | 19.071 | 36.607 |
| ATOM | 1324 | O | GLU | 235 | 15.538 | 18.025 | 37.103 |
| ATOM | 1325 | N | ILE | 236 | 15.547 | 19.463 | 35.401 |
| ATOM | 1326 | CA | ILE | 236 | 16.316 | 18.588 | 34.534 |
| ATOM | 1327 | CB | ILE | 236 | 16.147 | 18.903 | 33.037 |
| ATOM | 1328 | CG2 | ILE | 236 | 14.757 | 18.479 | 32.572 |
| ATOM | 1329 | CG1 | ILE | 236 | 16.514 | 20.369 | 32.716 |
| ATOM | 1330 | CD1 | ILE | 236 | 15.435 | 21.446 | 32.982 |
| ATOM | 1331 | C | ILE | 236 | 17.784 | 18.526 | 34.840 |
| ATOM | 1332 | O | ILE | 236 | 18.383 | 17.480 | 34.680 |
| ATOM | 1333 | N | GLU | 237 | 18.379 | 19.633 | 35.258 |
| ATOM | 1334 | CA | GLU | 237 | 19.805 | 19.626 | 35.590 |
| ATOM | 1335 | CB | GLU | 237 | 20.240 | 20.953 | 36.221 |
| ATOM | 1336 | CG | GLU | 237 | 20.463 | 22.051 | 35.248 |
| ATOM | 1337 | CD | GLU | 237 | 19.412 | 22.033 | 34.153 |
| ATOM | 1338 | OE1 | GLU | 237 | 18.259 | 22.473 | 34.424 |
| ATOM | 1339 | OE2 | GLU | 237 | 19.731 | 21.551 | 33.027 |
| ATOM | 1340 | C | GLU | 237 | 19.976 | 18.560 | 36.637 |
| ATOM | 1341 | O | GLU | 237 | 20.854 | 17.691 | 36.558 |
| ATOM | 1342 | N | TRP | 238 | 19.091 | 18.615 | 37.616 |

FIGURE 1CC

| Atom | | | Residue AA | No. | X | Y | Z |
|---|---|---|---|---|---|---|---|
| ATOM | 1343 | CA | TRP | 238 | 19.183 | 17.676 | 38.662 |
| ATOM | 1344 | CB | TRP | 238 | 18.478 | 18.199 | 39.890 |
| ATOM | 1345 | CG | TRP | 238 | 19.248 | 19.380 | 40.414 |
| ATOM | 1346 | CD2 | TRP | 238 | 20.565 | 19.364 | 40.981 |
| ATOM | 1347 | CE2 | TRP | 238 | 20.940 | 20.703 | 41.209 |
| ATOM | 1348 | CE3 | TRP | 238 | 21.466 | 18.349 | 41.308 |
| ATOM | 1349 | CD1 | TRP | 238 | 18.886 | 20.691 | 40.340 |
| ATOM | 1350 | NE1 | TRP | 238 | 19.896 | 21.495 | 40.812 |
| ATOM | 1351 | CZ2 | TRP | 238 | 22.172 | 21.049 | 41.744 |
| ATOM | 1352 | CZ3 | TRP | 238 | 22.687 | 18.696 | 41.838 |
| ATOM | 1353 | CH2 | TRP | 238 | 23.030 | 20.033 | 42.050 |
| ATOM | 1354 | C | TRP | 238 | 18.721 | 16.361 | 38.144 |
| ATOM | 1355 | O | TRP | 238 | 19.518 | 15.436 | 38.117 |
| ATOM | 1356 | N | GLN | 239 | 17.555 | 16.327 | 37.522 |
| ATOM | 1357 | CA | GLN | 239 | 17.040 | 15.074 | 36.995 |
| ATOM | 1358 | CB | GLN | 239 | 15.904 | 15.346 | 36.031 |
| ATOM | 1359 | CG | GLN | 239 | 15.656 | 14.255 | 35.009 |
| ATOM | 1360 | CD | GLN | 239 | 15.320 | 12.921 | 35.619 |
| ATOM | 1361 | OE1 | GLN | 239 | 15.860 | 11.884 | 35.228 |
| ATOM | 1362 | NE2 | GLN | 239 | 14.417 | 12.932 | 36.571 |
| ATOM | 1363 | C | GLN | 239 | 18.101 | 14.194 | 36.341 |
| ATOM | 1364 | O | GLN | 239 | 17.953 | 12.982 | 36.241 |
| ATOM | 1365 | N | ASN | 240 | 19.187 | 14.795 | 35.901 |
| ATOM | 1366 | CA | ASN | 240 | 20.232 | 14.002 | 35.303 |
| ATOM | 1367 | CB | ASN | 240 | 20.692 | 14.591 | 33.970 |
| ATOM | 1368 | CG | ASN | 240 | 19.662 | 14.399 | 32.858 |
| ATOM | 1369 | OD1 | ASN | 240 | 19.467 | 15.285 | 32.021 |
| ATOM | 1370 | ND2 | ASN | 240 | 18.994 | 13.241 | 32.848 |
| ATOM | 1371 | C | ASN | 240 | 21.405 | 13.861 | 36.222 |
| ATOM | 1372 | O | ASN | 240 | 22.094 | 12.852 | 36.175 |
| ATOM | 1373 | N | TYR | 241 | 21.648 | 14.869 | 37.049 |
| ATOM | 1374 | CA | TYR | 241 | 22.772 | 14.821 | 37.970 |
| ATOM | 1375 | CB | TYR | 241 | 22.748 | 16.017 | 38.922 |
| ATOM | 1376 | CG | TYR | 241 | 23.771 | 15.895 | 40.018 |
| ATOM | 1377 | CD1 | TYR | 241 | 23.390 | 15.596 | 41.327 |
| ATOM | 1378 | CE1 | TYR | 241 | 24.339 | 15.400 | 42.319 |
| ATOM | 1379 | CD2 | TYR | 241 | 25.127 | 15.998 | 39.736 |
| ATOM | 1380 | CE2 | TYR | 241 | 26.085 | 15.798 | 40.722 |
| ATOM | 1381 | CZ | TYR | 241 | 25.687 | 15.498 | 42.002 |
| ATOM | 1382 | OH | TYR | 241 | 26.655 | 15.252 | 42.934 |
| ATOM | 1383 | C | TYR | 241 | 22.732 | 13.522 | 38.760 |
| ATOM | 1384 | O | TYR | 241 | 23.714 | 12.786 | 38.876 |
| ATOM | 1385 | N | TRP | 242 | 21.561 | 13.221 | 39.268 |
| ATOM | 1386 | CA | TRP | 242 | 21.390 | 12.013 | 40.037 |
| ATOM | 1387 | CB | TRP | 242 | 20.100 | 12.115 | 40.879 |
| ATOM | 1388 | CG | TRP | 242 | 20.209 | 13.205 | 41.905 |
| ATOM | 1389 | CD2 | TRP | 242 | 21.014 | 13.180 | 43.087 |
| ATOM | 1390 | CE2 | TRP | 242 | 20.955 | 14.458 | 43.658 |

FIGURE 1DD

| | Atom | | Residue AA | No. | X | Y | Z |
|---|---|---|---|---|---|---|---|
| ATOM | 1391 | CE3 | TRP | 242 | 21.788 | 12.201 | 43.711 |
| ATOM | 1392 | CD1 | TRP | 242 | 19.686 | 14.456 | 41.822 |
| ATOM | 1393 | NE1 | TRP | 242 | 20.137 | 15.220 | 42.862 |
| ATOM | 1394 | CZ2 | TRP | 242 | 21.651 | 14.794 | 44.837 |
| ATOM | 1395 | CZ3 | TRP | 242 | 22.482 | 12.533 | 44.883 |
| ATOM | 1396 | CH2 | TRP | 242 | 22.408 | 13.819 | 45.432 |
| ATOM | 1397 | C | TRP | 242 | 21.454 | 10.739 | 39.176 |
| ATOM | 1398 | O | TRP | 242 | 21.989 | 9.731 | 39.620 |
| ATOM | 1399 | N | ALA | 243 | 20.946 | 10.798 | 37.940 |
| ATOM | 1400 | CA | ALA | 243 | 20.968 | 9.642 | 37.027 |
| ATOM | 1401 | CB | ALA | 243 | 20.304 | 9.991 | 35.648 |
| ATOM | 1402 | C | ALA | 243 | 22.426 | 9.229 | 36.846 |
| ATOM | 1403 | O | ALA | 243 | 22.793 | 8.073 | 37.062 |
| ATOM | 1404 | N | THR | 244 | 23.261 | 10.216 | 36.556 |
| ATOM | 1405 | CA | THR | 244 | 24.688 | 9.995 | 36.366 |
| ATOM | 1406 | CB | THR | 244 | 25.408 | 11.328 | 35.976 |
| ATOM | 1407 | OG1 | THR | 244 | 24.783 | 11.914 | 34.822 |
| ATOM | 1408 | CG2 | THR | 244 | 26.874 | 11.081 | 35.690 |
| ATOM | 1409 | C | THR | 244 | 25.296 | 9.462 | 37.677 |
| ATOM | 1410 | O | THR | 244 | 26.005 | 8.448 | 37.696 |
| ATOM | 1411 | N | PHE | 245 | 24.940 | 10.123 | 38.776 |
| ATOM | 1412 | CA | PHE | 245 | 25.424 | 9.796 | 40.111 |
| ATOM | 1413 | CB | PHE | 245 | 24.855 | 10.805 | 41.081 |
| ATOM | 1414 | CG | PHE | 245 | 25.399 | 10.671 | 42.438 |
| ATOM | 1415 | CD1 | PHE | 245 | 26.781 | 10.635 | 42.638 |
| ATOM | 1416 | CD2 | PHE | 245 | 24.544 | 10.550 | 43.525 |
| ATOM | 1417 | CE1 | PHE | 245 | 27.309 | 10.479 | 43.915 |
| ATOM | 1418 | CE2 | PHE | 245 | 25.042 | 10.395 | 44.807 |
| ATOM | 1419 | CZ | PHE | 245 | 26.432 | 10.358 | 45.007 |
| ATOM | 1420 | C | PHE | 245 | 25.070 | 8.405 | 40.595 |
| ATOM | 1421 | O | PHE | 245 | 25.924 | 7.669 | 41.070 |
| ATOM | 1422 | N | ALA | 246 | 23.776 | 8.116 | 40.544 |
| ATOM | 1423 | CA | ALA | 246 | 23.191 | 6.848 | 40.944 |
| ATOM | 1424 | CB | ALA | 246 | 21.685 | 6.886 | 40.740 |
| ATOM | 1425 | C | ALA | 246 | 23.790 | 5.743 | 40.110 |
| ATOM | 1426 | O | ALA | 246 | 24.143 | 4.686 | 40.619 |
| ATOM | 1427 | N | SER | 247 | 23.927 | 6.002 | 38.820 |
| ATOM | 1428 | CA | SER | 247 | 24.474 | 5.011 | 37.918 |
| ATOM | 1429 | CB | SER | 247 | 24.133 | 5.368 | 36.486 |
| ATOM | 1430 | OG | SER | 247 | 22.720 | 5.425 | 36.368 |
| ATOM | 1431 | C | SER | 247 | 25.953 | 4.870 | 38.120 |
| ATOM | 1432 | O | SER | 247 | 26.490 | 3.772 | 38.096 |
| ATOM | 1433 | N | ASP | 248 | 26.616 | 5.988 | 38.339 |
| ATOM | 1434 | CA | ASP | 248 | 28.047 | 5.938 | 38.602 |
| ATOM | 1435 | CB | ASP | 248 | 28.613 | 7.352 | 38.842 |
| ATOM | 1436 | CG | ASP | 248 | 29.437 | 7.878 | 37.666 |
| ATOM | 1437 | OD1 | ASP | 248 | 30.252 | 7.128 | 37.070 |
| ATOM | 1438 | OD2 | ASP | 248 | 29.279 | 9.078 | 37.367 |

FIGURE 1EE

| | Atom | | Residue AA | Residue No. | X | Y | Z |
|---|---|---|---|---|---|---|---|
| ATOM | 1439 | C | ASP | 248 | 28.208 | 5.094 | 39.887 |
| ATOM | 1440 | O | ASP | 248 | 29.075 | 4.217 | 39.984 |
| ATOM | 1441 | N | TRP | 249 | 27.328 | 5.333 | 40.851 |
| ATOM | 1442 | CA | TRP | 249 | 27.371 | 4.604 | 42.098 |
| ATOM | 1443 | CB | TRP | 249 | 26.151 | 4.970 | 42.941 |
| ATOM | 1444 | CG | TRP | 249 | 26.263 | 4.536 | 44.351 |
| ATOM | 1445 | CD2 | TRP | 249 | 25.592 | 3.424 | 44.977 |
| ATOM | 1446 | CE2 | TRP | 249 | 26.070 | 3.342 | 46.290 |
| ATOM | 1447 | CE3 | TRP | 249 | 24.647 | 2.481 | 44.548 |
| ATOM | 1448 | CD1 | TRP | 249 | 27.080 | 5.070 | 45.288 |
| ATOM | 1449 | NE1 | TRP | 249 | 26.976 | 4.358 | 46.453 |
| ATOM | 1450 | CZ2 | TRP | 249 | 25.637 | 2.353 | 47.187 |
| ATOM | 1451 | CZ3 | TRP | 249 | 24.218 | 1.490 | 45.446 |
| ATOM | 1452 | CH2 | TRP | 249 | 24.714 | 1.440 | 46.741 |
| ATOM | 1453 | C | TRP | 249 | 27.395 | 3.096 | 41.836 |
| ATOM | 1454 | O | TRP | 249 | 28.339 | 2.403 | 42.185 |
| ATOM | 1455 | N | LEU | 250 | 26.376 | 2.599 | 41.161 |
| ATOM | 1456 | CA | LEU | 250 | 26.306 | 1.183 | 40.899 |
| ATOM | 1457 | CB | LEU | 250 | 25.200 | 0.878 | 39.905 |
| ATOM | 1458 | CG | LEU | 250 | 23.877 | 0.851 | 40.643 |
| ATOM | 1459 | CD1 | LEU | 250 | 22.761 | 1.285 | 39.763 |
| ATOM | 1460 | CD2 | LEU | 250 | 23.638 | -0.519 | 41.155 |
| ATOM | 1461 | C | LEU | 250 | 27.615 | 0.563 | 40.475 |
| ATOM | 1462 | O | LEU | 250 | 28.200 | -0.209 | 41.213 |
| ATOM | 1463 | N | THR | 251 | 28.144 | 0.965 | 39.340 |
| ATOM | 1464 | CA | THR | 251 | 29.382 | 0.352 | 38.908 |
| ATOM | 1465 | CB | THR | 251 | 29.783 | 0.720 | 37.422 |
| ATOM | 1466 | OG1 | THR | 251 | 30.107 | 2.119 | 37.309 |
| ATOM | 1467 | CG2 | THR | 251 | 28.639 | 0.356 | 36.440 |
| ATOM | 1468 | C | THR | 251 | 30.535 | 0.588 | 39.881 |
| ATOM | 1469 | O | THR | 251 | 31.386 | -0.284 | 40.009 |
| ATOM | 1470 | N | SER | 252 | 30.519 | 1.695 | 40.630 |
| ATOM | 1471 | CA | SER | 252 | 31.610 | 1.992 | 41.581 |
| ATOM | 1472 | CB | SER | 252 | 31.506 | 3.410 | 42.142 |
| ATOM | 1473 | OG | SER | 252 | 30.281 | 3.623 | 42.819 |
| ATOM | 1474 | C | SER | 252 | 31.693 | 0.986 | 42.715 |
| ATOM | 1475 | O | SER | 252 | 32.787 | 0.727 | 43.233 |
| ATOM | 1476 | N | ALA | 253 | 30.523 | 0.455 | 43.105 |
| ATOM | 1477 | CA | ALA | 253 | 30.412 | -0.588 | 44.138 |
| ATOM | 1478 | CB | ALA | 253 | 29.017 | -0.561 | 44.821 |
| ATOM | 1479 | C | ALA | 253 | 30.678 | -1.939 | 43.412 |
| ATOM | 1480 | O | ALA | 253 | 30.624 | -3.014 | 44.036 |
| ATOM | 1481 | N | ASN | 254 | 30.981 | -1.835 | 42.098 |
| ATOM | 1482 | CA | ASN | 254 | 31.346 | -2.936 | 41.163 |
| ATOM | 1483 | CB | ASN | 254 | 32.108 | -4.041 | 41.905 |
| ATOM | 1484 | CG | ASN | 254 | 33.538 | -4.152 | 41.470 |
| ATOM | 1485 | OD1 | ASN | 254 | 34.057 | -5.259 | 41.294 |
| ATOM | 1486 | ND2 | ASN | 254 | 34.205 | -3.007 | 41.315 |

FIGURE 1FF

| | Atom | | Residue AA | No. | X | Y | Z |
|---|---|---|---|---|---|---|---|
| ATOM | 1487 | C | ASN | 254 | 30.320 | -3.598 | 40.228 |
| ATOM | 1488 | O | ASN | 254 | 30.503 | -4.758 | 39.828 |
| ATOM | 1489 | N | MET | 255 | 29.292 | -2.875 | 39.804 |
| ATOM | 1490 | CA | MET | 255 | 28.303 | -3.529 | 38.966 |
| ATOM | 1491 | CB | MET | 255 | 26.905 | -3.196 | 39.424 |
| ATOM | 1492 | CG | MET | 255 | 25.957 | -4.284 | 39.099 |
| ATOM | 1493 | SD | MET | 255 | 24.359 | -3.711 | 39.469 |
| ATOM | 1494 | CE | MET | 255 | 24.212 | -2.604 | 38.133 |
| ATOM | 1495 | C | MET | 255 | 28.409 | -3.350 | 37.462 |
| ATOM | 1496 | O | MET | 255 | 27.691 | -2.546 | 36.866 |
| ATOM | 1497 | N | SER | 256 | 29.250 | -4.181 | 36.856 |
| ATOM | 1498 | CA | SER | 256 | 29.501 | -4.194 | 35.420 |
| ATOM | 1499 | CB | SER | 256 | 29.735 | -5.635 | 34.949 |
| ATOM | 1500 | OG | SER | 256 | 28.661 | -6.486 | 35.311 |
| ATOM | 1501 | C | SER | 256 | 28.445 | -3.541 | 34.536 |
| ATOM | 1502 | O | SER | 256 | 27.298 | -3.996 | 34.457 |
| ATOM | 1503 | N | SER | 257 | 28.872 | -2.497 | 33.833 |
| ATOM | 1504 | CA | SER | 257 | 28.010 | -1.743 | 32.922 |
| ATOM | 1505 | CB | SER | 257 | 28.822 | -0.671 | 32.163 |
| ATOM | 1506 | OG | SER | 257 | 30.083 | -1.164 | 31.734 |
| ATOM | 1507 | C | SER | 257 | 27.312 | -2.660 | 31.933 |
| ATOM | 1508 | O | SER | 257 | 26.105 | -2.582 | 31.752 |
| ATOM | 1509 | N | GLU | 258 | 28.077 | -3.600 | 31.393 |
| ATOM | 1510 | CA | GLU | 258 | 27.596 | -4.553 | 30.408 |
| ATOM | 1511 | CB | GLU | 258 | 28.780 | -5.371 | 29.845 |
| ATOM | 1512 | CG | GLU | 258 | 29.612 | -4.612 | 28.722 |
| ATOM | 1513 | CD | GLU | 258 | 31.114 | -4.221 | 29.084 |
| ATOM | 1514 | OE1 | GLU | 258 | 31.696 | -4.773 | 30.091 |
| ATOM | 1515 | OE2 | GLU | 258 | 31.706 | -3.368 | 28.323 |
| ATOM | 1516 | C | GLU | 258 | 26.454 | -5.449 | 30.886 |
| ATOM | 1517 | O | GLU | 258 | 26.151 | -6.464 | 30.257 |
| ATOM | 1518 | N | ASN | 259 | 25.804 | -5.063 | 31.980 |
| ATOM | 1519 | CA | ASN | 259 | 24.685 | -5.822 | 32.492 |
| ATOM | 1520 | CB | ASN | 259 | 25.123 | -6.641 | 33.671 |
| ATOM | 1521 | CG | ASN | 259 | 24.896 | -8.098 | 33.451 |
| ATOM | 1522 | OD1 | ASN | 259 | 23.878 | -8.482 | 32.891 |
| ATOM | 1523 | ND2 | ASN | 259 | 25.845 | -8.930 | 33.879 |
| ATOM | 1524 | C | ASN | 259 | 23.503 | -4.965 | 32.877 |
| ATOM | 1525 | O | ASN | 259 | 22.448 | -5.485 | 33.212 |
| ATOM | 1526 | N | MET | 260 | 23.659 | -3.652 | 32.712 |
| ATOM | 1527 | CA | MET | 260 | 22.638 | -2.642 | 33.046 |
| ATOM | 1528 | CB | MET | 260 | 23.008 | -1.993 | 34.401 |
| ATOM | 1529 | CG | MET | 260 | 24.510 | -1.716 | 34.529 |
| ATOM | 1530 | SD | MET | 260 | 25.009 | -0.529 | 35.750 |
| ATOM | 1531 | CE | MET | 260 | 23.922 | 0.714 | 35.447 |
| ATOM | 1532 | C | MET | 260 | 22.532 | -1.519 | 31.982 |
| ATOM | 1533 | O | MET | 260 | 23.546 | -1.092 | 31.419 |
| ATOM | 1534 | N | ARG | 261 | 21.322 | -0.989 | 31.782 |

FIGURE 1GG

| Atom | | | Residue AA | No. | X | Y | Z |
|---|---|---|---|---|---|---|---|
| ATOM | 1535 | CA | ARG | 261 | 21.064 | 0.104 | 30.826 |
| ATOM | 1536 | CB | ARG | 261 | 20.359 | -0.454 | 29.603 |
| ATOM | 1537 | CG | ARG | 261 | 18.869 | -0.802 | 29.811 |
| ATOM | 1538 | CD | ARG | 261 | 18.265 | -1.409 | 28.535 |
| ATOM | 1539 | NE | ARG | 261 | 16.822 | -1.660 | 28.586 |
| ATOM | 1540 | CZ | ARG | 261 | 16.263 | -2.831 | 28.299 |
| ATOM | 1541 | NH1 | ARG | 261 | 14.949 | -2.998 | 28.338 |
| ATOM | 1542 | NH2 | ARG | 261 | 17.026 | -3.856 | 27.993 |
| ATOM | 1543 | C | ARG | 261 | 20.105 | 1.087 | 31.469 |
| ATOM | 1544 | O | ARG | 261 | 19.618 | 0.838 | 32.550 |
| ATOM | 1545 | N | LEU | 262 | 19.789 | 2.190 | 30.820 |
| ATOM | 1546 | CA | LEU | 262 | 18.811 | 3.091 | 31.422 |
| ATOM | 1547 | CB | LEU | 262 | 19.395 | 4.453 | 31.775 |
| ATOM | 1548 | CG | LEU | 262 | 20.861 | 4.672 | 32.107 |
| ATOM | 1549 | CD1 | LEU | 262 | 20.945 | 6.044 | 32.733 |
| ATOM | 1550 | CD2 | LEU | 262 | 21.427 | 3.621 | 33.025 |
| ATOM | 1551 | C | LEU | 262 | 17.647 | 3.299 | 30.469 |
| ATOM | 1552 | O | LEU | 262 | 17.708 | 4.155 | 29.601 |
| ATOM | 1553 | N | ARG | 263 | 16.589 | 2.513 | 30.632 |
| ATOM | 1554 | CA | ARG | 263 | 15.392 | 2.596 | 29.785 |
| ATOM | 1555 | CB | ARG | 263 | 14.568 | 1.304 | 29.912 |
| ATOM | 1556 | CG | ARG | 263 | 13.254 | 1.283 | 29.177 |
| ATOM | 1557 | CD | ARG | 263 | 12.112 | 1.303 | 30.156 |
| ATOM | 1558 | NE | ARG | 263 | 10.949 | 1.973 | 29.589 |
| ATOM | 1559 | CZ | ARG | 263 | 9.709 | 1.930 | 30.084 |
| ATOM | 1560 | NH1 | ARG | 263 | 8.742 | 2.585 | 29.455 |
| ATOM | 1561 | NH2 | ARG | 263 | 9.425 | 1.288 | 31.212 |
| ATOM | 1562 | C | ARG | 263 | 14.538 | 3.814 | 30.096 |
| ATOM | 1563 | O | ARG | 263 | 13.363 | 3.698 | 30.386 |
| ATOM | 1564 | N | ASP | 264 | 15.167 | 4.978 | 30.063 |
| ATOM | 1565 | CA | ASP | 264 | 14.534 | 6.278 | 30.306 |
| ATOM | 1566 | CB | ASP | 264 | 15.381 | 7.336 | 29.593 |
| ATOM | 1567 | CG | ASP | 264 | 14.935 | 8.744 | 29.864 |
| ATOM | 1568 | OD1 | ASP | 264 | 14.001 | 8.997 | 30.664 |
| ATOM | 1569 | OD2 | ASP | 264 | 15.557 | 9.616 | 29.244 |
| ATOM | 1570 | C | ASP | 264 | 13.145 | 6.209 | 29.683 |
| ATOM | 1571 | O | ASP | 264 | 13.039 | 6.187 | 28.457 |
| ATOM | 1572 | N | HIS | 265 | 12.078 | 6.244 | 30.486 |
| ATOM | 1573 | CA | HIS | 265 | 10.772 | 6.058 | 29.864 |
| ATOM | 1574 | CB | HIS | 265 | 10.021 | 4.881 | 30.468 |
| ATOM | 1575 | CG | HIS | 265 | 9.525 | 5.088 | 31.858 |
| ATOM | 1576 | CD2 | HIS | 265 | 8.478 | 5.804 | 32.330 |
| ATOM | 1577 | ND1 | HIS | 265 | 10.011 | 4.364 | 32.927 |
| ATOM | 1578 | CE1 | HIS | 265 | 9.273 | 4.614 | 33.991 |
| ATOM | 1579 | NE2 | HIS | 265 | 8.337 | 5.485 | 33.657 |
| ATOM | 1580 | C | HIS | 265 | 9.796 | 7.072 | 29.344 |
| ATOM | 1581 | O | HIS | 265 | 9.833 | 8.264 | 29.635 |
| ATOM | 1582 | N | ASP | 266 | 8.931 | 6.497 | 28.518 |

FIGURE 1HH

| | Atom | | Residue AA | No. | X | Y | Z |
|---|---|---|---|---|---|---|---|
| ATOM | 1583 | CA | ASP | 266 | 7.868 | 7.143 | 27.745 |
| ATOM | 1584 | CB | ASP | 266 | 7.461 | 6.200 | 26.581 |
| ATOM | 1585 | CG | ASP | 266 | 6.823 | 4.857 | 27.074 |
| ATOM | 1586 | OD1 | ASP | 266 | 7.497 | 4.090 | 27.825 |
| ATOM | 1587 | OD2 | ASP | 266 | 5.659 | 4.572 | 26.681 |
| ATOM | 1588 | C | ASP | 266 | 6.580 | 7.648 | 28.415 |
| ATOM | 1589 | O | ASP | 266 | 6.234 | 7.257 | 29.548 |
| ATOM | 1590 | N | ALA | 267 | 5.811 | 8.379 | 27.595 |
| ATOM | 1591 | CA | ALA | 267 | 4.533 | 8.973 | 27.973 |
| ATOM | 1592 | CB | ALA | 267 | 4.179 | 10.130 | 27.011 |
| ATOM | 1593 | C | ALA | 267 | 3.385 | 7.956 | 28.051 |
| ATOM | 1594 | O | ALA | 267 | 2.212 | 8.309 | 27.841 |
| ATOM | 1595 | N | ASP | 268 | 3.732 | 6.681 | 28.231 |
| ATOM | 1596 | CA | ASP | 268 | 2.706 | 5.653 | 28.406 |
| ATOM | 1597 | CB | ASP | 268 | 3.244 | 4.222 | 28.094 |
| ATOM | 1598 | CG | ASP | 268 | 2.406 | 3.065 | 28.771 |
| ATOM | 1599 | OD1 | ASP | 268 | 3.040 | 2.068 | 29.218 |
| ATOM | 1600 | OD2 | ASP | 268 | 1.142 | 3.135 | 28.851 |
| ATOM | 1601 | C | ASP | 268 | 2.458 | 5.789 | 29.890 |
| ATOM | 1602 | O | ASP | 268 | 1.449 | 6.362 | 30.329 |
| ATOM | 1603 | N | GLU | 269 | 3.500 | 5.379 | 30.619 |
| ATOM | 1604 | CA | GLU | 269 | 3.534 | 5.364 | 32.073 |
| ATOM | 1605 | CB | GLU | 269 | 4.167 | 4.038 | 32.568 |
| ATOM | 1606 | CG | GLU | 269 | 5.695 | 3.891 | 32.399 |
| ATOM | 1607 | CD | GLU | 269 | 6.132 | 3.584 | 30.986 |
| ATOM | 1608 | OE1 | GLU | 269 | 6.450 | 4.541 | 30.257 |
| ATOM | 1609 | OE2 | GLU | 269 | 6.187 | 2.388 | 30.628 |
| ATOM | 1610 | C | GLU | 269 | 4.230 | 6.592 | 32.704 |
| ATOM | 1611 | O | GLU | 269 | 4.494 | 6.613 | 33.929 |
| ATOM | 1612 | N | LEU | 270 | 4.595 | 7.577 | 31.877 |
| ATOM | 1613 | CA | LEU | 270 | 5.217 | 8.782 | 32.425 |
| ATOM | 1614 | CB | LEU | 270 | 5.771 | 9.720 | 31.361 |
| ATOM | 1615 | CG | LEU | 270 | 6.348 | 10.967 | 32.019 |
| ATOM | 1616 | CD1 | LEU | 270 | 7.645 | 11.375 | 31.344 |
| ATOM | 1617 | CD2 | LEU | 270 | 5.321 | 12.068 | 31.962 |
| ATOM | 1618 | C | LEU | 270 | 4.039 | 9.405 | 33.108 |
| ATOM | 1619 | O | LEU | 270 | 2.893 | 9.329 | 32.620 |
| ATOM | 1620 | N | SER | 271 | 4.298 | 9.973 | 34.268 |
| ATOM | 1621 | CA | SER | 271 | 3.186 | 10.511 | 34.995 |
| ATOM | 1622 | CB | SER | 271 | 3.398 | 10.425 | 36.510 |
| ATOM | 1623 | OG | SER | 271 | 2.333 | 9.690 | 37.127 |
| ATOM | 1624 | C | SER | 271 | 2.775 | 11.877 | 34.575 |
| ATOM | 1625 | O | SER | 271 | 3.579 | 12.646 | 34.058 |
| ATOM | 1626 | N | ALA | 272 | 1.469 | 12.097 | 34.723 |
| ATOM | 1627 | CA | ALA | 272 | 0.793 | 13.356 | 34.430 |
| ATOM | 1628 | CB | ALA | 272 | -0.648 | 13.297 | 35.010 |
| ATOM | 1629 | C | ALA | 272 | 1.587 | 14.523 | 35.070 |
| ATOM | 1630 | O | ALA | 272 | 1.733 | 15.609 | 34.460 |

FIGURE III

| Atom | | | Residue AA | No. | X | Y | Z |
|---|---|---|---|---|---|---|---|
| ATOM | 1631 | N | TYR | 273 | 2.073 | 14.276 | 36.300 |
| ATOM | 1632 | CA | TYR | 273 | 2.863 | 15.239 | 37.086 |
| ATOM | 1633 | CB | TYR | 273 | 2.734 | 14.953 | 38.590 |
| ATOM | 1634 | CG | TYR | 273 | 3.112 | 13.532 | 39.053 |
| ATOM | 1635 | CD1 | TYR | 273 | 2.118 | 12.519 | 39.164 |
| ATOM | 1636 | CE1 | TYR | 273 | 2.421 | 11.236 | 39.679 |
| ATOM | 1637 | CD2 | TYR | 273 | 4.436 | 13.218 | 39.466 |
| ATOM | 1638 | CE2 | TYR | 273 | 4.750 | 11.934 | 39.980 |
| ATOM | 1639 | CZ | TYR | 273 | 3.728 | 10.950 | 40.085 |
| ATOM | 1640 | OH | TYR | 273 | 3.981 | 9.691 | 40.606 |
| ATOM | 1641 | C | TYR | 273 | 4.328 | 15.206 | 36.703 |
| ATOM | 1642 | O | TYR | 273 | 5.019 | 16.228 | 36.747 |
| ATOM | 1643 | N | SER | 274 | 4.791 | 13.993 | 36.415 |
| ATOM | 1644 | CA | SER | 274 | 6.159 | 13.749 | 36.021 |
| ATOM | 1645 | CB | SER | 274 | 6.424 | 12.245 | 35.965 |
| ATOM | 1646 | OG | SER | 274 | 7.731 | 11.964 | 35.479 |
| ATOM | 1647 | C | SER | 274 | 6.384 | 14.354 | 34.648 |
| ATOM | 1648 | O | SER | 274 | 5.480 | 14.928 | 34.030 |
| ATOM | 1649 | N | ASN | 275 | 7.605 | 14.193 | 34.175 |
| ATOM | 1650 | CA | ASN | 275 | 8.027 | 14.699 | 32.884 |
| ATOM | 1651 | CB | ASN | 275 | 7.801 | 16.211 | 32.812 |
| ATOM | 1652 | CG | ASN | 275 | 8.227 | 16.921 | 34.088 |
| ATOM | 1653 | OD1 | ASN | 275 | 7.437 | 17.071 | 35.011 |
| ATOM | 1654 | ND2 | ASN | 275 | 9.498 | 17.308 | 34.165 |
| ATOM | 1655 | C | ASN | 275 | 9.509 | 14.370 | 32.873 |
| ATOM | 1656 | O | ASN | 275 | 10.368 | 15.226 | 32.592 |
| ATOM | 1657 | N | ALA | 276 | 9.790 | 13.133 | 33.285 |
| ATOM | 1658 | CA | ALA | 276 | 11.142 | 12.564 | 33.385 |
| ATOM | 1659 | CB | ALA | 276 | 12.163 | 13.575 | 33.945 |
| ATOM | 1660 | C | ALA | 276 | 11.013 | 11.412 | 34.343 |
| ATOM | 1661 | O | ALA | 276 | 10.428 | 11.542 | 35.423 |
| ATOM | 1662 | N | THR | 277 | 11.565 | 10.289 | 33.940 |
| ATOM | 1663 | CA | THR | 277 | 11.493 | 9.111 | 34.748 |
| ATOM | 1664 | CB | THR | 277 | 9.994 | 8.708 | 35.025 |
| ATOM | 1665 | OG1 | THR | 277 | 9.948 | 7.375 | 35.533 |
| ATOM | 1666 | CG2 | THR | 277 | 9.079 | 8.855 | 33.787 |
| ATOM | 1667 | C | THR | 277 | 12.306 | 8.032 | 34.048 |
| ATOM | 1668 | O | THR | 277 | 11.783 | 7.170 | 33.317 |
| ATOM | 1669 | N | THR | 278 | 13.617 | 8.169 | 34.208 |
| ATOM | 1670 | CA | THR | 278 | 14.572 | 7.244 | 33.620 |
| ATOM | 1671 | CB | THR | 278 | 15.908 | 7.965 | 33.266 |
| ATOM | 1672 | OG1 | THR | 278 | 17.000 | 7.053 | 33.372 |
| ATOM | 1673 | CG2 | THR | 278 | 16.151 | 9.155 | 34.157 |
| ATOM | 1674 | C | THR | 278 | 14.837 | 6.109 | 34.593 |
| ATOM | 1675 | O | THR | 278 | 15.385 | 6.352 | 35.651 |
| ATOM | 1676 | N | ASP | 279 | 14.349 | 4.904 | 34.318 |
| ATOM | 1677 | CA | ASP | 279 | 14.639 | 3.772 | 35.201 |
| ATOM | 1678 | CB | ASP | 279 | 13.700 | 2.601 | 34.934 |

FIGURE 1JJ

| Atom | | | Residue AA | No. | X | Y | Z |
|---|---|---|---|---|---|---|---|
| ATOM | 1679 | CG | ASP | 279 | 12.310 | 2.839 | 35.416 |
| ATOM | 1680 | OD1 | ASP | 279 | 12.056 | 3.903 | 36.011 |
| ATOM | 1681 | OD2 | ASP | 279 | 11.468 | 1.941 | 35.206 |
| ATOM | 1682 | C | ASP | 279 | 16.046 | 3.310 | 34.823 |
| ATOM | 1683 | O | ASP | 279 | 16.563 | 3.722 | 33.782 |
| ATOM | 1684 | N | ILE | 280 | 16.687 | 2.515 | 35.677 |
| ATOM | 1685 | CA | ILE | 280 | 18.005 | 1.953 | 35.391 |
| ATOM | 1686 | CB | ILE | 280 | 19.051 | 2.331 | 36.438 |
| ATOM | 1687 | CG2 | ILE | 280 | 20.359 | 1.707 | 36.079 |
| ATOM | 1688 | CG1 | ILE | 280 | 19.200 | 3.848 | 36.516 |
| ATOM | 1689 | CD1 | ILE | 280 | 20.356 | 4.316 | 37.324 |
| ATOM | 1690 | C | ILE | 280 | 17.638 | 0.505 | 35.534 |
| ATOM | 1691 | O | ILE | 280 | 16.909 | 0.171 | 36.450 |
| ATOM | 1692 | N | GLU | 281 | 18.072 | -0.361 | 34.638 |
| ATOM | 1693 | CA | GLU | 281 | 17.658 | -1.752 | 34.749 |
| ATOM | 1694 | CB | GLU | 281 | 16.801 | -2.159 | 33.538 |
| ATOM | 1695 | CG | GLU | 281 | 15.723 | -1.142 | 33.081 |
| ATOM | 1696 | CD | GLU | 281 | 14.796 | -1.672 | 31.972 |
| ATOM | 1697 | OE1 | GLU | 281 | 13.717 | -1.103 | 31.749 |
| ATOM | 1698 | OE2 | GLU | 281 | 15.129 | -2.669 | 31.321 |
| ATOM | 1699 | C | GLU | 281 | 18.802 | -2.720 | 34.885 |
| ATOM | 1700 | O | GLU | 281 | 19.942 | -2.384 | 34.625 |
| ATOM | 1701 | N | TYR | 282 | 18.488 | -3.934 | 35.297 |
| ATOM | 1702 | CA | TYR | 282 | 19.495 | -4.957 | 35.434 |
| ATOM | 1703 | CB | TYR | 282 | 19.728 | -5.369 | 36.899 |
| ATOM | 1704 | CG | TYR | 282 | 20.931 | -6.287 | 37.093 |
| ATOM | 1705 | CD1 | TYR | 282 | 20.804 | -7.658 | 37.012 |
| ATOM | 1706 | CE1 | TYR | 282 | 21.903 | -8.483 | 37.070 |
| ATOM | 1707 | CD2 | TYR | 282 | 22.210 | -5.767 | 37.255 |
| ATOM | 1708 | CE2 | TYR | 282 | 23.320 | -6.586 | 37.314 |
| ATOM | 1709 | CZ | TYR | 282 | 23.155 | -7.940 | 37.210 |
| ATOM | 1710 | OH | TYR | 282 | 24.250 | -8.754 | 37.187 |
| ATOM | 1711 | C | TYR | 282 | 19.072 | -6.167 | 34.631 |
| ATOM | 1712 | O | TYR | 282 | 17.890 | -6.474 | 34.467 |
| ATOM | 1713 | N | ALA | 283 | 20.073 | -6.830 | 34.097 |
| ATOM | 1714 | CA | ALA | 283 | 19.886 | -8.018 | 33.314 |
| ATOM | 1715 | CB | ALA | 283 | 21.008 | -8.113 | 32.286 |
| ATOM | 1716 | C | ALA | 283 | 19.913 | -9.213 | 34.257 |
| ATOM | 1717 | O | ALA | 283 | 20.888 | -9.962 | 34.318 |
| ATOM | 1718 | N | PHE | 284 | 18.858 | -9.357 | 35.037 |
| ATOM | 1719 | CA | PHE | 284 | 18.780 | -10.462 | 35.974 |
| ATOM | 1720 | CB | PHE | 284 | 17.571 | -10.285 | 36.878 |
| ATOM | 1721 | CG | PHE | 284 | 17.664 | -9.124 | 37.805 |
| ATOM | 1722 | CD1 | PHE | 284 | 18.755 | -8.970 | 38.631 |
| ATOM | 1723 | CD2 | PHE | 284 | 16.648 | -8.193 | 37.861 |
| ATOM | 1724 | CE1 | PHE | 284 | 18.838 | -7.906 | 39.500 |
| ATOM | 1725 | CE2 | PHE | 284 | 16.721 | -7.123 | 38.729 |
| ATOM | 1726 | CZ | PHE | 284 | 17.824 | -6.981 | 39.553 |

FIGURE 1KK

| Atom | | | Residue AA | No. | X | Y | Z |
|---|---|---|---|---|---|---|---|
| ATOM | 1727 | C | PHE | 284 | 18.626 | -11.761 | 35.212 |
| ATOM | 1728 | O | PHE | 284 | 18.194 | -11.757 | 34.085 |
| ATOM | 1729 | N | PRO | 285 | 18.909 | -12.900 | 35.844 |
| ATOM | 1730 | CD | PRO | 285 | 19.370 | -13.126 | 37.225 |
| ATOM | 1731 | CA | PRO | 285 | 18.765 | -14.172 | 35.127 |
| ATOM | 1732 | CB | PRO | 285 | 19.022 | -15.213 | 36.221 |
| ATOM | 1733 | CG | PRO | 285 | 19.971 | -14.510 | 37.137 |
| ATOM | 1734 | C | PRO | 285 | 17.360 | -14.323 | 34.569 |
| ATOM | 1735 | O | PRO | 285 | 17.158 | -14.859 | 33.492 |
| ATOM | 1736 | N | PHE | 286 | 16.387 | -13.820 | 35.303 |
| ATOM | 1737 | CA | PHE | 286 | 15.001 | -13.912 | 34.866 |
| ATOM | 1738 | CB | PHE | 286 | 14.048 | -13.963 | 36.073 |
| ATOM | 1739 | CG | PHE | 286 | 14.215 | -12.813 | 37.011 |
| ATOM | 1740 | CD1 | PHE | 286 | 13.475 | -11.664 | 36.845 |
| ATOM | 1741 | CD2 | PHE | 286 | 15.201 | -12.838 | 37.978 |
| ATOM | 1742 | CE1 | PHE | 286 | 13.726 | -10.561 | 37.611 |
| ATOM | 1743 | CE2 | PHE | 286 | 15.455 | -11.740 | 38.744 |
| ATOM | 1744 | CZ | PHE | 286 | 14.719 | -10.595 | 38.559 |
| ATOM | 1745 | C | PHE | 286 | 14.584 | -12.778 | 33.926 |
| ATOM | 1746 | O | PHE | 286 | 13.399 | -12.627 | 33.640 |
| ATOM | 1747 | N | GLY | 287 | 15.526 | -11.958 | 33.477 |
| ATOM | 1748 | CA | GLY | 287 | 15.159 | -10.887 | 32.572 |
| ATOM | 1749 | C | GLY | 287 | 15.624 | -9.493 | 32.930 |
| ATOM | 1750 | O | GLY | 287 | 16.579 | -9.296 | 33.686 |
| ATOM | 1751 | N | TRP | 288 | 14.998 | -8.510 | 32.302 |
| ATOM | 1752 | CA | TRP | 288 | 15.347 | -7.135 | 32.576 |
| ATOM | 1753 | CB | TRP | 288 | 15.071 | -6.246 | 31.366 |
| ATOM | 1754 | CG | TRP | 288 | 16.130 | -6.372 | 30.352 |
| ATOM | 1755 | CD2 | TRP | 288 | 17.318 | -5.559 | 30.229 |
| ATOM | 1756 | CE2 | TRP | 288 | 18.104 | -6.118 | 29.195 |
| ATOM | 1757 | CE3 | TRP | 288 | 17.795 | -4.420 | 30.892 |
| ATOM | 1758 | CD1 | TRP | 288 | 16.233 | -7.351 | 29.405 |
| ATOM | 1759 | NE1 | TRP | 288 | 17.424 | -7.208 | 28.710 |
| ATOM | 1760 | CZ2 | TRP | 288 | 19.345 | -5.569 | 28.809 |
| ATOM | 1761 | CZ3 | TRP | 288 | 19.044 | -3.876 | 30.502 |
| ATOM | 1762 | CH2 | TRP | 288 | 19.791 | -4.452 | 29.477 |
| ATOM | 1763 | C | TRP | 288 | 14.485 | -6.727 | 33.737 |
| ATOM | 1764 | O | TRP | 288 | 13.378 | -7.256 | 33.907 |
| ATOM | 1765 | N | GLY | 289 | 15.006 | -5.820 | 34.556 |
| ATOM | 1766 | CA | GLY | 289 | 14.263 | -5.333 | 35.708 |
| ATOM | 1767 | C | GLY | 289 | 14.839 | -4.017 | 36.189 |
| ATOM | 1768 | O | GLY | 289 | 15.984 | -3.701 | 35.884 |
| ATOM | 1769 | N | GLU | 290 | 14.061 | -3.246 | 36.935 |
| ATOM | 1770 | CA | GLU | 290 | 14.561 | -1.978 | 37.402 |
| ATOM | 1771 | CB | GLU | 290 | 13.425 | -0.977 | 37.537 |
| ATOM | 1772 | CG | GLU | 290 | 12.391 | -1.284 | 38.611 |
| ATOM | 1773 | CD | GLU | 290 | 11.205 | -0.284 | 38.607 |
| ATOM | 1774 | OE1 | GLU | 290 | 10.212 | -0.542 | 37.867 |

FIGURE 1LL

| Atom | | | Residue AA | No. | X | Y | Z |
|---|---|---|---|---|---|---|---|
| ATOM | 1775 | OE2 | GLU | 290 | 11.260 | 0.749 | 39.338 |
| ATOM | 1776 | C | GLU | 290 | 15.324 | -2.075 | 38.700 |
| ATOM | 1777 | O | GLU | 290 | 15.162 | -3.026 | 39.450 |
| ATOM | 1778 | N | LEU | 291 | 16.258 | -1.155 | 38.882 |
| ATOM | 1779 | CA | LEU | 291 | 17.030 | -1.073 | 40.100 |
| ATOM | 1780 | CB | LEU | 291 | 18.528 | -0.882 | 39.824 |
| ATOM | 1781 | CG | LEU | 291 | 19.369 | -2.096 | 39.455 |
| ATOM | 1782 | CD1 | LEU | 291 | 20.739 | -1.973 | 40.076 |
| ATOM | 1783 | CD2 | LEU | 291 | 18.683 | -3.342 | 39.925 |
| ATOM | 1784 | C | LEU | 291 | 16.466 | 0.189 | 40.699 |
| ATOM | 1785 | O | LEU | 291 | 15.445 | 0.171 | 41.387 |
| ATOM | 1786 | N | TRP | 292 | 17.096 | 1.296 | 40.335 |
| ATOM | 1787 | CA | TRP | 292 | 16.708 | 2.612 | 40.786 |
| ATOM | 1788 | CB | TRP | 292 | 17.849 | 3.558 | 40.488 |
| ATOM | 1789 | CG | TRP | 292 | 18.441 | 4.205 | 41.645 |
| ATOM | 1790 | CD2 | TRP | 292 | 19.746 | 3.991 | 42.135 |
| ATOM | 1791 | CE2 | TRP | 292 | 19.943 | 4.895 | 43.205 |
| ATOM | 1792 | CE3 | TRP | 292 | 20.785 | 3.130 | 41.772 |
| ATOM | 1793 | CD1 | TRP | 292 | 17.896 | 5.193 | 42.408 |
| ATOM | 1794 | NE1 | TRP | 292 | 18.787 | 5.615 | 43.357 |
| ATOM | 1795 | CZ2 | TRP | 292 | 21.137 | 4.960 | 43.910 |
| ATOM | 1796 | CZ3 | TRP | 292 | 21.971 | 3.194 | 42.474 |
| ATOM | 1797 | CH2 | TRP | 292 | 22.140 | 4.103 | 43.530 |
| ATOM | 1798 | C | TRP | 292 | 15.463 | 3.096 | 40.035 |
| ATOM | 1799 | O | TRP | 292 | 14.832 | 2.348 | 39.304 |
| ATOM | 1800 | N | GLY | 293 | 15.149 | 4.372 | 40.197 |
| ATOM | 1801 | CA | GLY | 293 | 14.017 | 4.961 | 39.521 |
| ATOM | 1802 | C | GLY | 293 | 14.083 | 6.468 | 39.675 |
| ATOM | 1803 | O | GLY | 293 | 13.268 | 7.029 | 40.398 |
| ATOM | 1804 | N | ILE | 294 | 15.061 | 7.121 | 39.043 |
| ATOM | 1805 | CA | ILE | 294 | 15.203 | 8.573 | 39.129 |
| ATOM | 1806 | CB | ILE | 294 | 16.519 | 9.044 | 38.513 |
| ATOM | 1807 | CG2 | ILE | 294 | 16.741 | 10.486 | 38.784 |
| ATOM | 1808 | CG1 | ILE | 294 | 17.696 | 8.287 | 39.095 |
| ATOM | 1809 | CD1 | ILE | 294 | 17.975 | 6.992 | 38.390 |
| ATOM | 1810 | C | ILE | 294 | 14.039 | 9.178 | 38.348 |
| ATOM | 1811 | O | ILE | 294 | 13.725 | 8.715 | 37.247 |
| ATOM | 1812 | N | ALA | 295 | 13.392 | 10.201 | 38.897 |
| ATOM | 1813 | CA | ALA | 295 | 12.241 | 10.786 | 38.216 |
| ATOM | 1814 | CB | ALA | 295 | 11.018 | 9.921 | 38.432 |
| ATOM | 1815 | C | ALA | 295 | 11.936 | 12.199 | 38.655 |
| ATOM | 1816 | O | ALA | 295 | 12.083 | 12.512 | 39.826 |
| ATOM | 1817 | N | SER | 296 | 11.496 | 13.038 | 37.709 |
| ATOM | 1818 | CA | SER | 296 | 11.145 | 14.447 | 37.973 |
| ATOM | 1819 | CB | SER | 296 | 11.615 | 15.375 | 36.833 |
| ATOM | 1820 | OG | SER | 296 | 11.480 | 16.759 | 37.157 |
| ATOM | 1821 | C | SER | 296 | 9.629 | 14.528 | 38.132 |
| ATOM | 1822 | O | SER | 296 | 8.871 | 14.319 | 37.177 |

FIGURE 1MM

| Atom | | | Residue AA | No. | X | Y | Z |
|---|---|---|---|---|---|---|---|
| ATOM | 1823 | N | ARG | 297 | 9.206 | 14.779 | 39.366 |
| ATOM | 1824 | CA | ARG | 297 | 7.788 | 14.867 | 39.709 |
| ATOM | 1825 | CB | ARG | 297 | 7.520 | 14.064 | 40.992 |
| ATOM | 1826 | CG | ARG | 297 | 8.285 | 12.757 | 41.123 |
| ATOM | 1827 | CD | ARG | 297 | 8.166 | 12.209 | 42.539 |
| ATOM | 1828 | NE | ARG | 297 | 6.771 | 12.005 | 42.935 |
| ATOM | 1829 | CZ | ARG | 297 | 6.197 | 10.821 | 43.126 |
| ATOM | 1830 | NH1 | ARG | 297 | 6.901 | 9.720 | 42.958 |
| ATOM | 1831 | NH2 | ARG | 297 | 4.913 | 10.735 | 43.479 |
| ATOM | 1832 | C | ARG | 297 | 7.342 | 16.333 | 39.927 |
| ATOM | 1833 | O | ARG | 297 | 6.193 | 16.585 | 40.372 |
| ATOM | 1834 | N | THR | 298 | 8.236 | 17.277 | 39.590 |
| ATOM | 1835 | CA | THR | 298 | 7.991 | 18.713 | 39.753 |
| ATOM | 1836 | CB | THR | 298 | 6.844 | 19.232 | 38.828 |
| ATOM | 1837 | OG1 | THR | 298 | 5.579 | 18.626 | 39.159 |
| ATOM | 1838 | CG2 | THR | 298 | 7.192 | 18.933 | 37.396 |
| ATOM | 1839 | C | THR | 298 | 7.710 | 19.050 | 41.217 |
| ATOM | 1840 | O | THR | 298 | 8.589 | 18.896 | 42.072 |
| ATOM | 1841 | N | ASP | 299 | 6.507 | 19.531 | 41.509 |
| ATOM | 1842 | CA | ASP | 299 | 6.170 | 19.833 | 42.891 |
| ATOM | 1843 | CB | ASP | 299 | 5.839 | 21.319 | 43.116 |
| ATOM | 1844 | CG | ASP | 299 | 4.999 | 21.929 | 42.004 |
| ATOM | 1845 | OD1 | ASP | 299 | 5.489 | 22.940 | 41.421 |
| ATOM | 1846 | OD2 | ASP | 299 | 3.854 | 21.435 | 41.761 |
| ATOM | 1847 | C | ASP | 299 | 5.091 | 18.882 | 43.418 |
| ATOM | 1848 | O | ASP | 299 | 5.273 | 18.278 | 44.478 |
| ATOM | 1849 | N | PHE | 300 | 4.012 | 18.713 | 42.656 |
| ATOM | 1850 | CA | PHE | 300 | 2.904 | 17.791 | 42.977 |
| ATOM | 1851 | CB | PHE | 300 | 3.029 | 16.527 | 42.114 |
| ATOM | 1852 | CG | PHE | 300 | 1.930 | 15.519 | 42.337 |
| ATOM | 1853 | CD1 | PHE | 300 | 0.590 | 15.893 | 42.203 |
| ATOM | 1854 | CD2 | PHE | 300 | 2.234 | 14.185 | 42.636 |
| ATOM | 1855 | CE1 | PHE | 300 | -0.440 | 14.953 | 42.357 |
| ATOM | 1856 | CE2 | PHE | 300 | 1.213 | 13.237 | 42.793 |
| ATOM | 1857 | CZ | PHE | 300 | -0.127 | 13.625 | 42.651 |
| ATOM | 1858 | C | PHE | 300 | 2.648 | 17.342 | 44.429 |
| ATOM | 1859 | O | PHE | 300 | 1.565 | 17.594 | 44.973 |
| ATOM | 1860 | N | ASP | 301 | 3.599 | 16.585 | 44.996 |
| ATOM | 1861 | CA | ASP | 301 | 3.513 | 16.052 | 46.360 |
| ATOM | 1862 | CB | ASP | 301 | 4.661 | 15.114 | 46.604 |
| ATOM | 1863 | CG | ASP | 301 | 4.748 | 14.082 | 45.564 |
| ATOM | 1864 | OD1 | ASP | 301 | 5.578 | 14.293 | 44.651 |
| ATOM | 1865 | OD2 | ASP | 301 | 3.952 | 13.107 | 45.651 |
| ATOM | 1866 | C | ASP | 301 | 3.479 | 17.094 | 47.461 |
| ATOM | 1867 | O | ASP | 301 | 2.508 | 17.113 | 48.228 |
| ATOM | 1868 | N | LEU | 302 | 4.524 | 17.932 | 47.575 |
| ATOM | 1869 | CA | LEU | 302 | 4.518 | 18.976 | 48.604 |
| ATOM | 1870 | CB | LEU | 302 | 5.638 | 19.988 | 48.429 |

FIGURE 1NN

| | Atom | | Residue AA | No. | X | Y | Z |
|---|---|---|---|---|---|---|---|
| ATOM | 1871 | CG | LEU | 302 | 7.086 | 19.562 | 48.585 |
| ATOM | 1872 | CD1 | LEU | 302 | 7.187 | 18.570 | 49.750 |
| ATOM | 1873 | CD2 | LEU | 302 | 7.571 | 18.947 | 47.269 |
| ATOM | 1874 | C | LEU | 302 | 3.211 | 19.698 | 48.402 |
| ATOM | 1875 | O | LEU | 302 | 2.411 | 19.807 | 49.325 |
| ATOM | 1876 | N | ALA | 303 | 2.955 | 20.061 | 47.145 |
| ATOM | 1877 | CA | ALA | 303 | 1.728 | 20.759 | 46.734 |
| ATOM | 1878 | CB | ALA | 303 | 1.864 | 21.285 | 45.295 |
| ATOM | 1879 | C | ALA | 303 | 0.407 | 19.985 | 46.888 |
| ATOM | 1880 | O | ALA | 303 | -0.654 | 20.579 | 46.735 |
| ATOM | 1881 | N | ALA | 304 | 0.466 | 18.673 | 47.118 |
| ATOM | 1882 | CA | ALA | 304 | -0.741 | 17.864 | 47.325 |
| ATOM | 1883 | CB | ALA | 304 | -0.491 | 16.424 | 46.897 |
| ATOM | 1884 | C | ALA | 304 | -1.068 | 17.929 | 48.826 |
| ATOM | 1885 | O | ALA | 304 | -2.226 | 17.908 | 49.245 |
| ATOM | 1886 | N | HIS | 305 | -0.010 | 18.038 | 49.618 |
| ATOM | 1887 | CA | HIS | 305 | -0.096 | 18.131 | 51.056 |
| ATOM | 1888 | CB | HIS | 305 | 1.240 | 17.731 | 51.647 |
| ATOM | 1889 | CG | HIS | 305 | 1.541 | 16.276 | 51.497 |
| ATOM | 1890 | CD2 | HIS | 305 | 2.718 | 15.616 | 51.377 |
| ATOM | 1891 | ND1 | HIS | 305 | 0.555 | 15.311 | 51.488 |
| ATOM | 1892 | CE1 | HIS | 305 | 1.110 | 14.116 | 51.376 |
| ATOM | 1893 | NE2 | HIS | 305 | 2.423 | 14.273 | 51.307 |
| ATOM | 1894 | C | HIS | 305 | -0.401 | 19.567 | 51.402 |
| ATOM | 1895 | O | HIS | 305 | -1.396 | 19.859 | 52.059 |
| ATOM | 1896 | N | ALA | 306 | 0.467 | 20.455 | 50.925 |
| ATOM | 1897 | CA | ALA | 306 | 0.341 | 21.894 | 51.117 |
| ATOM | 1898 | CB | ALA | 306 | 1.293 | 22.651 | 50.181 |
| ATOM | 1899 | C | ALA | 306 | -1.077 | 22.347 | 50.851 |
| ATOM | 1900 | O | ALA | 306 | -1.523 | 23.352 | 51.412 |
| ATOM | 1901 | N | GLU | 307 | -1.764 | 21.642 | 49.956 |
| ATOM | 1902 | CA | GLU | 307 | -3.127 | 22.002 | 49.629 |
| ATOM | 1903 | CB | GLU | 307 | -3.392 | 21.901 | 48.126 |
| ATOM | 1904 | CG | GLU | 307 | -4.834 | 22.345 | 47.677 |
| ATOM | 1905 | CD | GLU | 307 | -5.836 | 21.173 | 47.397 |
| ATOM | 1906 | OE1 | GLU | 307 | -5.879 | 20.722 | 46.204 |
| ATOM | 1907 | OE2 | GLU | 307 | -6.582 | 20.746 | 48.352 |
| ATOM | 1908 | C | GLU | 307 | -4.111 | 21.138 | 50.360 |
| ATOM | 1909 | O | GLU | 307 | -4.858 | 21.631 | 51.201 |
| ATOM | 1910 | N | HIS | 308 | -4.109 | 19.851 | 50.039 |
| ATOM | 1911 | CA | HIS | 308 | -5.047 | 18.920 | 50.631 |
| ATOM | 1912 | CB | HIS | 308 | -4.795 | 17.532 | 50.054 |
| ATOM | 1913 | CG | HIS | 308 | -5.713 | 16.467 | 50.570 |
| ATOM | 1914 | CD2 | HIS | 308 | -6.942 | 16.068 | 50.158 |
| ATOM | 1915 | ND1 | HIS | 308 | -5.353 | 15.608 | 51.591 |
| ATOM | 1916 | CE1 | HIS | 308 | -6.316 | 14.720 | 51.780 |
| ATOM | 1917 | NE2 | HIS | 308 | -7.292 | 14.977 | 50.921 |
| ATOM | 1918 | C | HIS | 308 | -5.021 | 18.916 | 52.165 |

FIGURE 10O

| Atom | | | Residue AA | No. | X | Y | Z |
|---|---|---|---|---|---|---|---|
| ATOM | 1919 | O | HIS | 308 | -6.006 | 18.487 | 52.792 |
| ATOM | 1920 | N | SER | 309 | -3.935 | 19.419 | 52.770 |
| ATOM | 1921 | CA | SER | 309 | -3.837 | 19.463 | 54.235 |
| ATOM | 1922 | CB | SER | 309 | -3.303 | 18.135 | 54.800 |
| ATOM | 1923 | OG | SER | 309 | -4.244 | 17.071 | 54.627 |
| ATOM | 1924 | C | SER | 309 | -3.147 | 20.678 | 54.889 |
| ATOM | 1925 | O | SER | 309 | -1.968 | 20.649 | 55.312 |
| ATOM | 1926 | N | GLY | 310 | -3.945 | 21.741 | 54.948 |
| ATOM | 1927 | CA | GLY | 310 | -3.594 | 23.016 | 55.560 |
| ATOM | 1928 | C | GLY | 310 | -2.275 | 23.765 | 55.432 |
| ATOM | 1929 | O | GLY | 310 | -2.265 | 24.976 | 55.103 |
| ATOM | 1930 | N | GLU | 311 | -1.184 | 23.067 | 55.742 |
| ATOM | 1931 | CA | GLU | 311 | 0.154 | 23.640 | 55.753 |
| ATOM | 1932 | CB | GLU | 311 | 1.178 | 22.509 | 55.827 |
| ATOM | 1933 | CG | GLU | 311 | 2.379 | 22.844 | 56.726 |
| ATOM | 1934 | CD | GLU | 311 | 2.018 | 22.932 | 58.228 |
| ATOM | 1935 | OE1 | GLU | 311 | 2.977 | 22.925 | 59.059 |
| ATOM | 1936 | OE2 | GLU | 311 | 0.794 | 22.993 | 58.584 |
| ATOM | 1937 | C | GLU | 311 | 0.649 | 24.782 | 54.810 |
| ATOM | 1938 | O | GLU | 311 | 0.638 | 25.955 | 55.215 |
| ATOM | 1939 | N | ASP | 312 | 1.100 | 24.412 | 53.600 |
| ATOM | 1940 | CA | ASP | 312 | 1.694 | 25.267 | 52.539 |
| ATOM | 1941 | CB | ASP | 312 | 1.387 | 26.772 | 52.687 |
| ATOM | 1942 | CG | ASP | 312 | 2.566 | 27.583 | 53.262 |
| ATOM | 1943 | OD1 | ASP | 312 | 2.605 | 27.795 | 54.504 |
| ATOM | 1944 | OD2 | ASP | 312 | 3.434 | 28.032 | 52.474 |
| ATOM | 1945 | C | ASP | 312 | 3.207 | 24.968 | 52.614 |
| ATOM | 1946 | O | ASP | 312 | 3.770 | 24.785 | 53.701 |
| ATOM | 1947 | N | PHE | 313 | 3.870 | 24.872 | 51.471 |
| ATOM | 1948 | CA | PHE | 313 | 5.293 | 24.519 | 51.514 |
| ATOM | 1949 | CB | PHE | 313 | 5.443 | 23.014 | 51.214 |
| ATOM | 1950 | CG | PHE | 313 | 4.750 | 22.077 | 52.228 |
| ATOM | 1951 | CD1 | PHE | 313 | 3.450 | 21.600 | 52.005 |
| ATOM | 1952 | CD2 | PHE | 313 | 5.450 | 21.578 | 53.336 |
| ATOM | 1953 | CE1 | PHE | 313 | 2.875 | 20.655 | 52.841 |
| ATOM | 1954 | CE2 | PHE | 313 | 4.874 | 20.626 | 54.178 |
| ATOM | 1955 | CZ | PHE | 313 | 3.590 | 20.169 | 53.923 |
| ATOM | 1956 | C | PHE | 313 | 6.240 | 25.316 | 50.593 |
| ATOM | 1957 | O | PHE | 313 | 7.373 | 24.895 | 50.332 |
| ATOM | 1958 | N | ALA | 314 | 5.788 | 26.475 | 50.132 |
| ATOM | 1959 | CA | ALA | 314 | 6.581 | 27.302 | 49.237 |
| ATOM | 1960 | CB | ALA | 314 | 5.733 | 28.433 | 48.718 |
| ATOM | 1961 | C | ALA | 314 | 7.843 | 27.856 | 49.873 |
| ATOM | 1962 | O | ALA | 314 | 7.819 | 28.339 | 51.011 |
| ATOM | 1963 | N | TYR | 315 | 8.949 | 27.764 | 49.140 |
| ATOM | 1964 | CA | TYR | 315 | 10.230 | 28.303 | 49.598 |
| ATOM | 1965 | CB | TYR | 315 | 11.361 | 27.706 | 48.778 |
| ATOM | 1966 | CG | TYR | 315 | 12.711 | 28.236 | 49.132 |

FIGURE 1PP

| Atom | | | Residue AA | No. | X | Y | Z |
|---|---|---|---|---|---|---|---|
| ATOM | 1967 | CD1 | TYR | 315 | 13.248 | 29.317 | 48.468 |
| ATOM | 1968 | CE1 | TYR | 315 | 14.548 | 29.778 | 48.744 |
| ATOM | 1969 | CD2 | TYR | 315 | 13.484 | 27.621 | 50.089 |
| ATOM | 1970 | CE2 | TYR | 315 | 14.792 | 28.067 | 50.380 |
| ATOM | 1971 | CZ | TYR | 315 | 15.320 | 29.147 | 49.697 |
| ATOM | 1972 | OH | TYR | 315 | 16.618 | 29.567 | 49.931 |
| ATOM | 1973 | C | TYR | 315 | 10.136 | 29.806 | 49.336 |
| ATOM | 1974 | O | TYR | 315 | 9.267 | 30.236 | 48.583 |
| ATOM | 1975 | N | ALA | 316 | 11.006 | 30.615 | 49.925 |
| ATOM | 1976 | CA | ALA | 316 | 10.906 | 32.056 | 49.678 |
| ATOM | 1977 | CB | ALA | 316 | 10.104 | 32.733 | 50.794 |
| ATOM | 1978 | C | ALA | 316 | 12.262 | 32.707 | 49.555 |
| ATOM | 1979 | O | ALA | 316 | 12.939 | 32.884 | 50.584 |
| ATOM | 1980 | N | ASP | 317 | 12.645 | 33.053 | 48.315 |
| ATOM | 1981 | CA | ASP | 317 | 13.934 | 33.687 | 48.045 |
| ATOM | 1982 | CB | ASP | 317 | 14.968 | 33.187 | 49.070 |
| ATOM | 1983 | CG | ASP | 317 | 16.282 | 33.868 | 48.964 |
| ATOM | 1984 | OD1 | ASP | 317 | 17.136 | 33.395 | 48.183 |
| ATOM | 1985 | OD2 | ASP | 317 | 16.479 | 34.845 | 49.702 |
| ATOM | 1986 | C | ASP | 317 | 14.522 | 33.472 | 46.637 |
| ATOM | 1987 | O | ASP | 317 | 15.109 | 32.411 | 46.374 |
| ATOM | 1988 | N | PRO | 318 | 14.323 | 34.427 | 45.688 |
| ATOM | 1989 | CD | PRO | 318 | 13.500 | 35.646 | 45.723 |
| ATOM | 1990 | CA | PRO | 318 | 14.896 | 34.284 | 44.344 |
| ATOM | 1991 | CB | PRO | 318 | 13.818 | 34.910 | 43.467 |
| ATOM | 1992 | CG | PRO | 318 | 13.475 | 36.131 | 44.264 |
| ATOM | 1993 | C | PRO | 318 | 16.104 | 35.246 | 44.525 |
| ATOM | 1994 | O | PRO | 318 | 16.187 | 36.299 | 43.861 |
| ATOM | 1995 | N | ALA | 319 | 16.918 | 34.921 | 45.553 |
| ATOM | 1996 | CA | ALA | 319 | 18.107 | 35.668 | 46.029 |
| ATOM | 1997 | CB | ALA | 319 | 18.826 | 36.472 | 44.882 |
| ATOM | 1998 | C | ALA | 319 | 17.622 | 36.636 | 47.119 |
| ATOM | 1999 | O | ALA | 319 | 18.305 | 36.892 | 48.122 |
| ATOM | 2000 | N | THR | 320 | 16.422 | 37.157 | 46.909 |
| ATOM | 2001 | CA | THR | 320 | 15.789 | 38.113 | 47.813 |
| ATOM | 2002 | CB | THR | 320 | 15.256 | 39.312 | 46.962 |
| ATOM | 2003 | OG1 | THR | 320 | 14.538 | 38.800 | 45.807 |
| ATOM | 2004 | CG2 | THR | 320 | 16.431 | 40.213 | 46.511 |
| ATOM | 2005 | C | THR | 320 | 14.623 | 37.380 | 48.500 |
| ATOM | 2006 | O | THR | 320 | 14.794 | 36.730 | 49.543 |
| ATOM | 2007 | N | ASN | 321 | 13.438 | 37.528 | 47.901 |
| ATOM | 2008 | CA | ASN | 321 | 12.206 | 36.864 | 48.329 |
| ATOM | 2009 | CB | ASN | 321 | 11.566 | 37.502 | 49.608 |
| ATOM | 2010 | CG | ASN | 321 | 11.175 | 36.431 | 50.694 |
| ATOM | 2011 | OD1 | ASN | 321 | 9.999 | 36.022 | 50.816 |
| ATOM | 2012 | ND2 | ASN | 321 | 12.177 | 35.970 | 51.456 |
| ATOM | 2013 | C | ASN | 321 | 11.233 | 36.794 | 47.107 |
| ATOM | 2014 | O | ASN | 321 | 11.143 | 37.744 | 46.294 |

FIGURE 1QQ

| | Atom | | Residue AA | No. | X | Y | Z |
|---|---|---|---|---|---|---|---|
| ATOM | 2015 | N | ALA | 322 | 10.833 | 35.538 | 46.851 |
| ATOM | 2016 | CA | ALA | 322 | 9.886 | 35.084 | 45.812 |
| ATOM | 2017 | CB | ALA | 322 | 10.557 | 34.849 | 44.439 |
| ATOM | 2018 | C | ALA | 322 | 9.430 | 33.745 | 46.391 |
| ATOM | 2019 | O | ALA | 322 | 10.261 | 32.954 | 46.890 |
| ATOM | 2020 | N | ALA | 323 | 8.116 | 33.540 | 46.384 |
| ATOM | 2021 | CA | ALA | 323 | 7.520 | 32.324 | 46.914 |
| ATOM | 2022 | CB | ALA | 323 | 6.292 | 32.672 | 47.834 |
| ATOM | 2023 | C | ALA | 323 | 7.130 | 31.383 | 45.754 |
| ATOM | 2024 | O | ALA | 323 | 6.478 | 31.787 | 44.800 |
| ATOM | 2025 | N | TYR | 324 | 7.595 | 30.141 | 45.841 |
| ATOM | 2026 | CA | TYR | 324 | 7.355 | 29.105 | 44.847 |
| ATOM | 2027 | CB | TYR | 324 | 8.306 | 29.297 | 43.688 |
| ATOM | 2028 | CG | TYR | 324 | 9.749 | 29.510 | 44.094 |
| ATOM | 2029 | CD1 | TYR | 324 | 10.196 | 30.775 | 44.465 |
| ATOM | 2030 | CE1 | TYR | 324 | 11.537 | 31.020 | 44.724 |
| ATOM | 2031 | CD2 | TYR | 324 | 10.684 | 28.478 | 44.005 |
| ATOM | 2032 | CE2 | TYR | 324 | 12.031 | 28.705 | 44.256 |
| ATOM | 2033 | CZ | TYR | 324 | 12.454 | 29.992 | 44.612 |
| ATOM | 2034 | OH | TYR | 324 | 13.789 | 30.301 | 44.809 |
| ATOM | 2035 | C | TYR | 324 | 7.659 | 27.741 | 45.453 |
| ATOM | 2036 | O | TYR | 324 | 8.797 | 27.481 | 45.867 |
| ATOM | 2037 | N | ILE | 325 | 6.657 | 26.871 | 45.522 |
| ATOM | 2038 | CA | ILE | 325 | 6.866 | 25.535 | 46.077 |
| ATOM | 2039 | CB | ILE | 325 | 5.586 | 24.729 | 46.045 |
| ATOM | 2040 | CG2 | ILE | 325 | 4.990 | 24.748 | 44.649 |
| ATOM | 2041 | CG1 | ILE | 325 | 5.859 | 23.306 | 46.495 |
| ATOM | 2042 | CD1 | ILE | 325 | 4.604 | 22.592 | 46.833 |
| ATOM | 2043 | C | ILE | 325 | 7.952 | 24.845 | 45.252 |
| ATOM | 2044 | O | ILE | 325 | 7.991 | 24.992 | 44.016 |
| ATOM | 2045 | N | PRO | 326 | 8.879 | 24.128 | 45.924 |
| ATOM | 2046 | CD | PRO | 326 | 9.070 | 24.042 | 47.385 |
| ATOM | 2047 | CA | PRO | 326 | 9.977 | 23.437 | 45.223 |
| ATOM | 2048 | CB | PRO | 326 | 10.910 | 22.994 | 46.372 |
| ATOM | 2049 | CG | PRO | 326 | 10.579 | 23.959 | 47.489 |
| ATOM | 2050 | C | PRO | 326 | 9.617 | 22.261 | 44.293 |
| ATOM | 2051 | O | PRO | 326 | 8.501 | 21.695 | 44.308 |
| ATOM | 2052 | N | TYR | 327 | 10.607 | 21.905 | 43.491 |
| ATOM | 2053 | CA | TYR | 327 | 10.475 | 20.814 | 42.560 |
| ATOM | 2054 | CB | TYR | 327 | 11.029 | 21.237 | 41.204 |
| ATOM | 2055 | CG | TYR | 327 | 10.027 | 21.756 | 40.195 |
| ATOM | 2056 | CD1 | TYR | 327 | 10.174 | 21.447 | 38.828 |
| ATOM | 2057 | CE1 | TYR | 327 | 9.303 | 21.967 | 37.883 |
| ATOM | 2058 | CD2 | TYR | 327 | 8.965 | 22.598 | 40.590 |
| ATOM | 2059 | CE2 | TYR | 327 | 8.082 | 23.126 | 39.648 |
| ATOM | 2060 | CZ | TYR | 327 | 8.256 | 22.812 | 38.294 |
| ATOM | 2061 | OH | TYR | 327 | 7.397 | 23.371 | 37.362 |
| ATOM | 2062 | C | TYR | 327 | 11.382 | 19.728 | 43.074 |

FIGURE 1RR

| Atom | | | Residue AA | No. | X | Y | Z |
|---|---|---|---|---|---|---|---|
| ATOM | 2063 | O | TYR | 327 | 12.514 | 20.034 | 43.438 |
| ATOM | 2064 | N | CYS | 328 | 10.923 | 18.478 | 43.116 |
| ATOM | 2065 | CA | CYS | 328 | 11.818 | 17.414 | 43.561 |
| ATOM | 2066 | CB | CYS | 328 | 11.314 | 16.699 | 44.816 |
| ATOM | 2067 | SG | CYS | 328 | 10.065 | 15.451 | 44.552 |
| ATOM | 2068 | C | CYS | 328 | 12.123 | 16.413 | 42.455 |
| ATOM | 2069 | O | CYS | 328 | 11.555 | 16.475 | 41.351 |
| ATOM | 2070 | N | ILE | 329 | 13.069 | 15.527 | 42.743 |
| ATOM | 2071 | CA | ILE | 329 | 13.512 | 14.486 | 41.819 |
| ATOM | 2072 | CB | ILE | 329 | 14.893 | 14.853 | 41.235 |
| ATOM | 2073 | CG2 | ILE | 329 | 15.558 | 13.660 | 40.655 |
| ATOM | 2074 | CG1 | ILE | 329 | 14.766 | 15.948 | 40.191 |
| ATOM | 2075 | CD1 | ILE | 329 | 14.855 | 17.328 | 40.746 |
| ATOM | 2076 | C | ILE | 329 | 13.667 | 13.280 | 42.732 |
| ATOM | 2077 | O | ILE | 329 | 14.456 | 13.339 | 43.643 |
| ATOM | 2078 | N | GLU | 330 | 12.945 | 12.193 | 42.536 |
| ATOM | 2079 | CA | GLU | 330 | 13.135 | 11.123 | 43.481 |
| ATOM | 2080 | CB | GLU | 330 | 11.811 | 10.733 | 44.128 |
| ATOM | 2081 | CG | GLU | 330 | 10.940 | 9.803 | 43.354 |
| ATOM | 2082 | CD | GLU | 330 | 9.806 | 9.249 | 44.179 |
| ATOM | 2083 | OE1 | GLU | 330 | 9.784 | 8.026 | 44.433 |
| ATOM | 2084 | OE2 | GLU | 330 | 8.930 | 10.041 | 44.563 |
| ATOM | 2085 | C | GLU | 330 | 13.907 | 9.910 | 43.026 |
| ATOM | 2086 | O | GLU | 330 | 13.355 | 9.017 | 42.433 |
| ATOM | 2087 | N | PRO | 331 | 15.222 | 9.891 | 43.225 |
| ATOM | 2088 | CD | PRO | 331 | 16.137 | 11.017 | 43.425 |
| ATOM | 2089 | CA | PRO | 331 | 15.955 | 8.704 | 42.793 |
| ATOM | 2090 | CB | PRO | 331 | 17.404 | 9.189 | 42.790 |
| ATOM | 2091 | CG | PRO | 331 | 17.417 | 10.331 | 43.721 |
| ATOM | 2092 | C | PRO | 331 | 15.746 | 7.502 | 43.724 |
| ATOM | 2093 | O | PRO | 331 | 16.674 | 7.072 | 44.412 |
| ATOM | 2094 | N | SER | 332 | 14.529 | 6.954 | 43.725 |
| ATOM | 2095 | CA | SER | 332 | 14.141 | 5.801 | 44.558 |
| ATOM | 2096 | CB | SER | 332 | 12.663 | 5.457 | 44.335 |
| ATOM | 2097 | OG | SER | 332 | 12.375 | 4.105 | 44.611 |
| ATOM | 2098 | C | SER | 332 | 15.000 | 4.581 | 44.297 |
| ATOM | 2099 | O | SER | 332 | 15.668 | 4.512 | 43.289 |
| ATOM | 2100 | N | LEU | 333 | 14.943 | 3.591 | 45.181 |
| ATOM | 2101 | CA | LEU | 333 | 15.747 | 2.372 | 45.027 |
| ATOM | 2102 | CB | LEU | 333 | 17.147 | 2.552 | 45.646 |
| ATOM | 2103 | CG | LEU | 333 | 18.249 | 1.616 | 45.133 |
| ATOM | 2104 | CD1 | LEU | 333 | 18.199 | 1.532 | 43.645 |
| ATOM | 2105 | CD2 | LEU | 333 | 19.617 | 2.065 | 45.564 |
| ATOM | 2106 | C | LEU | 333 | 15.043 | 1.126 | 45.594 |
| ATOM | 2107 | O | LEU | 333 | 13.803 | 1.017 | 45.567 |
| ATOM | 2108 | N | GLY | 334 | 15.827 | 0.171 | 46.065 |
| ATOM | 2109 | CA | GLY | 334 | 15.250 | -1.037 | 46.595 |
| ATOM | 2110 | C | GLY | 334 | 16.440 | -1.718 | 47.194 |

FIGURE 1SS

| Atom | | | Residue AA | No. | X | Y | Z |
|---|---|---|---|---|---|---|---|
| ATOM | 2111 | O | GLY | 334 | 17.310 | -2.206 | 46.480 |
| ATOM | 2112 | N | ALA | 335 | 16.535 | -1.689 | 48.509 |
| ATOM | 2113 | CA | ALA | 335 | 17.674 | -2.295 | 49.156 |
| ATOM | 2114 | CB | ALA | 335 | 17.639 | -2.008 | 50.620 |
| ATOM | 2115 | C | ALA | 335 | 17.639 | -3.774 | 48.897 |
| ATOM | 2116 | O | ALA | 335 | 18.650 | -4.383 | 48.561 |
| ATOM | 2117 | N | ASP | 336 | 16.442 | -4.334 | 49.007 |
| ATOM | 2118 | CA | ASP | 336 | 16.280 | -5.750 | 48.781 |
| ATOM | 2119 | CB | ASP | 336 | 14.814 | -6.192 | 48.973 |
| ATOM | 2120 | CG | ASP | 336 | 14.438 | -6.480 | 50.470 |
| ATOM | 2121 | OD1 | ASP | 336 | 14.333 | -7.675 | 50.870 |
| ATOM | 2122 | OD2 | ASP | 336 | 14.174 | -5.512 | 51.225 |
| ATOM | 2123 | C | ASP | 336 | 16.824 | -6.050 | 47.379 |
| ATOM | 2124 | O | ASP | 336 | 17.803 | -6.786 | 47.267 |
| ATOM | 2125 | N | ARG | 337 | 16.296 | -5.378 | 46.343 |
| ATOM | 2126 | CA | ARG | 337 | 16.744 | -5.561 | 44.936 |
| ATOM | 2127 | CB | ARG | 337 | 15.916 | -4.737 | 43.957 |
| ATOM | 2128 | CG | ARG | 337 | 14.513 | -5.233 | 43.711 |
| ATOM | 2129 | CD | ARG | 337 | 14.111 | -5.006 | 42.230 |
| ATOM | 2130 | NE | ARG | 337 | 12.699 | -4.631 | 42.080 |
| ATOM | 2131 | CZ | ARG | 337 | 12.236 | -3.377 | 42.170 |
| ATOM | 2132 | NH1 | ARG | 337 | 13.073 | -2.349 | 42.389 |
| ATOM | 2133 | NH2 | ARG | 337 | 10.919 | -3.156 | 42.147 |
| ATOM | 2134 | C | ARG | 337 | 18.207 | -5.259 | 44.655 |
| ATOM | 2135 | O | ARG | 337 | 18.920 | -6.130 | 44.188 |
| ATOM | 2136 | N | VAL | 338 | 18.648 | -4.033 | 44.912 |
| ATOM | 2137 | CA | VAL | 338 | 20.032 | -3.666 | 44.676 |
| ATOM | 2138 | CB | VAL | 338 | 20.424 | -2.330 | 45.346 |
| ATOM | 2139 | CG1 | VAL | 338 | 21.871 | -1.970 | 45.067 |
| ATOM | 2140 | CG2 | VAL | 338 | 19.570 | -1.251 | 44.841 |
| ATOM | 2141 | C | VAL | 338 | 20.957 | -4.758 | 45.176 |
| ATOM | 2142 | O | VAL | 338 | 22.036 | -4.918 | 44.632 |
| ATOM | 2143 | N | THR | 339 | 20.543 | -5.538 | 46.179 |
| ATOM | 2144 | CA | THR | 339 | 21.418 | -6.596 | 46.680 |
| ATOM | 2145 | CB | THR | 339 | 21.220 | -6.915 | 48.193 |
| ATOM | 2146 | OG1 | THR | 339 | 20.013 | -7.635 | 48.403 |
| ATOM | 2147 | CG2 | THR | 339 | 21.138 | -5.644 | 48.990 |
| ATOM | 2148 | C | THR | 339 | 21.349 | -7.830 | 45.809 |
| ATOM | 2149 | O | THR | 339 | 22.365 | -8.481 | 45.585 |
| ATOM | 2150 | N | LEU | 340 | 20.178 | -8.106 | 45.246 |
| ATOM | 2151 | CA | LEU | 340 | 20.029 | -9.253 | 44.366 |
| ATOM | 2152 | CB | LEU | 340 | 18.582 | -9.411 | 43.928 |
| ATOM | 2153 | CG | LEU | 340 | 18.267 | -10.709 | 43.191 |
| ATOM | 2154 | CD1 | LEU | 340 | 18.944 | -11.865 | 43.863 |
| ATOM | 2155 | CD2 | LEU | 340 | 16.778 | -10.936 | 43.124 |
| ATOM | 2156 | C | LEU | 340 | 20.948 | -9.037 | 43.164 |
| ATOM | 2157 | O | LEU | 340 | 21.635 | -9.952 | 42.715 |
| ATOM | 2158 | N | ALA | 341 | 21.002 | -7.800 | 42.683 |

FIGURE 1TT

| Atom | | | Residue AA | No. | X | Y | Z |
|---|---|---|---|---|---|---|---|
| ATOM | 2159 | CA | ALA | 341 | 21.854 | -7.444 | 41.565 |
| ATOM | 2160 | CB | ALA | 341 | 21.843 | -5.961 | 41.337 |
| ATOM | 2161 | C | ALA | 341 | 23.224 | -7.879 | 41.960 |
| ATOM | 2162 | O | ALA | 341 | 23.667 | -8.950 | 41.611 |
| ATOM | 2163 | N | PHE | 342 | 23.841 | -7.079 | 42.798 |
| ATOM | 2164 | CA | PHE | 342 | 25.175 | -7.352 | 43.306 |
| ATOM | 2165 | CB | PHE | 342 | 25.425 | -6.519 | 44.577 |
| ATOM | 2166 | CG | PHE | 342 | 25.659 | -5.052 | 44.326 |
| ATOM | 2167 | CD1 | PHE | 342 | 24.662 | -4.125 | 44.571 |
| ATOM | 2168 | CD2 | PHE | 342 | 26.903 | -4.598 | 43.916 |
| ATOM | 2169 | CE1 | PHE | 342 | 24.897 | -2.772 | 44.422 |
| ATOM | 2170 | CE2 | PHE | 342 | 27.155 | -3.251 | 43.761 |
| ATOM | 2171 | CZ | PHE | 342 | 26.154 | -2.334 | 44.016 |
| ATOM | 2172 | C | PHE | 342 | 25.471 | -8.842 | 43.583 |
| ATOM | 2173 | O | PHE | 342 | 26.602 | -9.282 | 43.398 |
| ATOM | 2174 | N | LEU | 343 | 24.472 | -9.604 | 44.028 |
| ATOM | 2175 | CA | LEU | 343 | 24.671 | -11.021 | 44.310 |
| ATOM | 2176 | CB | LEU | 343 | 23.483 | -11.619 | 45.083 |
| ATOM | 2177 | CG | LEU | 343 | 23.668 | -12.770 | 46.087 |
| ATOM | 2178 | CD1 | LEU | 343 | 22.353 | -13.475 | 46.298 |
| ATOM | 2179 | CD2 | LEU | 343 | 24.675 | -13.772 | 45.631 |
| ATOM | 2180 | C | LEU | 343 | 24.833 | -11.728 | 42.966 |
| ATOM | 2181 | O | LEU | 343 | 25.859 | -12.370 | 42.726 |
| ATOM | 2182 | N | CYS | 344 | 23.838 | -11.577 | 42.082 |
| ATOM | 2183 | CA | CYS | 344 | 23.842 | -12.191 | 40.751 |
| ATOM | 2184 | CB | CYS | 344 | 22.588 | -11.787 | 40.006 |
| ATOM | 2185 | SG | CYS | 344 | 21.156 | -12.665 | 40.492 |
| ATOM | 2186 | C | CYS | 344 | 25.048 | -11.775 | 39.911 |
| ATOM | 2187 | O | CYS | 344 | 25.808 | -12.598 | 39.401 |
| ATOM | 2188 | N | ASP | 345 | 25.199 | -10.473 | 39.775 |
| ATOM | 2189 | CA | ASP | 345 | 26.261 | -9.863 | 39.024 |
| ATOM | 2190 | CB | ASP | 345 | 26.220 | -8.386 | 39.301 |
| ATOM | 2191 | CG | ASP | 345 | 26.975 | -7.610 | 38.300 |
| ATOM | 2192 | OD1 | ASP | 345 | 28.168 | -7.318 | 38.566 |
| ATOM | 2193 | OD2 | ASP | 345 | 26.375 | -7.298 | 37.247 |
| ATOM | 2194 | C | ASP | 345 | 27.603 | -10.391 | 39.441 |
| ATOM | 2195 | O | ASP | 345 | 28.558 | -10.396 | 38.663 |
| ATOM | 2196 | N | ALA | 346 | 27.675 | -10.811 | 40.695 |
| ATOM | 2197 | CA | ALA | 346 | 28.904 | -11.332 | 41.275 |
| ATOM | 2198 | CB | ALA | 346 | 29.060 | -10.839 | 42.708 |
| ATOM | 2199 | C | ALA | 346 | 29.027 | -12.844 | 41.216 |
| ATOM | 2200 | O | ALA | 346 | 30.127 | -13.375 | 41.325 |
| ATOM | 2201 | N | TYR | 347 | 27.910 | -13.537 | 41.068 |
| ATOM | 2202 | CA | TYR | 347 | 27.966 | -14.968 | 40.978 |
| ATOM | 2203 | CB | TYR | 347 | 26.615 | -15.555 | 40.687 |
| ATOM | 2204 | CG | TYR | 347 | 26.713 | -17.037 | 40.698 |
| ATOM | 2205 | CD1 | TYR | 347 | 26.688 | -17.777 | 39.527 |
| ATOM | 2206 | CE1 | TYR | 347 | 26.839 | -19.146 | 39.558 |

FIGURE 1UU

| Atom | | | Residue AA | No. | X | Y | Z |
|---|---|---|---|---|---|---|---|
| ATOM | 2207 | CD2 | TYR | 347 | 26.889 | -17.703 | 41.890 |
| ATOM | 2208 | CE2 | TYR | 347 | 27.039 | -19.058 | 41.932 |
| ATOM | 2209 | CZ | TYR | 347 | 27.012 | -19.777 | 40.770 |
| ATOM | 2210 | OH | TYR | 347 | 27.151 | -21.135 | 40.859 |
| ATOM | 2211 | C | TYR | 347 | 28.857 | -15.284 | 39.818 |
| ATOM | 2212 | O | TYR | 347 | 29.067 | -14.435 | 38.965 |
| ATOM | 2213 | N | ASP | 348 | 29.346 | -16.510 | 39.744 |
| ATOM | 2214 | CA | ASP | 348 | 30.235 | -16.926 | 38.652 |
| ATOM | 2215 | CB | ASP | 348 | 31.536 | -16.108 | 38.693 |
| ATOM | 2216 | CG | ASP | 348 | 32.523 | -16.496 | 37.602 |
| ATOM | 2217 | OD1 | ASP | 348 | 32.410 | -16.026 | 36.429 |
| ATOM | 2218 | OD2 | ASP | 348 | 33.449 | -17.256 | 37.933 |
| ATOM | 2219 | C | ASP | 348 | 30.529 | -18.396 | 38.847 |
| ATOM | 2220 | O | ASP | 348 | 30.116 | -18.959 | 39.846 |
| ATOM | 2221 | N | GLU | 349 | 31.134 | -19.040 | 37.863 |
| ATOM | 2222 | CA | GLU | 349 | 31.501 | -20.447 | 37.964 |
| ATOM | 2223 | CB | GLU | 349 | 30.478 | -21.373 | 37.285 |
| ATOM | 2224 | CG | GLU | 349 | 29.083 | -21.371 | 37.982 |
| ATOM | 2225 | CD | GLU | 349 | 27.975 | -22.187 | 37.270 |
| ATOM | 2226 | OE1 | GLU | 349 | 27.469 | -23.164 | 37.878 |
| ATOM | 2227 | OE2 | GLU | 349 | 27.565 | -21.827 | 36.137 |
| ATOM | 2228 | C | GLU | 349 | 32.807 | -20.407 | 37.235 |
| ATOM | 2229 | O | GLU | 349 | 32.882 | -19.877 | 36.136 |
| ATOM | 2230 | N | GLU | 350 | 33.865 | -20.813 | 37.917 |
| ATOM | 2231 | CA | GLU | 350 | 35.202 | -20.768 | 37.358 |
| ATOM | 2232 | CB | GLU | 350 | 36.158 | -20.041 | 38.307 |
| ATOM | 2233 | CG | GLU | 350 | 36.464 | -18.652 | 37.855 |
| ATOM | 2234 | CD | GLU | 350 | 37.859 | -18.210 | 38.202 |
| ATOM | 2235 | OE1 | GLU | 350 | 38.028 | -17.011 | 38.508 |
| ATOM | 2236 | OE2 | GLU | 350 | 38.792 | -19.044 | 38.143 |
| ATOM | 2237 | C | GLU | 350 | 35.847 | -22.069 | 36.934 |
| ATOM | 2238 | O | GLU | 350 | 35.198 | -23.134 | 36.814 |
| ATOM | 2239 | N | GLY | 351 | 37.145 | -21.905 | 36.665 |
| ATOM | 2240 | CA | GLY | 351 | 38.073 | -22.949 | 36.249 |
| ATOM | 2241 | C | GLY | 351 | 37.632 | -24.094 | 35.356 |
| ATOM | 2242 | O | GLY | 351 | 38.037 | -24.177 | 34.182 |
| ATOM | 2243 | N | VAL | 352 | 36.843 | -24.980 | 35.971 |
| ATOM | 2244 | CA | VAL | 352 | 36.286 | -26.212 | 35.397 |
| ATOM | 2245 | CB | VAL | 352 | 35.570 | -25.956 | 34.034 |
| ATOM | 2246 | CG1 | VAL | 352 | 35.077 | -27.297 | 33.405 |
| ATOM | 2247 | CG2 | VAL | 352 | 34.389 | -24.952 | 34.255 |
| ATOM | 2248 | C | VAL | 352 | 37.269 | -27.423 | 35.370 |
| ATOM | 2249 | O | VAL | 352 | 38.458 | -27.285 | 34.969 |
| ATOM | 2250 | OT | VAL | 352 | 36.854 | -28.503 | 35.871 |
| ATOM | 2251 | CB | ALA | 356 | 39.926 | -30.567 | 35.981 |
| ATOM | 2252 | C | ALA | 356 | 39.381 | -29.620 | 38.330 |
| ATOM | 2253 | O | ALA | 356 | 38.988 | -29.716 | 39.523 |
| ATOM | 2254 | N | ALA | 356 | 37.664 | -30.912 | 37.046 |

FIGURE 1VV

| Atom | | | Residue AA | No. | X | Y | Z |
|---|---|---|---|---|---|---|---|
| ATOM | 2255 | CA | ALA | 356 | 39.134 | -30.788 | 37.329 |
| ATOM | 2256 | N | ALA | 357 | 39.924 | -28.506 | 37.797 |
| ATOM | 2257 | CA | ALA | 357 | 40.255 | -27.273 | 38.542 |
| ATOM | 2258 | CB | ALA | 357 | 41.542 | -26.613 | 37.895 |
| ATOM | 2259 | C | ALA | 357 | 39.066 | -26.244 | 38.635 |
| ATOM | 2260 | O | ALA | 357 | 39.256 | -25.031 | 38.459 |
| ATOM | 2261 | N | ALA | 358 | 37.864 | -26.735 | 38.963 |
| ATOM | 2262 | CA | ALA | 358 | 36.673 | -25.885 | 39.061 |
| ATOM | 2263 | CB | ALA | 358 | 35.416 | -26.755 | 39.155 |
| ATOM | 2264 | C | ALA | 358 | 36.736 | -24.865 | 40.217 |
| ATOM | 2265 | O | ALA | 358 | 37.792 | -24.708 | 40.861 |
| ATOM | 2266 | N | ARG | 359 | 35.613 | -24.176 | 40.466 |
| ATOM | 2267 | CA | ARG | 359 | 35.519 | -23.169 | 41.527 |
| ATOM | 2268 | CB | ARG | 359 | 36.722 | -22.204 | 41.437 |
| ATOM | 2269 | CG | ARG | 359 | 36.587 | -20.902 | 42.218 |
| ATOM | 2270 | CD | ARG | 359 | 37.928 | -20.201 | 42.416 |
| ATOM | 2271 | NE | ARG | 359 | 37.823 | -18.763 | 42.184 |
| ATOM | 2272 | CZ | ARG | 359 | 38.575 | -17.824 | 42.752 |
| ATOM | 2273 | NH1 | ARG | 359 | 39.528 | -18.153 | 43.600 |
| ATOM | 2274 | NH2 | ARG | 359 | 38.346 | -16.542 | 42.489 |
| ATOM | 2275 | C | ARG | 359 | 34.248 | -22.362 | 41.362 |
| ATOM | 2276 | O | ARG | 359 | 33.836 | -22.172 | 40.246 |
| ATOM | 2277 | N | THR | 360 | 33.579 | -21.989 | 42.454 |
| ATOM | 2278 | CA | THR | 360 | 32.401 | -21.102 | 42.408 |
| ATOM | 2279 | CB | THR | 360 | 31.155 | -21.592 | 43.179 |
| ATOM | 2280 | OG1 | THR | 360 | 30.459 | -22.601 | 42.430 |
| ATOM | 2281 | CG2 | THR | 360 | 30.212 | -20.421 | 43.430 |
| ATOM | 2282 | C | THR | 360 | 32.919 | -19.919 | 43.188 |
| ATOM | 2283 | O | THR | 360 | 33.452 | -20.088 | 44.288 |
| ATOM | 2284 | N | VAL | 361 | 32.806 | -18.733 | 42.621 |
| ATOM | 2285 | CA | VAL | 361 | 33.288 | -17.544 | 43.292 |
| ATOM | 2286 | CB | VAL | 361 | 34.433 | -16.878 | 42.515 |
| ATOM | 2287 | CG1 | VAL | 361 | 35.342 | -16.123 | 43.445 |
| ATOM | 2288 | CG2 | VAL | 361 | 35.183 | -17.876 | 41.743 |
| ATOM | 2289 | C | VAL | 361 | 32.142 | -16.572 | 43.304 |
| ATOM | 2290 | O | VAL | 361 | 31.098 | -16.853 | 42.742 |
| ATOM | 2291 | N | LEU | 362 | 32.292 | -15.506 | 44.068 |
| ATOM | 2292 | CA | LEU | 362 | 31.333 | -14.421 | 44.109 |
| ATOM | 2293 | CB | LEU | 362 | 30.454 | -14.409 | 45.360 |
| ATOM | 2294 | CG | LEU | 362 | 29.303 | -15.419 | 45.481 |
| ATOM | 2295 | CD1 | LEU | 362 | 28.180 | -14.852 | 46.308 |
| ATOM | 2296 | CD2 | LEU | 362 | 28.760 | -15.760 | 44.134 |
| ATOM | 2297 | C | LEU | 362 | 32.371 | -13.355 | 44.171 |
| ATOM | 2298 | O | LEU | 362 | 33.378 | -13.512 | 44.843 |
| ATOM | 2299 | N | HIS | 363 | 32.248 | -12.363 | 43.321 |
| ATOM | 2300 | CA | HIS | 363 | 33.251 | -11.321 | 43.318 |
| ATOM | 2301 | CB | HIS | 363 | 33.851 | -11.130 | 41.905 |
| ATOM | 2302 | CG | HIS | 363 | 34.677 | -12.289 | 41.388 |

FIGURE 1WW

| | Atom | | Residue AA | No. | X | Y | Z |
|---|---|---|---|---|---|---|---|
| ATOM | 2303 | CD2 | HIS | 363 | 36.018 | -12.493 | 41.375 |
| ATOM | 2304 | ND1 | HIS | 363 | 34.129 | -13.370 | 40.722 |
| ATOM | 2305 | CE1 | HIS | 363 | 35.092 | -14.185 | 40.327 |
| ATOM | 2306 | NE2 | HIS | 363 | 36.248 | -13.675 | 40.712 |
| ATOM | 2307 | C | HIS | 363 | 32.619 | -10.025 | 43.820 |
| ATOM | 2308 | O | HIS | 363 | 32.205 | -9.186 | 43.023 |
| ATOM | 2309 | N | PHE | 364 | 32.496 | -9.898 | 45.146 |
| ATOM | 2310 | CA | PHE | 364 | 31.911 | -8.712 | 45.800 |
| ATOM | 2311 | CB | PHE | 364 | 31.427 | -9.057 | 47.227 |
| ATOM | 2312 | CG | PHE | 364 | 30.232 | -9.974 | 47.296 |
| ATOM | 2313 | CD1 | PHE | 364 | 30.348 | -11.230 | 47.824 |
| ATOM | 2314 | CD2 | PHE | 364 | 28.979 | -9.546 | 46.928 |
| ATOM | 2315 | CE1 | PHE | 364 | 29.241 | -12.031 | 47.986 |
| ATOM | 2316 | CE2 | PHE | 364 | 27.869 | -10.357 | 47.097 |
| ATOM | 2317 | CZ | PHE | 364 | 28.004 | -11.590 | 47.624 |
| ATOM | 2318 | C | PHE | 364 | 32.985 | -7.629 | 45.946 |
| ATOM | 2319 | O | PHE | 364 | 34.147 | -7.933 | 46.209 |
| ATOM | 2320 | N | HIS | 365 | 32.630 | -6.374 | 45.731 |
| ATOM | 2321 | CA | HIS | 365 | 33.616 | -5.325 | 45.949 |
| ATOM | 2322 | CB | HIS | 365 | 32.993 | -3.980 | 45.598 |
| ATOM | 2323 | CG | HIS | 365 | 33.803 | -2.811 | 46.035 |
| ATOM | 2324 | CD2 | HIS | 365 | 35.066 | -2.437 | 45.723 |
| ATOM | 2325 | ND1 | HIS | 365 | 33.336 | -1.877 | 46.927 |
| ATOM | 2326 | CE1 | HIS | 365 | 34.279 | -0.981 | 47.152 |
| ATOM | 2327 | NE2 | HIS | 365 | 35.337 | -1.297 | 46.434 |
| ATOM | 2328 | C | HIS | 365 | 33.871 | -5.431 | 47.468 |
| ATOM | 2329 | O | HIS | 365 | 32.929 | -5.642 | 48.222 |
| ATOM | 2330 | N | PRO | 366 | 35.121 | -5.295 | 47.946 |
| ATOM | 2331 | CD | PRO | 366 | 36.362 | -4.966 | 47.237 |
| ATOM | 2332 | CA | PRO | 366 | 35.382 | -5.399 | 49.391 |
| ATOM | 2333 | CB | PRO | 366 | 36.734 | -4.748 | 49.523 |
| ATOM | 2334 | CG | PRO | 366 | 37.405 | -5.200 | 48.303 |
| ATOM | 2335 | C | PRO | 366 | 34.359 | -4.708 | 50.283 |
| ATOM | 2336 | O | PRO | 366 | 33.693 | -5.351 | 51.077 |
| ATOM | 2337 | N | ALA | 367 | 34.180 | -3.409 | 50.092 |
| ATOM | 2338 | CA | ALA | 367 | 33.226 | -2.629 | 50.866 |
| ATOM | 2339 | CB | ALA | 367 | 33.407 | -1.165 | 50.557 |
| ATOM | 2340 | C | ALA | 367 | 31.775 | -3.028 | 50.648 |
| ATOM | 2341 | O | ALA | 367 | 30.883 | -2.215 | 50.818 |
| ATOM | 2342 | N | LEU | 368 | 31.544 | -4.270 | 50.254 |
| ATOM | 2343 | CA | LEU | 368 | 30.209 | -4.788 | 50.012 |
| ATOM | 2344 | CB | LEU | 368 | 29.817 | -4.588 | 48.552 |
| ATOM | 2345 | CG | LEU | 368 | 28.578 | -3.808 | 48.134 |
| ATOM | 2346 | CD1 | LEU | 368 | 27.370 | -4.520 | 48.543 |
| ATOM | 2347 | CD2 | LEU | 368 | 28.591 | -2.430 | 48.688 |
| ATOM | 2348 | C | LEU | 368 | 30.220 | -6.282 | 50.335 |
| ATOM | 2349 | O | LEU | 368 | 29.171 | -6.911 | 50.464 |
| ATOM | 2350 | N | ALA | 369 | 31.411 | -6.853 | 50.454 |

FIGURE 1XX

| Atom | | | Residue AA | No. | X | Y | Z |
|---|---|---|---|---|---|---|---|
| ATOM | 2351 | CA | ALA | 369 | 31.560 | -8.269 | 50.766 |
| ATOM | 2352 | CB | ALA | 369 | 32.989 | -8.662 | 50.606 |
| ATOM | 2353 | C | ALA | 369 | 31.143 | -8.495 | 52.198 |
| ATOM | 2354 | O | ALA | 369 | 31.469 | -7.695 | 53.059 |
| ATOM | 2355 | N | PRO | 370 | 30.447 | -9.600 | 52.488 |
| ATOM | 2356 | CD | PRO | 370 | 30.119 | -10.765 | 51.660 |
| ATOM | 2357 | CA | PRO | 370 | 30.038 | -9.836 | 53.872 |
| ATOM | 2358 | CB | PRO | 370 | 29.336 | -11.201 | 53.781 |
| ATOM | 2359 | CG | PRO | 370 | 30.060 | -11.876 | 52.689 |
| ATOM | 2360 | C | PRO | 370 | 31.231 | -9.799 | 54.880 |
| ATOM | 2361 | O | PRO | 370 | 31.186 | -9.064 | 55.891 |
| ATOM | 2362 | N | TYR | 371 | 32.277 | -10.585 | 54.613 |
| ATOM | 2363 | CA | TYR | 371 | 33.463 | -10.598 | 55.471 |
| ATOM | 2364 | CB | TYR | 371 | 33.934 | -12.015 | 55.768 |
| ATOM | 2365 | CG | TYR | 371 | 33.016 | -12.805 | 56.649 |
| ATOM | 2366 | CD1 | TYR | 371 | 33.096 | -12.717 | 58.026 |
| ATOM | 2367 | CE1 | TYR | 371 | 32.251 | -13.464 | 58.847 |
| ATOM | 2368 | CD2 | TYR | 371 | 32.080 | -13.653 | 56.106 |
| ATOM | 2369 | CE2 | TYR | 371 | 31.241 | -14.402 | 56.909 |
| ATOM | 2370 | CZ | TYR | 371 | 31.323 | -14.309 | 58.276 |
| ATOM | 2371 | OH | TYR | 371 | 30.478 | -15.083 | 59.049 |
| ATOM | 2372 | C | TYR | 371 | 34.556 | -9.865 | 54.718 |
| ATOM | 2373 | O | TYR | 371 | 34.562 | -9.898 | 53.501 |
| ATOM | 2374 | N | LYS | 372 | 35.490 | -9.236 | 55.418 |
| ATOM | 2375 | CA | LYS | 372 | 36.532 | -8.497 | 54.747 |
| ATOM | 2376 | CB | LYS | 372 | 36.777 | -7.195 | 55.462 |
| ATOM | 2377 | CG | LYS | 372 | 35.570 | -6.331 | 55.487 |
| ATOM | 2378 | CD | LYS | 372 | 35.193 | -5.952 | 54.103 |
| ATOM | 2379 | CE | LYS | 372 | 33.713 | -6.084 | 53.903 |
| ATOM | 2380 | NZ | LYS | 372 | 32.904 | -5.224 | 54.803 |
| ATOM | 2381 | C | LYS | 372 | 37.802 | -9.258 | 54.627 |
| ATOM | 2382 | O | LYS | 372 | 38.680 | -8.892 | 53.877 |
| ATOM | 2383 | N | ALA | 373 | 37.912 | -10.315 | 55.394 |
| ATOM | 2384 | CA | ALA | 373 | 39.103 | -11.138 | 55.361 |
| ATOM | 2385 | CB | ALA | 373 | 40.283 | -10.443 | 56.058 |
| ATOM | 2386 | C | ALA | 373 | 38.690 | -12.359 | 56.125 |
| ATOM | 2387 | O | ALA | 373 | 37.514 | -12.493 | 56.462 |
| ATOM | 2388 | N | ALA | 374 | 39.635 | -13.257 | 56.366 |
| ATOM | 2389 | CA | ALA | 374 | 39.364 | -14.461 | 57.125 |
| ATOM | 2390 | CB | ALA | 374 | 38.708 | -15.498 | 56.259 |
| ATOM | 2391 | C | ALA | 374 | 40.693 | -14.960 | 57.650 |
| ATOM | 2392 | O | ALA | 374 | 41.696 | -14.905 | 56.931 |
| ATOM | 2393 | N | ILE | 375 | 40.734 | -15.312 | 58.936 |
| ATOM | 2394 | CA | ILE | 375 | 41.955 | -15.826 | 59.524 |
| ATOM | 2395 | CB | ILE | 375 | 42.247 | -15.237 | 60.884 |
| ATOM | 2396 | CG2 | ILE | 375 | 43.723 | -15.121 | 61.045 |
| ATOM | 2397 | CG1 | ILE | 375 | 41.658 | -13.848 | 61.000 |
| ATOM | 2398 | CD1 | ILE | 375 | 42.374 | -12.866 | 60.198 |

FIGURE 1YY

| Atom | | | Residue AA | No. | X | Y | Z |
|---|---|---|---|---|---|---|---|
| ATOM | 2399 | C | ILE | 375 | 41.771 | -17.324 | 59.644 |
| ATOM | 2400 | O | ILE | 375 | 40.902 | -17.797 | 60.348 |
| ATOM | 2401 | N | LEU | 376 | 42.474 | -18.053 | 58.799 |
| ATOM | 2402 | CA | LEU | 376 | 42.431 | -19.507 | 58.792 |
| ATOM | 2403 | CB | LEU | 376 | 42.522 | -20.048 | 57.355 |
| ATOM | 2404 | CG | LEU | 376 | 41.466 | -19.777 | 56.289 |
| ATOM | 2405 | CD1 | LEU | 376 | 40.203 | -20.509 | 56.594 |
| ATOM | 2406 | CD2 | LEU | 376 | 41.212 | -18.321 | 56.206 |
| ATOM | 2407 | C | LEU | 376 | 43.730 | -19.827 | 59.493 |
| ATOM | 2408 | O | LEU | 376 | 44.752 | -19.206 | 59.197 |
| ATOM | 2409 | N | PRO | 377 | 43.712 | -20.712 | 60.489 |
| ATOM | 2410 | CD | PRO | 377 | 42.659 | -21.453 | 61.189 |
| ATOM | 2411 | CA | PRO | 377 | 45.007 | -20.962 | 61.100 |
| ATOM | 2412 | CB | PRO | 377 | 44.653 | -21.858 | 62.272 |
| ATOM | 2413 | CG | PRO | 377 | 43.442 | -22.571 | 61.788 |
| ATOM | 2414 | C | PRO | 377 | 45.763 | -21.700 | 60.047 |
| ATOM | 2415 | O | PRO | 377 | 46.073 | -21.150 | 59.004 |
| ATOM | 2416 | N | LEU | 378 | 46.018 | -22.965 | 60.309 |
| ATOM | 2417 | CA | LEU | 378 | 46.711 | -23.850 | 59.390 |
| ATOM | 2418 | CB | LEU | 378 | 48.238 | -23.695 | 59.477 |
| ATOM | 2419 | CG | LEU | 378 | 49.124 | -24.377 | 58.414 |
| ATOM | 2420 | CD1 | LEU | 378 | 48.721 | -25.823 | 58.128 |
| ATOM | 2421 | CD2 | LEU | 378 | 49.088 | -23.596 | 57.147 |
| ATOM | 2422 | C | LEU | 378 | 46.315 | -25.172 | 59.996 |
| ATOM | 2423 | O | LEU | 378 | 45.710 | -26.029 | 59.332 |
| ATOM | 2424 | N | SER | 379 | 46.616 | -25.276 | 61.299 |
| ATOM | 2425 | CA | SER | 379 | 46.356 | -26.460 | 62.118 |
| ATOM | 2426 | CB | SER | 379 | 47.671 | -27.174 | 62.427 |
| ATOM | 2427 | OG | SER | 379 | 47.432 | -28.504 | 62.821 |
| ATOM | 2428 | C | SER | 379 | 45.758 | -25.987 | 63.415 |
| ATOM | 2429 | O | SER | 379 | 46.160 | -24.934 | 63.914 |
| ATOM | 2430 | N | ALA | 380 | 44.848 | -26.785 | 63.975 |
| ATOM | 2431 | CA | ALA | 380 | 44.192 | -26.455 | 65.232 |
| ATOM | 2432 | CB | ALA | 380 | 43.411 | -27.663 | 65.762 |
| ATOM | 2433 | C | ALA | 380 | 45.232 | -25.964 | 66.255 |
| ATOM | 2434 | O | ALA | 380 | 44.918 | -25.167 | 67.142 |
| ATOM | 2435 | N | ALA | 381 | 46.481 | -26.391 | 66.077 |
| ATOM | 2436 | CA | ALA | 381 | 47.582 | -25.980 | 66.941 |
| ATOM | 2437 | CB | ALA | 381 | 48.875 | -26.610 | 66.461 |
| ATOM | 2438 | C | ALA | 381 | 47.709 | -24.451 | 66.956 |
| ATOM | 2439 | O | ALA | 381 | 47.575 | -23.817 | 67.998 |
| ATOM | 2440 | N | LEU | 382 | 47.897 | -23.845 | 65.795 |
| ATOM | 2441 | CA | LEU | 382 | 48.018 | -22.399 | 65.765 |
| ATOM | 2442 | CB | LEU | 382 | 48.704 | -21.913 | 64.470 |
| ATOM | 2443 | CG | LEU | 382 | 50.038 | -22.469 | 63.945 |
| ATOM | 2444 | CD1 | LEU | 382 | 50.986 | -22.774 | 65.117 |
| ATOM | 2445 | CD2 | LEU | 382 | 49.767 | -23.719 | 63.097 |
| ATOM | 2446 | C | LEU | 382 | 46.668 | -21.694 | 65.932 |

FIGURE 1ZZ

| Atom | | | Residue AA | No. | X | Y | Z |
|---|---|---|---|---|---|---|---|
| ATOM | 2447 | O | LEU | 382 | 46.529 | -20.548 | 65.500 |
| ATOM | 2448 | N | SER | 383 | 45.674 | -22.365 | 66.522 |
| ATOM | 2449 | CA | SER | 383 | 44.359 | -21.748 | 66.725 |
| ATOM | 2450 | CB | SER | 383 | 43.393 | -22.689 | 67.442 |
| ATOM | 2451 | OG | SER | 383 | 42.847 | -23.643 | 66.551 |
| ATOM | 2452 | C | SER | 383 | 44.602 | -20.516 | 67.566 |
| ATOM | 2453 | O | SER | 383 | 44.196 | -19.400 | 67.225 |
| ATOM | 2454 | N | GLY | 384 | 45.257 | -20.718 | 68.692 |
| ATOM | 2455 | CA | GLY | 384 | 45.605 | -19.571 | 69.493 |
| ATOM | 2456 | C | GLY | 384 | 46.709 | -18.939 | 68.651 |
| ATOM | 2457 | O | GLY | 384 | 47.477 | -19.670 | 67.996 |
| ATOM | 2458 | N | ALA | 385 | 46.773 | -17.603 | 68.664 |
| ATOM | 2459 | CA | ALA | 385 | 47.735 | -16.765 | 67.910 |
| ATOM | 2460 | CB | ALA | 385 | 49.022 | -17.517 | 67.502 |
| ATOM | 2461 | C | ALA | 385 | 46.983 | -16.279 | 66.692 |
| ATOM | 2462 | O | ALA | 385 | 47.015 | -15.097 | 66.368 |
| ATOM | 2463 | N | ALA | 386 | 46.261 | -17.188 | 66.054 |
| ATOM | 2464 | CA | ALA | 386 | 45.460 | -16.820 | 64.913 |
| ATOM | 2465 | CB | ALA | 386 | 44.984 | -18.064 | 64.193 |
| ATOM | 2466 | C | ALA | 386 | 44.278 | -16.004 | 65.473 |
| ATOM | 2467 | O | ALA | 386 | 43.918 | -14.947 | 64.937 |
| ATOM | 2468 | N | ILE | 387 | 43.749 | -16.429 | 66.614 |
| ATOM | 2469 | CA | ILE | 387 | 42.634 | -15.720 | 67.200 |
| ATOM | 2470 | CB | ILE | 387 | 42.149 | -16.394 | 68.437 |
| ATOM | 2471 | CG2 | ILE | 387 | 40.886 | -15.709 | 68.922 |
| ATOM | 2472 | CG1 | ILE | 387 | 41.850 | -17.859 | 68.123 |
| ATOM | 2473 | CD1 | ILE | 387 | 41.715 | -18.777 | 69.334 |
| ATOM | 2474 | C | ILE | 387 | 43.068 | -14.339 | 67.553 |
| ATOM | 2475 | O | ILE | 387 | 42.259 | -13.432 | 67.630 |
| ATOM | 2476 | N | ALA | 388 | 44.372 | -14.182 | 67.716 |
| ATOM | 2477 | CA | ALA | 388 | 44.958 | -12.894 | 68.063 |
| ATOM | 2478 | CB | ALA | 388 | 46.423 | -13.076 | 68.488 |
| ATOM | 2479 | C | ALA | 388 | 44.827 | -11.844 | 66.941 |
| ATOM | 2480 | O | ALA | 388 | 44.355 | -10.708 | 67.183 |
| ATOM | 2481 | N | ILE | 389 | 45.259 | -12.193 | 65.729 |
| ATOM | 2482 | CA | ILE | 389 | 45.122 | -11.255 | 64.626 |
| ATOM | 2483 | CB | ILE | 389 | 45.777 | -11.729 | 63.339 |
| ATOM | 2484 | CG2 | ILE | 389 | 46.949 | -10.841 | 63.015 |
| ATOM | 2485 | CG1 | ILE | 389 | 46.076 | -13.222 | 63.406 |
| ATOM | 2486 | CD1 | ILE | 389 | 47.212 | -13.660 | 62.521 |
| ATOM | 2487 | C | ILE | 389 | 43.637 | -11.078 | 64.378 |
| ATOM | 2488 | O | ILE | 389 | 43.177 | -9.991 | 64.009 |
| ATOM | 2489 | N | PHE | 390 | 42.880 | -12.142 | 64.613 |
| ATOM | 2490 | CA | PHE | 390 | 41.458 | -12.065 | 64.423 |
| ATOM | 2491 | CB | PHE | 390 | 40.756 | -13.281 | 64.990 |
| ATOM | 2492 | CG | PHE | 390 | 39.298 | -13.081 | 65.118 |
| ATOM | 2493 | CD1 | PHE | 390 | 38.781 | -12.387 | 66.191 |
| ATOM | 2494 | CD2 | PHE | 390 | 38.441 | -13.469 | 64.117 |

FIGURE 1AAA

| Atom | | | Residue AA | No. | X | Y | Z |
|---|---|---|---|---|---|---|---|
| ATOM | 2495 | CE1 | PHE | 390 | 37.434 | -12.071 | 66.264 |
| ATOM | 2496 | CE2 | PHE | 390 | 37.085 | -13.151 | 64.190 |
| ATOM | 2497 | CZ | PHE | 390 | 36.590 | -12.448 | 65.267 |
| ATOM | 2498 | C | PHE | 390 | 40.936 | -10.825 | 65.113 |
| ATOM | 2499 | O | PHE | 390 | 40.362 | -9.962 | 64.478 |
| ATOM | 2500 | N | GLU | 391 | 41.176 | -10.735 | 66.412 |
| ATOM | 2501 | CA | GLU | 391 | 40.713 | -9.606 | 67.220 |
| ATOM | 2502 | CB | GLU | 391 | 41.049 | -9.820 | 68.684 |
| ATOM | 2503 | CG | GLU | 391 | 40.226 | -10.892 | 69.351 |
| ATOM | 2504 | CD | GLU | 391 | 40.769 | -11.295 | 70.721 |
| ATOM | 2505 | OE1 | GLU | 391 | 41.947 | -10.967 | 71.044 |
| ATOM | 2506 | OE2 | GLU | 391 | 40.001 | -11.960 | 71.464 |
| ATOM | 2507 | C | GLU | 391 | 41.230 | -8.237 | 66.829 |
| ATOM | 2508 | O | GLU | 391 | 40.448 | -7.279 | 66.719 |
| ATOM | 2509 | N | GLN | 392 | 42.550 | -8.124 | 66.687 |
| ATOM | 2510 | CA | GLN | 392 | 43.178 | -6.852 | 66.315 |
| ATOM | 2511 | CB | GLN | 392 | 44.630 | -7.108 | 65.875 |
| ATOM | 2512 | CG | GLN | 392 | 45.429 | -5.866 | 65.377 |
| ATOM | 2513 | CD | GLN | 392 | 46.524 | -6.219 | 64.315 |
| ATOM | 2514 | OE1 | GLN | 392 | 46.652 | -5.532 | 63.269 |
| ATOM | 2515 | NE2 | GLN | 392 | 47.303 | -7.299 | 64.579 |
| ATOM | 2516 | C | GLN | 392 | 42.396 | -6.156 | 65.196 |
| ATOM | 2517 | O | GLN | 392 | 42.256 | -4.938 | 65.191 |
| ATOM | 2518 | N | LEU | 393 | 41.848 | -6.964 | 64.295 |
| ATOM | 2519 | CA | LEU | 393 | 41.101 | -6.474 | 63.163 |
| ATOM | 2520 | CB | LEU | 393 | 41.378 | -7.344 | 61.937 |
| ATOM | 2521 | CG | LEU | 393 | 42.877 | -7.450 | 61.629 |
| ATOM | 2522 | CD1 | LEU | 393 | 43.114 | -8.526 | 60.642 |
| ATOM | 2523 | CD2 | LEU | 393 | 43.469 | -6.139 | 61.131 |
| ATOM | 2524 | C | LEU | 393 | 39.625 | -6.355 | 63.409 |
| ATOM | 2525 | O | LEU | 393 | 39.025 | -5.422 | 62.920 |
| ATOM | 2526 | N | SER | 394 | 39.043 | -7.261 | 64.189 |
| ATOM | 2527 | CA | SER | 394 | 37.608 | -7.239 | 64.475 |
| ATOM | 2528 | CB | SER | 394 | 37.277 | -8.224 | 65.574 |
| ATOM | 2529 | OG | SER | 394 | 37.910 | -9.458 | 65.333 |
| ATOM | 2530 | C | SER | 394 | 37.159 | -5.855 | 64.898 |
| ATOM | 2531 | O | SER | 394 | 36.024 | -5.440 | 64.668 |
| ATOM | 2532 | N | SER | 395 | 38.098 | -5.122 | 65.469 |
| ATOM | 2533 | CA | SER | 395 | 37.888 | -3.769 | 65.951 |
| ATOM | 2534 | CB | SER | 395 | 39.243 | -3.199 | 66.349 |
| ATOM | 2535 | OG | SER | 395 | 40.244 | -3.708 | 65.484 |
| ATOM | 2536 | C | SER | 395 | 37.280 | -2.886 | 64.906 |
| ATOM | 2537 | O | SER | 395 | 36.723 | -1.841 | 65.208 |
| ATOM | 2538 | N | LYS | 396 | 37.432 | -3.301 | 63.662 |
| ATOM | 2539 | CA | LYS | 396 | 36.940 | -2.531 | 62.537 |
| ATOM | 2540 | CB | LYS | 396 | 38.097 | -1.690 | 61.974 |
| ATOM | 2541 | CG | LYS | 396 | 38.359 | -0.366 | 62.721 |
| ATOM | 2542 | CD | LYS | 396 | 39.205 | -0.492 | 64.001 |

FIGURE 1BBB

| Atom | | | Residue AA | No. | X | Y | Z |
|---|---|---|---|---|---|---|---|
| ATOM | 2543 | CE | LYS | 396 | 40.693 | -0.523 | 63.711 |
| ATOM | 2544 | NZ | LYS | 396 | 41.053 | -1.693 | 62.889 |
| ATOM | 2545 | C | LYS | 396 | 36.243 | -3.280 | 61.385 |
| ATOM | 2546 | O | LYS | 396 | 35.223 | -2.815 | 60.865 |
| ATOM | 2547 | N | PHE | 397 | 36.776 | -4.434 | 60.993 |
| ATOM | 2548 | CA | PHE | 397 | 36.231 | -5.197 | 59.859 |
| ATOM | 2549 | CB | PHE | 397 | 37.376 | -5.564 | 58.892 |
| ATOM | 2550 | CG | PHE | 397 | 38.309 | -4.424 | 58.575 |
| ATOM | 2551 | CD1 | PHE | 397 | 37.810 | -3.160 | 58.270 |
| ATOM | 2552 | CD2 | PHE | 397 | 39.676 | -4.615 | 58.623 |
| ATOM | 2553 | CE1 | PHE | 397 | 38.658 | -2.113 | 58.028 |
| ATOM | 2554 | CE2 | PHE | 397 | 40.535 | -3.572 | 58.383 |
| ATOM | 2555 | CZ | PHE | 397 | 40.032 | -2.313 | 58.086 |
| ATOM | 2556 | C | PHE | 397 | 35.456 | -6.472 | 60.173 |
| ATOM | 2557 | O | PHE | 397 | 35.856 | -7.246 | 61.010 |
| ATOM | 2558 | N | SER | 398 | 34.412 | -6.749 | 59.414 |
| ATOM | 2559 | CA | SER | 398 | 33.626 | -7.953 | 59.640 |
| ATOM | 2560 | CB | SER | 398 | 32.318 | -7.889 | 58.839 |
| ATOM | 2561 | OG | SER | 398 | 31.964 | -6.561 | 58.468 |
| ATOM | 2562 | C | SER | 398 | 34.396 | -9.174 | 59.178 |
| ATOM | 2563 | O | SER | 398 | 34.072 | -9.726 | 58.150 |
| ATOM | 2564 | N | ILE | 399 | 35.392 | -9.628 | 59.921 |
| ATOM | 2565 | CA | ILE | 399 | 36.160 | -10.787 | 59.482 |
| ATOM | 2566 | CB | ILE | 399 | 37.658 | -10.544 | 59.661 |
| ATOM | 2567 | CG2 | ILE | 399 | 37.992 | -9.121 | 59.291 |
| ATOM | 2568 | CG1 | ILE | 399 | 38.089 | -10.836 | 61.089 |
| ATOM | 2569 | CD1 | ILE | 399 | 39.554 | -10.631 | 61.313 |
| ATOM | 2570 | C | ILE | 399 | 35.766 | -12.148 | 60.069 |
| ATOM | 2571 | O | ILE | 399 | 35.197 | -12.230 | 61.143 |
| ATOM | 2572 | N | ASP | 400 | 36.034 | -13.212 | 59.325 |
| ATOM | 2573 | CA | ASP | 400 | 35.723 | -14.577 | 59.747 |
| ATOM | 2574 | CB | ASP | 400 | 35.226 | -15.378 | 58.521 |
| ATOM | 2575 | CG | ASP | 400 | 34.501 | -16.702 | 58.873 |
| ATOM | 2576 | OD1 | ASP | 400 | 34.906 | -17.450 | 59.779 |
| ATOM | 2577 | OD2 | ASP | 400 | 33.527 | -17.046 | 58.175 |
| ATOM | 2578 | C | ASP | 400 | 37.016 | -15.195 | 60.289 |
| ATOM | 2579 | O | ASP | 400 | 38.094 | -14.617 | 60.193 |
| ATOM | 2580 | N | PHE | 401 | 36.871 | -16.337 | 60.938 |
| ATOM | 2581 | CA | PHE | 401 | 37.975 | -17.113 | 61.476 |
| ATOM | 2582 | CB | PHE | 401 | 38.140 | -16.855 | 62.990 |
| ATOM | 2583 | CG | PHE | 401 | 39.299 | -17.595 | 63.624 |
| ATOM | 2584 | CD1 | PHE | 401 | 40.558 | -17.019 | 63.678 |
| ATOM | 2585 | CD2 | PHE | 401 | 39.138 | -18.887 | 64.123 |
| ATOM | 2586 | CE1 | PHE | 401 | 41.642 | -17.724 | 64.211 |
| ATOM | 2587 | CE2 | PHE | 401 | 40.212 | -19.593 | 64.657 |
| ATOM | 2588 | CZ | PHE | 401 | 41.465 | -19.014 | 64.699 |
| ATOM | 2589 | C | PHE | 401 | 37.555 | -18.574 | 61.203 |
| ATOM | 2590 | O | PHE | 401 | 36.422 | -18.969 | 61.498 |

FIGURE 1CCC

| | Atom | | Residue AA | No. | X | Y | Z |
|---|---|---|---|---|---|---|---|
| ATOM | 2591 | N | ASP | 402 | 38.422 | -19.345 | 60.556 |
| ATOM | 2592 | CA | ASP | 402 | 38.099 | -20.730 | 60.283 |
| ATOM | 2593 | CB | ASP | 402 | 37.442 | -20.893 | 58.926 |
| ATOM | 2594 | CG | ASP | 402 | 36.662 | -22.167 | 58.824 |
| ATOM | 2595 | OD1 | ASP | 402 | 35.913 | -22.318 | 57.845 |
| ATOM | 2596 | OD2 | ASP | 402 | 36.776 | -23.012 | 59.740 |
| ATOM | 2597 | C | ASP | 402 | 39.302 | -21.634 | 60.384 |
| ATOM | 2598 | O | ASP | 402 | 40.323 | -21.430 | 59.746 |
| ATOM | 2599 | N | GLU | 403 | 39.152 | -22.640 | 61.222 |
| ATOM | 2600 | CA | GLU | 403 | 40.197 | -23.599 | 61.457 |
| ATOM | 2601 | CB | GLU | 403 | 40.547 | -23.628 | 62.943 |
| ATOM | 2602 | CG | GLU | 403 | 39.325 | -23.670 | 63.866 |
| ATOM | 2603 | CD | GLU | 403 | 39.684 | -23.753 | 65.355 |
| ATOM | 2604 | OE1 | GLU | 403 | 39.179 | -24.686 | 66.017 |
| ATOM | 2605 | OE2 | GLU | 403 | 40.449 | -22.896 | 65.865 |
| ATOM | 2606 | C | GLU | 403 | 39.713 | -24.960 | 61.020 |
| ATOM | 2607 | O | GLU | 403 | 40.466 | -25.746 | 60.434 |
| ATOM | 2608 | N | SER | 404 | 38.446 | -25.240 | 61.301 |
| ATOM | 2609 | CA | SER | 404 | 37.869 | -26.538 | 60.943 |
| ATOM | 2610 | CB | SER | 404 | 36.371 | -26.583 | 61.320 |
| ATOM | 2611 | OG | SER | 404 | 35.874 | -27.921 | 61.503 |
| ATOM | 2612 | C | SER | 404 | 38.068 | -26.846 | 59.458 |
| ATOM | 2613 | O | SER | 404 | 37.861 | -25.973 | 58.604 |
| ATOM | 2614 | N | GLN | 405 | 38.470 | -28.089 | 59.183 |
| ATOM | 2615 | CA | GLN | 405 | 38.726 | -28.602 | 57.834 |
| ATOM | 2616 | CB | GLN | 405 | 37.820 | -27.926 | 56.784 |
| ATOM | 2617 | CG | GLN | 405 | 36.316 | -27.963 | 57.090 |
| ATOM | 2618 | CD | GLN | 405 | 35.883 | -29.281 | 57.733 |
| ATOM | 2619 | OE1 | GLN | 405 | 35.090 | -29.285 | 58.678 |
| ATOM | 2620 | NE2 | GLN | 405 | 36.415 | -30.406 | 57.233 |
| ATOM | 2621 | C | GLN | 405 | 40.206 | -28.529 | 57.407 |
| ATOM | 2622 | O | GLN | 405 | 41.101 | -28.370 | 58.243 |
| ATOM | 2623 | N | SER | 406 | 40.459 | -28.728 | 56.117 |
| ATOM | 2624 | CA | SER | 406 | 41.813 | -28.699 | 55.591 |
| ATOM | 2625 | CB | SER | 406 | 41.866 | -29.375 | 54.202 |
| ATOM | 2626 | OG | SER | 406 | 41.045 | -28.705 | 53.257 |
| ATOM | 2627 | C | SER | 406 | 42.319 | -27.252 | 55.541 |
| ATOM | 2628 | O | SER | 406 | 42.620 | -26.657 | 56.580 |
| ATOM | 2629 | N | ILE | 407 | 42.419 | -26.711 | 54.323 |
| ATOM | 2630 | CA | ILE | 407 | 42.864 | -25.341 | 54.057 |
| ATOM | 2631 | CB | ILE | 407 | 44.420 | -25.169 | 54.156 |
| ATOM | 2632 | CG2 | ILE | 407 | 45.082 | -25.129 | 52.793 |
| ATOM | 2633 | CG1 | ILE | 407 | 44.762 | -23.866 | 54.873 |
| ATOM | 2634 | CD1 | ILE | 407 | 44.063 | -22.656 | 54.346 |
| ATOM | 2635 | C | ILE | 407 | 42.362 | -25.080 | 52.646 |
| ATOM | 2636 | O | ILE | 407 | 41.743 | -24.056 | 52.383 |
| ATOM | 2637 | N | GLY | 408 | 42.553 | -26.060 | 51.768 |
| ATOM | 2638 | CA | GLY | 408 | 42.097 | -25.926 | 50.400 |

FIGURE 1DDD

| Atom | | | Residue AA | No. | X | Y | Z |
|---|---|---|---|---|---|---|---|
| ATOM | 2639 | C | GLY | 408 | 40.582 | -25.970 | 50.402 |
| ATOM | 2640 | O | GLY | 408 | 39.941 | -25.179 | 49.719 |
| ATOM | 2641 | N | LYS | 409 | 40.014 | -26.874 | 51.195 |
| ATOM | 2642 | CA | LYS | 409 | 38.578 | -27.006 | 51.282 |
| ATOM | 2643 | CB | LYS | 409 | 38.221 | -28.276 | 52.038 |
| ATOM | 2644 | CG | LYS | 409 | 37.477 | -29.335 | 51.226 |
| ATOM | 2645 | CD | LYS | 409 | 36.001 | -28.948 | 50.956 |
| ATOM | 2646 | CE | LYS | 409 | 35.238 | -30.090 | 50.222 |
| ATOM | 2647 | NZ | LYS | 409 | 33.770 | -29.814 | 49.977 |
| ATOM | 2648 | C | LYS | 409 | 38.052 | -25.788 | 52.010 |
| ATOM | 2649 | O | LYS | 409 | 36.909 | -25.379 | 51.796 |
| ATOM | 2650 | N | ARG | 410 | 38.913 | -25.201 | 52.844 |
| ATOM | 2651 | CA | ARG | 410 | 38.589 | -24.005 | 53.637 |
| ATOM | 2652 | CB | ARG | 410 | 39.655 | -23.740 | 54.730 |
| ATOM | 2653 | CG | ARG | 410 | 39.163 | -23.950 | 56.214 |
| ATOM | 2654 | CD | ARG | 410 | 40.214 | -24.538 | 57.168 |
| ATOM | 2655 | NE | ARG | 410 | 41.167 | -23.547 | 57.640 |
| ATOM | 2656 | CZ | ARG | 410 | 42.214 | -23.818 | 58.416 |
| ATOM | 2657 | NH1 | ARG | 410 | 43.036 | -22.848 | 58.800 |
| ATOM | 2658 | NH2 | ARG | 410 | 42.447 | -25.060 | 58.817 |
| ATOM | 2659 | C | ARG | 410 | 38.501 | -22.836 | 52.698 |
| ATOM | 2660 | O | ARG | 410 | 37.545 | -22.074 | 52.726 |
| ATOM | 2661 | N | TYR | 411 | 39.499 | -22.723 | 51.843 |
| ATOM | 2662 | CA | TYR | 411 | 39.533 | -21.684 | 50.845 |
| ATOM | 2663 | CB | TYR | 411 | 40.747 | -21.882 | 49.958 |
| ATOM | 2664 | CG | TYR | 411 | 42.044 | -21.421 | 50.545 |
| ATOM | 2665 | CD1 | TYR | 411 | 43.228 | -22.116 | 50.290 |
| ATOM | 2666 | CE1 | TYR | 411 | 44.476 | -21.641 | 50.733 |
| ATOM | 2667 | CD2 | TYR | 411 | 42.123 | -20.248 | 51.268 |
| ATOM | 2668 | CE2 | TYR | 411 | 43.367 | -19.760 | 51.717 |
| ATOM | 2669 | CZ | TYR | 411 | 44.542 | -20.462 | 51.439 |
| ATOM | 2670 | OH | TYR | 411 | 45.779 | -19.973 | 51.809 |
| ATOM | 2671 | C | TYR | 411 | 38.244 | -21.775 | 50.000 |
| ATOM | 2672 | O | TYR | 411 | 37.490 | -20.820 | 49.909 |
| ATOM | 2673 | N | ARG | 412 | 37.953 | -22.939 | 49.438 |
| ATOM | 2674 | CA | ARG | 412 | 36.759 | -23.088 | 48.626 |
| ATOM | 2675 | CB | ARG | 412 | 36.429 | -24.581 | 48.347 |
| ATOM | 2676 | CG | ARG | 412 | 35.053 | -24.859 | 47.579 |
| ATOM | 2677 | CD | ARG | 412 | 34.181 | -26.099 | 48.110 |
| ATOM | 2678 | NE | ARG | 412 | 33.519 | -25.933 | 49.436 |
| ATOM | 2679 | CZ | ARG | 412 | 32.249 | -26.266 | 49.725 |
| ATOM | 2680 | NH1 | ARG | 412 | 31.776 | -26.079 | 50.959 |
| ATOM | 2681 | NH2 | ARG | 412 | 31.429 | -26.746 | 48.785 |
| ATOM | 2682 | C | ARG | 412 | 35.562 | -22.424 | 49.283 |
| ATOM | 2683 | O | ARG | 412 | 35.027 | -21.465 | 48.746 |
| ATOM | 2684 | N | ARG | 413 | 35.177 | -22.883 | 50.464 |
| ATOM | 2685 | CA | ARG | 413 | 33.995 | -22.338 | 51.116 |
| ATOM | 2686 | CB | ARG | 413 | 33.813 | -22.948 | 52.517 |

FIGURE 1EEE

| | Atom | | Residue AA | No. | X | Y | Z |
|---|---|---|---|---|---|---|---|
| ATOM | 2687 | CG | ARG | 413 | 32.540 | -22.457 | 53.225 |
| ATOM | 2688 | CD | ARG | 413 | 32.709 | -22.241 | 54.750 |
| ATOM | 2689 | NE | ARG | 413 | 31.700 | -21.314 | 55.330 |
| ATOM | 2690 | CZ | ARG | 413 | 30.378 | -21.561 | 55.459 |
| ATOM | 2691 | NH1 | ARG | 413 | 29.839 | -22.724 | 55.053 |
| ATOM | 2692 | NH2 | ARG | 413 | 29.569 | -20.637 | 55.990 |
| ATOM | 2693 | C | ARG | 413 | 33.945 | -20.814 | 51.196 |
| ATOM | 2694 | O | ARG | 413 | 32.872 | -20.212 | 51.123 |
| ATOM | 2695 | N | ALA | 414 | 35.115 | -20.205 | 51.321 |
| ATOM | 2696 | CA | ALA | 414 | 35.224 | -18.762 | 51.450 |
| ATOM | 2697 | CB | ALA | 414 | 36.651 | -18.382 | 51.902 |
| ATOM | 2698 | C | ALA | 414 | 34.832 | -18.024 | 50.173 |
| ATOM | 2699 | O | ALA | 414 | 34.101 | -17.028 | 50.194 |
| ATOM | 2700 | N | ASP | 415 | 35.305 | -18.529 | 49.050 |
| ATOM | 2701 | CA | ASP | 415 | 35.009 | -17.923 | 47.770 |
| ATOM | 2702 | CB | ASP | 415 | 35.813 | -18.607 | 46.675 |
| ATOM | 2703 | CG | ASP | 415 | 37.307 | -18.467 | 46.900 |
| ATOM | 2704 | OD1 | ASP | 415 | 37.700 | -17.360 | 47.335 |
| ATOM | 2705 | OD2 | ASP | 415 | 38.075 | -19.446 | 46.694 |
| ATOM | 2706 | C | ASP | 415 | 33.519 | -17.993 | 47.515 |
| ATOM | 2707 | O | ASP | 415 | 32.897 | -16.964 | 47.334 |
| ATOM | 2708 | N | GLU | 416 | 32.910 | -19.164 | 47.626 |
| ATOM | 2709 | CA | GLU | 416 | 31.486 | -19.240 | 47.381 |
| ATOM | 2710 | CB | GLU | 416 | 31.016 | -20.671 | 47.442 |
| ATOM | 2711 | CG | GLU | 416 | 31.569 | -21.400 | 48.619 |
| ATOM | 2712 | CD | GLU | 416 | 30.878 | -22.724 | 48.879 |
| ATOM | 2713 | OE1 | GLU | 416 | 29.797 | -22.981 | 48.293 |
| ATOM | 2714 | OE2 | GLU | 416 | 31.411 | -23.503 | 49.701 |
| ATOM | 2715 | C | GLU | 416 | 30.613 | -18.338 | 48.256 |
| ATOM | 2716 | O | GLU | 416 | 29.431 | -18.206 | 47.987 |
| ATOM | 2717 | N | ILE | 417 | 31.162 | -17.770 | 49.333 |
| ATOM | 2718 | CA | ILE | 417 | 30.382 | -16.843 | 50.185 |
| ATOM | 2719 | CB | ILE | 417 | 30.587 | -17.002 | 51.748 |
| ATOM | 2720 | CG2 | ILE | 417 | 30.668 | -18.484 | 52.159 |
| ATOM | 2721 | CG1 | ILE | 417 | 31.815 | -16.208 | 52.215 |
| ATOM | 2722 | CD1 | ILE | 417 | 32.057 | -16.280 | 53.689 |
| ATOM | 2723 | C | ILE | 417 | 30.830 | -15.454 | 49.778 |
| ATOM | 2724 | O | ILE | 417 | 30.209 | -14.463 | 50.133 |
| ATOM | 2725 | N | GLY | 418 | 32.002 | -15.403 | 49.166 |
| ATOM | 2726 | CA | GLY | 418 | 32.513 | -14.166 | 48.636 |
| ATOM | 2727 | C | GLY | 418 | 33.395 | -13.262 | 49.434 |
| ATOM | 2728 | O | GLY | 418 | 33.170 | -12.067 | 49.453 |
| ATOM | 2729 | N | THR | 419 | 34.463 | -13.773 | 50.002 |
| ATOM | 2730 | CA | THR | 419 | 35.292 | -12.883 | 50.772 |
| ATOM | 2731 | CB | THR | 419 | 35.314 | -13.309 | 52.267 |
| ATOM | 2732 | OG1 | THR | 419 | 35.857 | -14.625 | 52.421 |
| ATOM | 2733 | CG2 | THR | 419 | 33.874 | -13.335 | 52.808 |
| ATOM | 2734 | C | THR | 419 | 36.660 | -12.619 | 50.173 |

FIGURE 1FFF

| | Atom | | Residue AA | No. | X | Y | Z |
|---|---|---|---|---|---|---|---|
| ATOM | 2735 | O | THR | 419 | 37.371 | -13.538 | 49.814 |
| ATOM | 2736 | N | PRO | 420 | 37.014 | -11.342 | 50.010 |
| ATOM | 2737 | CD | PRO | 420 | 36.044 | -10.301 | 50.376 |
| ATOM | 2738 | CA | PRO | 420 | 38.232 | -10.727 | 49.470 |
| ATOM | 2739 | CB | PRO | 420 | 38.076 | -9.271 | 49.867 |
| ATOM | 2740 | CG | PRO | 420 | 36.635 | -9.065 | 49.765 |
| ATOM | 2741 | C | PRO | 420 | 39.624 | -11.238 | 49.851 |
| ATOM | 2742 | O | PRO | 420 | 40.543 | -11.092 | 49.041 |
| ATOM | 2743 | N | TYR | 421 | 39.815 | -11.754 | 51.077 |
| ATOM | 2744 | CA | TYR | 421 | 41.136 | -12.267 | 51.516 |
| ATOM | 2745 | CB | TYR | 421 | 42.010 | -11.147 | 52.059 |
| ATOM | 2746 | CG | TYR | 421 | 42.172 | -10.022 | 51.105 |
| ATOM | 2747 | CD1 | TYR | 421 | 41.328 | -8.921 | 51.174 |
| ATOM | 2748 | CE1 | TYR | 421 | 41.415 | -7.905 | 50.275 |
| ATOM | 2749 | CD2 | TYR | 421 | 43.128 | -10.073 | 50.105 |
| ATOM | 2750 | CE2 | TYR | 421 | 43.238 | -9.062 | 49.198 |
| ATOM | 2751 | CZ | TYR | 421 | 42.371 | -7.977 | 49.286 |
| ATOM | 2752 | OH | TYR | 421 | 42.445 | -6.952 | 48.380 |
| ATOM | 2753 | C | TYR | 421 | 41.178 | -13.388 | 52.547 |
| ATOM | 2754 | O | TYR | 421 | 40.396 | -13.426 | 53.488 |
| ATOM | 2755 | N | CYS | 422 | 42.177 | -14.244 | 52.406 |
| ATOM | 2756 | CA | CYS | 422 | 42.362 | -15.338 | 53.322 |
| ATOM | 2757 | CB | CYS | 422 | 42.178 | -16.661 | 52.623 |
| ATOM | 2758 | SG | CYS | 422 | 40.482 | -16.979 | 52.303 |
| ATOM | 2759 | C | CYS | 422 | 43.735 | -15.277 | 53.935 |
| ATOM | 2760 | O | CYS | 422 | 44.733 | -15.599 | 53.287 |
| ATOM | 2761 | N | VAL | 423 | 43.781 | -14.814 | 55.180 |
| ATOM | 2762 | CA | VAL | 423 | 45.028 | -14.713 | 55.935 |
| ATOM | 2763 | CB | VAL | 423 | 44.989 | -13.569 | 56.960 |
| ATOM | 2764 | CG1 | VAL | 423 | 46.360 | -13.424 | 57.630 |
| ATOM | 2765 | CG2 | VAL | 423 | 44.570 | -12.280 | 56.285 |
| ATOM | 2766 | C | VAL | 423 | 45.287 | -16.018 | 56.684 |
| ATOM | 2767 | O | VAL | 423 | 44.627 | -16.322 | 57.683 |
| ATOM | 2768 | N | THR | 424 | 46.236 | -16.793 | 56.178 |
| ATOM | 2769 | CA | THR | 424 | 46.567 | -18.065 | 56.784 |
| ATOM | 2770 | CB | THR | 424 | 46.846 | -19.139 | 55.713 |
| ATOM | 2771 | OG1 | THR | 424 | 47.728 | -18.603 | 54.713 |
| ATOM | 2772 | CG2 | THR | 424 | 45.542 | -19.569 | 55.057 |
| ATOM | 2773 | C | THR | 424 | 47.743 | -17.938 | 57.734 |
| ATOM | 2774 | O | THR | 424 | 48.769 | -17.330 | 57.409 |
| ATOM | 2775 | N | PHE | 425 | 47.550 | -18.444 | 58.942 |
| ATOM | 2776 | CA | PHE | 425 | 48.584 | -18.414 | 59.943 |
| ATOM | 2777 | CB | PHE | 425 | 48.013 | -18.034 | 61.311 |
| ATOM | 2778 | CG | PHE | 425 | 49.072 | -17.767 | 62.350 |
| ATOM | 2779 | CD1 | PHE | 425 | 49.432 | -16.460 | 62.673 |
| ATOM | 2780 | CD2 | PHE | 425 | 49.771 | -18.817 | 62.941 |
| ATOM | 2781 | CE1 | PHE | 425 | 50.472 | -16.205 | 63.553 |
| ATOM | 2782 | CE2 | PHE | 425 | 50.812 | -18.564 | 63.822 |

FIGURE 1GGG

| | Atom | | Residue AA | No. | X | Y | Z |
|---|---|---|---|---|---|---|---|
| ATOM | 2783 | CZ | PHE | 425 | 51.163 | -17.255 | 64.125 |
| ATOM | 2784 | C | PHE | 425 | 49.113 | -19.816 | 60.001 |
| ATOM | 2785 | O | PHE | 425 | 48.387 | -20.743 | 60.306 |
| ATOM | 2786 | N | ASP | 426 | 50.372 | -19.994 | 59.684 |
| ATOM | 2787 | CA | ASP | 426 | 50.930 | -21.321 | 59.739 |
| ATOM | 2788 | CB | ASP | 426 | 51.483 | -21.694 | 58.382 |
| ATOM | 2789 | CG | ASP | 426 | 52.779 | -21.021 | 58.102 |
| ATOM | 2790 | OD1 | ASP | 426 | 53.788 | -21.743 | 58.138 |
| ATOM | 2791 | OD2 | ASP | 426 | 52.795 | -19.783 | 57.900 |
| ATOM | 2792 | C | ASP | 426 | 52.053 | -21.292 | 60.728 |
| ATOM | 2793 | O | ASP | 426 | 52.244 | -20.313 | 61.419 |
| ATOM | 2794 | N | PHE | 427 | 52.887 | -22.310 | 60.672 |
| ATOM | 2795 | CA | PHE | 427 | 54.015 | -22.410 | 61.564 |
| ATOM | 2796 | CB | PHE | 427 | 54.616 | -23.796 | 61.442 |
| ATOM | 2797 | CG | PHE | 427 | 53.644 | -24.892 | 61.802 |
| ATOM | 2798 | CD1 | PHE | 427 | 53.860 | -25.700 | 62.910 |
| ATOM | 2799 | CD2 | PHE | 427 | 52.514 | -25.121 | 61.031 |
| ATOM | 2800 | CE1 | PHE | 427 | 52.960 | -26.728 | 63.239 |
| ATOM | 2801 | CE2 | PHE | 427 | 51.608 | -26.145 | 61.353 |
| ATOM | 2802 | CZ | PHE | 427 | 51.827 | -26.946 | 62.449 |
| ATOM | 2803 | C | PHE | 427 | 55.033 | -21.297 | 61.331 |
| ATOM | 2804 | O | PHE | 427 | 55.477 | -20.634 | 62.262 |
| ATOM | 2805 | N | ASP | 428 | 55.402 | -21.057 | 60.094 |
| ATOM | 2806 | CA | ASP | 428 | 56.334 | -19.981 | 59.859 |
| ATOM | 2807 | CB | ASP | 428 | 56.855 | -19.989 | 58.434 |
| ATOM | 2808 | CG | ASP | 428 | 57.649 | -21.239 | 58.121 |
| ATOM | 2809 | OD1 | ASP | 428 | 57.157 | -22.354 | 58.439 |
| ATOM | 2810 | OD2 | ASP | 428 | 58.765 | -21.108 | 57.561 |
| ATOM | 2811 | C | ASP | 428 | 55.667 | -18.672 | 60.167 |
| ATOM | 2812 | O | ASP | 428 | 56.341 | -17.726 | 60.517 |
| ATOM | 2813 | N | SER | 429 | 54.347 | -18.619 | 60.089 |
| ATOM | 2814 | CA | SER | 429 | 53.670 | -17.375 | 60.386 |
| ATOM | 2815 | CB | SER | 429 | 52.154 | -17.542 | 60.337 |
| ATOM | 2816 | OG | SER | 429 | 51.685 | -17.668 | 59.003 |
| ATOM | 2817 | C | SER | 429 | 54.121 | -16.856 | 61.754 |
| ATOM | 2818 | O | SER | 429 | 54.445 | -15.673 | 61.902 |
| ATOM | 2819 | N | LEU | 430 | 54.187 | -17.734 | 62.752 |
| ATOM | 2820 | CA | LEU | 430 | 54.644 | -17.287 | 64.066 |
| ATOM | 2821 | CB | LEU | 430 | 54.304 | -18.264 | 65.219 |
| ATOM | 2822 | CG | LEU | 430 | 54.560 | -19.767 | 65.427 |
| ATOM | 2823 | CD1 | LEU | 430 | 53.561 | -20.590 | 64.657 |
| ATOM | 2824 | CD2 | LEU | 430 | 55.984 | -20.161 | 65.132 |
| ATOM | 2825 | C | LEU | 430 | 56.126 | -17.016 | 63.976 |
| ATOM | 2826 | O | LEU | 430 | 56.543 | -15.894 | 64.196 |
| ATOM | 2827 | N | ALA | 431 | 56.880 | -17.997 | 63.491 |
| ATOM | 2828 | CA | ALA | 431 | 58.332 | -17.883 | 63.345 |
| ATOM | 2829 | CB | ALA | 431 | 58.863 | -19.038 | 62.479 |
| ATOM | 2830 | C | ALA | 431 | 58.794 | -16.533 | 62.766 |

FIGURE 1HHH

| Atom | | | Residue AA | No. | X | Y | Z |
|---|---|---|---|---|---|---|---|
| ATOM | 2831 | O | ALA | 431 | 59.544 | -15.796 | 63.407 |
| ATOM | 2832 | N | ASP | 432 | 58.355 | -16.221 | 61.553 |
| ATOM | 2833 | CA | ASP | 432 | 58.742 | -14.987 | 60.914 |
| ATOM | 2834 | CB | ASP | 432 | 58.832 | -15.158 | 59.379 |
| ATOM | 2835 | CG | ASP | 432 | 57.465 | -15.189 | 58.678 |
| ATOM | 2836 | OD1 | ASP | 432 | 56.435 | -15.545 | 59.295 |
| ATOM | 2837 | OD2 | ASP | 432 | 57.426 | -14.848 | 57.474 |
| ATOM | 2838 | C | ASP | 432 | 57.807 | -13.870 | 61.303 |
| ATOM | 2839 | O | ASP | 432 | 58.091 | -12.728 | 61.055 |
| ATOM | 2840 | N | ASN | 433 | 56.676 | -14.202 | 61.891 |
| ATOM | 2841 | CA | ASN | 433 | 55.715 | -13.196 | 62.304 |
| ATOM | 2842 | CB | ASN | 433 | 56.354 | -12.239 | 63.320 |
| ATOM | 2843 | CG | ASN | 433 | 55.501 | -12.066 | 64.591 |
| ATOM | 2844 | OD1 | ASN | 433 | 55.530 | -11.002 | 65.236 |
| ATOM | 2845 | ND2 | ASN | 433 | 54.746 | -13.120 | 64.965 |
| ATOM | 2846 | C | ASN | 433 | 55.051 | -12.441 | 61.144 |
| ATOM | 2847 | O | ASN | 433 | 54.727 | -11.251 | 61.251 |
| ATOM | 2848 | N | GLN | 434 | 54.795 | -13.163 | 60.056 |
| ATOM | 2849 | CA | GLN | 434 | 54.142 | -12.619 | 58.872 |
| ATOM | 2850 | CB | GLN | 434 | 55.152 | -12.317 | 57.775 |
| ATOM | 2851 | CG | GLN | 434 | 56.102 | -11.215 | 58.134 |
| ATOM | 2852 | CD | GLN | 434 | 56.985 | -10.787 | 56.982 |
| ATOM | 2853 | OE1 | GLN | 434 | 58.193 | -10.518 | 57.170 |
| ATOM | 2854 | NE2 | GLN | 434 | 56.395 | -10.698 | 55.777 |
| ATOM | 2855 | C | GLN | 434 | 53.178 | -13.678 | 58.395 |
| ATOM | 2856 | O | GLN | 434 | 53.330 | -14.847 | 58.735 |
| ATOM | 2857 | N | VAL | 435 | 52.214 | -13.288 | 57.573 |
| ATOM | 2858 | CA | VAL | 435 | 51.220 | -14.237 | 57.080 |
| ATOM | 2859 | CB | VAL | 435 | 49.903 | -14.087 | 57.893 |
| ATOM | 2860 | CG1 | VAL | 435 | 50.067 | -14.674 | 59.279 |
| ATOM | 2861 | CG2 | VAL | 435 | 49.538 | -12.621 | 58.014 |
| ATOM | 2862 | C | VAL | 435 | 50.933 | -14.185 | 55.558 |
| ATOM | 2863 | O | VAL | 435 | 51.247 | -13.214 | 54.888 |
| ATOM | 2864 | N | THR | 436 | 50.346 | -15.252 | 55.029 |
| ATOM | 2865 | CA | THR | 436 | 50.006 | -15.352 | 53.619 |
| ATOM | 2866 | CB | THR | 436 | 50.081 | -16.802 | 53.150 |
| ATOM | 2867 | OG1 | THR | 436 | 49.883 | -17.675 | 54.262 |
| ATOM | 2868 | CG2 | THR | 436 | 51.428 | -17.092 | 52.538 |
| ATOM | 2869 | C | THR | 436 | 48.623 | -14.808 | 53.271 |
| ATOM | 2870 | O | THR | 436 | 47.607 | -15.411 | 53.611 |
| ATOM | 2871 | N | VAL | 437 | 48.601 | -13.653 | 52.613 |
| ATOM | 2872 | CA | VAL | 437 | 47.374 | -12.991 | 52.178 |
| ATOM | 2873 | CB | VAL | 437 | 47.519 | -11.447 | 52.204 |
| ATOM | 2874 | CG1 | VAL | 437 | 46.230 | -10.787 | 51.755 |
| ATOM | 2875 | CG2 | VAL | 437 | 47.891 | -10.978 | 53.577 |
| ATOM | 2876 | C | VAL | 437 | 47.084 | -13.395 | 50.737 |
| ATOM | 2877 | O | VAL | 437 | 47.748 | -12.927 | 49.816 |
| ATOM | 2878 | N | ARG | 438 | 46.132 | -14.300 | 50.544 |

FIGURE 1III

| Atom | | | Residue AA | No. | X | Y | Z |
|---|---|---|---|---|---|---|---|
| ATOM | 2879 | CA | ARG | 438 | 45.771 | -14.738 | 49.212 |
| ATOM | 2880 | CB | ARG | 438 | 45.418 | -16.218 | 49.236 |
| ATOM | 2881 | CG | ARG | 438 | 44.008 | -16.553 | 48.879 |
| ATOM | 2882 | CD | ARG | 438 | 43.969 | -17.893 | 48.201 |
| ATOM | 2883 | NE | ARG | 438 | 42.615 | -18.325 | 47.873 |
| ATOM | 2884 | CZ | ARG | 438 | 42.324 | -19.323 | 47.042 |
| ATOM | 2885 | NH1 | ARG | 438 | 43.302 | -19.993 | 46.445 |
| ATOM | 2886 | NH2 | ARG | 438 | 41.056 | -19.669 | 46.821 |
| ATOM | 2887 | C | ARG | 438 | 44.604 | -13.901 | 48.719 |
| ATOM | 2888 | O | ARG | 438 | 43.750 | -13.513 | 49.525 |
| ATOM | 2889 | N | ASP | 439 | 44.603 | -13.574 | 47.420 |
| ATOM | 2890 | CA | ASP | 439 | 43.525 | -12.790 | 46.791 |
| ATOM | 2891 | CB | ASP | 439 | 44.070 | -11.999 | 45.586 |
| ATOM | 2892 | CG | ASP | 439 | 42.969 | -11.184 | 44.845 |
| ATOM | 2893 | OD1 | ASP | 439 | 41.994 | -11.810 | 44.370 |
| ATOM | 2894 | OD2 | ASP | 439 | 43.085 | -9.925 | 44.706 |
| ATOM | 2895 | C | ASP | 439 | 42.414 | -13.723 | 46.317 |
| ATOM | 2896 | O | ASP | 439 | 42.701 | -14.813 | 45.868 |
| ATOM | 2897 | N | ARG | 440 | 41.164 | -13.286 | 46.362 |
| ATOM | 2898 | CA | ARG | 440 | 40.086 | -14.142 | 45.902 |
| ATOM | 2899 | CB | ARG | 440 | 38.712 | -13.526 | 46.199 |
| ATOM | 2900 | CG | ARG | 440 | 37.527 | -14.337 | 45.597 |
| ATOM | 2901 | CD | ARG | 440 | 36.295 | -13.498 | 45.438 |
| ATOM | 2902 | NE | ARG | 440 | 36.663 | -12.123 | 45.150 |
| ATOM | 2903 | CZ | ARG | 440 | 35.925 | -11.071 | 45.459 |
| ATOM | 2904 | NH1 | ARG | 440 | 34.757 | -11.229 | 46.055 |
| ATOM | 2905 | NH2 | ARG | 440 | 36.405 | -9.856 | 45.256 |
| ATOM | 2906 | C | ARG | 440 | 40.183 | -14.492 | 44.402 |
| ATOM | 2907 | O | ARG | 440 | 40.614 | -15.585 | 44.026 |
| ATOM | 2908 | N | ASP | 441 | 39.732 | -13.571 | 43.549 |
| ATOM | 2909 | CA | ASP | 441 | 39.750 | -13.770 | 42.108 |
| ATOM | 2910 | CB | ASP | 441 | 39.335 | -12.484 | 41.335 |
| ATOM | 2911 | CG | ASP | 441 | 39.027 | -11.240 | 42.245 |
| ATOM | 2912 | OD1 | ASP | 441 | 39.889 | -10.347 | 42.391 |
| ATOM | 2913 | OD2 | ASP | 441 | 37.897 | -11.086 | 42.735 |
| ATOM | 2914 | C | ASP | 441 | 41.143 | -14.250 | 41.705 |
| ATOM | 2915 | O | ASP | 441 | 41.312 | -15.387 | 41.316 |
| ATOM | 2916 | N | SER | 442 | 42.141 | -13.416 | 41.974 |
| ATOM | 2917 | CA | SER | 442 | 43.556 | -13.672 | 41.678 |
| ATOM | 2918 | CB | SER | 442 | 44.409 | -12.531 | 42.275 |
| ATOM | 2919 | OG | SER | 442 | 45.672 | -12.950 | 42.790 |
| ATOM | 2920 | C | SER | 442 | 44.163 | -15.025 | 42.070 |
| ATOM | 2921 | O | SER | 442 | 45.065 | -15.516 | 41.382 |
| ATOM | 2922 | N | MET | 443 | 43.764 | -15.562 | 43.223 |
| ATOM | 2923 | CA | MET | 443 | 44.282 | -16.840 | 43.708 |
| ATOM | 2924 | CB | MET | 443 | 44.058 | -17.917 | 42.661 |
| ATOM | 2925 | CG | MET | 443 | 42.621 | -18.111 | 42.320 |
| ATOM | 2926 | SD | MET | 443 | 42.329 | -19.816 | 42.524 |

FIGURE 1JJJ

| | Atom | | Residue AA | No. | X | Y | Z |
|---|---|---|---|---|---|---|---|
| ATOM | 2927 | CE | MET | 443 | 40.905 | -20.019 | 41.597 |
| ATOM | 2928 | C | MET | 443 | 45.759 | -16.805 | 44.093 |
| ATOM | 2929 | O | MET | 443 | 46.307 | -17.793 | 44.593 |
| ATOM | 2930 | N | GLU | 444 | 46.415 | -15.680 | 43.837 |
| ATOM | 2931 | CA | GLU | 444 | 47.819 | -15.555 | 44.169 |
| ATOM | 2932 | CB | GLU | 444 | 48.527 | -14.586 | 43.220 |
| ATOM | 2933 | CG | GLU | 444 | 49.780 | -15.214 | 42.554 |
| ATOM | 2934 | CD | GLU | 444 | 49.593 | -16.710 | 42.068 |
| ATOM | 2935 | OE1 | GLU | 444 | 48.883 | -16.936 | 41.029 |
| ATOM | 2936 | OE2 | GLU | 444 | 50.174 | -17.651 | 42.713 |
| ATOM | 2937 | C | GLU | 444 | 47.872 | -15.073 | 45.585 |
| ATOM | 2938 | O | GLU | 444 | 46.917 | -14.424 | 46.039 |
| ATOM | 2939 | N | GLN | 445 | 48.952 | -15.421 | 46.292 |
| ATOM | 2940 | CA | GLN | 445 | 49.124 | -15.039 | 47.699 |
| ATOM | 2941 | CB | GLN | 445 | 48.738 | -16.197 | 48.612 |
| ATOM | 2942 | CG | GLN | 445 | 49.290 | -17.534 | 48.199 |
| ATOM | 2943 | CD | GLN | 445 | 48.754 | -18.647 | 49.057 |
| ATOM | 2944 | OE1 | GLN | 445 | 49.528 | -19.385 | 49.643 |
| ATOM | 2945 | NE2 | GLN | 445 | 47.426 | -18.768 | 49.154 |
| ATOM | 2946 | C | GLN | 445 | 50.507 | -14.560 | 48.075 |
| ATOM | 2947 | O | GLN | 445 | 51.498 | -15.184 | 47.724 |
| ATOM | 2948 | N | VAL | 446 | 50.558 | -13.476 | 48.837 |
| ATOM | 2949 | CA | VAL | 446 | 51.815 | -12.888 | 49.294 |
| ATOM | 2950 | CB | VAL | 446 | 51.877 | -11.411 | 48.895 |
| ATOM | 2951 | CG1 | VAL | 446 | 50.557 | -10.737 | 49.206 |
| ATOM | 2952 | CG2 | VAL | 446 | 53.003 | -10.701 | 49.644 |
| ATOM | 2953 | C | VAL | 446 | 51.943 | -12.966 | 50.821 |
| ATOM | 2954 | O | VAL | 446 | 50.932 | -12.868 | 51.521 |
| ATOM | 2955 | N | ARG | 447 | 53.156 | -13.163 | 51.345 |
| ATOM | 2956 | CA | ARG | 447 | 53.338 | -13.204 | 52.802 |
| ATOM | 2957 | CB | ARG | 447 | 54.431 | -14.209 | 53.209 |
| ATOM | 2958 | CG | ARG | 447 | 54.635 | -14.312 | 54.721 |
| ATOM | 2959 | CD | ARG | 447 | 55.613 | -15.414 | 55.152 |
| ATOM | 2960 | NE | ARG | 447 | 55.053 | -16.769 | 55.064 |
| ATOM | 2961 | CZ | ARG | 447 | 54.758 | -17.564 | 56.104 |
| ATOM | 2962 | NH1 | ARG | 447 | 54.960 | -17.167 | 57.365 |
| ATOM | 2963 | NH2 | ARG | 447 | 54.243 | -18.774 | 55.872 |
| ATOM | 2964 | C | ARG | 447 | 53.691 | -11.789 | 53.278 |
| ATOM | 2965 | O | ARG | 447 | 54.704 | -11.228 | 52.851 |
| ATOM | 2966 | N | MET | 448 | 52.841 | -11.197 | 54.118 |
| ATOM | 2967 | CA | MET | 448 | 53.075 | -9.849 | 54.624 |
| ATOM | 2968 | CB | MET | 448 | 51.982 | -8.896 | 54.131 |
| ATOM | 2969 | CG | MET | 448 | 50.585 | -9.289 | 54.480 |
| ATOM | 2970 | SD | MET | 448 | 49.405 | -8.187 | 53.662 |
| ATOM | 2971 | CE | MET | 448 | 50.057 | -6.557 | 54.214 |
| ATOM | 2972 | C | MET | 448 | 53.214 | -9.767 | 56.143 |
| ATOM | 2973 | O | MET | 448 | 52.792 | -10.663 | 56.866 |
| ATOM | 2974 | N | PRO | 449 | 53.893 | -8.725 | 56.638 |

FIGURE 1KKK

| | Atom | | Residue AA | No. | X | Y | Z |
|---|---|---|---|---|---|---|---|
| ATOM | 2975 | CD | PRO | 449 | 54.571 | -7.706 | 55.820 |
| ATOM | 2976 | CA | PRO | 449 | 54.120 | -8.478 | 58.065 |
| ATOM | 2977 | CB | PRO | 449 | 54.839 | -7.138 | 58.062 |
| ATOM | 2978 | CG | PRO | 449 | 55.605 | -7.168 | 56.774 |
| ATOM | 2979 | C | PRO | 449 | 52.783 | -8.365 | 58.759 |
| ATOM | 2980 | O | PRO | 449 | 52.064 | -7.383 | 58.569 |
| ATOM | 2981 | N | ILE | 450 | 52.476 | -9.358 | 59.586 |
| ATOM | 2982 | CA | ILE | 450 | 51.204 | -9.429 | 60.294 |
| ATOM | 2983 | CB | ILE | 450 | 51.291 | -10.337 | 61.531 |
| ATOM | 2984 | CG2 | ILE | 450 | 49.949 | -10.403 | 62.205 |
| ATOM | 2985 | CG1 | ILE | 450 | 51.678 | -11.751 | 61.108 |
| ATOM | 2986 | CD1 | ILE | 450 | 51.636 | -12.769 | 62.209 |
| ATOM | 2987 | C | ILE | 450 | 50.649 | -8.073 | 60.676 |
| ATOM | 2988 | O | ILE | 450 | 49.446 | -7.819 | 60.593 |
| ATOM | 2989 | N | SER | 451 | 51.559 | -7.188 | 61.034 |
| ATOM | 2990 | CA | SER | 451 | 51.216 | -5.832 | 61.414 |
| ATOM | 2991 | CB | SER | 451 | 52.515 | -5.064 | 61.712 |
| ATOM | 2992 | OG | SER | 451 | 52.536 | -3.769 | 61.105 |
| ATOM | 2993 | C | SER | 451 | 50.407 | -5.095 | 60.332 |
| ATOM | 2994 | O | SER | 451 | 49.286 | -4.626 | 60.573 |
| ATOM | 2995 | N | GLU | 452 | 50.983 | -5.020 | 59.141 |
| ATOM | 2996 | CA | GLU | 452 | 50.380 | -4.313 | 58.029 |
| ATOM | 2997 | CB | GLU | 452 | 51.337 | -4.342 | 56.837 |
| ATOM | 2998 | CG | GLU | 452 | 52.761 | -3.815 | 57.217 |
| ATOM | 2999 | CD | GLU | 452 | 53.670 | -3.370 | 56.002 |
| ATOM | 3000 | OE1 | GLU | 452 | 53.998 | -4.223 | 55.110 |
| ATOM | 3001 | OE2 | GLU | 452 | 54.084 | -2.165 | 55.969 |
| ATOM | 3002 | C | GLU | 452 | 48.958 | -4.703 | 57.617 |
| ATOM | 3003 | O | GLU | 452 | 48.255 | -3.925 | 56.951 |
| ATOM | 3004 | N | LEU | 453 | 48.514 | -5.873 | 58.058 |
| ATOM | 3005 | CA | LEU | 453 | 47.173 | -6.347 | 57.742 |
| ATOM | 3006 | CB | LEU | 453 | 46.836 | -7.542 | 58.635 |
| ATOM | 3007 | CG | LEU | 453 | 47.393 | -8.928 | 58.290 |
| ATOM | 3008 | CD1 | LEU | 453 | 46.564 | -9.562 | 57.173 |
| ATOM | 3009 | CD2 | LEU | 453 | 48.875 | -8.848 | 57.927 |
| ATOM | 3010 | C | LEU | 453 | 46.122 | -5.245 | 57.932 |
| ATOM | 3011 | O | LEU | 453 | 45.138 | -5.172 | 57.194 |
| ATOM | 3012 | N | GLU | 454 | 46.359 | -4.383 | 58.917 |
| ATOM | 3013 | CA | GLU | 454 | 45.456 | -3.276 | 59.243 |
| ATOM | 3014 | CB | GLU | 454 | 45.946 | -2.492 | 60.476 |
| ATOM | 3015 | CG | GLU | 454 | 45.305 | -2.925 | 61.818 |
| ATOM | 3016 | CD | GLU | 454 | 44.315 | -1.903 | 62.398 |
| ATOM | 3017 | OE1 | GLU | 454 | 44.060 | -1.997 | 63.630 |
| ATOM | 3018 | OE2 | GLU | 454 | 43.801 | -1.031 | 61.638 |
| ATOM | 3019 | C | GLU | 454 | 45.370 | -2.328 | 58.090 |
| ATOM | 3020 | O | GLU | 454 | 44.301 | -2.156 | 57.505 |
| ATOM | 3021 | N | ALA | 455 | 46.510 | -1.724 | 57.769 |
| ATOM | 3022 | CA | ALA | 455 | 46.598 | -0.769 | 56.677 |

FIGURE 1LLL

| Atom | | | Residue AA | No. | X | Y | Z |
|---|---|---|---|---|---|---|---|
| ATOM | 3023 | CB | ALA | 455 | 48.043 | -0.336 | 56.492 |
| ATOM | 3024 | C | ALA | 455 | 46.043 | -1.366 | 55.372 |
| ATOM | 3025 | O | ALA | 455 | 45.217 | -0.718 | 54.692 |
| ATOM | 3026 | N | PHE | 456 | 46.470 | -2.599 | 55.057 |
| ATOM | 3027 | CA | PHE | 456 | 46.035 | -3.315 | 53.856 |
| ATOM | 3028 | CB | PHE | 456 | 46.591 | -4.746 | 53.864 |
| ATOM | 3029 | CG | PHE | 456 | 46.280 | -5.542 | 52.613 |
| ATOM | 3030 | CD1 | PHE | 456 | 47.296 | -6.125 | 51.877 |
| ATOM | 3031 | CD2 | PHE | 456 | 44.973 | -5.702 | 52.166 |
| ATOM | 3032 | CE1 | PHE | 456 | 47.019 | -6.846 | 50.720 |
| ATOM | 3033 | CE2 | PHE | 456 | 44.690 | -6.421 | 51.012 |
| ATOM | 3034 | CZ | PHE | 456 | 45.711 | -6.993 | 50.287 |
| ATOM | 3035 | C | PHE | 456 | 44.507 | -3.345 | 53.733 |
| ATOM | 3036 | O | PHE | 456 | 43.936 | -2.659 | 52.886 |
| ATOM | 3037 | N | LEU | 457 | 43.848 | -4.138 | 54.571 |
| ATOM | 3038 | CA | LEU | 457 | 42.394 | -4.265 | 54.532 |
| ATOM | 3039 | CB | LEU | 457 | 41.901 | -5.133 | 55.678 |
| ATOM | 3040 | CG | LEU | 457 | 42.297 | -6.579 | 55.536 |
| ATOM | 3041 | CD1 | LEU | 457 | 41.790 | -7.337 | 56.710 |
| ATOM | 3042 | CD2 | LEU | 457 | 41.714 | -7.117 | 54.256 |
| ATOM | 3043 | C | LEU | 457 | 41.628 | -2.952 | 54.539 |
| ATOM | 3044 | O | LEU | 457 | 40.470 | -2.930 | 54.138 |
| ATOM | 3045 | N | THR | 458 | 42.269 | -1.877 | 55.009 |
| ATOM | 3046 | CA | THR | 458 | 41.665 | -0.552 | 55.069 |
| ATOM | 3047 | CB | THR | 458 | 42.476 | 0.351 | 55.926 |
| ATOM | 3048 | OG1 | THR | 458 | 42.616 | -0.258 | 57.200 |
| ATOM | 3049 | CG2 | THR | 458 | 41.786 | 1.677 | 56.080 |
| ATOM | 3050 | C | THR | 458 | 41.587 | 0.108 | 53.710 |
| ATOM | 3051 | O | THR | 458 | 40.536 | 0.623 | 53.321 |
| ATOM | 3052 | N | ALA | 459 | 42.725 | 0.134 | 53.014 |
| ATOM | 3053 | CA | ALA | 459 | 42.847 | 0.728 | 51.674 |
| ATOM | 3054 | CB | ALA | 459 | 44.294 | 0.776 | 51.231 |
| ATOM | 3055 | C | ALA | 459 | 42.070 | -0.055 | 50.671 |
| ATOM | 3056 | O | ALA | 459 | 41.257 | 0.510 | 49.958 |
| ATOM | 3057 | N | LYS | 460 | 42.298 | -1.364 | 50.649 |
| ATOM | 3058 | CA | LYS | 460 | 41.626 | -2.251 | 49.722 |
| ATOM | 3059 | CB | LYS | 460 | 42.255 | -3.638 | 49.759 |
| ATOM | 3060 | CG | LYS | 460 | 42.538 | -4.191 | 48.384 |
| ATOM | 3061 | CD | LYS | 460 | 43.941 | -3.793 | 47.841 |
| ATOM | 3062 | CE | LYS | 460 | 44.026 | -3.698 | 46.253 |
| ATOM | 3063 | NZ | LYS | 460 | 43.888 | -4.962 | 45.401 |
| ATOM | 3064 | C | LYS | 460 | 40.149 | -2.370 | 49.996 |
| ATOM | 3065 | O | LYS | 460 | 39.558 | -3.375 | 49.660 |
| ATOM | 3066 | N | THR | 461 | 39.545 | -1.314 | 50.520 |
| ATOM | 3067 | CA | THR | 461 | 38.145 | -1.311 | 50.860 |
| ATOM | 3068 | CB | THR | 461 | 37.995 | -1.413 | 52.350 |
| ATOM | 3069 | OG1 | THR | 461 | 38.624 | -2.607 | 52.815 |
| ATOM | 3070 | CG2 | THR | 461 | 36.524 | -1.402 | 52.726 |

FIGURE 1MMM

| | Atom | | Residue AA | No. | X | Y | Z |
|---|---|---|---|---|---|---|---|
| ATOM | 3071 | C | THR | 461 | 37.449 | -0.029 | 50.465 |
| ATOM | 3072 | O | THR | 461 | 36.322 | -0.068 | 49.976 |
| ATOM | 3073 | N | ALA | 462 | 38.089 | 1.087 | 50.820 |
| ATOM | 3074 | CA | ALA | 462 | 37.653 | 2.473 | 50.586 |
| ATOM | 3075 | CB | ALA | 462 | 38.752 | 3.242 | 49.885 |
| ATOM | 3076 | C | ALA | 462 | 36.302 | 2.777 | 49.927 |
| ATOM | 3077 | O | ALA | 462 | 35.662 | 3.787 | 50.269 |
| ATOM | 3078 | N | PHE | 463 | 35.918 | 1.961 | 48.944 |
| ATOM | 3079 | CA | PHE | 463 | 34.645 | 2.111 | 48.225 |
| ATOM | 3080 | CB | PHE | 463 | 33.463 | 2.190 | 49.195 |
| ATOM | 3081 | CG | PHE | 463 | 32.130 | 2.120 | 48.519 |
| ATOM | 3082 | CD1 | PHE | 463 | 31.717 | 0.935 | 47.895 |
| ATOM | 3083 | CD2 | PHE | 463 | 31.291 | 3.223 | 48.511 |
| ATOM | 3084 | CE1 | PHE | 463 | 30.484 | 0.836 | 47.270 |
| ATOM | 3085 | CE2 | PHE | 463 | 30.069 | 3.155 | 47.902 |
| ATOM | 3086 | CZ | PHE | 463 | 29.653 | 1.942 | 47.269 |
| ATOM | 3087 | C | PHE | 463 | 34.649 | 3.321 | 47.279 |
| ATOM | 3088 | O | PHE | 463 | 35.708 | 3.485 | 46.614 |
| ATOM | 3089 | OT | PHE | 463 | 33.632 | 4.068 | 47.193 |
| ATOM | 3090 | CB | MET | 1001 | 21.009 | 13.671 | 84.565 |
| ATOM | 3091 | CG | MET | 1001 | 19.537 | 13.254 | 85.037 |
| ATOM | 3092 | SD | MET | 1001 | 18.432 | 12.056 | 84.091 |
| ATOM | 3093 | CE | MET | 1001 | 16.748 | 12.318 | 84.896 |
| ATOM | 3094 | C | MET | 1001 | 20.000 | 15.514 | 83.107 |
| ATOM | 3095 | O | MET | 1001 | 19.992 | 16.640 | 83.663 |
| ATOM | 3096 | N | MET | 1001 | 22.497 | 15.237 | 83.191 |
| ATOM | 3097 | CA | MET | 1001 | 21.161 | 14.532 | 83.261 |
| ATOM | 3098 | N | ALA | 1002 | 19.018 | 15.059 | 82.342 |
| ATOM | 3099 | CA | ALA | 1002 | 17.822 | 15.839 | 82.060 |
| ATOM | 3100 | CB | ALA | 1002 | 16.957 | 15.132 | 81.009 |
| ATOM | 3101 | C | ALA | 1002 | 16.979 | 16.198 | 83.284 |
| ATOM | 3102 | O | ALA | 1002 | 16.456 | 15.324 | 84.005 |
| ATOM | 3103 | N | LYS | 1003 | 16.892 | 17.503 | 83.507 |
| ATOM | 3104 | CA | LYS | 1003 | 16.105 | 18.049 | 84.582 |
| ATOM | 3105 | CB | LYS | 1003 | 16.406 | 19.549 | 84.712 |
| ATOM | 3106 | CG | LYS | 1003 | 17.272 | 20.152 | 83.582 |
| ATOM | 3107 | CD | LYS | 1003 | 16.474 | 20.468 | 82.305 |
| ATOM | 3108 | CE | LYS | 1003 | 15.331 | 21.477 | 82.540 |
| ATOM | 3109 | NZ | LYS | 1003 | 15.723 | 22.913 | 82.519 |
| ATOM | 3110 | C | LYS | 1003 | 14.627 | 17.799 | 84.213 |
| ATOM | 3111 | O | LYS | 1003 | 14.004 | 16.807 | 84.624 |
| ATOM | 3112 | N | ASP | 1004 | 14.101 | 18.674 | 83.373 |
| ATOM | 3113 | CA | ASP | 1004 | 12.729 | 18.589 | 82.925 |
| ATOM | 3114 | CB | ASP | 1004 | 12.317 | 19.994 | 82.391 |
| ATOM | 3115 | CG | ASP | 1004 | 10.824 | 20.364 | 82.673 |
| ATOM | 3116 | OD1 | ASP | 1004 | 9.972 | 19.454 | 82.877 |
| ATOM | 3117 | OD2 | ASP | 1004 | 10.494 | 21.586 | 82.682 |
| ATOM | 3118 | C | ASP | 1004 | 12.696 | 17.539 | 81.791 |

FIGURE 1NNN

| Atom | | | Residue AA | No. | X | Y | Z |
|---|---|---|---|---|---|---|---|
| ATOM | 3119 | O | ASP | 1004 | 13.748 | 17.185 | 81.254 |
| ATOM | 3120 | N | MET | 1005 | 11.528 | 16.941 | 81.534 |
| ATOM | 3121 | CA | MET | 1005 | 11.387 | 16.036 | 80.382 |
| ATOM | 3122 | CB | MET | 1005 | 10.287 | 14.972 | 80.562 |
| ATOM | 3123 | CG | MET | 1005 | 10.034 | 14.109 | 79.283 |
| ATOM | 3124 | SD | MET | 1005 | 11.007 | 12.551 | 79.076 |
| ATOM | 3125 | CE | MET | 1005 | 12.685 | 13.162 | 78.685 |
| ATOM | 3126 | C | MET | 1005 | 10.982 | 16.995 | 79.248 |
| ATOM | 3127 | O | MET | 1005 | 11.500 | 16.901 | 78.142 |
| ATOM | 3128 | N | ASP | 1006 | 10.122 | 17.964 | 79.581 |
| ATOM | 3129 | CA | ASP | 1006 | 9.626 | 18.978 | 78.648 |
| ATOM | 3130 | CB | ASP | 1006 | 8.651 | 19.954 | 79.320 |
| ATOM | 3131 | CG | ASP | 1006 | 7.462 | 19.247 | 79.993 |
| ATOM | 3132 | OD1 | ASP | 1006 | 6.903 | 19.812 | 80.982 |
| ATOM | 3133 | OD2 | ASP | 1006 | 7.088 | 18.128 | 79.543 |
| ATOM | 3134 | C | ASP | 1006 | 10.755 | 19.779 | 78.064 |
| ATOM | 3135 | O | ASP | 1006 | 10.698 | 20.182 | 76.916 |
| ATOM | 3136 | N | THR | 1007 | 11.773 | 20.056 | 78.849 |
| ATOM | 3137 | CA | THR | 1007 | 12.865 | 20.810 | 78.296 |
| ATOM | 3138 | CB | THR | 1007 | 13.894 | 21.162 | 79.343 |
| ATOM | 3139 | OG1 | THR | 1007 | 13.382 | 22.216 | 80.180 |
| ATOM | 3140 | CG2 | THR | 1007 | 15.208 | 21.583 | 78.672 |
| ATOM | 3141 | C | THR | 1007 | 13.514 | 19.954 | 77.259 |
| ATOM | 3142 | O | THR | 1007 | 13.824 | 20.436 | 76.183 |
| ATOM | 3143 | N | ILE | 1008 | 13.671 | 18.672 | 77.579 |
| ATOM | 3144 | CA | ILE | 1008 | 14.304 | 17.724 | 76.666 |
| ATOM | 3145 | CB | ILE | 1008 | 14.726 | 16.407 | 77.393 |
| ATOM | 3146 | CG2 | ILE | 1008 | 14.560 | 15.200 | 76.483 |
| ATOM | 3147 | CG1 | ILE | 1008 | 16.183 | 16.527 | 77.877 |
| ATOM | 3148 | CD1 | ILE | 1008 | 16.429 | 17.695 | 78.780 |
| ATOM | 3149 | C | ILE | 1008 | 13.530 | 17.474 | 75.357 |
| ATOM | 3150 | O | ILE | 1008 | 14.107 | 17.599 | 74.275 |
| ATOM | 3151 | N | VAL | 1009 | 12.242 | 17.156 | 75.421 |
| ATOM | 3152 | CA | VAL | 1009 | 11.494 | 16.958 | 74.180 |
| ATOM | 3153 | CB | VAL | 1009 | 9.981 | 16.690 | 74.432 |
| ATOM | 3154 | CG1 | VAL | 1009 | 9.146 | 17.085 | 73.241 |
| ATOM | 3155 | CG2 | VAL | 1009 | 9.751 | 15.235 | 74.698 |
| ATOM | 3156 | C | VAL | 1009 | 11.662 | 18.215 | 73.331 |
| ATOM | 3157 | O | VAL | 1009 | 11.929 | 18.131 | 72.138 |
| ATOM | 3158 | N | SER | 1010 | 11.586 | 19.376 | 73.964 |
| ATOM | 3159 | CA | SER | 1010 | 11.724 | 20.621 | 73.231 |
| ATOM | 3160 | CB | SER | 1010 | 11.536 | 21.822 | 74.150 |
| ATOM | 3161 | OG | SER | 1010 | 11.625 | 23.039 | 73.420 |
| ATOM | 3162 | C | SER | 1010 | 13.046 | 20.727 | 72.479 |
| ATOM | 3163 | O | SER | 1010 | 13.065 | 20.964 | 71.281 |
| ATOM | 3164 | N | LEU | 1011 | 14.160 | 20.547 | 73.152 |
| ATOM | 3165 | CA | LEU | 1011 | 15.412 | 20.649 | 72.444 |
| ATOM | 3166 | CB | LEU | 1011 | 16.597 | 20.562 | 73.393 |

FIGURE 1OOO

| Atom | | | Residue AA | No. | X | Y | Z |
|---|---|---|---|---|---|---|---|
| ATOM | 3167 | CG | LEU | 1011 | 17.933 | 20.560 | 72.656 |
| ATOM | 3168 | CD1 | LEU | 1011 | 18.599 | 21.935 | 72.688 |
| ATOM | 3169 | CD2 | LEU | 1011 | 18.810 | 19.472 | 73.268 |
| ATOM | 3170 | C | LEU | 1011 | 15.489 | 19.547 | 71.415 |
| ATOM | 3171 | O | LEU | 1011 | 16.263 | 19.633 | 70.487 |
| ATOM | 3172 | N | ALA | 1012 | 14.692 | 18.503 | 71.568 |
| ATOM | 3173 | CA | ALA | 1012 | 14.725 | 17.417 | 70.585 |
| ATOM | 3174 | CB | ALA | 1012 | 14.063 | 16.146 | 71.138 |
| ATOM | 3175 | C | ALA | 1012 | 14.000 | 17.883 | 69.328 |
| ATOM | 3176 | O | ALA | 1012 | 14.624 | 18.113 | 68.286 |
| ATOM | 3177 | N | LYS | 1013 | 12.682 | 18.035 | 69.435 |
| ATOM | 3178 | CA | LYS | 1013 | 11.867 | 18.496 | 68.322 |
| ATOM | 3179 | CB | LYS | 1013 | 10.461 | 18.911 | 68.825 |
| ATOM | 3180 | CG | LYS | 1013 | 9.662 | 19.879 | 67.893 |
| ATOM | 3181 | CD | LYS | 1013 | 9.374 | 19.302 | 66.461 |
| ATOM | 3182 | CE | LYS | 1013 | 8.556 | 20.273 | 65.562 |
| ATOM | 3183 | NZ | LYS | 1013 | 7.900 | 19.639 | 64.367 |
| ATOM | 3184 | C | LYS | 1013 | 12.549 | 19.639 | 67.557 |
| ATOM | 3185 | O | LYS | 1013 | 13.187 | 19.414 | 66.532 |
| ATOM | 3186 | N | HIS | 1014 | 12.513 | 20.829 | 68.129 |
| ATOM | 3187 | CA | HIS | 1014 | 13.065 | 21.981 | 67.492 |
| ATOM | 3188 | CB | HIS | 1014 | 13.011 | 23.161 | 68.446 |
| ATOM | 3189 | CG | HIS | 1014 | 14.227 | 24.041 | 68.371 |
| ATOM | 3190 | CD2 | HIS | 1014 | 14.422 | 25.256 | 67.796 |
| ATOM | 3191 | ND1 | HIS | 1014 | 15.461 | 23.658 | 68.870 |
| ATOM | 3192 | CE1 | HIS | 1014 | 16.359 | 24.592 | 68.602 |
| ATOM | 3193 | NE2 | HIS | 1014 | 15.755 | 25.572 | 67.952 |
| ATOM | 3194 | C | HIS | 1014 | 14.477 | 21.856 | 66.946 |
| ATOM | 3195 | O | HIS | 1014 | 14.849 | 22.587 | 66.027 |
| ATOM | 3196 | N | ARG | 1015 | 15.312 | 21.022 | 67.540 |
| ATOM | 3197 | CA | ARG | 1015 | 16.698 | 20.963 | 67.063 |
| ATOM | 3198 | CB | ARG | 1015 | 17.642 | 20.758 | 68.265 |
| ATOM | 3199 | CG | ARG | 1015 | 19.111 | 20.909 | 67.998 |
| ATOM | 3200 | CD | ARG | 1015 | 19.316 | 21.902 | 66.916 |
| ATOM | 3201 | NE | ARG | 1015 | 18.880 | 23.218 | 67.308 |
| ATOM | 3202 | CZ | ARG | 1015 | 19.718 | 24.138 | 67.762 |
| ATOM | 3203 | NH1 | ARG | 1015 | 21.015 | 23.850 | 67.877 |
| ATOM | 3204 | NH2 | ARG | 1015 | 19.280 | 25.364 | 68.035 |
| ATOM | 3205 | C | ARG | 1015 | 16.904 | 19.928 | 65.969 |
| ATOM | 3206 | O | ARG | 1015 | 17.977 | 19.790 | 65.402 |
| ATOM | 3207 | N | GLY | 1016 | 15.828 | 19.249 | 65.625 |
| ATOM | 3208 | CA | GLY | 1016 | 15.928 | 18.249 | 64.602 |
| ATOM | 3209 | C | GLY | 1016 | 16.545 | 16.999 | 65.179 |
| ATOM | 3210 | O | GLY | 1016 | 17.617 | 16.552 | 64.770 |
| ATOM | 3211 | N | PHE | 1017 | 15.900 | 16.473 | 66.204 |
| ATOM | 3212 | CA | PHE | 1017 | 16.360 | 15.239 | 66.814 |
| ATOM | 3213 | CB | PHE | 1017 | 16.721 | 15.414 | 68.301 |
| ATOM | 3214 | CG | PHE | 1017 | 18.206 | 15.551 | 68.582 |

FIGURE 1PPP

| | Atom | | Residue AA | No. | X | Y | Z |
|---|---|---|---|---|---|---|---|
| ATOM | 3215 | CD1 | PHE | 1017 | 18.815 | 16.795 | 68.632 |
| ATOM | 3216 | CD2 | PHE | 1017 | 18.965 | 14.448 | 68.916 |
| ATOM | 3217 | CE1 | PHE | 1017 | 20.165 | 16.936 | 69.025 |
| ATOM | 3218 | CE2 | PHE | 1017 | 20.309 | 14.586 | 69.306 |
| ATOM | 3219 | CZ | PHE | 1017 | 20.901 | 15.832 | 69.361 |
| ATOM | 3220 | C | PHE | 1017 | 15.149 | 14.342 | 66.634 |
| ATOM | 3221 | O | PHE | 1017 | 15.284 | 13.239 | 66.135 |
| ATOM | 3222 | N | VAL | 1018 | 13.959 | 14.833 | 66.969 |
| ATOM | 3223 | CA | VAL | 1018 | 12.747 | 14.028 | 66.805 |
| ATOM | 3224 | CB | VAL | 1018 | 12.423 | 13.140 | 68.079 |
| ATOM | 3225 | CG1 | VAL | 1018 | 11.304 | 12.166 | 67.786 |
| ATOM | 3226 | CG2 | VAL | 1018 | 13.618 | 12.339 | 68.509 |
| ATOM | 3227 | C | VAL | 1018 | 11.569 | 14.975 | 66.522 |
| ATOM | 3228 | O | VAL | 1018 | 11.442 | 15.994 | 67.200 |
| ATOM | 3229 | N | PHE | 1019 | 10.778 | 14.680 | 65.476 |
| ATOM | 3230 | CA | PHE | 1019 | 9.600 | 15.475 | 65.096 |
| ATOM | 3231 | CB | PHE | 1019 | 9.588 | 15.846 | 63.614 |
| ATOM | 3232 | CG | PHE | 1019 | 10.804 | 16.555 | 63.147 |
| ATOM | 3233 | CD1 | PHE | 1019 | 11.161 | 17.797 | 63.662 |
| ATOM | 3234 | CD2 | PHE | 1019 | 11.621 | 15.969 | 62.192 |
| ATOM | 3235 | CE1 | PHE | 1019 | 12.340 | 18.449 | 63.224 |
| ATOM | 3236 | CE2 | PHE | 1019 | 12.804 | 16.614 | 61.749 |
| ATOM | 3237 | CZ | PHE | 1019 | 13.160 | 17.856 | 62.270 |
| ATOM | 3238 | C | PHE | 1019 | 8.429 | 14.552 | 65.285 |
| ATOM | 3239 | O | PHE | 1019 | 8.550 | 13.346 | 65.077 |
| ATOM | 3240 | N | PRO | 1020 | 7.257 | 15.104 | 65.591 |
| ATOM | 3241 | CD | PRO | 1020 | 6.947 | 16.520 | 65.814 |
| ATOM | 3242 | CA | PRO | 1020 | 6.075 | 14.271 | 65.790 |
| ATOM | 3243 | CB | PRO | 1020 | 5.083 | 15.243 | 66.420 |
| ATOM | 3244 | CG | PRO | 1020 | 5.446 | 16.527 | 65.807 |
| ATOM | 3245 | C | PRO | 1020 | 5.547 | 13.666 | 64.497 |
| ATOM | 3246 | O | PRO | 1020 | 5.394 | 14.358 | 63.481 |
| ATOM | 3247 | N | GLY | 1021 | 5.255 | 12.369 | 64.558 |
| ATOM | 3248 | CA | GLY | 1021 | 4.738 | 11.646 | 63.406 |
| ATOM | 3249 | C | GLY | 1021 | 3.443 | 12.207 | 62.830 |
| ATOM | 3250 | O | GLY | 1021 | 2.609 | 12.742 | 63.574 |
| ATOM | 3251 | N | SER | 1022 | 3.270 | 12.067 | 61.513 |
| ATOM | 3252 | CA | SER | 1022 | 2.086 | 12.569 | 60.826 |
| ATOM | 3253 | CB | SER | 1022 | 0.917 | 11.609 | 61.012 |
| ATOM | 3254 | OG | SER | 1022 | 1.244 | 10.319 | 60.533 |
| ATOM | 3255 | C | SER | 1022 | 1.702 | 13.947 | 61.340 |
| ATOM | 3256 | O | SER | 1022 | 0.540 | 14.339 | 61.266 |
| ATOM | 3257 | N | ASP | 1023 | 2.702 | 14.701 | 61.781 |
| ATOM | 3258 | CA | ASP | 1023 | 2.463 | 16.008 | 62.342 |
| ATOM | 3259 | CB | ASP | 1023 | 3.792 | 16.756 | 62.551 |
| ATOM | 3260 | CG | ASP | 1023 | 3.627 | 18.060 | 63.393 |
| ATOM | 3261 | OD1 | ASP | 1023 | 2.512 | 18.240 | 63.973 |
| ATOM | 3262 | OD2 | ASP | 1023 | 4.601 | 18.889 | 63.475 |

FIGURE 1QQQ

| | Atom | | Residue AA | No. | X | Y | Z |
|---|---|---|---|---|---|---|---|
| ATOM | 3263 | C | ASP | 1023 | 1.465 | 16.884 | 61.581 |
| ATOM | 3264 | O | ASP | 1023 | 0.292 | 16.941 | 61.932 |
| ATOM | 3265 | N | ILE | 1024 | 1.927 | 17.503 | 60.500 |
| ATOM | 3266 | CA | ILE | 1024 | 1.124 | 18.438 | 59.727 |
| ATOM | 3267 | CB | ILE | 1024 | 1.800 | 18.824 | 58.403 |
| ATOM | 3268 | CG2 | ILE | 1024 | 3.235 | 19.322 | 58.646 |
| ATOM | 3269 | CG1 | ILE | 1024 | 1.803 | 17.621 | 57.467 |
| ATOM | 3270 | CD1 | ILE | 1024 | 2.054 | 17.964 | 56.017 |
| ATOM | 3271 | C | ILE | 1024 | -0.317 | 18.061 | 59.459 |
| ATOM | 3272 | O | ILE | 1024 | -1.149 | 18.932 | 59.247 |
| ATOM | 3273 | N | TYR | 1025 | -0.622 | 16.778 | 59.436 |
| ATOM | 3274 | CA | TYR | 1025 | -2.005 | 16.392 | 59.187 |
| ATOM | 3275 | CB | TYR | 1025 | -2.125 | 15.018 | 58.487 |
| ATOM | 3276 | CG | TYR | 1025 | -2.003 | 15.118 | 56.982 |
| ATOM | 3277 | CD1 | TYR | 1025 | -0.920 | 15.792 | 56.410 |
| ATOM | 3278 | CE1 | TYR | 1025 | -0.802 | 15.945 | 55.046 |
| ATOM | 3279 | CD2 | TYR | 1025 | -2.978 | 14.588 | 56.133 |
| ATOM | 3280 | CE2 | TYR | 1025 | -2.869 | 14.734 | 54.748 |
| ATOM | 3281 | CZ | TYR | 1025 | -1.770 | 15.420 | 54.214 |
| ATOM | 3282 | OH | TYR | 1025 | -1.622 | 15.620 | 52.860 |
| ATOM | 3283 | C | TYR | 1025 | -2.772 | 16.400 | 60.493 |
| ATOM | 3284 | O | TYR | 1025 | -3.908 | 16.890 | 60.565 |
| ATOM | 3285 | N | GLY | 1026 | -2.123 | 15.914 | 61.542 |
| ATOM | 3286 | CA | GLY | 1026 | -2.768 | 15.850 | 62.839 |
| ATOM | 3287 | C | GLY | 1026 | -1.974 | 14.958 | 63.760 |
| ATOM | 3288 | O | GLY | 1026 | -2.016 | 15.130 | 64.978 |
| ATOM | 3289 | N | GLY | 1027 | -1.264 | 13.992 | 63.179 |
| ATOM | 3290 | CA | GLY | 1027 | -0.440 | 13.095 | 63.964 |
| ATOM | 3291 | C | GLY | 1027 | -1.010 | 11.712 | 64.131 |
| ATOM | 3292 | O | GLY | 1027 | -1.892 | 11.269 | 63.403 |
| ATOM | 3293 | N | LEU | 1028 | -0.418 | 11.000 | 65.065 |
| ATOM | 3294 | CA | LEU | 1028 | -0.837 | 9.661 | 65.400 |
| ATOM | 3295 | CB | LEU | 1028 | -0.308 | 8.658 | 64.381 |
| ATOM | 3296 | CG | LEU | 1028 | -0.895 | 7.267 | 64.617 |
| ATOM | 3297 | CD1 | LEU | 1028 | -2.359 | 7.304 | 64.264 |
| ATOM | 3298 | CD2 | LEU | 1028 | -0.191 | 6.220 | 63.800 |
| ATOM | 3299 | C | LEU | 1028 | -0.281 | 9.367 | 66.806 |
| ATOM | 3300 | O | LEU | 1028 | 0.860 | 9.758 | 67.144 |
| ATOM | 3301 | N | SER | 1029 | -1.128 | 8.775 | 67.645 |
| ATOM | 3302 | CA | SER | 1029 | -0.776 | 8.418 | 69.014 |
| ATOM | 3303 | CB | SER | 1029 | -1.790 | 7.399 | 69.532 |
| ATOM | 3304 | OG | SER | 1029 | -2.098 | 6.439 | 68.531 |
| ATOM | 3305 | C | SER | 1029 | 0.666 | 7.909 | 69.250 |
| ATOM | 3306 | O | SER | 1029 | 1.082 | 6.839 | 68.753 |
| ATOM | 3307 | N | ASN | 1030 | 1.412 | 8.735 | 69.985 |
| ATOM | 3308 | CA | ASN | 1030 | 2.797 | 8.475 | 70.367 |
| ATOM | 3309 | CB | ASN | 1030 | 2.847 | 7.686 | 71.675 |
| ATOM | 3310 | CG | ASN | 1030 | 3.887 | 8.247 | 72.679 |

FIGURE 1RRR

| Atom | | | Residue AA | No. | X | Y | Z |
|---|---|---|---|---|---|---|---|
| ATOM | 3311 | OD1 | ASN | 1030 | 5.073 | 8.472 | 72.335 |
| ATOM | 3312 | ND2 | ASN | 1030 | 3.430 | 8.503 | 73.920 |
| ATOM | 3313 | C | ASN | 1030 | 3.580 | 7.738 | 69.319 |
| ATOM | 3314 | O | ASN | 1030 | 3.973 | 6.594 | 69.505 |
| ATOM | 3315 | N | THR | 1031 | 3.748 | 8.387 | 68.189 |
| ATOM | 3316 | CA | THR | 1031 | 4.481 | 7.808 | 67.084 |
| ATOM | 3317 | CB | THR | 1031 | 3.493 | 7.214 | 65.993 |
| ATOM | 3318 | OG1 | THR | 1031 | 2.355 | 8.069 | 65.840 |
| ATOM | 3319 | CG2 | THR | 1031 | 2.960 | 5.823 | 66.429 |
| ATOM | 3320 | C | THR | 1031 | 5.384 | 8.969 | 66.621 |
| ATOM | 3321 | O | THR | 1031 | 4.920 | 10.107 | 66.439 |
| ATOM | 3322 | N | TRP | 1032 | 6.687 | 8.697 | 66.544 |
| ATOM | 3323 | CA | TRP | 1032 | 7.702 | 9.716 | 66.214 |
| ATOM | 3324 | CB | TRP | 1032 | 8.655 | 9.893 | 67.434 |
| ATOM | 3325 | CG | TRP | 1032 | 7.926 | 10.244 | 68.681 |
| ATOM | 3326 | CD2 | TRP | 1032 | 7.780 | 11.563 | 69.228 |
| ATOM | 3327 | CE2 | TRP | 1032 | 6.765 | 11.495 | 70.209 |
| ATOM | 3328 | CE3 | TRP | 1032 | 8.393 | 12.802 | 68.965 |
| ATOM | 3329 | CD1 | TRP | 1032 | 7.055 | 9.439 | 69.376 |
| ATOM | 3330 | NE1 | TRP | 1032 | 6.344 | 10.190 | 70.278 |
| ATOM | 3331 | CZ2 | TRP | 1032 | 6.346 | 12.616 | 70.920 |
| ATOM | 3332 | CZ3 | TRP | 1032 | 7.981 | 13.910 | 69.668 |
| ATOM | 3333 | CH2 | TRP | 1032 | 6.962 | 13.811 | 70.637 |
| ATOM | 3334 | C | TRP | 1032 | 8.554 | 9.538 | 64.942 |
| ATOM | 3335 | O | TRP | 1032 | 8.884 | 8.415 | 64.510 |
| ATOM | 3336 | N | ASP | 1033 | 8.925 | 10.668 | 64.364 |
| ATOM | 3337 | CA | ASP | 1033 | 9.761 | 10.648 | 63.196 |
| ATOM | 3338 | CB | ASP | 1033 | 9.198 | 11.566 | 62.089 |
| ATOM | 3339 | CG | ASP | 1033 | 7.923 | 11.003 | 61.398 |
| ATOM | 3340 | OD1 | ASP | 1033 | 7.109 | 11.826 | 60.932 |
| ATOM | 3341 | OD2 | ASP | 1033 | 7.722 | 9.770 | 61.274 |
| ATOM | 3342 | C | ASP | 1033 | 11.124 | 11.139 | 63.677 |
| ATOM | 3343 | O | ASP | 1033 | 11.212 | 12.133 | 64.392 |
| ATOM | 3344 | N | TYR | 1034 | 12.167 | 10.376 | 63.377 |
| ATOM | 3345 | CA | TYR | 1034 | 13.519 | 10.756 | 63.749 |
| ATOM | 3346 | CB | TYR | 1034 | 14.451 | 9.542 | 63.830 |
| ATOM | 3347 | CG | TYR | 1034 | 14.262 | 8.753 | 65.100 |
| ATOM | 3348 | CD1 | TYR | 1034 | 13.007 | 8.235 | 65.442 |
| ATOM | 3349 | CE1 | TYR | 1034 | 12.803 | 7.565 | 66.655 |
| ATOM | 3350 | CD2 | TYR | 1034 | 15.313 | 8.578 | 65.998 |
| ATOM | 3351 | CE2 | TYR | 1034 | 15.114 | 7.907 | 67.221 |
| ATOM | 3352 | CZ | TYR | 1034 | 13.855 | 7.405 | 67.538 |
| ATOM | 3353 | OH | TYR | 1034 | 13.634 | 6.746 | 68.727 |
| ATOM | 3354 | C | TYR | 1034 | 14.033 | 11.725 | 62.729 |
| ATOM | 3355 | O | TYR | 1034 | 14.210 | 11.379 | 61.581 |
| ATOM | 3356 | N | GLY | 1035 | 14.242 | 12.952 | 63.168 |
| ATOM | 3357 | CA | GLY | 1035 | 14.738 | 13.995 | 62.304 |
| ATOM | 3358 | C | GLY | 1035 | 16.183 | 13.774 | 61.969 |

FIGURE 1SSS

| | Atom | | Residue AA | No. | X | Y | Z |
|---|---|---|---|---|---|---|---|
| ATOM | 3359 | O | GLY | 1035 | 16.791 | 12.861 | 62.501 |
| ATOM | 3360 | N | PRO | 1036 | 16.783 | 14.674 | 61.181 |
| ATOM | 3361 | CD | PRO | 1036 | 16.112 | 15.961 | 60.949 |
| ATOM | 3362 | CA | PRO | 1036 | 18.160 | 14.727 | 60.672 |
| ATOM | 3363 | CB | PRO | 1036 | 18.328 | 16.187 | 60.325 |
| ATOM | 3364 | CG | PRO | 1036 | 16.971 | 16.570 | 59.899 |
| ATOM | 3365 | C | PRO | 1036 | 19.203 | 14.293 | 61.662 |
| ATOM | 3366 | O | PRO | 1036 | 20.117 | 13.552 | 61.319 |
| ATOM | 3367 | N | LEU | 1037 | 19.080 | 14.780 | 62.886 |
| ATOM | 3368 | CA | LEU | 1037 | 20.013 | 14.430 | 63.922 |
| ATOM | 3369 | CB | LEU | 1037 | 20.137 | 15.586 | 64.888 |
| ATOM | 3370 | CG | LEU | 1037 | 20.931 | 16.710 | 64.230 |
| ATOM | 3371 | CD1 | LEU | 1037 | 21.078 | 17.942 | 65.103 |
| ATOM | 3372 | CD2 | LEU | 1037 | 22.288 | 16.152 | 63.923 |
| ATOM | 3373 | C | LEU | 1037 | 19.626 | 13.138 | 64.628 |
| ATOM | 3374 | O | LEU | 1037 | 20.491 | 12.327 | 64.981 |
| ATOM | 3375 | N | GLY | 1038 | 18.320 | 12.913 | 64.753 |
| ATOM | 3376 | CA | GLY | 1038 | 17.805 | 11.716 | 65.408 |
| ATOM | 3377 | C | GLY | 1038 | 18.267 | 10.413 | 64.806 |
| ATOM | 3378 | O | GLY | 1038 | 18.590 | 9. | 65.525 |
| ATOM | 3379 | N | VAL | 1039 | 18.259 | 10.347 | 63.479 |
| ATOM | 3380 | CA | VAL | 1039 | 18.714 | 9.159 | 62.750 |
| ATOM | 3381 | CB | VAL | 1039 | 18.710 | 9.318 | 61.236 |
| ATOM | 3382 | CG1 | VAL | 1039 | 17.493 | 8.695 | 60.667 |
| ATOM | 3383 | CG2 | VAL | 1039 | 18.822 | 10.759 | 60.842 |
| ATOM | 3384 | C | VAL | 1039 | 20.141 | 8.855 | 63.069 |
| ATOM | 3385 | O | VAL | 1039 | 20.462 | 7.748 | 63.477 |
| ATOM | 3386 | N | GLU | 1040 | 21.008 | 9.830 | 62.840 |
| ATOM | 3387 | CA | GLU | 1040 | 22.420 | 9.644 | 63.122 |
| ATOM | 3388 | CB | GLU | 1040 | 23.193 | 10.959 | 62.921 |
| ATOM | 3389 | CG | GLU | 1040 | 24.292 | 10.919 | 61.809 |
| ATOM | 3390 | CD | GLU | 1040 | 23.766 | 10.636 | 60.374 |
| ATOM | 3391 | OE1 | GLU | 1040 | 22.823 | 11.326 | 59.912 |
| ATOM | 3392 | OE2 | GLU | 1040 | 24.326 | 9.737 | 59.694 |
| ATOM | 3393 | C | GLU | 1040 | 22.618 | 9.055 | 64.530 |
| ATOM | 3394 | O | GLU | 1040 | 23.083 | 7.911 | 64.656 |
| ATOM | 3395 | N | LEU | 1041 | 22.148 | 9.763 | 65.563 |
| ATOM | 3396 | CA | LEU | 1041 | 22.267 | 9.264 | 66.945 |
| ATOM | 3397 | CB | LEU | 1041 | 21.535 | 10.170 | 67.942 |
| ATOM | 3398 | CG | LEU | 1041 | 21.648 | 9.783 | 69.408 |
| ATOM | 3399 | CD1 | LEU | 1041 | 22.933 | 10.273 | 69.901 |
| ATOM | 3400 | CD2 | LEU | 1041 | 20.541 | 10.395 | 70.188 |
| ATOM | 3401 | C | LEU | 1041 | 21.718 | 7.831 | 67.066 |
| ATOM | 3402 | O | LEU | 1041 | 22.452 | 6.922 | 67.486 |
| ATOM | 3403 | N | LYS | 1042 | 20.467 | 7.614 | 66.638 |
| ATOM | 3404 | CA | LYS | 1042 | 19.854 | 6.285 | 66.721 |
| ATOM | 3405 | CB | LYS | 1042 | 18.446 | 6.272 | 66.159 |
| ATOM | 3406 | CG | LYS | 1042 | 17.727 | 4.983 | 66.419 |

FIGURE 1TTT

| Atom | | | Residue AA | No. | X | Y | Z |
|---|---|---|---|---|---|---|---|
| ATOM | 3407 | CD | LYS | 1042 | 16.323 | 5.100 | 65.901 |
| ATOM | 3408 | CE | LYS | 1042 | 15.472 | 3.874 | 66.186 |
| ATOM | 3409 | NZ | LYS | 1042 | 14.131 | 3.905 | 65.508 |
| ATOM | 3410 | C | LYS | 1042 | 20.679 | 5.247 | 66.004 |
| ATOM | 3411 | O | LYS | 1042 | 20.679 | 4.078 | 66.387 |
| ATOM | 3412 | N | ASN | 1043 | 21.421 | 5.692 | 64.992 |
| ATOM | 3413 | CA | ASN | 1043 | 22.262 | 4.809 | 64.210 |
| ATOM | 3414 | CB | ASN | 1043 | 22.296 | 5.231 | 62.749 |
| ATOM | 3415 | CG | ASN | 1043 | 21.194 | 4.560 | 61.940 |
| ATOM | 3416 | OD1 | ASN | 1043 | 20.269 | 5.207 | 61.433 |
| ATOM | 3417 | ND2 | ASN | 1043 | 21.264 | 3.241 | 61.856 |
| ATOM | 3418 | C | ASN | 1043 | 23.639 | 4.612 | 64.779 |
| ATOM | 3419 | O | ASN | 1043 | 24.239 | 3.571 | 64.576 |
| ATOM | 3420 | N | ASN | 1044 | 24.139 | 5.593 | 65.509 |
| ATOM | 3421 | CA | ASN | 1044 | 25.434 | 5.438 | 66.140 |
| ATOM | 3422 | CB | ASN | 1044 | 25.948 | 6.764 | 66.691 |
| ATOM | 3423 | CG | ASN | 1044 | 26.359 | 7.736 | 65.605 |
| ATOM | 3424 | OD1 | ASN | 1044 | 25.509 | 8.362 | 64.982 |
| ATOM | 3425 | ND2 | ASN | 1044 | 27.670 | 7.899 | 65.401 |
| ATOM | 3426 | C | ASN | 1044 | 25.182 | 4.478 | 67.289 |
| ATOM | 3427 | O | ASN | 1044 | 26.061 | 3.715 | 67.696 |
| ATOM | 3428 | N | VAL | 1045 | 23.967 | 4.541 | 67.820 |
| ATOM | 3429 | CA | VAL | 1045 | 23.553 | 3.674 | 68.908 |
| ATOM | 3430 | CB | VAL | 1045 | 22.146 | 4.066 | 69.433 |
| ATOM | 3431 | CG1 | VAL | 1045 | 21.584 | 2.982 | 70.313 |
| ATOM | 3432 | CG2 | VAL | 1045 | 22.205 | 5.351 | 70.202 |
| ATOM | 3433 | C | VAL | 1045 | 23.464 | 2.300 | 68.280 |
| ATOM | 3434 | O | VAL | 1045 | 24.164 | 1.356 | 68.677 |
| ATOM | 3435 | N | LYS | 1046 | 22.691 | 2.261 | 67.203 |
| ATOM | 3436 | CA | LYS | 1046 | 22.408 | 1.049 | 66.460 |
| ATOM | 3437 | CB | LYS | 1046 | 21.339 | 1.354 | 65.406 |
| ATOM | 3438 | CG | LYS | 1046 | 20.245 | 0.275 | 65.273 |
| ATOM | 3439 | CD | LYS | 1046 | 18.847 | 0.821 | 64.882 |
| ATOM | 3440 | CE | LYS | 1046 | 18.769 | 1.322 | 63.435 |
| ATOM | 3441 | NZ | LYS | 1046 | 17.477 | 1.993 | 63.125 |
| ATOM | 3442 | C | LYS | 1046 | 23.614 | 0.360 | 65.841 |
| ATOM | 3443 | O | LYS | 1046 | 23.584 | -0.822 | 65.528 |
| ATOM | 3444 | N | ALA | 1047 | 24.704 | 1.080 | 65.711 |
| ATOM | 3445 | CA | ALA | 1047 | 25.880 | 0.483 | 65.122 |
| ATOM | 3446 | CB | ALA | 1047 | 26.516 | 1.460 | 64.160 |
| ATOM | 3447 | C | ALA | 1047 | 26.899 | -0.004 | 66.149 |
| ATOM | 3448 | O | ALA | 1047 | 27.506 | -1.050 | 65.963 |
| ATOM | 3449 | N | ALA | 1048 | 27.089 | 0.752 | 67.227 |
| ATOM | 3450 | CA | ALA | 1048 | 28.033 | 0.391 | 68.264 |
| ATOM | 3451 | CB | ALA | 1048 | 28.036 | 1.432 | 69.304 |
| ATOM | 3452 | C | ALA | 1048 | 27.605 | -0.930 | 68.837 |
| ATOM | 3453 | O | ALA | 1048 | 28.428 | -1.737 | 69.227 |
| ATOM | 3454 | N | TRP | 1049 | 26.302 | -1.149 | 68.845 |

FIGURE 1UUU

| Atom | | | Residue AA | No. | X | Y | Z |
|---|---|---|---|---|---|---|---|
| ATOM | 3455 | CA | TRP | 1049 | 25.731 | -2.376 | 69.337 |
| ATOM | 3456 | CB | TRP | 1049 | 24.226 | -2.294 | 69.247 |
| ATOM | 3457 | CG | TRP | 1049 | 23.570 | -3.354 | 69.978 |
| ATOM | 3458 | CD2 | TRP | 1049 | 23.235 | -4.654 | 69.503 |
| ATOM | 3459 | CE2 | TRP | 1049 | 22.637 | -5.340 | 70.556 |
| ATOM | 3460 | CE3 | TRP | 1049 | 23.374 | -5.305 | 68.287 |
| ATOM | 3461 | CD1 | TRP | 1049 | 23.171 | -3.304 | 71.253 |
| ATOM | 3462 | NE1 | TRP | 1049 | 22.607 | -4.490 | 71.622 |
| ATOM | 3463 | CZ2 | TRP | 1049 | 22.180 | -6.654 | 70.433 |
| ATOM | 3464 | CZ3 | TRP | 1049 | 22.911 | -6.619 | 68.167 |
| ATOM | 3465 | CH2 | TRP | 1049 | 22.327 | -7.269 | 69.229 |
| ATOM | 3466 | C | TRP | 1049 | 26.199 | -3.541 | 68.493 |
| ATOM | 3467 | O | TRP | 1049 | 26.765 | -4.500 | 68.993 |
| ATOM | 3468 | N | TRP | 1050 | 25.921 | -3.457 | 67.200 |
| ATOM | 3469 | CA | TRP | 1050 | 26.281 | -4.507 | 66.249 |
| ATOM | 3470 | CB | TRP | 1050 | 25.881 | -4.098 | 64.807 |
| ATOM | 3471 | CG | TRP | 1050 | 25.739 | -5.264 | 63.853 |
| ATOM | 3472 | CD2 | TRP | 1050 | 24.538 | -5.990 | 63.552 |
| ATOM | 3473 | CE2 | TRP | 1050 | 24.901 | -7.088 | 62.752 |
| ATOM | 3474 | CE3 | TRP | 1050 | 23.202 | -5.826 | 63.891 |
| ATOM | 3475 | CD1 | TRP | 1050 | 26.744 | -5.919 | 63.216 |
| ATOM | 3476 | NE1 | TRP | 1050 | 26.251 | -7.021 | 62.558 |
| ATOM | 3477 | CZ2 | TRP | 1050 | 23.982 | -8.014 | 62.299 |
| ATOM | 3478 | CZ3 | TRP | 1050 | 22.289 | -6.745 | 63.438 |
| ATOM | 3479 | CH2 | TRP | 1050 | 22.680 | -7.827 | 62.653 |
| ATOM | 3480 | C | TRP | 1050 | 27.778 | -4.745 | 66.340 |
| ATOM | 3481 | O | TRP | 1050 | 28.246 | -5.880 | 66.429 |
| ATOM | 3482 | N | GLN | 1051 | 28.509 | -3.641 | 66.369 |
| ATOM | 3483 | CA | GLN | 1051 | 29.951 | -3.628 | 66.423 |
| ATOM | 3484 | CB | GLN | 1051 | 30.418 | -2.223 | 66.755 |
| ATOM | 3485 | CG | GLN | 1051 | 31.529 | -1.714 | 65.899 |
| ATOM | 3486 | CD | GLN | 1051 | 32.839 | -2.399 | 66.175 |
| ATOM | 3487 | OE1 | GLN | 1051 | 33.586 | -2.013 | 67.081 |
| ATOM | 3488 | NE2 | GLN | 1051 | 33.144 | -3.413 | 65.381 |
| ATOM | 3489 | C | GLN | 1051 | 30.428 | -4.594 | 67.468 |
| ATOM | 3490 | O | GLN | 1051 | 30.946 | -5.646 | 67.116 |
| ATOM | 3491 | N | LYS | 1052 | 30.102 | -4.296 | 68.727 |
| ATOM | 3492 | CA | LYS | 1052 | 30.514 | -5.085 | 69.889 |
| ATOM | 3493 | CB | LYS | 1052 | 30.470 | -4.214 | 71.143 |
| ATOM | 3494 | CG | LYS | 1052 | 31.187 | -2.869 | 71.052 |
| ATOM | 3495 | CD | LYS | 1052 | 32.667 | -3.058 | 70.865 |
| ATOM | 3496 | CE | LYS | 1052 | 33.428 | -1.754 | 71.023 |
| ATOM | 3497 | NZ | LYS | 1052 | 34.874 | -1.806 | 70.568 |
| ATOM | 3498 | C | LYS | 1052 | 29.755 | -6.382 | 70.145 |
| ATOM | 3499 | O | LYS | 1052 | 30.364 | -7.407 | 70.418 |
| ATOM | 3500 | N | PHE | 1053 | 28.436 | -6.344 | 70.055 |
| ATOM | 3501 | CA | PHE | 1053 | 27.632 | -7.536 | 70.286 |
| ATOM | 3502 | CB | PHE | 1053 | 26.182 | -7.153 | 70.521 |

FIGURE 1VVV

| | Atom | | Residue AA | No. | X | Y | Z |
|---|---|---|---|---|---|---|---|
| ATOM | 3503 | CG | PHE | 1053 | 25.843 | -6.979 | 71.961 |
| ATOM | 3504 | CD1 | PHE | 1053 | 25.881 | -5.730 | 72.543 |
| ATOM | 3505 | CD2 | PHE | 1053 | 25.517 | -8.073 | 72.756 |
| ATOM | 3506 | CE1 | PHE | 1053 | 25.599 | -5.570 | 73.910 |
| ATOM | 3507 | CE2 | PHE | 1053 | 25.237 | -7.916 | 74.116 |
| ATOM | 3508 | CZ | PHE | 1053 | 25.278 | -6.669 | 74.690 |
| ATOM | 3509 | C | PHE | 1053 | 27.667 | -8.672 | 69.269 |
| ATOM | 3510 | O | PHE | 1053 | 27.268 | -9.787 | 69.578 |
| ATOM | 3511 | N | ILE | 1054 | 28.119 | -8.396 | 68.053 |
| ATOM | 3512 | CA | ILE | 1054 | 28.158 | -9.416 | 66.995 |
| ATOM | 3513 | CB | ILE | 1054 | 27.085 | -9.142 | 65.942 |
| ATOM | 3514 | CG2 | ILE | 1054 | 26.901 | -10.351 | 65.075 |
| ATOM | 3515 | CG1 | ILE | 1054 | 25.773 | -8.725 | 66.592 |
| ATOM | 3516 | CD1 | ILE | 1054 | 25.062 | -9.805 | 67.306 |
| ATOM | 3517 | C | ILE | 1054 | 29.467 | -9.495 | 66.211 |
| ATOM | 3518 | O | ILE | 1054 | 30.024 | -10.584 | 65.965 |
| ATOM | 3519 | N | THR | 1055 | 29.911 | -8.328 | 65.762 |
| ATOM | 3520 | CA | THR | 1055 | 31.115 | -8.273 | 64.969 |
| ATOM | 3521 | CB | THR | 1055 | 31.374 | -6.848 | 64.368 |
| ATOM | 3522 | OG1 | THR | 1055 | 30.339 | -6.527 | 63.420 |
| ATOM | 3523 | CG2 | THR | 1055 | 32.724 | -6.809 | 63.637 |
| ATOM | 3524 | C | THR | 1055 | 32.315 | -8.820 | 65.721 |
| ATOM | 3525 | O | THR | 1055 | 32.998 | -9.715 | 65.231 |
| ATOM | 3526 | N | GLN | 1056 | 32.530 | -8.337 | 66.935 |
| ATOM | 3527 | CA | GLN | 1056 | 33.663 | -8.784 | 67.720 |
| ATOM | 3528 | CB | GLN | 1056 | 34.167 | -7.646 | 68.600 |
| ATOM | 3529 | CG | GLN | 1056 | 34.785 | -6.526 | 67.791 |
| ATOM | 3530 | CD | GLN | 1056 | 34.650 | -5.175 | 68.454 |
| ATOM | 3531 | OE1 | GLN | 1056 | 33.572 | -4.605 | 68.502 |
| ATOM | 3532 | NE2 | GLN | 1056 | 35.746 | -4.655 | 68.969 |
| ATOM | 3533 | C | GLN | 1056 | 33.470 | -10.067 | 68.520 |
| ATOM | 3534 | O | GLN | 1056 | 34.394 | -10.853 | 68.621 |
| ATOM | 3535 | N | SER | 1057 | 32.277 | -10.316 | 69.047 |
| ATOM | 3536 | CA | SER | 1057 | 32.034 | -11.515 | 69.844 |
| ATOM | 3537 | CB | SER | 1057 | 30.842 | -11.284 | 70.757 |
| ATOM | 3538 | OG | SER | 1057 | 29.737 | -10.882 | 69.977 |
| ATOM | 3539 | C | SER | 1057 | 31.773 | -12.722 | 68.984 |
| ATOM | 3540 | O | SER | 1057 | 30.644 | -12.970 | 68.622 |
| ATOM | 3541 | N | PRO | 1058 | 32.782 | -13.575 | 68.793 |
| ATOM | 3542 | CD | PRO | 1058 | 34.055 | -13.526 | 69.510 |
| ATOM | 3543 | CA | PRO | 1058 | 32.729 | -14.796 | 67.989 |
| ATOM | 3544 | CB | PRO | 1058 | 34.023 | -15.494 | 68.359 |
| ATOM | 3545 | CG | PRO | 1058 | 34.906 | -14.388 | 68.639 |
| ATOM | 3546 | C | PRO | 1058 | 31.543 | -15.689 | 68.303 |
| ATOM | 3547 | O | PRO | 1058 | 31.174 | -16.556 | 67.532 |
| ATOM | 3548 | N | PHE | 1059 | 30.956 | -15.493 | 69.462 |
| ATOM | 3549 | CA | PHE | 1059 | 29.812 | -16.288 | 69.846 |
| ATOM | 3550 | CB | PHE | 1059 | 29.321 | -15.873 | 71.242 |

FIGURE 1WWW

| | Atom | | Residue AA | No. | X | Y | Z |
|---|---|---|---|---|---|---|---|
| ATOM | 3551 | CG | PHE | 1059 | 30.318 | -16.081 | 72.317 |
| ATOM | 3552 | CD1 | PHE | 1059 | 30.733 | -17.367 | 72.656 |
| ATOM | 3553 | CD2 | PHE | 1059 | 30.827 | -14.986 | 73.016 |
| ATOM | 3554 | CE1 | PHE | 1059 | 31.652 | -17.578 | 73.696 |
| ATOM | 3555 | CE2 | PHE | 1059 | 31.752 | -15.163 | 74.065 |
| ATOM | 3556 | CZ | PHE | 1059 | 32.168 | -16.470 | 74.412 |
| ATOM | 3557 | C | PHE | 1059 | 28.640 | -16.112 | 68.897 |
| ATOM | 3558 | O | PHE | 1059 | 28.062 | -17.073 | 68.418 |
| ATOM | 3559 | N | ASN | 1060 | 28.321 | -14.870 | 68.604 |
| ATOM | 3560 | CA | ASN | 1060 | 27.143 | -14.595 | 67.826 |
| ATOM | 3561 | CB | ASN | 1060 | 26.298 | -13.595 | 68.593 |
| ATOM | 3562 | CG | ASN | 1060 | 26.832 | -13.324 | 69.961 |
| ATOM | 3563 | OD1 | ASN | 1060 | 26.202 | -13.659 | 70.944 |
| ATOM | 3564 | ND2 | ASN | 1060 | 28.018 | -12.750 | 70.036 |
| ATOM | 3565 | C | ASN | 1060 | 27.233 | -14.173 | 66.364 |
| ATOM | 3566 | O | ASN | 1060 | 28.276 | -13.706 | 65.873 |
| ATOM | 3567 | N | VAL | 1061 | 26.083 | -14.305 | 65.701 |
| ATOM | 3568 | CA | VAL | 1061 | 25.896 | -13.971 | 64.306 |
| ATOM | 3569 | CB | VAL | 1061 | 25.641 | -15.228 | 63.468 |
| ATOM | 3570 | CG1 | VAL | 1061 | 26.875 | -16.099 | 63.424 |
| ATOM | 3571 | CG2 | VAL | 1061 | 24.468 | -16.001 | 64.024 |
| ATOM | 3572 | C | VAL | 1061 | 24.648 | -13.140 | 64.265 |
| ATOM | 3573 | O | VAL | 1061 | 23.841 | -13.223 | 65.168 |
| ATOM | 3574 | N | GLY | 1062 | 24.483 | -12.338 | 63.230 |
| ATOM | 3575 | CA | GLY | 1062 | 23.291 | -11.533 | 63.160 |
| ATOM | 3576 | C | GLY | 1062 | 22.385 | -12.065 | 62.095 |
| ATOM | 3577 | O | GLY | 1062 | 22.748 | -13.010 | 61.414 |
| ATOM | 3578 | N | ILE | 1063 | 21.153 | -11.575 | 62.077 |
| ATOM | 3579 | CA | ILE | 1063 | 20.173 | -11.915 | 61.054 |
| ATOM | 3580 | CB | ILE | 1063 | 19.431 | -13.277 | 61.289 |
| ATOM | 3581 | CG2 | ILE | 1063 | 20.326 | -14.290 | 61.870 |
| ATOM | 3582 | CG1 | ILE | 1063 | 18.250 | -13.128 | 62.209 |
| ATOM | 3583 | CD1 | ILE | 1063 | 17.295 | -14.279 | 62.064 |
| ATOM | 3584 | C | ILE | 1063 | 19.190 | -10.719 | 60.845 |
| ATOM | 3585 | O | ILE | 1063 | 19.408 | -9.602 | 61.339 |
| ATOM | 3586 | N | ASP | 1064 | 18.210 | -10.907 | 59.976 |
| ATOM | 3587 | CA | ASP | 1064 | 17.207 | -9.890 | 59.702 |
| ATOM | 3588 | CB | ASP | 1064 | 17.657 | -8.958 | 58.567 |
| ATOM | 3589 | CG | ASP | 1064 | 16.753 | -7.731 | 58.400 |
| ATOM | 3590 | OD1 | ASP | 1064 | 15.524 | -7.882 | 58.274 |
| ATOM | 3591 | OD2 | ASP | 1064 | 17.276 | -6.599 | 58.374 |
| ATOM | 3592 | C | ASP | 1064 | 15.975 | -10.677 | 59.276 |
| ATOM | 3593 | O | ASP | 1064 | 15.893 | -11.125 | 58.135 |
| ATOM | 3594 | N | ALA | 1065 | 15.071 | -10.924 | 60.223 |
| ATOM | 3595 | CA | ALA | 1065 | 13.849 | -11.655 | 59.949 |
| ATOM | 3596 | CB | ALA | 1065 | 13.348 | -12.314 | 61.179 |
| ATOM | 3597 | C | ALA | 1065 | 12.795 | -10.723 | 59.390 |
| ATOM | 3598 | O | ALA | 1065 | 12.952 | -9.500 | 59.399 |

FIGURE 1XXX

| Atom | | | Residue AA | No. | X | Y | Z |
|---|---|---|---|---|---|---|---|
| ATOM | 3599 | N | ALA | 1066 | 11.683 | -11.310 | 58.981 |
| ATOM | 3600 | CA | ALA | 1066 | 10.593 | -10.568 | 58.373 |
| ATOM | 3601 | CB | ALA | 1066 | 9.923 | -11.466 | 57.329 |
| ATOM | 3602 | C | ALA | 1066 | 9.546 | -10.040 | 59.363 |
| ATOM | 3603 | O | ALA | 1066 | 9.060 | -10.784 | 60.194 |
| ATOM | 3604 | N | ILE | 1067 | 9.173 | -8.772 | 59.266 |
| ATOM | 3605 | CA | ILE | 1067 | 8.163 | -8.265 | 60.158 |
| ATOM | 3606 | CB | ILE | 1067 | 7.889 | -6.832 | 59.885 |
| ATOM | 3607 | CG2 | ILE | 1067 | 6.698 | -6.378 | 60.633 |
| ATOM | 3608 | CG1 | ILE | 1067 | 9.080 | -6.005 | 60.300 |
| ATOM | 3609 | CD1 | ILE | 1067 | 8.840 | -4.563 | 60.098 |
| ATOM | 3610 | C | ILE | 1067 | 6.896 | -9.076 | 59.950 |
| ATOM | 3611 | O | ILE | 1067 | 6.111 | -9.251 | 60.853 |
| ATOM | 3612 | N | LEU | 1068 | 6.705 | -9.599 | 58.757 |
| ATOM | 3613 | CA | LEU | 1068 | 5.525 | -10.408 | 58.469 |
| ATOM | 3614 | CB | LEU | 1068 | 4.983 | -10.089 | 57.062 |
| ATOM | 3615 | CG | LEU | 1068 | 4.171 | -8.836 | 56.686 |
| ATOM | 3616 | CD1 | LEU | 1068 | 2.824 | -8.875 | 57.365 |
| ATOM | 3617 | CD2 | LEU | 1068 | 4.915 | -7.564 | 57.024 |
| ATOM | 3618 | C | LEU | 1068 | 5.846 | -11.904 | 58.550 |
| ATOM | 3619 | O | LEU | 1068 | 6.740 | -12.409 | 57.852 |
| ATOM | 3620 | N | MET | 1069 | 5.118 | -12.622 | 59.393 |
| ATOM | 3621 | CA | MET | 1069 | 5.337 | -14.058 | 59.504 |
| ATOM | 3622 | CB | MET | 1069 | 6.527 | -14.410 | 60.429 |
| ATOM | 3623 | CG | MET | 1069 | 6.660 | -13.695 | 61.790 |
| ATOM | 3624 | SD | MET | 1069 | 8.204 | -14.269 | 62.657 |
| ATOM | 3625 | CE | MET | 1069 | 9.378 | -12.878 | 62.538 |
| ATOM | 3626 | C | MET | 1069 | 4.115 | -14.915 | 59.811 |
| ATOM | 3627 | O | MET | 1069 | 3.081 | -14.428 | 60.277 |
| ATOM | 3628 | N | ASN | 1070 | 4.231 | -16.171 | 59.395 |
| ATOM | 3629 | CA | ASN | 1070 | 3.232 | -17.214 | 59.565 |
| ATOM | 3630 | CB | ASN | 1070 | 3.883 | -18.581 | 59.295 |
| ATOM | 3631 | CG | ASN | 1070 | 2.879 | -19.721 | 59.268 |
| ATOM | 3632 | OD1 | ASN | 1070 | 3.036 | -20.727 | 59.959 |
| ATOM | 3633 | ND2 | ASN | 1070 | 1.848 | -19.573 | 58.461 |
| ATOM | 3634 | C | ASN | 1070 | 2.609 | -17.200 | 60.958 |
| ATOM | 3635 | O | ASN | 1070 | 3.222 | -17.627 | 61.934 |
| ATOM | 3636 | N | PRO | 1071 | 1.333 | -16.820 | 61.046 |
| ATOM | 3637 | CD | PRO | 1071 | 0.430 | -16.583 | 59.913 |
| ATOM | 3638 | CA | PRO | 1071 | 0.607 | -16.748 | 62.316 |
| ATOM | 3639 | CB | PRO | 1071 | -0.843 | -16.599 | 61.888 |
| ATOM | 3640 | CG | PRO | 1071 | -0.737 | -15.885 | 60.591 |
| ATOM | 3641 | C | PRO | 1071 | 0.783 | -17.960 | 63.189 |
| ATOM | 3642 | O | PRO | 1071 | 0.831 | -17.796 | 64.400 |
| ATOM | 3643 | N | ALA | 1072 | 0.909 | -19.155 | 62.596 |
| ATOM | 3644 | CA | ALA | 1072 | 1.078 | -20.390 | 63.377 |
| ATOM | 3645 | CB | ALA | 1072 | 1.395 | -21.592 | 62.475 |
| ATOM | 3646 | C | ALA | 1072 | 2.148 | -20.202 | 64.459 |

FIGURE 1YYY

| Atom | | | Residue AA | No. | X | Y | Z |
|---|---|---|---|---|---|---|---|
| ATOM | 3647 | O | ALA | 1072 | 2.017 | -20.728 | 65.572 |
| ATOM | 3648 | N | VAL | 1073 | 3.159 | -19.390 | 64.161 |
| ATOM | 3649 | CA | VAL | 1073 | 4.202 | -19.105 | 65.131 |
| ATOM | 3650 | CB | VAL | 1073 | 5.247 | -18.146 | 64.572 |
| ATOM | 3651 | CG1 | VAL | 1073 | 5.878 | -17.312 | 65.670 |
| ATOM | 3652 | CG2 | VAL | 1073 | 6.298 | -18.941 | 63.866 |
| ATOM | 3653 | C | VAL | 1073 | 3.583 | -18.478 | 66.360 |
| ATOM | 3654 | O | VAL | 1073 | 3.705 | -18.996 | 67.466 |
| ATOM | 3655 | N | TRP | 1074 | 2.839 | -17.407 | 66.150 |
| ATOM | 3656 | CA | TRP | 1074 | 2.208 | -16.681 | 67.244 |
| ATOM | 3657 | CB | TRP | 1074 | 1.464 | -15.468 | 66.702 |
| ATOM | 3658 | CG | TRP | 1074 | 2.434 | -14.506 | 66.057 |
| ATOM | 3659 | CD2 | TRP | 1074 | 3.554 | -13.868 | 66.690 |
| ATOM | 3660 | CE2 | TRP | 1074 | 4.214 | -13.102 | 65.700 |
| ATOM | 3661 | CE3 | TRP | 1074 | 4.063 | -13.874 | 67.997 |
| ATOM | 3662 | CD1 | TRP | 1074 | 2.459 | -14.108 | 64.747 |
| ATOM | 3663 | NE1 | TRP | 1074 | 3.528 | -13.267 | 64.526 |
| ATOM | 3664 | CZ2 | TRP | 1074 | 5.362 | -12.346 | 65.976 |
| ATOM | 3665 | CZ3 | TRP | 1074 | 5.207 | -13.124 | 68.276 |
| ATOM | 3666 | CH2 | TRP | 1074 | 5.844 | -12.369 | 67.268 |
| ATOM | 3667 | C | TRP | 1074 | 1.371 | -17.510 | 68.200 |
| ATOM | 3668 | O | TRP | 1074 | 0.939 | -17.014 | 69.240 |
| ATOM | 3669 | N | GLU | 1075 | 1.206 | -18.786 | 67.875 |
| ATOM | 3670 | CA | GLU | 1075 | 0.482 | -19.700 | 68.733 |
| ATOM | 3671 | CB | GLU | 1075 | -0.276 | -20.713 | 67.917 |
| ATOM | 3672 | CG | GLU | 1075 | -1.314 | -20.100 | 67.030 |
| ATOM | 3673 | CD | GLU | 1075 | -1.974 | -21.142 | 66.138 |
| ATOM | 3674 | OE1 | GLU | 1075 | -1.229 | -21.854 | 65.403 |
| ATOM | 3675 | OE2 | GLU | 1075 | -3.230 | -21.254 | 66.193 |
| ATOM | 3676 | C | GLU | 1075 | 1.496 | -20.437 | 69.579 |
| ATOM | 3677 | O | GLU | 1075 | 1.320 | -20.621 | 70.794 |
| ATOM | 3678 | N | ALA | 1076 | 2.564 | -20.883 | 68.933 |
| ATOM | 3679 | CA | ALA | 1076 | 3.614 | -21.581 | 69.663 |
| ATOM | 3680 | CB | ALA | 1076 | 4.616 | -22.185 | 68.720 |
| ATOM | 3681 | C | ALA | 1076 | 4.296 | -20.589 | 70.576 |
| ATOM | 3682 | O | ALA | 1076 | 5.158 | -20.962 | 71.365 |
| ATOM | 3683 | N | SER | 1077 | 3.988 | -19.312 | 70.362 |
| ATOM | 3684 | CA | SER | 1077 | 4.530 | -18.234 | 71.177 |
| ATOM | 3685 | CB | SER | 1077 | 4.853 | -16.980 | 70.312 |
| ATOM | 3686 | OG | SER | 1077 | 3.700 | -16.209 | 69.986 |
| ATOM | 3687 | C | SER | 1077 | 3.519 | -17.915 | 72.313 |
| ATOM | 3688 | O | SER | 1077 | 3.899 | -17.362 | 73.370 |
| ATOM | 3689 | N | GLY | 1078 | 2.250 | -18.292 | 72.100 |
| ATOM | 3690 | CA | GLY | 1078 | 1.195 | -18.026 | 73.069 |
| ATOM | 3691 | C | GLY | 1078 | 0.729 | -16.578 | 73.030 |
| ATOM | 3692 | O | GLY | 1078 | -0.236 | -16.226 | 73.691 |
| ATOM | 3693 | N | HIS | 1079 | 1.394 | -15.748 | 72.225 |
| ATOM | 3694 | CA | HIS | 1079 | 1.063 | -14.336 | 72.111 |

FIGURE 1ZZZ

| | Atom | | Residue AA | No. | X | Y | Z |
|---|---|---|---|---|---|---|---|
| ATOM | 3695 | CB | HIS | 1079 | 1.971 | -13.634 | 71.103 |
| ATOM | 3696 | CG | HIS | 1079 | 3.228 | -13.075 | 71.695 |
| ATOM | 3697 | CD2 | HIS | 1079 | 3.977 | -12.002 | 71.346 |
| ATOM | 3698 | ND1 | HIS | 1079 | 3.878 | -13.664 | 72.760 |
| ATOM | 3699 | CE1 | HIS | 1079 | 4.977 | -12.981 | 73.037 |
| ATOM | 3700 | NE2 | HIS | 1079 | 5.061 | -11.968 | 72.193 |
| ATOM | 3701 | C | HIS | 1079 | -0.352 | -14.205 | 71.650 |
| ATOM | 3702 | O | HIS | 1079 | -0.989 | -13.196 | 71.887 |
| ATOM | 3703 | N | LEU | 1080 | -0.827 | -15.234 | 70.967 |
| ATOM | 3704 | CA | LEU | 1080 | -2.185 | -15.259 | 70.457 |
| ATOM | 3705 | CB | LEU | 1080 | -2.520 | -16.675 | 69.975 |
| ATOM | 3706 | CG | LEU | 1080 | -3.005 | -16.863 | 68.525 |
| ATOM | 3707 | CD1 | LEU | 1080 | -4.457 | -16.329 | 68.400 |
| ATOM | 3708 | CD2 | LEU | 1080 | -2.037 | -16.206 | 67.498 |
| ATOM | 3709 | C | LEU | 1080 | -3.130 | -14.848 | 71.567 |
| ATOM | 3710 | O | LEU | 1080 | -4.083 | -14.102 | 71.332 |
| ATOM | 3711 | N | ASN | 1081 | -2.810 | -15.298 | 72.788 |
| ATOM | 3712 | CA | ASN | 1081 | -3.612 | -15.026 | 74.016 |
| ATOM | 3713 | CB | ASN | 1081 | -4.473 | -16.252 | 74.416 |
| ATOM | 3714 | CG | ASN | 1081 | -3.829 | -17.599 | 74.031 |
| ATOM | 3715 | OD1 | ASN | 1081 | -2.727 | -17.947 | 74.508 |
| ATOM | 3716 | ND2 | ASN | 1081 | -4.513 | -18.354 | 73.146 |
| ATOM | 3717 | C | ASN | 1081 | -2.837 | -14.545 | 75.250 |
| ATOM | 3718 | O | ASN | 1081 | -3.168 | -13.510 | 75.841 |
| ATOM | 3719 | N | ASN | 1082 | -1.832 | -15.316 | 75.650 |
| ATOM | 3720 | CA | ASN | 1082 | -1.010 | -14.948 | 76.802 |
| ATOM | 3721 | CB | ASN | 1082 | 0.126 | -15.964 | 77.017 |
| ATOM | 3722 | CG | ASN | 1082 | -0.380 | -17.403 | 77.172 |
| ATOM | 3723 | OD1 | ASN | 1082 | 0.340 | -18.359 | 76.822 |
| ATOM | 3724 | ND2 | ASN | 1082 | -1.608 | -17.568 | 77.714 |
| ATOM | 3725 | C | ASN | 1082 | -0.431 | -13.524 | 76.664 |
| ATOM | 3726 | O | ASN | 1082 | -0.189 | -12.860 | 77.674 |
| ATOM | 3727 | N | PHE | 1083 | -0.160 | -13.079 | 75.429 |
| ATOM | 3728 | CA | PHE | 1083 | 0.351 | -11.724 | 75.217 |
| ATOM | 3729 | CB | PHE | 1083 | 0.812 | -11.454 | 73.782 |
| ATOM | 3730 | CG | PHE | 1083 | 1.110 | -9.995 | 73.528 |
| ATOM | 3731 | CD1 | PHE | 1083 | 0.083 | -9.116 | 73.158 |
| ATOM | 3732 | CD2 | PHE | 1083 | 2.397 | -9.480 | 73.758 |
| ATOM | 3733 | CE1 | PHE | 1083 | 0.322 | -7.762 | 73.030 |
| ATOM | 3734 | CE2 | PHE | 1083 | 2.653 | -8.114 | 73.632 |
| ATOM | 3735 | CZ | PHE | 1083 | 1.602 | -7.247 | 73.266 |
| ATOM | 3736 | C | PHE | 1083 | -0.828 | -10.839 | 75.511 |
| ATOM | 3737 | O | PHE | 1083 | -1.793 | -10.787 | 74.743 |
| ATOM | 3738 | N | ASN | 1084 | -0.695 | -10.054 | 76.561 |
| ATOM | 3739 | CA | ASN | 1084 | -1.807 | -9.229 | 76.956 |
| ATOM | 3740 | CB | ASN | 1084 | -2.836 | -10.139 | 77.675 |
| ATOM | 3741 | CG | ASN | 1084 | -4.109 | -10.374 | 76.874 |
| ATOM | 3742 | OD1 | ASN | 1084 | -5.185 | -9.930 | 77.286 |

FIGURE 1AAAA

| | Atom | | Residue AA | No. | X | Y | Z |
|---|---|---|---|---|---|---|---|
| ATOM | 3743 | ND2 | ASN | 1084 | -4.016 | -11.140 | 75.785 |
| ATOM | 3744 | C | ASN | 1084 | -1.457 | -8.052 | 77.876 |
| ATOM | 3745 | O | ASN | 1084 | -0.299 | -7.841 | 78.302 |
| ATOM | 3746 | N | ALA | 1085 | -2.510 | -7.278 | 78.110 |
| ATOM | 3747 | CA | ALA | 1085 | -2.544 | -6.138 | 78.996 |
| ATOM | 3748 | CB | ALA | 1085 | -2.436 | -4.809 | 78.213 |
| ATOM | 3749 | C | ALA | 1085 | -3.969 | -6.334 | 79.546 |
| ATOM | 3750 | O | ALA | 1085 | -4.954 | -6.136 | 78.792 |
| ATOM | 3751 | N | PRO | 1086 | -4.080 | -6.992 | 80.742 |
| ATOM | 3752 | CD | PRO | 1086 | -3.006 | -7.791 | 81.385 |
| ATOM | 3753 | CA | PRO | 1086 | -5.372 | -7.251 | 81.419 |
| ATOM | 3754 | CB | PRO | 1086 | -4.962 | -8.071 | 82.659 |
| ATOM | 3755 | CG | PRO | 1086 | -3.797 | -8.869 | 82.148 |
| ATOM | 3756 | C | PRO | 1086 | -6.124 | -5.951 | 81.828 |
| ATOM | 3757 | O | PRO | 1086 | -5.455 | -4.940 | 82.204 |
| ATOM | 3758 | OT | PRO | 1086 | -7.383 | -5.965 | 81.731 |
| ATOM | 3759 | CB | ALA | 1150 | -7.496 | -10.159 | 79.486 |
| ATOM | 3760 | C | ALA | 1150 | -7.626 | -8.262 | 77.737 |
| ATOM | 3761 | O | ALA | 1150 | -8.642 | -8.564 | 77.046 |
| ATOM | 3762 | N | ALA | 1150 | -8.693 | -8.028 | 80.045 |
| ATOM | 3763 | CA | ALA | 1150 | -7.556 | -8.618 | 79.258 |
| ATOM | 3764 | N | ALA | 1151 | -6.547 | -7.636 | 77.232 |
| ATOM | 3765 | CA | ALA | 1151 | -6.446 | -7.204 | 75.816 |
| ATOM | 3766 | CB | ALA | 1151 | -6.531 | -5.645 | 75.746 |
| ATOM | 3767 | C | ALA | 1151 | -5.186 | -7.700 | 75.045 |
| ATOM | 3768 | O | ALA | 1151 | -4.045 | -7.487 | 75.513 |
| ATOM | 3769 | N | ASN | 1152 | -5.390 | -8.349 | 73.882 |
| ATOM | 3770 | CA | ASN | 1152 | -4.263 | -8.833 | 73.046 |
| ATOM | 3771 | CB | ASN | 1152 | -4.567 | -10.186 | 72.388 |
| ATOM | 3772 | CG | ASN | 1152 | -3.404 | -10.706 | 71.584 |
| ATOM | 3773 | OD1 | ASN | 1152 | -3.569 | -11.137 | 70.441 |
| ATOM | 3774 | ND2 | ASN | 1152 | -2.211 | -10.638 | 72.163 |
| ATOM | 3775 | C | ASN | 1152 | -3.854 | -7.767 | 72.003 |
| ATOM | 3776 | O | ASN | 1152 | -4.387 | -7.657 | 70.887 |
| ATOM | 3777 | N | LEU | 1153 | -2.850 | -7.011 | 72.409 |
| ATOM | 3778 | CA | LEU | 1153 | -2.304 | -5.871 | 71.681 |
| ATOM | 3779 | CB | LEU | 1153 | -1.532 | -5.003 | 72.717 |
| ATOM | 3780 | CG | LEU | 1153 | -1.585 | -5.320 | 74.245 |
| ATOM | 3781 | CD1 | LEU | 1153 | -0.292 | -4.869 | 74.968 |
| ATOM | 3782 | CD2 | LEU | 1153 | -2.836 | -4.693 | 74.876 |
| ATOM | 3783 | C | LEU | 1153 | -1.421 | -6.107 | 70.424 |
| ATOM | 3784 | O | LEU | 1153 | -0.600 | -5.243 | 70.068 |
| ATOM | 3785 | N | MET | 1154 | -1.529 | -7.262 | 69.779 |
| ATOM | 3786 | CA | MET | 1154 | -0.709 | -7.492 | 68.582 |
| ATOM | 3787 | CB | MET | 1154 | -0.651 | -8.980 | 68.247 |
| ATOM | 3788 | CG | MET | 1154 | -0.048 | -9.879 | 69.319 |
| ATOM | 3789 | SD | MET | 1154 | -0.115 | -11.612 | 68.764 |
| ATOM | 3790 | CE | MET | 1154 | 1.037 | -11.544 | 67.377 |

FIGURE 1BBBB

| Atom | | | Residue AA | No. | X | Y | Z |
|---|---|---|---|---|---|---|---|
| ATOM | 3791 | C | MET | 1154 | -1.392 | -6.732 | 67.434 |
| ATOM | 3792 | O | MET | 1154 | -2.637 | -6.677 | 67.400 |
| ATOM | 3793 | N | PHE | 1155 | -0.622 | -6.153 | 66.503 |
| ATOM | 3794 | CA | PHE | 1155 | -1.253 | -5.399 | 65.409 |
| ATOM | 3795 | CB | PHE | 1155 | -0.313 | -4.334 | 64.894 |
| ATOM | 3796 | CG | PHE | 1155 | -0.770 | -2.946 | 65.208 |
| ATOM | 3797 | CD1 | PHE | 1155 | -2.093 | -2.574 | 64.989 |
| ATOM | 3798 | CD2 | PHE | 1155 | 0.121 | -1.998 | 65.706 |
| ATOM | 3799 | CE1 | PHE | 1155 | -2.517 | -1.270 | 65.260 |
| ATOM | 3800 | CE2 | PHE | 1155 | -0.297 | -0.692 | 65.980 |
| ATOM | 3801 | CZ | PHE | 1155 | -1.617 | -0.330 | 65.755 |
| ATOM | 3802 | C | PHE | 1155 | -1.882 | -6.209 | 64.271 |
| ATOM | 3803 | O | PHE | 1155 | -1.199 | -6.874 | 63.495 |
| ATOM | 3804 | N | ALA | 1156 | -3.193 | -6.082 | 64.135 |
| ATOM | 3805 | CA | ALA | 1156 | -3.969 | -6.855 | 63.150 |
| ATOM | 3806 | CB | ALA | 1156 | -5.418 | -6.972 | 63.632 |
| ATOM | 3807 | C | ALA | 1156 | -3.973 | -6.479 | 61.672 |
| ATOM | 3808 | O | ALA | 1156 | -4.372 | -5.363 | 61.308 |
| ATOM | 3809 | N | THR | 1157 | -3.616 | -7.442 | 60.817 |
| ATOM | 3810 | CA | THR | 1157 | -3.624 | -7.216 | 59.353 |
| ATOM | 3811 | CB | THR | 1157 | -2.207 | -6.894 | 58.726 |
| ATOM | 3812 | OG1 | THR | 1157 | -2.386 | -6.093 | 57.551 |
| ATOM | 3813 | CG2 | THR | 1157 | -1.479 | -8.155 | 58.294 |
| ATOM | 3814 | C | THR | 1157 | -4.268 | -8.345 | 58.538 |
| ATOM | 3815 | O | THR | 1157 | -4.480 | -9.472 | 59.020 |
| ATOM | 3816 | N | ALA | 1158 | -4.605 | -8.012 | 57.302 |
| ATOM | 3817 | CA | ALA | 1158 | -5.209 | -8.970 | 56.403 |
| ATOM | 3818 | CB | ALA | 1158 | -6.675 | -8.634 | 56.177 |
| ATOM | 3819 | C | ALA | 1158 | -4.422 | -8.933 | 55.095 |
| ATOM | 3820 | O | ALA | 1158 | -4.085 | -7.860 | 54.586 |
| ATOM | 3821 | N | GLN | 1159 | -4.105 | -10.116 | 54.586 |
| ATOM | 3822 | CA | GLN | 1159 | -3.342 | -10.266 | 53.361 |
| ATOM | 3823 | CB | GLN | 1159 | -2.073 | -11.035 | 53.675 |
| ATOM | 3824 | CG | GLN | 1159 | -1.192 | -11.291 | 52.478 |
| ATOM | 3825 | CD | GLN | 1159 | -0.055 | -12.221 | 52.819 |
| ATOM | 3826 | OE1 | GLN | 1159 | 1.115 | -11.902 | 52.582 |
| ATOM | 3827 | NE2 | GLN | 1159 | -0.389 | -13.378 | 53.411 |
| ATOM | 3828 | C | GLN | 1159 | -4.119 | -10.987 | 52.247 |
| ATOM | 3829 | O | GLN | 1159 | -4.077 | -12.226 | 52.159 |
| ATOM | 3830 | N | GLY | 1160 | -4.785 | -10.200 | 51.389 |
| ATOM | 3831 | CA | GLY | 1160 | -5.601 | -10.720 | 50.286 |
| ATOM | 3832 | C | GLY | 1160 | -6.997 | -10.073 | 50.202 |
| ATOM | 3833 | O | GLY | 1160 | -7.168 | -9.080 | 49.451 |
| ATOM | 3834 | N | ALA | 1161 | -7.981 | -10.660 | 50.922 |
| ATOM | 3835 | CA | ALA | 1161 | -9.381 | -10.161 | 51.013 |
| ATOM | 3836 | CB | ALA | 1161 | -10.017 | -9.969 | 49.596 |
| ATOM | 3837 | C | ALA | 1161 | -10.318 | -10.999 | 51.937 |
| ATOM | 3838 | O | ALA | 1161 | -10.878 | -10.382 | 52.894 |

FIGURE 1CCCC

| Atom | | | Residue AA | No. | X | Y | Z |
|---|---|---|---|---|---|---|---|
| ATOM | 3839 | OT | ALA | 1161 | -10.455 | -12.249 | 51.736 |
| ATOM | 3840 | CB | ALA | 1164 | -13.078 | -13.598 | 55.906 |
| ATOM | 3841 | C | ALA | 1164 | -10.884 | -12.981 | 57.076 |
| ATOM | 3842 | O | ALA | 1164 | -9.875 | -12.267 | 57.330 |
| ATOM | 3843 | N | ALA | 1164 | -11.377 | -12.265 | 54.682 |
| ATOM | 3844 | CA | ALA | 1164 | -11.968 | -12.530 | 56.042 |
| ATOM | 3845 | N | ALA | 1165 | -11.131 | -14.135 | 57.707 |
| ATOM | 3846 | CA | ALA | 1165 | -10.184 | -14.728 | 58.658 |
| ATOM | 3847 | CB | ALA | 1165 | -10.942 | -15.364 | 59.852 |
| ATOM | 3848 | C | ALA | 1165 | -9.409 | -15.806 | 57.853 |
| ATOM | 3849 | O | ALA | 1165 | -10.044 | -16.632 | 57.160 |
| ATOM | 3850 | N | THR | 1166 | -8.068 | -15.708 | 57.894 |
| ATOM | 3851 | CA | THR | 1166 | -7.058 | -16.576 | 57.223 |
| ATOM | 3852 | CB | THR | 1166 | -7.595 | -17.461 | 56.059 |
| ATOM | 3853 | OG1 | THR | 1166 | -8.464 | -16.694 | 55.197 |
| ATOM | 3854 | CG2 | THR | 1166 | -8.270 | -18.765 | 56.620 |
| ATOM | 3855 | C | THR | 1166 | -6.002 | -15.645 | 56.638 |
| ATOM | 3856 | O | THR | 1166 | -4.797 | -15.953 | 56.579 |
| ATOM | 3857 | N | ASN | 1167 | -6.512 | -14.528 | 56.127 |
| ATOM | 3858 | CA | ASN | 1167 | -5.694 | -13.442 | 55.587 |
| ATOM | 3859 | CB | ASN | 1167 | -6.612 | -12.361 | 54.935 |
| ATOM | 3860 | CG | ASN | 1167 | -7.782 | -12.960 | 54.119 |
| ATOM | 3861 | OD1 | ASN | 1167 | -8.823 | -13.327 | 54.685 |
| ATOM | 3862 | ND2 | ASN | 1167 | -7.616 | -13.045 | 52.785 |
| ATOM | 3863 | C | ASN | 1167 | -5.047 | -12.874 | 56.889 |
| ATOM | 3864 | O | ASN | 1167 | -3.919 | -12.344 | 56.899 |
| ATOM | 3865 | N | ALA | 1168 | -5.825 | -13.016 | 57.972 |
| ATOM | 3866 | CA | ALA | 1168 | -5.501 | -12.595 | 59.330 |
| ATOM | 3867 | CB | ALA | 1168 | -6.592 | -13.138 | 60.310 |
| ATOM | 3868 | C | ALA | 1168 | -4.091 | -13.014 | 59.784 |
| ATOM | 3869 | O | ALA | 1168 | -3.874 | -14.119 | 60.285 |
| ATOM | 3870 | N | ILE | 1169 | -3.130 | -12.133 | 59.557 |
| ATOM | 3871 | CA | ILE | 1169 | -1.744 | -12.365 | 59.954 |
| ATOM | 3872 | CB | ILE | 1169 | -0.857 | -12.597 | 58.719 |
| ATOM | 3873 | CG2 | ILE | 1169 | -1.516 | -13.635 | 57.798 |
| ATOM | 3874 | CG1 | ILE | 1169 | -0.685 | -11.302 | 57.928 |
| ATOM | 3875 | CD1 | ILE | 1169 | 0.437 | -11.346 | 56.903 |
| ATOM | 3876 | C | ILE | 1169 | -1.365 | -11.072 | 60.682 |
| ATOM | 3877 | O | ILE | 1169 | -2.078 | -10.067 | 60.529 |
| ATOM | 3878 | N | PHE | 1170 | -0.307 | -11.052 | 61.487 |
| ATOM | 3879 | CA | PHE | 1170 | -0.022 | -9.795 | 62.183 |
| ATOM | 3880 | CB | PHE | 1170 | -0.381 | -9.878 | 63.663 |
| ATOM | 3881 | CG | PHE | 1170 | -1.596 | -10.647 | 63.924 |
| ATOM | 3882 | CD1 | PHE | 1170 | -2.838 | -10.169 | 63.492 |
| ATOM | 3883 | CD2 | PHE | 1170 | -1.506 | -11.892 | 64.514 |
| ATOM | 3884 | CE1 | PHE | 1170 | -3.983 | -10.939 | 63.639 |
| ATOM | 3885 | CE2 | PHE | 1170 | -2.631 | -12.675 | 64.672 |
| ATOM | 3886 | CZ | PHE | 1170 | -3.882 | -12.206 | 64.233 |

FIGURE 1DDDD

| Atom | | | Residue AA | No. | X | Y | Z |
|---|---|---|---|---|---|---|---|
| ATOM | 3887 | C | PHE | 1170 | 1.398 | -9.399 | 62.119 |
| ATOM | 3888 | O | PHE | 1170 | 2.226 | -10.147 | 61.599 |
| ATOM | 3889 | N | LEU | 1171 | 1.668 | -8.252 | 62.739 |
| ATOM | 3890 | CA | LEU | 1171 | 2.999 | -7.700 | 62.836 |
| ATOM | 3891 | CB | LEU | 1171 | 2.954 | -6.178 | 62.815 |
| ATOM | 3892 | CG | LEU | 1171 | 1.848 | -5.444 | 62.037 |
| ATOM | 3893 | CD1 | LEU | 1171 | 2.344 | -4.010 | 61.724 |
| ATOM | 3894 | CD2 | LEU | 1171 | 1.443 | -6.170 | 60.749 |
| ATOM | 3895 | C | LEU | 1171 | 3.596 | -8.175 | 64.148 |
| ATOM | 3896 | O | LEU | 1171 | 2.901 | -8.265 | 65.164 |
| ATOM | 3897 | N | ARG | 1172 | 4.884 | -8.493 | 64.106 |
| ATOM | 3898 | CA | ARG | 1172 | 5.618 | -8.983 | 65.264 |
| ATOM | 3899 | CB | ARG | 1172 | 7.047 | -9.406 | 64.854 |
| ATOM | 3900 | CG | ARG | 1172 | 8.017 | -8.255 | 64.463 |
| ATOM | 3901 | CD | ARG | 1172 | 9.386 | -8.816 | 64.107 |
| ATOM | 3902 | NE | ARG | 1172 | 10.273 | -7.860 | 63.454 |
| ATOM | 3903 | CZ | ARG | 1172 | 11.495 | -8.158 | 63.014 |
| ATOM | 3904 | NH1 | ARG | 1172 | 11.973 | -9.387 | 63.148 |
| ATOM | 3905 | NH2 | ARG | 1172 | 12.251 | -7.226 | 62.443 |
| ATOM | 3906 | C | ARG | 1172 | 5.717 | -7.978 | 66.418 |
| ATOM | 3907 | O | ARG | 1172 | 6.117 | -6.824 | 66.204 |
| ATOM | 3908 | N | PRO | 1173 | 5.278 | -8.373 | 67.634 |
| ATOM | 3909 | CD | PRO | 1173 | 4.355 | -9.486 | 67.899 |
| ATOM | 3910 | CA | PRO | 1173 | 5.354 | -7.484 | 68.808 |
| ATOM | 3911 | CB | PRO | 1173 | 4.210 | -7.985 | 69.701 |
| ATOM | 3912 | CG | PRO | 1173 | 3.345 | -8.819 | 68.777 |
| ATOM | 3913 | C | PRO | 1173 | 6.714 | -7.750 | 69.483 |
| ATOM | 3914 | O | PRO | 1173 | 7.199 | -6.976 | 70.319 |
| ATOM | 3915 | N | GLU | 1174 | 7.331 | -8.851 | 69.061 |
| ATOM | 3916 | CA | GLU | 1174 | 8.602 | -9.286 | 69.592 |
| ATOM | 3917 | CB | GLU | 1174 | 8.339 | -10.296 | 70.694 |
| ATOM | 3918 | CG | GLU | 1174 | 9.583 | -10.955 | 71.222 |
| ATOM | 3919 | CD | GLU | 1174 | 9.300 | -11.838 | 72.410 |
| ATOM | 3920 | OE1 | GLU | 1174 | 10.191 | -11.884 | 73.309 |
| ATOM | 3921 | OE2 | GLU | 1174 | 8.194 | -12.457 | 72.436 |
| ATOM | 3922 | C | GLU | 1174 | 9.526 | -9.881 | 68.517 |
| ATOM | 3923 | O | GLU | 1174 | 9.227 | -10.902 | 67.865 |
| ATOM | 3924 | N | THR | 1175 | 10.688 | -9.257 | 68.419 |
| ATOM | 3925 | CA | THR | 1175 | 11.731 | -9.597 | 67.465 |
| ATOM | 3926 | CB | THR | 1175 | 12.804 | -8.509 | 67.560 |
| ATOM | 3927 | OG1 | THR | 1175 | 12.182 | -7.224 | 67.388 |
| ATOM | 3928 | CG2 | THR | 1175 | 13.884 | -8.710 | 66.538 |
| ATOM | 3929 | C | THR | 1175 | 12.376 | -10.976 | 67.597 |
| ATOM | 3930 | O | THR | 1175 | 12.994 | -11.480 | 66.658 |
| ATOM | 3931 | N | ALA | 1176 | 12.175 | -11.608 | 68.744 |
| ATOM | 3932 | CA | ALA | 1176 | 12.783 | -12.904 | 69.032 |
| ATOM | 3933 | CB | ALA | 1176 | 12.656 | -13.228 | 70.510 |
| ATOM | 3934 | C | ALA | 1176 | 12.269 | -14.062 | 68.221 |

FIGURE 1EEEE

| | Atom | | Residue AA | No. | X | Y | Z |
|---|---|---|---|---|---|---|---|
| ATOM | 3935 | O | ALA | 1176 | 13.030 | -14.914 | 67.769 |
| ATOM | 3936 | N | GLN | 1177 | 10.964 | -14.129 | 68.076 |
| ATOM | 3937 | CA | GLN | 1177 | 10.406 | -15.219 | 67.339 |
| ATOM | 3938 | CB | GLN | 1177 | 8.928 | -14.975 | 67.154 |
| ATOM | 3939 | CG | GLN | 1177 | 8.195 | -15.045 | 68.463 |
| ATOM | 3940 | CD | GLN | 1177 | 8.703 | -16.182 | 69.310 |
| ATOM | 3941 | OE1 | GLN | 1177 | 8.703 | -17.336 | 68.882 |
| ATOM | 3942 | NE2 | GLN | 1177 | 9.208 | -15.859 | 70.491 |
| ATOM | 3943 | C | GLN | 1177 | 11.137 | -15.401 | 66.027 |
| ATOM | 3944 | O | GLN | 1177 | 11.512 | -16.523 | 65.679 |
| ATOM | 3945 | N | GLY | 1178 | 11.456 | -14.274 | 65.389 |
| ATOM | 3946 | CA | GLY | 1178 | 12.161 | -14.289 | 64.129 |
| ATOM | 3947 | C | GLY | 1178 | 13.474 | -15.019 | 64.261 |
| ATOM | 3948 | O | GLY | 1178 | 13.958 | -15.632 | 63.316 |
| ATOM | 3949 | N | ILE | 1179 | 14.073 | -14.943 | 65.433 |
| ATOM | 3950 | CA | ILE | 1179 | 15.319 | -15.644 | 65.640 |
| ATOM | 3951 | CB | ILE | 1179 | 16.132 | -15.073 | 66.792 |
| ATOM | 3952 | CG2 | ILE | 1179 | 17.541 | -15.597 | 66.711 |
| ATOM | 3953 | CG1 | ILE | 1179 | 16.130 | -13.545 | 66.750 |
| ATOM | 3954 | CD1 | ILE | 1179 | 16.937 | -12.886 | 67.857 |
| ATOM | 3955 | C | ILE | 1179 | 15.053 | -17.112 | 65.927 |
| ATOM | 3956 | O | ILE | 1179 | 15.607 | -17.980 | 65.275 |
| ATOM | 3957 | N | PHE | 1180 | 14.154 | -17.400 | 66.853 |
| ATOM | 3958 | CA | PHE | 1180 | 13.873 | -18.782 | 67.201 |
| ATOM | 3959 | CB | PHE | 1180 | 12.770 | -18.861 | 68.229 |
| ATOM | 3960 | CG | PHE | 1180 | 13.181 | -18.337 | 69.534 |
| ATOM | 3961 | CD1 | PHE | 1180 | 12.331 | -17.551 | 70.285 |
| ATOM | 3962 | CD2 | PHE | 1180 | 14.467 | -18.555 | 69.982 |
| ATOM | 3963 | CE1 | PHE | 1180 | 12.763 | -16.974 | 71.474 |
| ATOM | 3964 | CE2 | PHE | 1180 | 14.911 | -17.992 | 71.159 |
| ATOM | 3965 | CZ | PHE | 1180 | 14.061 | -17.197 | 71.910 |
| ATOM | 3966 | C | PHE | 1180 | 13.547 | -19.670 | 66.042 |
| ATOM | 3967 | O | PHE | 1180 | 14.037 | -20.791 | 65.944 |
| ATOM | 3968 | N | VAL | 1181 | 12.696 | -19.181 | 65.170 |
| ATOM | 3969 | CA | VAL | 1181 | 12.319 | -19.953 | 64.022 |
| ATOM | 3970 | CB | VAL | 1181 | 11.224 | -19.239 | 63.282 |
| ATOM | 3971 | CG1 | VAL | 1181 | 9.951 | -19.318 | 64.065 |
| ATOM | 3972 | CG2 | VAL | 1181 | 11.600 | -17.774 | 63.077 |
| ATOM | 3973 | C | VAL | 1181 | 13.517 | -20.175 | 63.099 |
| ATOM | 3974 | O | VAL | 1181 | 13.543 | -21.133 | 62.307 |
| ATOM | 3975 | N | ASN | 1182 | 14.503 | -19.287 | 63.201 |
| ATOM | 3976 | CA | ASN | 1182 | 15.704 | -19.372 | 62.376 |
| ATOM | 3977 | CB | ASN | 1182 | 16.078 | -17.994 | 61.772 |
| ATOM | 3978 | CG | ASN | 1182 | 15.217 | -17.604 | 60.562 |
| ATOM | 3979 | OD1 | ASN | 1182 | 15.674 | -17.597 | 59.420 |
| ATOM | 3980 | ND2 | ASN | 1182 | 13.986 | -17.238 | 60.825 |
| ATOM | 3981 | C | ASN | 1182 | 16.882 | -19.921 | 63.166 |
| ATOM | 3982 | O | ASN | 1182 | 18.025 | -19.608 | 62.869 |

FIGURE 1FFFF

| Atom | | | Residue AA | No. | X | Y | Z |
|---|---|---|---|---|---|---|---|
| ATOM | 3983 | N | TYR | 1183 | 16.616 | -20.743 | 64.169 |
| ATOM | 3984 | CA | TYR | 1183 | 17.706 | -21.301 | 64.961 |
| ATOM | 3985 | CB | TYR | 1183 | 17.205 | -21.910 | 66.271 |
| ATOM | 3986 | CG | TYR | 1183 | 18.199 | -22.845 | 66.941 |
| ATOM | 3987 | CD1 | TYR | 1183 | 17.882 | -24.193 | 67.165 |
| ATOM | 3988 | CE1 | TYR | 1183 | 18.797 | -25.077 | 67.776 |
| ATOM | 3989 | CD2 | TYR | 1183 | 19.453 | -22.395 | 67.346 |
| ATOM | 3990 | CE2 | TYR | 1183 | 20.377 | -23.271 | 67.962 |
| ATOM | 3991 | CZ | TYR | 1183 | 20.038 | -24.609 | 68.166 |
| ATOM | 3992 | OH | TYR | 1183 | 20.945 | -25.491 | 68.707 |
| ATOM | 3993 | C | TYR | 1183 | 18.432 | -22.363 | 64.184 |
| ATOM | 3994 | O | TYR | 1183 | 19.611 | -22.226 | 63.894 |
| ATOM | 3995 | N | ALA | 1184 | 17.713 | -23.423 | 63.836 |
| ATOM | 3996 | CA | ALA | 1184 | 18.306 | -24.530 | 63.126 |
| ATOM | 3997 | CB | ALA | 1184 | 17.245 | -25.534 | 62.768 |
| ATOM | 3998 | C | ALA | 1184 | 19.079 | -24.057 | 61.895 |
| ATOM | 3999 | O | ALA | 1184 | 20.212 | -24.485 | 61.683 |
| ATOM | 4000 | N | ASN | 1185 | 18.518 | -23.098 | 61.157 |
| ATOM | 4001 | CA | ASN | 1185 | 19.145 | -22.567 | 59.939 |
| ATOM | 4002 | CB | ASN | 1185 | 18.297 | -21.446 | 59.301 |
| ATOM | 4003 | CG | ASN | 1185 | 16.901 | -21.914 | 58.813 |
| ATOM | 4004 | OD1 | ASN | 1185 | 16.639 | -23.109 | 58.649 |
| ATOM | 4005 | ND2 | ASN | 1185 | 16.011 | -20.949 | 58.567 |
| ATOM | 4006 | C | ASN | 1185 | 20.538 | -22.029 | 60.207 |
| ATOM | 4007 | O | ASN | 1185 | 21.501 | -22.569 | 59.700 |
| ATOM | 4008 | N | VAL | 1186 | 20.644 | -20.974 | 61.007 |
| ATOM | 4009 | CA | VAL | 1186 | 21.932 | -20.354 | 61.320 |
| ATOM | 4010 | CB | VAL | 1186 | 21.816 | -19.310 | 62.422 |
| ATOM | 4011 | CG1 | VAL | 1186 | 23.187 | -18.763 | 62.765 |
| ATOM | 4012 | CG2 | VAL | 1186 | 20.872 | -18.211 | 62.012 |
| ATOM | 4013 | C | VAL | 1186 | 22.884 | -21.401 | 61.815 |
| ATOM | 4014 | O | VAL | 1186 | 24.085 | -21.338 | 61.574 |
| ATOM | 4015 | N | GLN | 1187 | 22.325 | -22.352 | 62.548 |
| ATOM | 4016 | CA | GLN | 1187 | 23.084 | -23.451 | 63.102 |
| ATOM | 4017 | CB | GLN | 1187 | 22.122 | -24.456 | 63.750 |
| ATOM | 4018 | CG | GLN | 1187 | 22.556 | -25.900 | 63.755 |
| ATOM | 4019 | CD | GLN | 1187 | 23.909 | -26.099 | 64.387 |
| ATOM | 4020 | OE1 | GLN | 1187 | 24.434 | -25.199 | 65.023 |
| ATOM | 4021 | NE2 | GLN | 1187 | 24.496 | -27.273 | 64.191 |
| ATOM | 4022 | C | GLN | 1187 | 23.894 | -24.061 | 61.975 |
| ATOM | 4023 | O | GLN | 1187 | 25.101 | -23.865 | 61.896 |
| ATOM | 4024 | N | ALA | 1188 | 23.194 | -24.679 | 61.034 |
| ATOM | 4025 | CA | ALA | 1188 | 23.802 | -25.341 | 59.870 |
| ATOM | 4026 | CB | ALA | 1188 | 22.730 | -26.114 | 59.087 |
| ATOM | 4027 | C | ALA | 1188 | 24.585 | -24.423 | 58.919 |
| ATOM | 4028 | O | ALA | 1188 | 25.802 | -24.565 | 58.789 |
| ATOM | 4029 | N | SER | 1189 | 23.886 | -23.495 | 58.260 |
| ATOM | 4030 | CA | SER | 1189 | 24.493 | -22.550 | 57.330 |

FIGURE 1GGGG

| Atom | | | Residue AA | No. | X | Y | Z |
|---|---|---|---|---|---|---|---|
| ATOM | 4031 | CB | SER | 1189 | 23.458 | -21.520 | 56.913 |
| ATOM | 4032 | OG | SER | 1189 | 23.027 | -20.781 | 58.032 |
| ATOM | 4033 | C | SER | 1189 | 25.737 | -21.842 | 57.900 |
| ATOM | 4034 | O | SER | 1189 | 26.569 | -21.320 | 57.150 |
| ATOM | 4035 | N | MET | 1190 | 25.860 | -21.832 | 59.225 |
| ATOM | 4036 | CA | MET | 1190 | 27.008 | -21.223 | 59.896 |
| ATOM | 4037 | CB | MET | 1190 | 26.535 | -20.155 | 60.865 |
| ATOM | 4038 | CG | MET | 1190 | 25.803 | -19.044 | 60.174 |
| ATOM | 4039 | SD | MET | 1190 | 26.726 | -18.377 | 58.805 |
| ATOM | 4040 | CE | MET | 1190 | 28.426 | -18.033 | 59.554 |
| ATOM | 4041 | C | MET | 1190 | 27.937 | -22.220 | 60.610 |
| ATOM | 4042 | O | MET | 1190 | 29.073 | -21.868 | 60.992 |
| ATOM | 4043 | N | ALA | 1191 | 27.443 | -23.452 | 60.769 |
| ATOM | 4044 | CA | ALA | 1191 | 28.164 | -24.563 | 61.410 |
| ATOM | 4045 | CB | ALA | 1191 | 29.403 | -24.925 | 60.593 |
| ATOM | 4046 | C | ALA | 1191 | 28.545 | -24.284 | 62.865 |
| ATOM | 4047 | O | ALA | 1191 | 29.715 | -24.426 | 63.252 |
| ATOM | 4048 | N | LYS | 1192 | 27.539 | -23.992 | 63.688 |
| ATOM | 4049 | CA | LYS | 1192 | 27.763 | -23.623 | 65.083 |
| ATOM | 4050 | CB | LYS | 1192 | 26.681 | -22.628 | 65.537 |
| ATOM | 4051 | CG | LYS | 1192 | 26.612 | -21.323 | 64.733 |
| ATOM | 4052 | CD | LYS | 1192 | 27.584 | -20.250 | 65.216 |
| ATOM | 4053 | CE | LYS | 1192 | 29.035 | -20.688 | 65.158 |
| ATOM | 4054 | NZ | LYS | 1192 | 29.984 | -19.582 | 65.414 |
| ATOM | 4055 | C | LYS | 1192 | 27.890 | -24.721 | 66.120 |
| ATOM | 4056 | O | LYS | 1192 | 27.266 | -25.774 | 66.016 |
| ATOM | 4057 | N | LYS | 1193 | 28.749 | -24.473 | 67.101 |
| ATOM | 4058 | CA | LYS | 1193 | 28.936 | -25.380 | 68.215 |
| ATOM | 4059 | CB | LYS | 1193 | 30.409 | -25.480 | 68.588 |
| ATOM | 4060 | CG | LYS | 1193 | 31.285 | -26.175 | 67.531 |
| ATOM | 4061 | CD | LYS | 1193 | 30.673 | -27.520 | 67.091 |
| ATOM | 4062 | CE | LYS | 1193 | 31.131 | -27.933 | 65.645 |
| ATOM | 4063 | NZ | LYS | 1193 | 30.128 | -28.782 | 64.836 |
| ATOM | 4064 | C | LYS | 1193 | 28.152 | -24.609 | 69.254 |
| ATOM | 4065 | O | LYS | 1193 | 28.229 | -23.375 | 69.265 |
| ATOM | 4066 | N | LEU | 1194 | 27.489 | -25.314 | 70.174 |
| ATOM | 4067 | CA | LEU | 1194 | 26.588 | -24.665 | 71.140 |
| ATOM | 4068 | CB | LEU | 1194 | 26.037 | -25.600 | 72.202 |
| ATOM | 4069 | CG | LEU | 1194 | 24.515 | -25.706 | 71.969 |
| ATOM | 4070 | CD1 | LEU | 1194 | 23.899 | -26.628 | 72.981 |
| ATOM | 4071 | CD2 | LEU | 1194 | 23.811 | -24.363 | 72.009 |
| ATOM | 4072 | C | LEU | 1194 | 26.812 | -23.277 | 71.691 |
| ATOM | 4073 | O | LEU | 1194 | 25.844 | -22.508 | 71.815 |
| ATOM | 4074 | N | PRO | 1195 | 28.022 | -22.964 | 72.152 |
| ATOM | 4075 | CD | PRO | 1195 | 29.222 | -23.770 | 72.404 |
| ATOM | 4076 | CA | PRO | 1195 | 28.160 | -21.584 | 72.643 |
| ATOM | 4077 | CB | PRO | 1195 | 29.536 | -21.602 | 73.279 |
| ATOM | 4078 | CG | PRO | 1195 | 30.261 | -22.708 | 72.483 |

FIGURE 1HHHH

| Atom | | | Residue AA | No. | X | Y | Z |
|---|---|---|---|---|---|---|---|
| ATOM | 4079 | C | PRO | 1195 | 28.089 | -20.626 | 71.408 |
| ATOM | 4080 | O | PRO | 1195 | 29.071 | -20.459 | 70.673 |
| ATOM | 4081 | N | PHE | 1196 | 26.903 | -20.086 | 71.129 |
| ATOM | 4082 | CA | PHE | 1196 | 26.725 | -19.200 | 69.993 |
| ATOM | 4083 | CB | PHE | 1196 | 26.767 | -20.006 | 68.693 |
| ATOM | 4084 | CG | PHE | 1196 | 25.436 | -20.596 | 68.280 |
| ATOM | 4085 | CD1 | PHE | 1196 | 24.463 | -19.806 | 67.648 |
| ATOM | 4086 | CD2 | PHE | 1196 | 25.157 | -21.936 | 68.489 |
| ATOM | 4087 | CE1 | PHE | 1196 | 23.249 | -20.344 | 67.239 |
| ATOM | 4088 | CE2 | PHE | 1196 | 23.940 | -22.480 | 68.082 |
| ATOM | 4089 | CZ | PHE | 1196 | 22.992 | -21.679 | 67.457 |
| ATOM | 4090 | C | PHE | 1196 | 25.423 | -18.417 | 70.116 |
| ATOM | 4091 | O | PHE | 1196 | 24.423 | -18.956 | 70.537 |
| ATOM | 4092 | N | GLY | 1197 | 25.428 | -17.157 | 69.707 |
| ATOM | 4093 | CA | GLY | 1197 | 24.235 | -16.342 | 69.811 |
| ATOM | 4094 | C | GLY | 1197 | 23.731 | -15.921 | 68.461 |
| ATOM | 4095 | O | GLY | 1197 | 24.375 | -16.231 | 67.484 |
| ATOM | 4096 | N | ILE | 1198 | 22.622 | -15.188 | 68.390 |
| ATOM | 4097 | CA | ILE | 1198 | 22.058 | -14.756 | 67.102 |
| ATOM | 4098 | CB | ILE | 1198 | 20.995 | -15.759 | 66.586 |
| ATOM | 4099 | CG2 | ILE | 1198 | 20.519 | -15.367 | 65.262 |
| ATOM | 4100 | CG1 | ILE | 1198 | 21.565 | -17.153 | 66.440 |
| ATOM | 4101 | CD1 | ILE | 1198 | 20.552 | -18.129 | 65.957 |
| ATOM | 4102 | C | ILE | 1198 | 21.367 | -13.399 | 67.211 |
| ATOM | 4103 | O | ILE | 1198 | 20.154 | -13.343 | 67.332 |
| ATOM | 4104 | N | GLY | 1199 | 22.110 | -12.307 | 67.103 |
| ATOM | 4105 | CA | GLY | 1199 | 21.501 | -10.992 | 67.226 |
| ATOM | 4106 | C | GLY | 1199 | 20.701 | -10.518 | 66.035 |
| ATOM | 4107 | O | GLY | 1199 | 20.740 | -11.157 | 65.012 |
| ATOM | 4108 | N | GLN | 1200 | 19.949 | -9.431 | 66.184 |
| ATOM | 4109 | CA | GLN | 1200 | 19.189 | -8.876 | 65.088 |
| ATOM | 4110 | CB | GLN | 1200 | 18.276 | -9.933 | 64.478 |
| ATOM | 4111 | CG | GLN | 1200 | 17.126 | -10.369 | 65.314 |
| ATOM | 4112 | CD | GLN | 1200 | 15.802 | -10.407 | 64.538 |
| ATOM | 4113 | OE1 | GLN | 1200 | 14.986 | -11.311 | 64.747 |
| ATOM | 4114 | NE2 | GLN | 1200 | 15.563 | -9.405 | 63.678 |
| ATOM | 4115 | C | GLN | 1200 | 18.384 | -7.633 | 65.422 |
| ATOM | 4116 | O | GLN | 1200 | 17.424 | -7.735 | 66.137 |
| ATOM | 4117 | N | ILE | 1201 | 18.735 | -6.470 | 64.872 |
| ATOM | 4118 | CA | ILE | 1201 | 17.985 | -5.237 | 65.144 |
| ATOM | 4119 | CB | ILE | 1201 | 18.726 | -4.058 | 64.682 |
| ATOM | 4120 | CG2 | ILE | 1201 | 17.903 | -2.825 | 64.848 |
| ATOM | 4121 | CG1 | ILE | 1201 | 20.003 | -3.975 | 65.473 |
| ATOM | 4122 | CD1 | ILE | 1201 | 20.883 | -2.895 | 65.035 |
| ATOM | 4123 | C | ILE | 1201 | 16.701 | -5.258 | 64.393 |
| ATOM | 4124 | O | ILE | 1201 | 16.646 | -5.855 | 63.342 |
| ATOM | 4125 | N | GLY | 1202 | 15.671 | -4.584 | 64.874 |
| ATOM | 4126 | CA | GLY | 1202 | 14.442 | -4.656 | 64.122 |

FIGURE 1IIII

| | Atom | | Residue AA | No. | X | Y | Z |
|---|---|---|---|---|---|---|---|
| ATOM | 4127 | C | GLY | 1202 | 13.217 | -3.901 | 64.558 |
| ATOM | 4128 | O | GLY | 1202 | 13.220 | -3.207 | 65.561 |
| ATOM | 4129 | N | LYS | 1203 | 12.164 | -4.039 | 63.764 |
| ATOM | 4130 | CA | LYS | 1203 | 10.918 | -3.369 | 64.036 |
| ATOM | 4131 | CB | LYS | 1203 | 10.307 | -2.842 | 62.727 |
| ATOM | 4132 | CG | LYS | 1203 | 9.913 | -1.349 | 62.736 |
| ATOM | 4133 | CD | LYS | 1203 | 11.136 | -0.448 | 62.588 |
| ATOM | 4134 | CE | LYS | 1203 | 10.899 | 0.968 | 63.099 |
| ATOM | 4135 | NZ | LYS | 1203 | 9.769 | 1.672 | 62.496 |
| ATOM | 4136 | C | LYS | 1203 | 9.967 | -4.339 | 64.718 |
| ATOM | 4137 | O | LYS | 1203 | 9.875 | -5.497 | 64.332 |
| ATOM | 4138 | N | SER | 1204 | 9.349 | -3.876 | 65.796 |
| ATOM | 4139 | CA | SER | 1204 | 8.371 | -4.644 | 66.556 |
| ATOM | 4140 | CB | SER | 1204 | 8.928 | -5.085 | 67.931 |
| ATOM | 4141 | OG | SER | 1204 | 9.731 | -6.261 | 67.875 |
| ATOM | 4142 | C | SER | 1204 | 7.243 | -3.629 | 66.718 |
| ATOM | 4143 | O | SER | 1204 | 7.507 | -2.432 | 66.707 |
| ATOM | 4144 | N | PHE | 1205 | 5.996 | -4.087 | 66.811 |
| ATOM | 4145 | CA | PHE | 1205 | 4.837 | -3.183 | 66.944 |
| ATOM | 4146 | CB | PHE | 1205 | 4.065 | -3.055 | 65.616 |
| ATOM | 4147 | CG | PHE | 1205 | 4.918 | -2.709 | 64.424 |
| ATOM | 4148 | CD1 | PHE | 1205 | 5.640 | -3.688 | 63.765 |
| ATOM | 4149 | CD2 | PHE | 1205 | 4.959 | -1.416 | 63.939 |
| ATOM | 4150 | CE1 | PHE | 1205 | 6.384 | -3.378 | 62.644 |
| ATOM | 4151 | CE2 | PHE | 1205 | 5.703 | -1.105 | 62.818 |
| ATOM | 4152 | CZ | PHE | 1205 | 6.418 | -2.085 | 62.167 |
| ATOM | 4153 | C | PHE | 1205 | 3.835 | -3.634 | 68.008 |
| ATOM | 4154 | O | PHE | 1205 | 3.332 | -4.767 | 67.962 |
| ATOM | 4155 | N | ARG | 1206 | 3.448 | -2.699 | 68.871 |
| ATOM | 4156 | CA | ARG | 1206 | 2.517 | -2.980 | 69.957 |
| ATOM | 4157 | CB | ARG | 1206 | 3.209 | -2.757 | 71.302 |
| ATOM | 4158 | CG | ARG | 1206 | 3.507 | -4.022 | 72.094 |
| ATOM | 4159 | CD | ARG | 1206 | 4.737 | -4.811 | 71.605 |
| ATOM | 4160 | NE | ARG | 1206 | 5.814 | -4.900 | 72.597 |
| ATOM | 4161 | CZ | ARG | 1206 | 5.668 | -5.215 | 73.893 |
| ATOM | 4162 | NH1 | ARG | 1206 | 4.470 | -5.479 | 74.415 |
| ATOM | 4163 | NH2 | ARG | 1206 | 6.744 | -5.301 | 74.683 |
| ATOM | 4164 | C | ARG | 1206 | 1.299 | -2.083 | 69.895 |
| ATOM | 4165 | O | ARG | 1206 | 1.428 | -0.858 | 69.903 |
| ATOM | 4166 | N | ASN | 1207 | 0.117 | -2.689 | 69.851 |
| ATOM | 4167 | CA | ASN | 1207 | -1.134 | -1.935 | 69.817 |
| ATOM | 4168 | CB | ASN | 1207 | -2.274 | -2.827 | 69.309 |
| ATOM | 4169 | CG | ASN | 1207 | -3.524 | -2.030 | 68.889 |
| ATOM | 4170 | OD1 | ASN | 1207 | -3.574 | -0.792 | 69.000 |
| ATOM | 4171 | ND2 | ASN | 1207 | -4.533 | -2.746 | 68.378 |
| ATOM | 4172 | C | ASN | 1207 | -1.383 | -1.524 | 71.265 |
| ATOM | 4173 | O | ASN | 1207 | -2.094 | -2.203 | 71.999 |
| ATOM | 4174 | N | GLU | 1208 | -0.759 | -0.420 | 71.668 |

FIGURE 1JJJJ

| | Atom | | Residue AA | No. | X | Y | Z |
|---|---|---|---|---|---|---|---|
| ATOM | 4175 | CA | GLU | 1208 | -0.827 | 0.108 | 73.043 |
| ATOM | 4176 | CB | GLU | 1208 | 0.235 | 1.203 | 73.232 |
| ATOM | 4177 | CG | GLU | 1208 | 1.028 | 1.022 | 74.489 |
| ATOM | 4178 | CD | GLU | 1208 | 1.462 | -0.422 | 74.712 |
| ATOM | 4179 | OE1 | GLU | 1208 | 2.668 | -0.695 | 74.521 |
| ATOM | 4180 | OE2 | GLU | 1208 | 0.615 | -1.278 | 75.081 |
| ATOM | 4181 | C | GLU | 1208 | -2.179 | 0.577 | 73.606 |
| ATOM | 4182 | O | GLU | 1208 | -3.248 | 0.181 | 73.100 |
| ATOM | 4183 | N | ILE | 1209 | -2.127 | 1.365 | 74.694 |
| ATOM | 4184 | CA | ILE | 1209 | -3.344 | 1.905 | 75.353 |
| ATOM | 4185 | CB | ILE | 1209 | -3.654 | 1.246 | 76.766 |
| ATOM | 4186 | CG2 | ILE | 1209 | -4.326 | -0.143 | 76.583 |
| ATOM | 4187 | CG1 | ILE | 1209 | -2.407 | 1.220 | 77.681 |
| ATOM | 4188 | CD1 | ILE | 1209 | -1.350 | 0.154 | 77.344 |
| ATOM | 4189 | C | ILE | 1209 | -3.264 | 3.421 | 75.519 |
| ATOM | 4190 | O | ILE | 1209 | -3.901 | 4.185 | 74.792 |
| ATOM | 4191 | N | THR | 1210 | -2.421 | 3.848 | 76.442 |
| ATOM | 4192 | CA | THR | 1210 | -2.231 | 5.257 | 76.707 |
| ATOM | 4193 | CB | THR | 1210 | -2.756 | 5.581 | 78.148 |
| ATOM | 4194 | OG1 | THR | 1210 | -2.551 | 6.973 | 78.449 |
| ATOM | 4195 | CG2 | THR | 1210 | -2.098 | 4.642 | 79.224 |
| ATOM | 4196 | C | THR | 1210 | -0.732 | 5.560 | 76.528 |
| ATOM | 4197 | O | THR | 1210 | -0.041 | 5.960 | 77.478 |
| ATOM | 4198 | N | PRO | 1211 | -0.202 | 5.327 | 75.302 |
| ATOM | 4199 | CD | PRO | 1211 | -0.867 | 4.892 | 74.046 |
| ATOM | 4200 | CA | PRO | 1211 | 1.225 | 5.586 | 75.064 |
| ATOM | 4201 | CB | PRO | 1211 | 1.280 | 5.777 | 73.547 |
| ATOM | 4202 | CG | PRO | 1211 | 0.315 | 4.686 | 73.085 |
| ATOM | 4203 | C | PRO | 1211 | 1.887 | 6.704 | 75.899 |
| ATOM | 4204 | O | PRO | 1211 | 1.574 | 7.913 | 75.790 |
| ATOM | 4205 | N | GLY | 1212 | 2.686 | 6.210 | 76.848 |
| ATOM | 4206 | CA | GLY | 1212 | 3.433 | 7.036 | 77.770 |
| ATOM | 4207 | C | GLY | 1212 | 4.434 | 7.918 | 77.067 |
| ATOM | 4208 | O | GLY | 1212 | 5.434 | 7.434 | 76.502 |
| ATOM | 4209 | N | ASN | 1213 | 4.100 | 9.210 | 77.086 |
| ATOM | 4210 | CA | ASN | 1213 | 4.877 | 10.302 | 76.486 |
| ATOM | 4211 | CB | ASN | 1213 | 4.906 | 11.527 | 77.430 |
| ATOM | 4212 | CG | ASN | 1213 | 5.157 | 11.143 | 78.900 |
| ATOM | 4213 | OD1 | ASN | 1213 | 4.521 | 10.211 | 79.430 |
| ATOM | 4214 | ND2 | ASN | 1213 | 6.090 | 11.857 | 79.564 |
| ATOM | 4215 | C | ASN | 1213 | 6.285 | 9.989 | 75.947 |
| ATOM | 4216 | O | ASN | 1213 | 7.017 | 9.170 | 76.475 |
| ATOM | 4217 | N | PHE | 1214 | 6.617 | 10.640 | 74.846 |
| ATOM | 4218 | CA | PHE | 1214 | 7.895 | 10.468 | 74.175 |
| ATOM | 4219 | CB | PHE | 1214 | 9.014 | 11.227 | 74.885 |
| ATOM | 4220 | CG | PHE | 1214 | 9.923 | 11.970 | 73.950 |
| ATOM | 4221 | CD1 | PHE | 1214 | 11.224 | 12.238 | 74.309 |
| ATOM | 4222 | CD2 | PHE | 1214 | 9.456 | 12.447 | 72.744 |

FIGURE 1KKKK

| Atom | | | Residue AA | No. | X | Y | Z |
|---|---|---|---|---|---|---|---|
| ATOM | 4223 | CE1 | PHE | 1214 | 12.044 | 12.981 | 73.481 |
| ATOM | 4224 | CE2 | PHE | 1214 | 10.258 | 13.179 | 71.920 |
| ATOM | 4225 | CZ | PHE | 1214 | 11.558 | 13.453 | 72.286 |
| ATOM | 4226 | C | PHE | 1214 | 8.324 | 9.032 | 73.902 |
| ATOM | 4227 | O | PHE | 1214 | 7.605 | 8.066 | 74.213 |
| ATOM | 4228 | N | ILE | 1215 | 9.541 | 8.930 | 73.367 |
| ATOM | 4229 | CA | ILE | 1215 | 10.153 | 7.679 | 72.973 |
| ATOM | 4230 | CB | ILE | 1215 | 11.641 | 7.875 | 72.650 |
| ATOM | 4231 | CG2 | ILE | 1215 | 12.090 | 6.837 | 71.672 |
| ATOM | 4232 | CG1 | ILE | 1215 | 11.892 | 9.206 | 71.960 |
| ATOM | 4233 | CD1 | ILE | 1215 | 13.368 | 9.401 | 71.583 |
| ATOM | 4234 | C | ILE | 1215 | 10.011 | 6.518 | 73.960 |
| ATOM | 4235 | O | ILE | 1215 | 10.216 | 5.356 | 73.575 |
| ATOM | 4236 | N | PHE | 1216 | 9.681 | 6.792 | 75.223 |
| ATOM | 4237 | CA | PHE | 1216 | 9.542 | 5.670 | 76.152 |
| ATOM | 4238 | CB | PHE | 1216 | 9.565 | 6.047 | 77.670 |
| ATOM | 4239 | CG | PHE | 1216 | 8.908 | 7.404 | 78.037 |
| ATOM | 4240 | CD1 | PHE | 1216 | 7.656 | 7.452 | 78.704 |
| ATOM | 4241 | CD2 | PHE | 1216 | 9.619 | 8.629 | 77.873 |
| ATOM | 4242 | CE1 | PHE | 1216 | 7.146 | 8.678 | 79.210 |
| ATOM | 4243 | CE2 | PHE | 1216 | 9.103 | 9.874 | 78.385 |
| ATOM | 4244 | CZ | PHE | 1216 | 7.883 | 9.888 | 79.048 |
| ATOM | 4245 | C | PHE | 1216 | 8.396 | 4.726 | 75.774 |
| ATOM | 4246 | O | PHE | 1216 | 8.603 | 3.505 | 75.729 |
| ATOM | 4247 | N | ARG | 1217 | 7.218 | 5.258 | 75.450 |
| ATOM | 4248 | CA | ARG | 1217 | 6.148 | 4.360 | 75.066 |
| ATOM | 4249 | CB | ARG | 1217 | 5.091 | 4.224 | 76.162 |
| ATOM | 4250 | CG | ARG | 1217 | 4.708 | 2.745 | 76.487 |
| ATOM | 4251 | CD | ARG | 1217 | 3.482 | 2.610 | 77.429 |
| ATOM | 4252 | NE | ARG | 1217 | 2.210 | 2.715 | 76.704 |
| ATOM | 4253 | CZ | ARG | 1217 | 0.998 | 2.658 | 77.261 |
| ATOM | 4254 | NH1 | ARG | 1217 | 0.842 | 2.502 | 78.567 |
| ATOM | 4255 | NH2 | ARG | 1217 | -0.074 | 2.727 | 76.491 |
| ATOM | 4256 | C | ARG | 1217 | 5.527 | 4.776 | 73.756 |
| ATOM | 4257 | O | ARG | 1217 | 4.594 | 5.577 | 73.731 |
| ATOM | 4258 | N | THR | 1218 | 6.050 | 4.187 | 72.675 |
| ATOM | 4259 | CA | THR | 1218 | 5.632 | 4.427 | 71.281 |
| ATOM | 4260 | CB | THR | 1218 | 6.864 | 4.725 | 70.364 |
| ATOM | 4261 | OG1 | THR | 1218 | 7.969 | 3.894 | 70.756 |
| ATOM | 4262 | CG2 | THR | 1218 | 7.280 | 6.204 | 70.428 |
| ATOM | 4263 | C | THR | 1218 | 4.930 | 3.187 | 70.744 |
| ATOM | 4264 | O | THR | 1218 | 5.350 | 2.063 | 71.026 |
| ATOM | 4265 | N | ARG | 1219 | 3.886 | 3.398 | 69.382 |
| ATOM | 4267 | CB | ARG | 1219 | 1.920 | 2.842 | 68.594 |
| ATOM | 4268 | CG | ARG | 1219 | 1.315 | 4.067 | 69.213 |
| ATOM | 4269 | CD | ARG | 1219 | -0.160 | 4.181 | 68.931 |
| ATOM | 4270 | NE | ARG | 1219 | -0.941 | 3.021 | 69.388 |

FIGURE 1LLLL

| Atom | | | Residue AA | No. | X | Y | Z |
|---|---|---|---|---|---|---|---|
| ATOM | 4271 | CZ | ARG | 1219 | -1.764 | 2.979 | 70.450 |
| ATOM | 4272 | NH1 | ARG | 1219 | -1.959 | 4.030 | 71.255 |
| ATOM | 4273 | NH2 | ARG | 1219 | -2.471 | 1.873 | 70.661 |
| ATOM | 4274 | C | ARG | 1219 | 3.981 | 1.458 | 68.459 |
| ATOM | 4275 | O | ARG | 1219 | 3.657 | 0.305 | 68.160 |
| ATOM | 4276 | N | GLU | 1220 | 5.112 | 2.023 | 68.051 |
| ATOM | 4277 | CA | GLU | 1220 | 6.021 | 1.359 | 67.131 |
| ATOM | 4278 | CB | GLU | 1220 | 5.799 | 1.965 | 65.744 |
| ATOM | 4279 | CG | GLU | 1220 | 6.755 | 1.516 | 64.672 |
| ATOM | 4280 | CD | GLU | 1220 | 6.724 | 2.425 | 63.482 |
| ATOM | 4281 | OE1 | GLU | 1220 | 7.798 | 2.952 | 63.118 |
| ATOM | 4282 | OE2 | GLU | 1220 | 5.622 | 2.622 | 62.936 |
| ATOM | 4283 | C | GLU | 1220 | 7.433 | 1.627 | 67.614 |
| ATOM | 4284 | O | GLU | 1220 | 7.725 | 2.747 | 68.008 |
| ATOM | 4285 | N | PHE | 1221 | 8.321 | 0.638 | 67.532 |
| ATOM | 4286 | CA | PHE | 1221 | 9.693 | 0.800 | 68.026 |
| ATOM | 4287 | CB | PHE | 1221 | 9.702 | 0.622 | 69.548 |
| ATOM | 4288 | CG | PHE | 1221 | 9.070 | -0.683 | 70.007 |
| ATOM | 4289 | CD1 | PHE | 1221 | 9.829 | -1.845 | 70.112 |
| ATOM | 4290 | CD2 | PHE | 1221 | 7.697 | -0.754 | 70.269 |
| ATOM | 4291 | CE1 | PHE | 1221 | 9.235 | -3.048 | 70.459 |
| ATOM | 4292 | CE2 | PHE | 1221 | 7.099 | -1.955 | 70.618 |
| ATOM | 4293 | CZ | PHE | 1221 | 7.870 | -3.106 | 70.710 |
| ATOM | 4294 | C | PHE | 1221 | 10.665 | -0.223 | 67.471 |
| ATOM | 4295 | O | PHE | 1221 | 10.264 | -1.255 | 66.949 |
| ATOM | 4296 | N | GLU | 1222 | 11.943 | 0.008 | 67.735 |
| ATOM | 4297 | CA | GLU | 1222 | 13.005 | -0.883 | 67.305 |
| ATOM | 4298 | CB | GLU | 1222 | 14.028 | -0.101 | 66.526 |
| ATOM | 4299 | CG | GLU | 1222 | 13.741 | 0.045 | 65.087 |
| ATOM | 4300 | CD | GLU | 1222 | 14.925 | 0.635 | 64.362 |
| ATOM | 4301 | OE1 | GLU | 1222 | 15.828 | -0.116 | 63.924 |
| ATOM | 4302 | OE2 | GLU | 1222 | 14.966 | 1.861 | 64.248 |
| ATOM | 4303 | C | GLU | 1222 | 13.691 | -1.533 | 68.513 |
| ATOM | 4304 | O | GLU | 1222 | 14.141 | -0.830 | 69.412 |
| ATOM | 4305 | N | GLN | 1223 | 13.795 | -2.862 | 68.502 |
| ATOM | 4306 | CA | GLN | 1223 | 14.407 | -3.647 | 69.567 |
| ATOM | 4307 | CB | GLN | 1223 | 13.912 | -5.070 | 69.502 |
| ATOM | 4308 | CG | GLN | 1223 | 12.436 | -5.166 | 69.348 |
| ATOM | 4309 | CD | GLN | 1223 | 11.742 | -5.556 | 70.621 |
| ATOM | 4310 | OE1 | GLN | 1223 | 12.170 | -5.170 | 71.700 |
| ATOM | 4311 | NE2 | GLN | 1223 | 10.646 | -6.320 | 70.504 |
| ATOM | 4312 | C | GLN | 1223 | 15.905 | -3.638 | 69.412 |
| ATOM | 4313 | O | GLN | 1223 | 16.478 | -2.600 | 69.158 |
| ATOM | 4314 | N | MET | 1224 | 16.539 | -4.786 | 69.595 |
| ATOM | 4315 | CA | MET | 1224 | 17.984 | -4.903 | 69.471 |
| ATOM | 4316 | CB | MET | 1224 | 18.671 | -3.718 | 70.101 |
| ATOM | 4317 | CG | MET | 1224 | 19.667 | -3.108 | 69.226 |
| ATOM | 4318 | SD | MET | 1224 | 19.537 | -1.389 | 69.461 |

FIGURE 1MMMM

| Atom | | | Residue AA | No. | X | Y | Z |
|---|---|---|---|---|---|---|---|
| ATOM | 4319 | CE | MET | 1224 | 21.150 | -1.001 | 69.569 |
| ATOM | 4320 | C | MET | 1224 | 18.396 | -6.122 | 70.239 |
| ATOM | 4321 | O | MET | 1224 | 19.353 | -6.076 | 70.972 |
| ATOM | 4322 | N | GLU | 1225 | 17.708 | -7.227 | 70.011 |
| ATOM | 4323 | CA | GLU | 1225 | 17.916 | -8.479 | 70.724 |
| ATOM | 4324 | CB | GLU | 1225 | 16.618 | -9.243 | 70.637 |
| ATOM | 4325 | CG | GLU | 1225 | 15.432 | -8.304 | 70.735 |
| ATOM | 4326 | CD | GLU | 1225 | 14.132 | -9.016 | 70.913 |
| ATOM | 4327 | OE1 | GLU | 1225 | 13.980 | -10.092 | 70.310 |
| ATOM | 4328 | OE2 | GLU | 1225 | 13.262 | -8.508 | 71.648 |
| ATOM | 4329 | C | GLU | 1225 | 19.058 | -9.379 | 70.322 |
| ATOM | 4330 | O | GLU | 1225 | 19.657 | -9.185 | 69.293 |
| ATOM | 4331 | N | LEU | 1226 | 19.360 | -10.365 | 71.148 |
| ATOM | 4332 | CA | LEU | 1226 | 20.414 | -11.317 | 70.855 |
| ATOM | 4333 | CB | LEU | 1226 | 21.767 | -10.809 | 71.329 |
| ATOM | 4334 | CG | LEU | 1226 | 22.959 | -11.780 | 71.360 |
| ATOM | 4335 | CD1 | LEU | 1226 | 24.240 | -10.999 | 71.262 |
| ATOM | 4336 | CD2 | LEU | 1226 | 22.991 | -12.622 | 72.597 |
| ATOM | 4337 | C | LEU | 1226 | 20.065 | -12.505 | 71.659 |
| ATOM | 4338 | O | LEU | 1226 | 19.815 | -12.359 | 72.818 |
| ATOM | 4339 | N | GLU | 1227 | 19.993 | -13.673 | 71.057 |
| ATOM | 4340 | CA | GLU | 1227 | 19.687 | -14.863 | 71.814 |
| ATOM | 4341 | CB | GLU | 1227 | 18.570 | -15.659 | 71.171 |
| ATOM | 4342 | CG | GLU | 1227 | 17.357 | -15.790 | 72.050 |
| ATOM | 4343 | CD | GLU | 1227 | 16.566 | -14.504 | 72.143 |
| ATOM | 4344 | OE1 | GLU | 1227 | 15.321 | -14.547 | 72.052 |
| ATOM | 4345 | OE2 | GLU | 1227 | 17.188 | -13.441 | 72.297 |
| ATOM | 4346 | C | GLU | 1227 | 20.921 | -15.716 | 71.886 |
| ATOM | 4347 | O | GLU | 1227 | 21.388 | -16.195 | 70.862 |
| ATOM | 4348 | N | PHE | 1228 | 21.453 | -15.879 | 73.093 |
| ATOM | 4349 | CA | PHE | 1228 | 22.641 | -16.680 | 73.342 |
| ATOM | 4350 | CB | PHE | 1228 | 23.432 | -16.084 | 74.501 |
| ATOM | 4351 | CG | PHE | 1228 | 24.833 | -16.611 | 74.620 |
| ATOM | 4352 | CD1 | PHE | 1228 | 25.090 | -17.807 | 75.265 |
| ATOM | 4353 | CD2 | PHE | 1228 | 25.905 | -15.900 | 74.081 |
| ATOM | 4354 | CE1 | PHE | 1228 | 26.397 | -18.290 | 75.375 |
| ATOM | 4355 | CE2 | PHE | 1228 | 27.211 | -16.370 | 74.185 |
| ATOM | 4356 | CZ | PHE | 1228 | 27.455 | -17.567 | 74.834 |
| ATOM | 4357 | C | PHE | 1228 | 22.228 | -18.099 | 73.680 |
| ATOM | 4358 | O | PHE | 1228 | 21.475 | -18.308 | 74.599 |
| ATOM | 4359 | N | PHE | 1229 | 22.672 | -19.062 | 72.890 |
| ATOM | 4360 | CA | PHE | 1229 | 22.346 | -20.461 | 73.118 |
| ATOM | 4361 | CB | PHE | 1229 | 22.065 | -21.182 | 71.796 |
| ATOM | 4362 | CG | PHE | 1229 | 20.811 | -20.696 | 71.148 |
| ATOM | 4363 | CD1 | PHE | 1229 | 20.776 | -19.443 | 70.554 |
| ATOM | 4364 | CD2 | PHE | 1229 | 19.630 | -21.377 | 71.324 |
| ATOM | 4365 | CE1 | PHE | 1229 | 19.599 | -18.877 | 70.177 |
| ATOM | 4366 | CE2 | PHE | 1229 | 18.450 | -20.809 | 70.943 |

FIGURE 1NNNN

| | Atom | | Residue AA | No. | X | Y | Z |
|---|---|---|---|---|---|---|---|
| ATOM | 4367 | CZ | PHE | 1229 | 18.434 | -19.554 | 70.373 |
| ATOM | 4368 | C | PHE | 1229 | 23.456 | -21.047 | 73.938 |
| ATOM | 4369 | O | PHE | 1229 | 24.637 | -20.906 | 73.625 |
| ATOM | 4370 | N | CYS | 1230 | 23.047 | -21.714 | 75.005 |
| ATOM | 4371 | CA | CYS | 1230 | 23.953 | -22.243 | 76.014 |
| ATOM | 4372 | CB | CYS | 1230 | 23.668 | -21.474 | 77.284 |
| ATOM | 4373 | SG | CYS | 1230 | 25.007 | -21.474 | 78.344 |
| ATOM | 4374 | C | CYS | 1230 | 23.767 | -23.696 | 76.328 |
| ATOM | 4375 | O | CYS | 1230 | 22.632 | -24.171 | 76.410 |
| ATOM | 4376 | N | LYS | 1231 | 24.868 | -24.400 | 76.546 |
| ATOM | 4377 | CA | LYS | 1231 | 24.762 | -25.807 | 76.893 |
| ATOM | 4378 | CB | LYS | 1231 | 26.164 | -26.408 | 77.028 |
| ATOM | 4379 | CG | LYS | 1231 | 26.210 | -27.896 | 77.444 |
| ATOM | 4380 | CD | LYS | 1231 | 26.078 | -28.111 | 78.978 |
| ATOM | 4381 | CE | LYS | 1231 | 27.348 | -27.676 | 79.784 |
| ATOM | 4382 | NZ | LYS | 1231 | 27.194 | -27.627 | 81.299 |
| ATOM | 4383 | C | LYS | 1231 | 24.015 | -25.790 | 78.236 |
| ATOM | 4384 | O | LYS | 1231 | 24.452 | -25.108 | 79.153 |
| ATOM | 4385 | N | PRO | 1232 | 22.911 | -26.559 | 78.381 |
| ATOM | 4386 | CD | PRO | 1232 | 22.552 | -27.573 | 77.373 |
| ATOM | 4387 | CA | PRO | 1232 | 22.025 | -26.704 | 79.546 |
| ATOM | 4388 | CB | PRO | 1232 | 21.381 | -28.074 | 79.312 |
| ATOM | 4389 | CG | PRO | 1232 | 21.202 | -28.095 | 77.869 |
| ATOM | 4390 | C | PRO | 1232 | 22.518 | -26.560 | 81.003 |
| ATOM | 4391 | O | PRO | 1232 | 21.707 | -26.682 | 81.926 |
| ATOM | 4392 | N | GLY | 1233 | 23.803 | -26.316 | 81.244 |
| ATOM | 4393 | CA | GLY | 1233 | 24.254 | -26.173 | 82.616 |
| ATOM | 4394 | C | GLY | 1233 | 24.700 | -24.773 | 82.946 |
| ATOM | 4395 | O | GLY | 1233 | 24.422 | -24.254 | 84.019 |
| ATOM | 4396 | N | GLU | 1234 | 25.247 | -24.099 | 81.959 |
| ATOM | 4397 | CA | GLU | 1234 | 25.768 | -22.770 | 82.181 |
| ATOM | 4398 | CB | GLU | 1234 | 26.896 | -22.542 | 81.191 |
| ATOM | 4399 | CG | GLU | 1234 | 27.840 | -23.721 | 81.151 |
| ATOM | 4400 | CD | GLU | 1234 | 28.260 | -24.119 | 79.745 |
| ATOM | 4401 | OE1 | GLU | 1234 | 27.681 | -23.601 | 78.754 |
| ATOM | 4402 | OE2 | GLU | 1234 | 29.179 | -24.967 | 79.627 |
| ATOM | 4403 | C | GLU | 1234 | 24.785 | -21.606 | 82.179 |
| ATOM | 4404 | O | GLU | 1234 | 25.184 | -20.450 | 82.291 |
| ATOM | 4405 | N | GLU | 1235 | 23.501 | -21.907 | 82.147 |
| ATOM | 4406 | CA | GLU | 1235 | 22.492 | -20.859 | 82.099 |
| ATOM | 4407 | CB | GLU | 1235 | 21.090 | -21.384 | 82.457 |
| ATOM | 4408 | CG | GLU | 1235 | 20.920 | -22.049 | 83.832 |
| ATOM | 4409 | CD | GLU | 1235 | 21.558 | -23.455 | 83.958 |
| ATOM | 4410 | OE1 | GLU | 1235 | 21.476 | -24.088 | 85.048 |
| ATOM | 4411 | OE2 | GLU | 1235 | 22.130 | -23.941 | 82.971 |
| ATOM | 4412 | C | GLU | 1235 | 22.835 | -19.637 | 82.905 |
| ATOM | 4413 | O | GLU | 1235 | 22.743 | -18.524 | 82.426 |
| ATOM | 4414 | N | ILE | 1236 | 23.372 | -19.854 | 84.083 |

FIGURE 10OOO

| Atom | | | Residue AA | No. | X | Y | Z |
|---|---|---|---|---|---|---|---|
| ATOM | 4415 | CA | ILE | 1236 | 23.713 | -18.737 | 84.932 |
| ATOM | 4416 | CB | ILE | 1236 | 23.659 | -19.067 | 86.439 |
| ATOM | 4417 | CG2 | ILE | 1236 | 22.236 | -19.199 | 86.878 |
| ATOM | 4418 | CG1 | ILE | 1236 | 24.526 | -20.288 | 86.786 |
| ATOM | 4419 | CD1 | ILE | 1236 | 23.944 | -21.685 | 86.490 |
| ATOM | 4420 | C | ILE | 1236 | 25.040 | -18.112 | 84.611 |
| ATOM | 4421 | O | ILE | 1236 | 25.187 | -16.909 | 84.742 |
| ATOM | 4422 | N | GLU | 1237 | 26.006 | -18.907 | 84.175 |
| ATOM | 4423 | CA | GLU | 1237 | 27.324 | -18.349 | 83.855 |
| ATOM | 4424 | CB | GLU | 1237 | 28.256 | -19.399 | 83.220 |
| ATOM | 4425 | CG | GLU | 1237 | 28.892 | -20.353 | 84.186 |
| ATOM | 4426 | CD | GLU | 1237 | 27.918 | -20.756 | 85.277 |
| ATOM | 4427 | OE1 | GLU | 1237 | 27.033 | -21.601 | 84.998 |
| ATOM | 4428 | OE2 | GLU | 1237 | 28.015 | -20.193 | 86.403 |
| ATOM | 4429 | C | GLU | 1237 | 27.089 | -17.265 | 82.843 |
| ATOM | 4430 | O | GLU | 1237 | 27.528 | -16.124 | 82.977 |
| ATOM | 4431 | N | TRP | 1238 | 26.313 | -17.627 | 81.849 |
| ATOM | 4432 | CA | TRP | 1238 | 26.041 | -16.704 | 80.807 |
| ATOM | 4433 | CB | TRP | 1238 | 25.593 | -17.475 | 79.575 |
| ATOM | 4434 | CG | TRP | 1238 | 26.763 | -18.286 | 79.050 |
| ATOM | 4435 | CD2 | TRP | 1238 | 27.960 | -17.769 | 78.472 |
| ATOM | 4436 | CE2 | TRP | 1238 | 28.791 | -18.857 | 78.198 |
| ATOM | 4437 | CE3 | TRP | 1238 | 28.408 | -16.483 | 78.157 |
| ATOM | 4438 | CD1 | TRP | 1238 | 26.915 | -19.630 | 79.097 |
| ATOM | 4439 | NE1 | TRP | 1238 | 28.125 | -19.985 | 78.589 |
| ATOM | 4440 | CZ2 | TRP | 1238 | 30.051 | -18.705 | 77.625 |
| ATOM | 4441 | CZ3 | TRP | 1238 | 29.657 | -16.331 | 77.588 |
| ATOM | 4442 | CH2 | TRP | 1238 | 30.464 | -17.433 | 77.329 |
| ATOM | 4443 | C | TRP | 1238 | 25.087 | -15.667 | 81.317 |
| ATOM | 4444 | O | TRP | 1238 | 25.420 | -14.495 | 81.302 |
| ATOM | 4445 | N | GLN | 1239 | 24.022 | -16.099 | 81.969 |
| ATOM | 4446 | CA | GLN | 1239 | 23.043 | -15.169 | 82.492 |
| ATOM | 4447 | CB | GLN | 1239 | 22.122 | -15.867 | 83.470 |
| ATOM | 4448 | CG | GLN | 1239 | 21.479 | -14.971 | 84.466 |
| ATOM | 4449 | CD | GLN | 1239 | 20.657 | -13.892 | 83.842 |
| ATOM | 4450 | OE1 | GLN | 1239 | 20.792 | -12.733 | 84.194 |
| ATOM | 4451 | NE2 | GLN | 1239 | 19.778 | -14.260 | 82.929 |
| ATOM | 4452 | C | GLN | 1239 | 23.675 | -13.973 | 83.128 |
| ATOM | 4453 | O | GLN | 1239 | 23.081 | -12.935 | 83.227 |
| ATOM | 4454 | N | ASN | 1240 | 24.907 | -14.110 | 83.547 |
| ATOM | 4455 | CA | ASN | 1240 | 25.562 | -12.982 | 84.151 |
| ATOM | 4456 | CB | ASN | 1240 | 26.206 | -13.354 | 85.485 |
| ATOM | 4457 | CG | ASN | 1240 | 25.166 | -13.567 | 86.614 |
| ATOM | 4458 | OD1 | ASN | 1240 | 25.334 | -14.486 | 87.453 |
| ATOM | 4459 | ND2 | ASN | 1240 | 24.084 | -12.727 | 86.641 |
| ATOM | 4460 | C | ASN | 1240 | 26.593 | -12.386 | 83.255 |
| ATOM | 4461 | O | ASN | 1240 | 26.842 | -11.193 | 83.311 |
| ATOM | 4462 | N | TYR | 1241 | 27.221 | -13.208 | 82.435 |

FIGURE 1PPPP

| | Atom | | Residue AA | No. | X | Y | Z |
|---|---|---|---|---|---|---|---|
| ATOM | 4463 | CA | TYR | 1241 | 28.247 | -12.708 | 81.535 |
| ATOM | 4464 | CB | TYR | 1241 | 28.673 | -13.797 | 80.563 |
| ATOM | 4465 | CG | TYR | 1241 | 29.562 | -13.275 | 79.469 |
| ATOM | 4466 | CD1 | TYR | 1241 | 29.098 | -13.166 | 78.154 |
| ATOM | 4467 | CE1 | TYR | 1241 | 29.887 | -12.641 | 77.162 |
| ATOM | 4468 | CD2 | TYR | 1241 | 30.846 | -12.848 | 79.753 |
| ATOM | 4469 | CE2 | TYR | 1241 | 31.645 | -12.323 | 78.770 |
| ATOM | 4470 | CZ | TYR | 1241 | 31.161 | -12.216 | 77.471 |
| ATOM | 4471 | OH | TYR | 1241 | 31.947 | -11.645 | 76.493 |
| ATOM | 4472 | C | TYR | 1241 | 27.700 | -11.543 | 80.753 |
| ATOM | 4473 | O | TYR | 1241 | 28.330 | -10.506 | 80.618 |
| ATOM | 4474 | N | TRP | 1242 | 26.484 | -11.717 | 80.276 |
| ATOM | 4475 | CA | TRP | 1242 | 25.857 | -10.689 | 79.492 |
| ATOM | 4476 | CB | TRP | 1242 | 24.723 | -11.284 | 78.622 |
| ATOM | 4477 | CG | TRP | 1242 | 25.268 | -12.246 | 77.579 |
| ATOM | 4478 | CD2 | TRP | 1242 | 26.030 | -11.905 | 76.419 |
| ATOM | 4479 | CE2 | TRP | 1242 | 26.502 | -13.092 | 75.872 |
| ATOM | 4480 | CE3 | TRP | 1242 | 26.368 | -10.700 | 75.799 |
| ATOM | 4481 | CD1 | TRP | 1242 | 25.287 | -13.593 | 77.658 |
| ATOM | 4482 | NE1 | TRP | 1242 | 26.035 | -14.112 | 76.650 |
| ATOM | 4483 | CZ2 | TRP | 1242 | 27.299 | -13.122 | 74.732 |
| ATOM | 4484 | CZ3 | TRP | 1242 | 27.162 | -10.726 | 74.664 |
| ATOM | 4485 | CH2 | TRP | 1242 | 27.618 | -11.926 | 74.144 |
| ATOM | 4486 | C | TRP | 1242 | 25.415 | -9.496 | 80.325 |
| ATOM | 4487 | O | TRP | 1242 | 25.512 | -8.364 | 79.853 |
| ATOM | 4488 | N | ALA | 1243 | 24.953 | -9.737 | 81.557 |
| ATOM | 4489 | CA | ALA | 1243 | 24.531 | -8.648 | 82.455 |
| ATOM | 4490 | CB | ALA | 1243 | 24.031 | -9.207 | 83.806 |
| ATOM | 4491 | C | ALA | 1243 | 25.737 | -7.716 | 82.666 |
| ATOM | 4492 | O | ALA | 1243 | 25.631 | -6.502 | 82.507 |
| ATOM | 4493 | N | THR | 1244 | 26.895 | -8.306 | 82.951 |
| ATOM | 4494 | CA | THR | 1244 | 28.130 | -7.558 | 83.158 |
| ATOM | 4495 | CB | THR | 1244 | 29.301 | -8.498 | 83.566 |
| ATOM | 4496 | OG1 | THR | 1244 | 28.942 | -9.270 | 84.724 |
| ATOM | 4497 | CG2 | THR | 1244 | 30.564 | -7.691 | 83.870 |
| ATOM | 4498 | C | THR | 1244 | 28.496 | -6.846 | 81.854 |
| ATOM | 4499 | O | THR | 1244 | 28.781 | -5.647 | 81.853 |
| ATOM | 4500 | N | PHE | 1245 | 28.418 | -7.582 | 80.746 |
| ATOM | 4501 | CA | PHE | 1245 | 28.732 | -7.083 | 79.404 |
| ATOM | 4502 | CB | PHE | 1245 | 28.603 | -8.225 | 78.422 |
| ATOM | 4503 | CG | PHE | 1245 | 29.045 | -7.878 | 77.057 |
| ATOM | 4504 | CD1 | PHE | 1245 | 30.292 | -7.331 | 76.857 |
| ATOM | 4505 | CD2 | PHE | 1245 | 28.214 | -8.090 | 75.975 |
| ATOM | 4506 | CE1 | PHE | 1245 | 30.702 | -7.000 | 75.606 |
| ATOM | 4507 | CE2 | PHE | 1245 | 28.612 | -7.767 | 74.717 |
| ATOM | 4508 | CZ | PHE | 1245 | 29.860 | -7.217 | 74.526 |
| ATOM | 4509 | C | PHE | 1245 | 27.863 | -5.936 | 78.909 |
| ATOM | 4510 | O | PHE | 1245 | 28.359 | -4.929 | 78.422 |

FIGURE 1QQQQ

| | | | Residue | | | | |
|---|---|---|---|---|---|---|---|
| | Atom | | AA | No. | X | Y | Z |
| ATOM | 4511 | N | ALA | 1246 | 26.564 | -6.182 | 78.933 |
| ATOM | 4512 | CA | ALA | 1246 | 25.545 | -5.231 | 78.547 |
| ATOM | 4513 | CB | ALA | 1246 | 24.176 | -5.852 | 78.746 |
| ATOM | 4514 | C | ALA | 1246 | 25.666 | -3.965 | 79.389 |
| ATOM | 4515 | O | ALA | 1246 | 25.579 | -2.853 | 78.874 |
| ATOM | 4516 | N | SER | 1247 | 25.878 | -4.137 | 80.690 |
| ATOM | 4517 | CA | SER | 1247 | 26.014 | -3.015 | 81.609 |
| ATOM | 4518 | CB | SER | 1247 | 25.881 | -3.502 | 83.029 |
| ATOM | 4519 | OG | SER | 1247 | 24.616 | -4.119 | 83.172 |
| ATOM | 4520 | C | SER | 1247 | 27.325 | -2.317 | 81.407 |
| ATOM | 4521 | O | SER | 1247 | 27.387 | -1.113 | 81.394 |
| ATOM | 4522 | N | ASP | 1248 | 28.378 | -3.083 | 81.230 |
| ATOM | 4523 | CA | ASP | 1248 | 29.654 | -2.489 | 80.960 |
| ATOM | 4524 | CB | ASP | 1248 | 30.711 | -3.557 | 80.738 |
| ATOM | 4525 | CG | ASP | 1248 | 31.627 | -3.736 | 81.937 |
| ATOM | 4526 | OD1 | ASP | 1248 | 32.027 | -2.729 | 82.565 |
| ATOM | 4527 | OD2 | ASP | 1248 | 31.972 | -4.895 | 82.246 |
| ATOM | 4528 | C | ASP | 1248 | 29.473 | -1.695 | 79.671 |
| ATOM | 4529 | O | ASP | 1248 | 29.948 | -0.574 | 79.554 |
| ATOM | 4530 | N | TRP | 1249 | 28.743 | -2.246 | 78.715 |
| ATOM | 4531 | CA | TRP | 1249 | 28.529 | -1.548 | 77.460 |
| ATOM | 4532 | CB | TRP | 1249 | 27.568 | -2.337 | 76.578 |
| ATOM | 4533 | CG | TRP | 1249 | 27.523 | -1.887 | 75.143 |
| ATOM | 4534 | CD2 | TRP | 1249 | 26.480 | -1.139 | 74.505 |
| ATOM | 4535 | CE2 | TRP | 1249 | 26.885 | -0.898 | 73.198 |
| ATOM | 4536 | CE3 | TRP | 1249 | 25.244 | -0.639 | 74.926 |
| ATOM | 4537 | CD1 | TRP | 1249 | 28.481 | -2.073 | 74.209 |
| ATOM | 4538 | NE1 | TRP | 1249 | 28.110 | -1.483 | 73.042 |
| ATOM | 4539 | CZ2 | TRP | 1249 | 26.108 | -0.174 | 72.297 |
| ATOM | 4540 | CZ3 | TRP | 1249 | 24.469 | 0.085 | 74.022 |
| ATOM | 4541 | CH2 | TRP | 1249 | 24.908 | 0.308 | 72.729 |
| ATOM | 4542 | C | TRP | 1249 | 27.967 | -0.166 | 77.713 |
| ATOM | 4543 | O | TRP | 1249 | 28.571 | 0.824 | 77.349 |
| ATOM | 4544 | N | LEU | 1250 | 26.856 | -0.093 | 78.418 |
| ATOM | 4545 | CA | LEU | 1250 | 26.242 | 1.186 | 78.660 |
| ATOM | 4546 | CB | LEU | 1250 | 25.112 | 1.036 | 79.636 |
| ATOM | 4547 | CG | LEU | 1250 | 23.892 | 0.564 | 78.889 |
| ATOM | 4548 | CD1 | LEU | 1250 | 23.021 | -0.280 | 79.772 |
| ATOM | 4549 | CD2 | LEU | 1250 | 23.159 | 1.762 | 78.371 |
| ATOM | 4550 | C | LEU | 1250 | 27.185 | 2.284 | 79.087 |
| ATOM | 4551 | O | LEU | 1250 | 27.371 | 3.263 | 78.369 |
| ATOM | 4552 | N | THR | 1251 | 27.853 | 2.109 | 80.215 |
| ATOM | 4553 | CA | THR | 1251 | 28.754 | 3.153 | 80.670 |
| ATOM | 4554 | CB | THR | 1251 | 29.245 | 2.965 | 82.168 |
| ATOM | 4555 | OG1 | THR | 1251 | 30.067 | 1.800 | 82.290 |
| ATOM | 4556 | CG2 | THR | 1251 | 28.063 | 2.839 | 83.141 |
| ATOM | 4557 | C | THR | 1251 | 29.915 | 3.397 | 79.692 |
| ATOM | 4558 | O | THR | 1251 | 30.352 | 4.533 | 79.570 |

FIGURE 1RRRR

| Atom | | | Residue AA | No. | X | Y | Z |
|---|---|---|---|---|---|---|---|
| ATOM | 4559 | N | SER | 1252 | 30.336 | 2.382 | 78.927 |
| ATOM | 4560 | CA | SER | 1252 | 31.447 | 2.530 | 77.954 |
| ATOM | 4561 | CB | SER | 1252 | 31.921 | 1.167 | 77.420 |
| ATOM | 4562 | OG | SER | 1252 | 30.897 | 0.461 | 76.729 |
| ATOM | 4563 | C | SER | 1252 | 31.127 | 3.486 | 76.783 |
| ATOM | 4564 | O | SER | 1252 | 32.026 | 4.115 | 76.203 |
| ATOM | 4565 | N | ALA | 1253 | 29.846 | 3.555 | 76.424 |
| ATOM | 4566 | CA | ALA | 1253 | 29.378 | 4.470 | 75.395 |
| ATOM | 4567 | CB | ALA | 1253 | 28.115 | 3.923 | 74.717 |
| ATOM | 4568 | C | ALA | 1253 | 29.105 | 5.808 | 76.129 |
| ATOM | 4569 | O | ALA | 1253 | 28.651 | 6.784 | 75.515 |
| ATOM | 4570 | N | ASN | 1254 | 29.384 | 5.808 | 77.447 |
| ATOM | 4571 | CA | ASN | 1254 | 29.295 | 6.947 | 78.388 |
| ATOM | 4572 | CB | ASN | 1254 | 29.566 | 8.255 | 77.677 |
| ATOM | 4573 | CG | ASN | 1254 | 30.828 | 8.907 | 78.154 |
| ATOM | 4574 | OD1 | ASN | 1254 | 30.893 | 10.130 | 78.266 |
| ATOM | 4575 | ND2 | ASN | 1254 | 31.863 | 8.106 | 78.408 |
| ATOM | 4576 | C | ASN | 1254 | 28.113 | 7.156 | 79.321 |
| ATOM | 4577 | O | ASN | 1254 | 27.873 | 8.277 | 79.767 |
| ATOM | 4578 | N | MET | 1255 | 27.425 | 6.101 | 79.724 |
| ATOM | 4579 | CA | MET | 1255 | 26.255 | 6.330 | 80.562 |
| ATOM | 4580 | CB | MET | 1255 | 25.092 | 5.491 | 80.094 |
| ATOM | 4581 | CG | MET | 1255 | 23.808 | 6.135 | 80.448 |
| ATOM | 4582 | SD | MET | 1255 | 22.593 | 4.998 | 80.090 |
| ATOM | 4583 | CE | MET | 1255 | 22.834 | 3.961 | 81.447 |
| ATOM | 4584 | C | MET | 1255 | 26.386 | 6.209 | 82.067 |
| ATOM | 4585 | O | MET | 1255 | 25.968 | 5.186 | 82.659 |
| ATOM | 4586 | N | SER | 1256 | 26.845 | 7.307 | 82.678 |
| ATOM | 4587 | CA | SER | 1256 | 27.068 | 7.424 | 84.132 |
| ATOM | 4588 | CB | SER | 1256 | 26.746 | 8.834 | 84.599 |
| ATOM | 4589 | OG | SER | 1256 | 25.424 | 9.177 | 84.230 |
| ATOM | 4590 | C | SER | 1256 | 26.341 | 6.415 | 85.020 |
| ATOM | 4591 | O | SER | 1256 | 25.102 | 6.369 | 85.086 |
| ATOM | 4592 | N | SER | 1257 | 27.149 | 5.624 | 85.713 |
| ATOM | 4593 | CA | SER | 1257 | 26.654 | 4.593 | 86.592 |
| ATOM | 4594 | CB | SER | 1257 | 27.838 | 3.944 | 87.317 |
| ATOM | 4595 | OG | SER | 1257 | 28.784 | 4.919 | 87.756 |
| ATOM | 4596 | C | SER | 1257 | 25.654 | 5.158 | 87.587 |
| ATOM | 4597 | O | SER | 1257 | 24.549 | 4.621 | 87.758 |
| ATOM | 4598 | N | GLU | 1258 | 26.011 | 6.304 | 88.154 |
| ATOM | 4599 | CA | GLU | 1258 | 25.185 | 6.976 | 89.144 |
| ATOM | 4600 | CB | GLU | 1258 | 25.959 | 8.182 | 89.715 |
| ATOM | 4601 | CG | GLU | 1258 | 27.006 | 7.797 | 90.834 |
| ATOM | 4602 | CD | GLU | 1258 | 28.522 | 8.041 | 90.479 |
| ATOM | 4603 | OE1 | GLU | 1258 | 28.844 | 8.792 | 89.509 |
| ATOM | 4604 | OE2 | GLU | 1258 | 29.394 | 7.486 | 91.216 |
| ATOM | 4605 | C | GLU | 1258 | 23.756 | 7.346 | 88.690 |
| ATOM | 4606 | O | GLU | 1258 | 23.043 | 8.095 | 89.383 |

FIGURE 1SSSS

| Atom | | | Residue AA | No. | X | Y | Z |
|---|---|---|---|---|---|---|---|
| ATOM | 4607 | N | ASN | 1259 | 23.333 | 6.775 | 87.555 |
| ATOM | 4608 | CA | ASN | 1259 | 22.008 | 7.012 | 87.001 |
| ATOM | 4609 | CB | ASN | 1259 | 22.114 | 7.956 | 85.825 |
| ATOM | 4610 | CG | ASN | 1259 | 21.360 | 9.211 | 86.054 |
| ATOM | 4611 | OD1 | ASN | 1259 | 20.260 | 9.174 | 86.598 |
| ATOM | 4612 | ND2 | ASN | 1259 | 21.939 | 10.344 | 85.667 |
| ATOM | 4613 | C | ASN | 1259 | 21.243 | 5.755 | 86.599 |
| ATOM | 4614 | O | ASN | 1259 | 20.069 | 5.826 | 86.250 |
| ATOM | 4615 | N | MET | 1260 | 21.871 | 4.604 | 86.799 |
| ATOM | 4616 | CA | MET | 1260 | 21.298 | 3.314 | 86.440 |
| ATOM | 4617 | CB | MET | 1260 | 21.913 | 2.872 | 85.106 |
| ATOM | 4618 | CG | MET | 1260 | 23.429 | 3.262 | 84.963 |
| ATOM | 4619 | SD | MET | 1260 | 24.505 | 2.346 | 84.068 |
| ATOM | 4621 | C | MET | 1260 | 21.625 | 2.257 | 87.489 |
| ATOM | 4622 | O | MET | 1260 | 22.704 | 2.306 | 88.080 |
| ATOM | 4623 | N | ARG | 1261 | 20.748 | 1.260 | 87.652 |
| ATOM | 4624 | CA | ARG | 1261 | 20.944 | 0.165 | 88.628 |
| ATOM | 4625 | CB | ARG | 1261 | 20.067 | 0.407 | 89.861 |
| ATOM | 4626 | CG | ARG | 1261 | 18.540 | 0.165 | 89.658 |
| ATOM | 4627 | CD | ARG | 1261 | 17.754 | 0.490 | 90.927 |
| ATOM | 4628 | NE | ARG | 1261 | 16.332 | 0.158 | 90.873 |
| ATOM | 4629 | CZ | ARG | 1261 | 15.355 | 1.012 | 91.183 |
| ATOM | 4630 | NH1 | ARG | 1261 | 14.080 | 0.650 | 91.148 |
| ATOM | 4631 | NH2 | ARG | 1261 | 15.637 | 2.259 | 91.476 |
| ATOM | 4632 | C | ARG | 1261 | 20.461 | -1.110 | 87.977 |
| ATOM | 4633 | O | ARG | 1261 | 19.993 | -1.058 | 86.867 |
| ATOM | 4634 | N | LEU | 1262 | 20.583 | -2.259 | 88.626 |
| ATOM | 4635 | CA | LEU | 1262 | 20.023 | -3.484 | 88.032 |
| ATOM | 4636 | CB | LEU | 1262 | 21.083 | -4.518 | 87.676 |
| ATOM | 4637 | CG | LEU | 1262 | 22.518 | -4.169 | 87.328 |
| ATOM | 4638 | CD1 | LEU | 1262 | 23.105 | -5.411 | 86.684 |
| ATOM | 4639 | CD2 | LEU | 1262 | 22.622 | -2.971 | 86.411 |
| ATOM | 4640 | C | LEU | 1262 | 19.018 | -4.141 | 88.992 |
| ATOM | 4641 | O | LEU | 1262 | 19.389 | -4.954 | 89.839 |
| ATOM | 4642 | N | ARG | 1263 | 17.747 | -3.777 | 88.865 |
| ATOM | 4643 | CA | ARG | 1263 | 16.683 | -4.313 | 89.712 |
| ATOM | 4644 | CB | ARG | 1263 | 15.432 | -3.423 | 89.581 |
| ATOM | 4645 | CG | ARG | 1263 | 14.186 | -3.921 | 90.285 |
| ATOM | 4646 | CD | ARG | 1263 | 13.137 | -4.390 | 89.292 |
| ATOM | 4647 | NE | ARG | 1263 | 12.335 | -5.466 | 89.863 |
| ATOM | 4648 | CZ | ARG | 1263 | 11.191 | -5.921 | 89.352 |
| ATOM | 4649 | NH1 | ARG | 1263 | 10.544 | -6.900 | 89.970 |
| ATOM | 4650 | NH2 | ARG | 1263 | 10.715 | -5.446 | 88.203 |
| ATOM | 4651 | C | ARG | 1263 | 16.375 | -5.787 | 89.388 |
| ATOM | 4652 | O | ARG | 1263 | 15.236 | -6.149 | 89.066 |
| ATOM | 4653 | N | ASP | 1264 | 17.411 | -6.622 | 89.438 |
| ATOM | 4654 | CA | ASP | 1264 | 17.321 | -8.066 | 89.184 |

FIGURE 1TTTT

| | Atom | | Residue AA | No. | X | Y | Z |
|---|---|---|---|---|---|---|---|
| ATOM | 4655 | CB | ASP | 1264 | 18.516 | -8.717 | 89.898 |
| ATOM | 4656 | CG | ASP | 1264 | 18.681 | -10.203 | 89.594 |
| ATOM | 4657 | OD1 | ASP | 1264 | 17.931 | -10.815 | 88.776 |
| ATOM | 4658 | OD2 | ASP | 1264 | 19.620 | -10.755 | 90.199 |
| ATOM | 4659 | C | ASP | 1264 | 15.986 | -8.544 | 89.782 |
| ATOM | 4660 | O | ASP | 1264 | 15.833 | -8.542 | 91.009 |
| ATOM | 4661 | N | HIS | 1265 | 15.034 | -8.987 | 88.958 |
| ATOM | 4662 | CA | HIS | 1265 | 13.753 | -9.320 | 89.559 |
| ATOM | 4663 | CB | HIS | 1265 | 12.617 | -8.503 | 88.949 |
| ATOM | 4664 | CG | HIS | 1265 | 12.242 | -8.877 | 87.558 |
| ATOM | 4665 | CD2 | HIS | 1265 | 11.577 | -9.953 | 87.075 |
| ATOM | 4666 | ND1 | HIS | 1265 | 12.422 | -8.024 | 86.491 |
| ATOM | 4667 | CE1 | HIS | 1265 | 11.875 | -8.551 | 85.412 |
| ATOM | 4668 | NE2 | HIS | 1265 | 11.356 | -9.722 | 85.740 |
| ATOM | 4669 | C | HIS | 1265 | 13.239 | -10.654 | 90.078 |
| ATOM | 4670 | O | HIS | 1265 | 13.770 | -11.743 | 89.808 |
| ATOM | 4671 | N | ASP | 1266 | 12.199 | -10.464 | 90.897 |
| ATOM | 4672 | CA | ASP | 1266 | 11.459 | -11.459 | 91.674 |
| ATOM | 4673 | CB | ASP | 1266 | 10.719 | -10.741 | 92.833 |
| ATOM | 4674 | CG | ASP | 1266 | 9.616 | -9.745 | 92.341 |
| ATOM | 4675 | OD1 | ASP | 1266 | 9.955 | -8.778 | 91.607 |
| ATOM | 4676 | OD2 | ASP | 1266 | 8.427 | -9.917 | 92.730 |
| ATOM | 4677 | C | ASP | 1266 | 10.480 | -12.404 | 91.024 |
| ATOM | 4678 | O | ASP | 1266 | 10.009 | -12.168 | 89.912 |
| ATOM | 4679 | N | ALA | 1267 | 10.051 | -13.365 | 91.846 |
| ATOM | 4680 | CA | ALA | 1267 | 9.101 | -14.397 | 91.464 |
| ATOM | 4681 | CB | ALA | 1267 | 9.218 | -15.600 | 92.390 |
| ATOM | 4682 | C | ALA | 1267 | 7.663 | -13.902 | 91.394 |
| ATOM | 4683 | O | ALA | 1267 | 6.721 | -14.677 | 91.594 |
| ATOM | 4684 | N | ASP | 1268 | 7.499 | -12.592 | 91.222 |
| ATOM | 4685 | CA | ASP | 1268 | 6.165 | -12.031 | 91.031 |
| ATOM | 4686 | CB | ASP | 1268 | 6.131 | -10.511 | 91.323 |
| ATOM | 4687 | CG | ASP | 1268 | 4.928 | -9.776 | 90.656 |
| ATOM | 4688 | OD1 | ASP | 1268 | 5.144 | -8.630 | 90.174 |
| ATOM | 4689 | OD2 | ASP | 1268 | 3.777 | -10.322 | 90.628 |
| ATOM | 4690 | C | ASP | 1268 | 5.995 | -12.261 | 89.534 |
| ATOM | 4691 | O | ASP | 1268 | 5.299 | -13.203 | 89.085 |
| ATOM | 4692 | N | GLU | 1269 | 6.771 | -11.461 | 88.798 |
| ATOM | 4693 | CA | GLU | 1269 | 6.790 | -11.454 | 87.346 |
| ATOM | 4694 | CB | GLU | 1269 | 6.855 | -9.996 | 86.835 |
| ATOM | 4695 | CG | GLU | 1269 | 8.220 | -9.262 | 87.017 |
| ATOM | 4696 | CD | GLU | 1269 | 8.517 | -8.821 | 88.452 |
| ATOM | 4697 | OE1 | GLU | 1269 | 9.195 | -9.574 | 89.184 |
| ATOM | 4698 | OE2 | GLU | 1269 | 8.100 | -7.706 | 88.827 |
| ATOM | 4699 | C | GLU | 1269 | 7.910 | -12.315 | 86.732 |
| ATOM | 4700 | O | GLU | 1269 | 8.167 | -12.218 | 85.519 |
| ATOM | 4701 | N | LEU | 1270 | 8.633 | -13.079 | 87.561 |
| ATOM | 4702 | CA | LEU | 1270 | 9.668 | -13.965 | 87.029 |

FIGURE 1UUUU

| Atom | | | Residue AA | No. | X | Y | Z |
|---|---|---|---|---|---|---|---|
| ATOM | 4703 | CB | LEU | 1270 | 10.541 | -14.615 | 88.103 |
| ATOM | 4704 | CG | LEU | 1270 | 11.569 | -15.559 | 87.474 |
| ATOM | 4705 | CD1 | LEU | 1270 | 12.922 | -15.470 | 88.126 |
| ATOM | 4706 | CD2 | LEU | 1270 | 11.051 | -16.963 | 87.515 |
| ATOM | 4707 | C | LEU | 1270 | 8.832 | -15.020 | 86.320 |
| ATOM | 4708 | O | LEU | 1270 | 7.763 | -15.439 | 86.811 |
| ATOM | 4709 | N | SER | 1271 | 9.281 | -15.414 | 85.138 |
| ATOM | 4710 | CA | SER | 1271 | 8.490 | -16.348 | 84.423 |
| ATOM | 4711 | CB | SER | 1271 | 8.643 | -16.169 | 82.922 |
| ATOM | 4712 | OG | SER | 1271 | 7.344 | -15.952 | 82.367 |
| ATOM | 4713 | C | SER | 1271 | 8.634 | -17.773 | 84.858 |
| ATOM | 4714 | O | SER | 1271 | 9.644 | -18.173 | 85.418 |
| ATOM | 4715 | N | ALA | 1272 | 7.518 | -18.477 | 84.689 |
| ATOM | 4716 | CA | ALA | 1272 | 7.367 | -19.897 | 84.968 |
| ATOM | 4717 | CB | ALA | 1272 | 6.043 | -20.380 | 84.363 |
| ATOM | 4718 | C | ALA | 1272 | 8.548 | -20.645 | 84.327 |
| ATOM | 4719 | O | ALA | 1272 | 9.114 | -21.569 | 84.928 |
| ATOM | 4720 | N | TYR | 1273 | 8.901 | -20.226 | 83.103 |
| ATOM | 4721 | CA | TYR | 1273 | 10.027 | -20.789 | 82.328 |
| ATOM | 4722 | CB | TYR | 1273 | 9.818 | -20.541 | 80.822 |
| ATOM | 4723 | CG | TYR | 1273 | 9.634 | -19.091 | 80.367 |
| ATOM | 4724 | CD1 | TYR | 1273 | 8.349 | -18.547 | 80.240 |
| ATOM | 4725 | CE1 | TYR | 1273 | 8.148 | -17.266 | 79.693 |
| ATOM | 4726 | CD2 | TYR | 1273 | 10.732 | -18.310 | 79.948 |
| ATOM | 4727 | CE2 | TYR | 1273 | 10.545 | -17.023 | 79.405 |
| ATOM | 4728 | CZ | TYR | 1273 | 9.246 | -16.504 | 79.277 |
| ATOM | 4729 | OH | TYR | 1273 | 9.031 | -15.236 | 78.749 |
| ATOM | 4730 | C | TYR | 1273 | 11.376 | -20.200 | 82.734 |
| ATOM | 4731 | O | TYR | 1273 | 12.409 | -20.877 | 82.724 |
| ATOM | 4732 | N | SER | 1274 | 11.335 | -18.898 | 82.984 |
| ATOM | 4733 | CA | SER | 1274 | 12.485 | -18.148 | 83.392 |
| ATOM | 4734 | CB | SER | 1274 | 12.119 | -16.652 | 83.444 |
| ATOM | 4735 | OG | SER | 1274 | 13.200 | -15.842 | 83.897 |
| ATOM | 4736 | C | SER | 1274 | 12.931 | -18.643 | 84.763 |
| ATOM | 4737 | O | SER | 1274 | 12.332 | -19.532 | 85.366 |
| ATOM | 4738 | N | ASN | 1275 | 13.993 | -18.027 | 85.245 |
| ATOM | 4739 | CA | ASN | 1275 | 14.576 | -18.321 | 86.534 |
| ATOM | 4740 | CB | ASN | 1275 | 14.951 | -19.790 | 86.625 |
| ATOM | 4741 | CG | ASN | 1275 | 15.622 | -20.263 | 85.403 |
| ATOM | 4742 | OD1 | ASN | 1275 | 14.948 | -20.650 | 84.467 |
| ATOM | 4743 | ND2 | ASN | 1275 | 16.951 | -20.160 | 85.353 |
| ATOM | 4744 | C | ASN | 1275 | 15.819 | -17.448 | 86.540 |
| ATOM | 4745 | O | ASN | 1275 | 16.946 | -17.909 | 86.781 |
| ATOM | 4746 | N | ALA | 1276 | 15.591 | -16.194 | 86.167 |
| ATOM | 4747 | CA | ALA | 1276 | 16.612 | -15.163 | 86.092 |
| ATOM | 4748 | CB | ALA | 1276 | 17.909 | -15.705 | 85.528 |
| ATOM | 4749 | C | ALA | 1276 | 16.033 | -14.154 | 85.146 |
| ATOM | 4750 | O | ALA | 1276 | 15.466 | -14.516 | 84.124 |

FIGURE 1VVVV

| | Atom | | Residue AA | No. | X | Y | Z |
|---|---|---|---|---|---|---|---|
| ATOM | 4751 | N | THR | 1277 | 16.129 | -12.894 | 85.514 |
| ATOM | 4752 | CA | THR | 1277 | 15.604 | -11.834 | 84.698 |
| ATOM | 4753 | CB | THR | 1277 | 14.087 | -11.994 | 84.422 |
| ATOM | 4754 | OG1 | THR | 1277 | 13.552 | -10.748 | 83.973 |
| ATOM | 4755 | CG2 | THR | 1277 | 13.328 | -12.484 | 85.635 |
| ATOM | 4756 | C | THR | 1277 | 15.928 | -10.537 | 85.388 |
| ATOM | 4757 | O | THR | 1277 | 15.094 | -9.938 | 86.076 |
| ATOM | 4758 | N | THR | 1278 | 17.193 | -10.168 | 85.264 |
| ATOM | 4759 | CA | THR | 1278 | 17.705 | -8.954 | 85.840 |
| ATOM | 4760 | CB | THR | 1278 | 19.199 | -9.121 | 86.193 |
| ATOM | 4761 | OG1 | THR | 1278 | 19.875 | -7.865 | 86.113 |
| ATOM | 4762 | CG2 | THR | 1278 | 19.870 | -10.101 | 85.294 |
| ATOM | 4763 | C | THR | 1278 | 17.518 | -7.806 | 84.864 |
| ATOM | 4764 | O | THR | 1278 | 18.108 | -7.824 | 83.803 |
| ATOM | 4765 | N | ASP | 1279 | 16.621 | -6.870 | 85.150 |
| ATOM | 4766 | CA | ASP | 1279 | 16.461 | -5.710 | 84.276 |
| ATOM | 4767 | CB | ASP | 1279 | 15.134 | -5.001 | 84.545 |
| ATOM | 4768 | CG | ASP | 1279 | 13.949 | -5.765 | 84.063 |
| ATOM | 4769 | OD1 | ASP | 1279 | 14.149 | -6.827 | 83.460 |
| ATOM | 4770 | OD2 | ASP | 1279 | 12.812 | -5.292 | 84.287 |
| ATOM | 4771 | C | ASP | 1279 | 17.581 | -4.726 | 84.660 |
| ATOM | 4772 | O | ASP | 1279 | 18.201 | -4.869 | 85.713 |
| ATOM | 4773 | N | ILE | 1280 | 17.880 | -3.768 | 83.791 |
| ATOM | 4774 | CA | ILE | 1280 | 18.855 | -2.719 | 84.090 |
| ATOM | 4775 | CB | ILE | 1280 | 19.989 | -2.653 | 83.071 |
| ATOM | 4776 | CG2 | ILE | 1280 | 20.973 | -1.557 | 83.460 |
| ATOM | 4777 | CG1 | ILE | 1280 | 20.689 | -4.002 | 82.985 |
| ATOM | 4778 | CD1 | ILE | 1280 | 21.921 | -3.987 | 82.139 |
| ATOM | 4779 | C | ILE | 1280 | 17.934 | -1.502 | 83.942 |
| ATOM | 4780 | O | ILE | 1280 | 17.115 | -1.467 | 83.041 |
| ATOM | 4781 | N | GLU | 1281 | 18.010 | -0.518 | 84.816 |
| ATOM | 4782 | CA | GLU | 1281 | 17.079 | 0.576 | 84.702 |
| ATOM | 4783 | CB | GLU | 1281 | 16.136 | 0.588 | 85.910 |
| ATOM | 4784 | CG | GLU | 1281 | 15.509 | -0.769 | 86.333 |
| ATOM | 4785 | CD | GLU | 1281 | 14.451 | -0.658 | 87.463 |
| ATOM | 4786 | OE1 | GLU | 1281 | 13.677 | -1.616 | 87.664 |
| ATOM | 4787 | OE2 | GLU | 1281 | 14.366 | 0.386 | 88.142 |
| ATOM | 4788 | C | GLU | 1281 | 17.767 | 1.896 | 84.599 |
| ATOM | 4789 | O | GLU | 1281 | 18.945 | 2.015 | 84.895 |
| ATOM | 4790 | N | TYR | 1282 | 17.013 | 2.899 | 84.197 |
| ATOM | 4791 | CA | TYR | 1282 | 17.551 | 4.217 | 84.080 |
| ATOM | 4792 | CB | TYR | 1282 | 17.635 | 4.698 | 82.622 |
| ATOM | 4793 | CG | TYR | 1282 | 18.405 | 6.013 | 82.436 |
| ATOM | 4794 | CD1 | TYR | 1282 | 17.752 | 7.248 | 82.448 |
| ATOM | 4796 | CD2 | TYR | 1282 | 19.793 | 6.025 | 82.262 |
| ATOM | 4797 | CE2 | TYR | 1282 | 20.505 | 7.229 | 82.190 |
| ATOM | 4798 | CZ | TYR | 1282 | 19.829 | 8.430 | 82.291 |

FIGURE 1WWWW

| Atom | | | Residue AA | No. | X | Y | Z |
|---|---|---|---|---|---|---|---|
| ATOM | 4799 | OH | TYR | 1282 | 20.521 | 9.604 | 82.300 |
| ATOM | 4800 | C | TYR | 1282 | 16.684 | 5.145 | 84.861 |
| ATOM | 4801 | O | TYR | 1282 | 15.479 | 4.963 | 84.966 |
| ATOM | 4802 | N | ALA | 1283 | 17.358 | 6.124 | 85.439 |
| ATOM | 4803 | CA | ALA | 1283 | 16.757 | 7.178 | 86.218 |
| ATOM | 4804 | CB | ALA | 1283 | 17.766 | 7.683 | 87.241 |
| ATOM | 4805 | C | ALA | 1283 | 16.331 | 8.313 | 85.271 |
| ATOM | 4806 | O | ALA | 1283 | 16.953 | 9.385 | 85.223 |
| ATOM | 4807 | N | PHE | 1284 | 15.306 | 8.041 | 84.470 |
| ATOM | 4808 | CA | PHE | 1284 | 14.784 | 9.040 | 83.531 |
| ATOM | 4809 | CB | PHE | 1284 | 13.733 | 8.412 | 82.602 |
| ATOM | 4810 | CG | PHE | 1284 | 14.275 | 7.383 | 81.673 |
| ATOM | 4811 | CD1 | PHE | 1284 | 15.347 | 7.671 | 80.851 |
| ATOM | 4812 | CD2 | PHE | 1284 | 13.699 | 6.118 | 81.614 |
| ATOM | 4813 | CE1 | PHE | 1284 | 15.844 | 6.710 | 79.983 |
| ATOM | 4814 | CE2 | PHE | 1284 | 14.190 | 5.145 | 80.742 |
| ATOM | 4815 | CZ | PHE | 1284 | 15.266 | 5.445 | 79.928 |
| ATOM | 4816 | C | PHE | 1284 | 14.126 | 10.201 | 84.305 |
| ATOM | 4817 | O | PHE | 1284 | 13.709 | 10.045 | 85.452 |
| ATOM | 4818 | N | PRO | 1285 | 13.966 | 11.361 | 83.656 |
| ATOM | 4819 | CD | PRO | 1285 | 14.279 | 11.749 | 82.268 |
| ATOM | 4820 | CA | PRO | 1285 | 13.342 | 12.464 | 84.375 |
| ATOM | 4821 | CB | PRO | 1285 | 13.184 | 13.519 | 83.271 |
| ATOM | 4822 | CG | PRO | 1285 | 14.339 | 13.240 | 82.375 |
| ATOM | 4823 | C | PRO | 1285 | 11.975 | 12.030 | 84.947 |
| ATOM | 4824 | O | PRO | 1285 | 11.596 | 12.392 | 86.064 |
| ATOM | 4825 | N | PHE | 1286 | 11.255 | 11.217 | 84.193 |
| ATOM | 4826 | CA | PHE | 1286 | 9.944 | 10.773 | 84.631 |
| ATOM | 4827 | CB | PHE | 1286 | 9.060 | 10.468 | 83.403 |
| ATOM | 4828 | CG | PHE | 1286 | 9.675 | 9.469 | 82.456 |
| ATOM | 4829 | CD1 | PHE | 1286 | 9.407 | 8.102 | 82.595 |
| ATOM | 4830 | CD2 | PHE | 1286 | 10.616 | 9.880 | 81.507 |
| ATOM | 4831 | CE1 | PHE | 1286 | 10.075 | 7.167 | 81.823 |
| ATOM | 4832 | CE2 | PHE | 1286 | 11.285 | 8.954 | 80.891 |
| ATOM | 4834 | C | PHE | 1286 | 9.995 | 9.564 | 85.583 |
| ATOM | 4835 | O | PHE | 1286 | 8.953 | 8.982 | 85.909 |
| ATOM | 4836 | N | GLY | 1287 | 11.183 | 9.141 | 85.993 |
| ATOM | 4837 | CA | GLY | 1287 | 11.238 | 8.009 | 86.900 |
| ATOM | 4838 | C | GLY | 1287 | 12.203 | 6.902 | 86.564 |
| ATOM | 4839 | O | GLY | 1287 | 13.154 | 7.093 | 85.818 |
| ATOM | 4840 | N | TRP | 1288 | 12.011 | 5.756 | 87.197 |
| ATOM | 4841 | CA | TRP | 1288 | 12.868 | 4.621 | 86.922 |
| ATOM | 4842 | CB | TRP | 1288 | 12.972 | 3.689 | 88.125 |
| ATOM | 4843 | CG | TRP | 1288 | 13.905 | 4.213 | 89.150 |
| ATOM | 4844 | CD2 | TRP | 1288 | 15.303 | 3.925 | 89.280 |
| ATOM | 4845 | CE2 | TRP | 1288 | 15.809 | 4.758 | 90.293 |
| ATOM | 4846 | CE3 | TRP | 1288 | 16.178 | 3.051 | 88.633 |

FIGURE 1XXXX

| Atom | | | Residue AA | No. | X | Y | Z |
|---|---|---|---|---|---|---|---|
| ATOM | 4847 | CD1 | TRP | 1288 | 13.628 | 5.159 | 90.079 |
| ATOM | 4848 | NE1 | TRP | 1288 | 14.765 | 5.500 | 90.767 |
| ATOM | 4849 | CZ2 | TRP | 1288 | 17.153 | 4.748 | 90.673 |
| ATOM | 4850 | CZ3 | TRP | 1288 | 17.518 | 3.041 | 89.014 |
| ATOM | 4851 | CH2 | TRP | 1288 | 17.989 | 3.883 | 90.022 |
| ATOM | 4852 | C | TRP | 1288 | 12.225 | 3.895 | 85.768 |
| ATOM | 4853 | O | TRP | 1288 | 10.992 | 3.928 | 85.629 |
| ATOM | 4854 | N | GLY | 1289 | 13.052 | 3.283 | 84.920 |
| ATOM | 4855 | CA | GLY | 1289 | 12.540 | 2.546 | 83.775 |
| ATOM | 4856 | C | GLY | 1289 | 13.591 | 1.583 | 83.292 |
| ATOM | 4857 | O | GLY | 1289 | 14.767 | 1.751 | 83.628 |
| ATOM | 4858 | N | GLU | 1290 | 13.192 | 0.586 | 82.512 |
| ATOM | 4859 | CA | GLU | 1290 | 14.158 | -0.382 | 82.030 |
| ATOM | 4860 | CB | GLU | 1290 | 13.525 | -1.764 | 81.915 |
| ATOM | 4861 | CG | GLU | 1290 | 12.445 | -1.909 | 80.851 |
| ATOM | 4862 | CD | GLU | 1290 | 11.737 | -3.283 | 80.901 |
| ATOM | 4863 | OE1 | GLU | 1290 | 10.747 | -3.420 | 81.666 |
| ATOM | 4864 | OE2 | GLU | 1290 | 12.169 | -4.224 | 80.184 |
| ATOM | 4865 | C | GLU | 1290 | 14.825 | 0.002 | 80.727 |
| ATOM | 4866 | O | GLU | 1290 | 14.314 | 0.817 | 79.978 |
| ATOM | 4867 | N | LEU | 1291 | 16.055 | -0.456 | 80.574 |
| ATOM | 4868 | CA | LEU | 1291 | 16.828 | -0.263 | 79.367 |
| ATOM | 4869 | CB | LEU | 1291 | 18.280 | 0.100 | 79.655 |
| ATOM | 4870 | CG | LEU | 1291 | 18.580 | 1.523 | 80.011 |
| ATOM | 4871 | CD1 | LEU | 1291 | 19.880 | 1.923 | 79.370 |
| ATOM | 4872 | CD2 | LEU | 1291 | 17.459 | 2.390 | 79.522 |
| ATOM | 4873 | C | LEU | 1291 | 16.798 | -1.665 | 78.785 |
| ATOM | 4874 | O | LEU | 1291 | 15.839 | -2.032 | 78.093 |
| ATOM | 4875 | N | TRP | 1292 | 17.813 | -2.460 | 79.142 |
| ATOM | 4876 | CA | TRP | 1292 | 17.962 | -3.833 | 78.714 |
| ATOM | 4877 | CB | TRP | 1292 | 19.366 | -4.264 | 79.020 |
| ATOM | 4878 | CG | TRP | 1292 | 20.165 | -4.612 | 77.853 |
| ATOM | 4879 | CD2 | TRP | 1292 | 21.281 | -3.892 | 77.341 |
| ATOM | 4880 | CE2 | TRP | 1292 | 21.810 | -4.645 | 76.274 |
| ATOM | 4881 | CE3 | TRP | 1292 | 21.898 | -2.683 | 77.686 |
| ATOM | 4882 | CD1 | TRP | 1292 | 20.059 | -5.723 | 77.103 |
| ATOM | 4883 | NE1 | TRP | 1292 | 21.035 | -5.761 | 76.145 |
| ATOM | 4884 | CZ2 | TRP | 1292 | 22.923 | -4.238 | 75.553 |
| ATOM | 4885 | CZ3 | TRP | 1292 | 23.010 | -2.278 | 76.965 |
| ATOM | 4886 | CH2 | TRP | 1292 | 23.509 | -3.055 | 75.914 |
| ATOM | 4887 | C | TRP | 1292 | 17.006 | -4.757 | 79.456 |
| ATOM | 4888 | O | TRP | 1292 | 16.148 | -4.335 | 80.200 |
| ATOM | 4889 | N | GLY | 1293 | 17.187 | -6.044 | 79.269 |
| ATOM | 4890 | CA | GLY | 1293 | 16.347 | -7.019 | 79.928 |
| ATOM | 4891 | C | GLY | 1293 | 16.998 | -8.386 | 79.773 |
| ATOM | 4892 | O | GLY | 1293 | 16.509 | -9.212 | 79.010 |
| ATOM | 4893 | N | ILE | 1294 | 18.126 | -8.609 | 80.445 |
| ATOM | 4894 | CA | ILE | 1294 | 18.825 | -9.880 | 80.368 |

FIGURE 1YYYY

| Atom | | | Residue AA | No. | X | Y | Z |
|---|---|---|---|---|---|---|---|
| ATOM | 4895 | CB | ILE | 1294 | 20.216 | -9.796 | 81.025 |
| ATOM | 4896 | CG2 | ILE | 1294 | 21.006 | -11.040 | 80.734 |
| ATOM | 4897 | CG1 | ILE | 1294 | 21.028 | -8.631 | 80.466 |
| ATOM | 4898 | CD1 | ILE | 1294 | 20.774 | -7.320 | 81.136 |
| ATOM | 4899 | C | ILE | 1294 | 17.984 | -10.892 | 81.129 |
| ATOM | 4900 | O | ILE | 1294 | 17.516 | -10.598 | 82.212 |
| ATOM | 4901 | N | ALA | 1295 | 17.810 | -12.091 | 80.593 |
| ATOM | 4902 | CA | ALA | 1295 | 16.983 | -13.083 | 81.265 |
| ATOM | 4903 | CB | ALA | 1295 | 15.514 | -12.746 | 81.055 |
| ATOM | 4904 | C | ALA | 1295 | 17.234 | -14.511 | 80.810 |
| ATOM | 4905 | O | ALA | 1295 | 17.409 | -14.761 | 79.625 |
| ATOM | 4906 | N | SER | 1296 | 17.188 | -15.450 | 81.753 |
| ATOM | 4907 | CA | SER | 1296 | 17.395 | -16.874 | 81.469 |
| ATOM | 4908 | CB | SER | 1296 | 18.155 | -17.548 | 82.637 |
| ATOM | 4909 | OG | SER | 1296 | 18.658 | -18.844 | 82.315 |
| ATOM | 4910 | C | SER | 1296 | 16.026 | -17.531 | 81.257 |
| ATOM | 4911 | O | SER | 1296 | 15.239 | -17.639 | 82.211 |
| ATOM | 4912 | N | ARG | 1297 | 15.732 | -17.925 | 80.015 |
| ATOM | 4913 | CA | ARG | 1297 | 14.453 | -18.562 | 79.689 |
| ATOM | 4914 | CB | ARG | 1297 | 13.869 | -17.935 | 78.429 |
| ATOM | 4915 | CG | ARG | 1297 | 14.052 | -16.449 | 78.328 |
| ATOM | 4916 | CD | ARG | 1297 | 13.754 | -16.023 | 76.908 |
| ATOM | 4917 | NE | ARG | 1297 | 12.398 | -16.366 | 76.498 |
| ATOM | 4918 | CZ | ARG | 1297 | 11.424 | -15.477 | 76.322 |
| ATOM | 4919 | NH1 | ARG | 1297 | 11.633 | -14.179 | 76.520 |
| ATOM | 4920 | NH2 | ARG | 1297 | 10.230 | -15.885 | 75.932 |
| ATOM | 4921 | C | ARG | 1297 | 14.593 | -20.073 | 79.469 |
| ATOM | 4922 | O | ARG | 1297 | 13.641 | -20.726 | 78.998 |
| ATOM | 4923 | N | THR | 1298 | 15.770 | -20.608 | 79.821 |
| ATOM | 4924 | CA | THR | 1298 | 16.118 | -22.027 | 79.666 |
| ATOM | 4925 | CB | THR | 1298 | 15.272 | -22.966 | 80.583 |
| ATOM | 4926 | OG1 | THR | 1298 | 13.875 | -22.886 | 80.254 |
| ATOM | 4927 | CG2 | THR | 1298 | 15.478 | -22.622 | 82.023 |
| ATOM | 4928 | C | THR | 1298 | 15.989 | -22.458 | 78.207 |
| ATOM | 4929 | O | THR | 1298 | 16.727 | -21.997 | 77.347 |
| ATOM | 4930 | N | ASP | 1299 | 15.070 | -23.357 | 77.921 |
| ATOM | 4931 | CA | ASP | 1299 | 14.899 | -23.747 | 76.554 |
| ATOM | 4932 | CB | ASP | 1299 | 15.163 | -25.247 | 76.330 |
| ATOM | 4933 | CG | ASP | 1299 | 14.591 | -26.138 | 77.422 |
| ATOM | 4934 | OD1 | ASP | 1299 | 15.390 | -26.905 | 78.015 |
| ATOM | 4935 | OD2 | ASP | 1299 | 13.350 | -26.109 | 77.646 |
| ATOM | 4936 | C | ASP | 1299 | 13.551 | -23.279 | 76.017 |
| ATOM | 4937 | O | ASP | 1299 | 13.511 | -22.664 | 74.939 |
| ATOM | 4938 | N | PHE | 1300 | 12.474 | -23.525 | 76.772 |
| ATOM | 4939 | CA | PHE | 1300 | 11.090 | -23.121 | 76.418 |
| ATOM | 4940 | CB | PHE | 1300 | 10.675 | -21.917 | 77.274 |
| ATOM | 4941 | CG | PHE | 1300 | 9.249 | -21.435 | 77.029 |
| ATOM | 4942 | CD1 | PHE | 1300 | 8.162 | -22.293 | 77.174 |

FIGURE 1ZZZZ

| | Atom | | Residue AA | No. | X | Y | Z |
|---|---|---|---|---|---|---|---|
| ATOM | 4943 | CD2 | PHE | 1300 | 9.002 | -20.098 | 76.735 |
| ATOM | 4944 | CE1 | PHE | 1300 | 6.872 | -21.830 | 77.041 |
| ATOM | 4945 | CE2 | PHE | 1300 | 7.701 | -19.628 | 76.601 |
| ATOM | 4946 | CZ | PHE | 1300 | 6.639 | -20.500 | 76.758 |
| ATOM | 4947 | C | PHE | 1300 | 10.696 | -22.826 | 74.947 |
| ATOM | 4948 | O | PHE | 1300 | 9.836 | -23.504 | 74.371 |
| ATOM | 4949 | N | ASP | 1301 | 11.275 | -21.758 | 74.391 |
| ATOM | 4950 | CA | ASP | 1301 | 11.012 | -21.304 | 73.031 |
| ATOM | 4951 | CB | ASP | 1301 | 11.687 | -19.975 | 72.812 |
| ATOM | 4952 | CG | ASP | 1301 | 11.315 | -18.986 | 73.872 |
| ATOM | 4953 | OD1 | ASP | 1301 | 12.118 | -18.824 | 74.831 |
| ATOM | 4954 | OD2 | ASP | 1301 | 10.199 | -18.414 | 73.757 |
| ATOM | 4955 | C | ASP | 1301 | 11.396 | -22.279 | 71.951 |
| ATOM | 4956 | O | ASP | 1301 | 10.527 | -22.701 | 71.183 |
| ATOM | 4957 | N | LEU | 1302 | 12.675 | -22.635 | 71.862 |
| ATOM | 4958 | CA | LEU | 1302 | 13.062 | -23.588 | 70.840 |
| ATOM | 4959 | CB | LEU | 1302 | 14.480 | -24.103 | 71.014 |
| ATOM | 4960 | CG | LEU | 1302 | 15.638 | -23.149 | 70.876 |
| ATOM | 4961 | CD1 | LEU | 1302 | 15.361 | -22.163 | 69.749 |
| ATOM | 4962 | CD2 | LEU | 1302 | 15.798 | -22.450 | 72.193 |
| ATOM | 4963 | C | LEU | 1302 | 12.121 | -24.743 | 71.031 |
| ATOM | 4964 | O | LEU | 1302 | 11.408 | -25.119 | 70.107 |
| ATOM | 4965 | N | ALA | 1303 | 12.001 | -25.169 | 72.285 |
| ATOM | 4966 | CA | ALA | 1303 | 11.153 | -26.296 | 72.664 |
| ATOM | 4967 | CB | ALA | 1303 | 11.473 | -26.743 | 74.087 |
| ATOM | 4968 | C | ALA | 1303 | 9.647 | -26.112 | 72.489 |
| ATOM | 4969 | O | ALA | 1303 | 8.896 | -27.087 | 72.588 |
| ATOM | 4970 | N | ALA | 1304 | 9.197 | -24.877 | 72.282 |
| ATOM | 4971 | CA | ALA | 1304 | 7.770 | -24.618 | 72.062 |
| ATOM | 4972 | CB | ALA | 1304 | 7.410 | -23.197 | 72.487 |
| ATOM | 4973 | C | ALA | 1304 | 7.500 | -24.813 | 70.566 |
| ATOM | 4974 | O | ALA | 1304 | 6.427 | -25.282 | 70.165 |
| ATOM | 4975 | N | HIS | 1305 | 8.516 | -24.484 | 69.764 |
| ATOM | 4976 | CA | HIS | 1305 | 8.496 | -24.591 | 68.319 |
| ATOM | 4977 | CB | HIS | 1305 | 9.583 | -23.706 | 67.766 |
| ATOM | 4978 | CG | HIS | 1305 | 9.313 | -22.248 | 67.947 |
| ATOM | 4979 | CD2 | HIS | 1305 | 10.153 | -21.197 | 68.101 |
| ATOM | 4980 | ND1 | HIS | 1305 | 8.040 | -21.723 | 67.923 |
| ATOM | 4981 | CE1 | HIS | 1305 | 8.108 | -20.411 | 68.048 |
| ATOM | 4982 | NE2 | HIS | 1305 | 9.378 | -20.068 | 68.158 |
| ATOM | 4983 | C | HIS | 1305 | 8.765 | -26.015 | 67.951 |
| ATOM | 4984 | O | HIS | 1305 | 7.979 | -26.631 | 67.272 |
| ATOM | 4985 | N | ALA | 1306 | 9.880 | -26.528 | 68.442 |
| ATOM | 4986 | CA | ALA | 1306 | 10.302 | -27.904 | 68.233 |
| ATOM | 4987 | CB | ALA | 1306 | 11.466 | -28.238 | 69.148 |
| ATOM | 4988 | C | ALA | 1306 | 9.173 | -28.871 | 68.520 |
| ATOM | 4989 | O | ALA | 1306 | 9.158 | -29.996 | 68.025 |
| ATOM | 4990 | N | GLU | 1307 | 8.267 | -28.467 | 69.393 |

FIGURE 1AAAAA

| Atom | | | Residue AA | No. | X | Y | Z |
|---|---|---|---|---|---|---|---|
| ATOM | 4991 | CA | GLU | 1307 | 7.153 | -29.333 | 69.737 |
| ATOM | 4992 | CB | GLU | 1307 | 6.851 | -29.304 | 71.247 |
| ATOM | 4993 | CG | GLU | 1307 | 5.717 | -30.260 | 71.698 |
| ATOM | 4994 | CD | GLU | 1307 | 4.365 | -29.550 | 71.929 |
| ATOM | 4995 | OE1 | GLU | 1307 | 4.116 | -29.111 | 73.081 |
| ATOM | 4996 | OE2 | GLU | 1307 | 3.541 | -29.457 | 70.976 |
| ATOM | 4997 | C | GLU | 1307 | 5.930 | -28.923 | 68.995 |
| ATOM | 4998 | O | GLU | 1307 | 5.440 | -29.672 | 68.154 |
| ATOM | 4999 | N | HIS | 1308 | 5.433 | -27.735 | 69.333 |
| ATOM | 5000 | CA | HIS | 1308 | 4.231 | -27.201 | 68.723 |
| ATOM | 5001 | CB | HIS | 1308 | 3.920 | -25.824 | 69.291 |
| ATOM | 5002 | CG | HIS | 1308 | 2.674 | -25.204 | 68.738 |
| ATOM | 5003 | CD2 | HIS | 1308 | 1.379 | -25.300 | 69.135 |
| ATOM | 5004 | ND1 | HIS | 1308 | 2.687 | -24.305 | 67.691 |
| ATOM | 5005 | CE1 | HIS | 1308 | 1.458 | -23.865 | 67.475 |
| ATOM | 5006 | NE2 | HIS | 1308 | 0.644 | -24.453 | 68.337 |
| ATOM | 5007 | C | HIS | 1308 | 4.256 | -27.166 | 67.197 |
| ATOM | 5008 | O | HIS | 1308 | 3.197 | -27.073 | 66.588 |
| ATOM | 5009 | N | SER | 1309 | 5.443 | -27.240 | 66.584 |
| ATOM | 5010 | CA | SER | 1309 | 5.548 | -27.254 | 65.119 |
| ATOM | 5011 | CB | SER | 1309 | 5.542 | -25.839 | 64.573 |
| ATOM | 5012 | OG | SER | 1309 | 4.281 | -25.238 | 64.836 |
| ATOM | 5013 | C | SER | 1309 | 6.642 | -28.114 | 64.452 |
| ATOM | 5014 | O | SER | 1309 | 7.695 | -27.624 | 64.027 |
| ATOM | 5015 | N | GLY | 1310 | 6.350 | -29.414 | 64.420 |
| ATOM | 5016 | CA | GLY | 1310 | 7.169 | -30.451 | 63.816 |
| ATOM | 5017 | C | GLY | 1310 | 8.672 | -30.652 | 63.940 |
| ATOM | 5018 | O | GLY | 1310 | 9.149 | -31.753 | 64.234 |
| ATOM | 5019 | N | GLU | 1311 | 9.412 | -29.596 | 63.659 |
| ATOM | 5020 | CA | GLU | 1311 | 10.860 | -29.612 | 63.629 |
| ATOM | 5021 | CB | GLU | 1311 | 11.364 | -28.163 | 63.561 |
| ATOM | 5022 | CG | GLU | 1311 | 12.587 | -27.959 | 62.640 |
| ATOM | 5023 | CD | GLU | 1311 | 12.298 | -28.201 | 61.141 |
| ATOM | 5024 | OE1 | GLU | 1311 | 13.157 | -27.806 | 60.301 |
| ATOM | 5025 | OE2 | GLU | 1311 | 11.236 | -28.783 | 60.795 |
| ATOM | 5026 | C | GLU | 1311 | 11.729 | -30.464 | 64.564 |
| ATOM | 5027 | O | GLU | 1311 | 12.165 | -31.542 | 64.177 |
| ATOM | 5028 | N | ASP | 1312 | 12.018 | -29.922 | 65.747 |
| ATOM | 5029 | CA | ASP | 1312 | 12.884 | -30.490 | 66.807 |
| ATOM | 5030 | CB | ASP | 1312 | 13.185 | -32.015 | 66.634 |
| ATOM | 5031 | CG | ASP | 1312 | 14.573 | -32.314 | 66.040 |
| ATOM | 5032 | OD1 | ASP | 1312 | 14.679 | -32.501 | 64.816 |
| ATOM | 5033 | OD2 | ASP | 1312 | 15.555 | -32.410 | 66.799 |
| ATOM | 5034 | C | ASP | 1312 | 14.151 | -29.608 | 66.779 |
| ATOM | 5035 | O | ASP | 1312 | 14.589 | -29.191 | 65.699 |
| ATOM | 5036 | N | PHE | 1313 | 14.708 | -29.261 | 67.938 |
| ATOM | 5037 | CA | PHE | 1313 | 15.883 | -28.394 | 67.929 |
| ATOM | 5038 | CB | PHE | 1313 | 15.442 | -26.948 | 68.238 |

FIGURE 1BBBBB

| | Atom | | Residue AA | No. | X | Y | Z |
|---|---|---|---|---|---|---|---|
| ATOM | 5039 | CG | PHE | 1313 | 14.483 | -26.335 | 67.217 |
| ATOM | 5040 | CD1 | PHE | 1313 | 13.111 | -26.433 | 67.396 |
| ATOM | 5041 | CD2 | PHE | 1313 | 14.957 | -25.569 | 66.142 |
| ATOM | 5042 | CE1 | PHE | 1313 | 12.221 | -25.780 | 66.542 |
| ATOM | 5043 | CE2 | PHE | 1313 | 14.073 | -24.909 | 65.281 |
| ATOM | 5044 | CZ | PHE | 1313 | 12.707 | -25.014 | 65.484 |
| ATOM | 5045 | C | PHE | 1313 | 17.072 | -28.797 | 68.840 |
| ATOM | 5046 | O | PHE | 1313 | 17.964 | -27.990 | 69.109 |
| ATOM | 5047 | N | ALA | 1314 | 17.122 | -30.050 | 69.259 |
| ATOM | 5048 | CA | ALA | 1314 | 18.176 | -30.504 | 70.149 |
| ATOM | 5049 | CB | ALA | 1314 | 17.845 | -31.863 | 70.684 |
| ATOM | 5050 | C | ALA | 1314 | 19.543 | -30.534 | 69.516 |
| ATOM | 5051 | O | ALA | 1314 | 19.698 | -30.995 | 68.409 |
| ATOM | 5052 | N | TYR | 1315 | 20.536 | -30.034 | 70.237 |
| ATOM | 5053 | CA | TYR | 1315 | 21.922 | -30.033 | 69.776 |
| ATOM | 5054 | CB | TYR | 1315 | 22.742 | -29.055 | 70.607 |
| ATOM | 5055 | CG | TYR | 1315 | 24.197 | -28.994 | 70.269 |
| ATOM | 5056 | CD1 | TYR | 1315 | 25.103 | -29.796 | 70.918 |
| ATOM | 5057 | CE1 | TYR | 1315 | 26.455 | -29.707 | 70.655 |
| ATOM | 5058 | CD2 | TYR | 1315 | 24.669 | -28.096 | 69.337 |
| ATOM | 5059 | CE2 | TYR | 1315 | 26.018 | -27.992 | 69.058 |
| ATOM | 5060 | CZ | TYR | 1315 | 26.919 | -28.799 | 69.721 |
| ATOM | 5061 | OH | TYR | 1315 | 28.280 | -28.679 | 69.461 |
| ATOM | 5062 | C | TYR | 1315 | 22.398 | -31.445 | 70.030 |
| ATOM | 5063 | O | TYR | 1315 | 21.736 | -32.194 | 70.740 |
| ATOM | 5064 | N | ALA | 1316 | 23.532 | -31.829 | 69.470 |
| ATOM | 5065 | CA | ALA | 1316 | 24.002 | -33.179 | 69.697 |
| ATOM | 5066 | CB | ALA | 1316 | 23.523 | -34.086 | 68.593 |
| ATOM | 5067 | C | ALA | 1316 | 25.507 | -33.252 | 69.832 |
| ATOM | 5068 | O | ALA | 1316 | 26.208 | -33.142 | 68.823 |
| ATOM | 5069 | N | ASP | 1317 | 25.982 | -33.431 | 71.077 |
| ATOM | 5070 | CA | ASP | 1317 | 27.407 | -33.526 | 71.376 |
| ATOM | 5071 | CB | ASP | 1317 | 28.173 | -32.703 | 70.337 |
| ATOM | 5072 | CG | ASP | 1317 | 29.636 | -32.832 | 70.459 |
| ATOM | 5073 | OD1 | ASP | 1317 | 30.238 | -32.060 | 71.243 |
| ATOM | 5074 | OD2 | ASP | 1317 | 30.186 | -33.682 | 69.747 |
| ATOM | 5075 | C | ASP | 1317 | 27.883 | -33.097 | 72.798 |
| ATOM | 5076 | O | ASP | 1317 | 28.071 | -31.896 | 73.055 |
| ATOM | 5077 | N | PRO | 1318 | 28.062 | -34.055 | 73.752 |
| ATOM | 5078 | CD | PRO | 1318 | 27.798 | -35.506 | 73.702 |
| ATOM | 5079 | CA | PRO | 1318 | 28.542 | -33.702 | 75.102 |
| ATOM | 5080 | CB | PRO | 1318 | 27.800 | -34.711 | 75.993 |
| ATOM | 5081 | CG | PRO | 1318 | 27.947 | -35.987 | 75.183 |
| ATOM | 5082 | C | PRO | 1318 | 30.022 | -34.107 | 74.929 |
| ATOM | 5083 | O | PRO | 1318 | 30.507 | -35.048 | 75.583 |
| ATOM | 5084 | N | ALA | 1319 | 30.646 | -33.485 | 73.914 |
| ATOM | 5085 | CA | ALA | 1319 | 32.032 | -33.732 | 73.448 |
| ATOM | 5086 | CB | ALA | 1319 | 32.965 | -34.207 | 74.600 |

FIGURE 1CCCCC

| Atom | | | Residue AA | No. | X | Y | Z |
|---|---|---|---|---|---|---|---|
| ATOM | 5087 | C | ALA | 1319 | 31.971 | -34.801 | 72.338 |
| ATOM | 5088 | O | ALA | 1319 | 32.704 | -34.747 | 71.334 |
| ATOM | 5089 | N | THR | 1320 | 31.052 | -35.744 | 72.538 |
| ATOM | 5090 | CA | THR | 1320 | 30.811 | -36.868 | 71.645 |
| ATOM | 5091 | CB | THR | 1320 | 30.750 | -38.161 | 72.507 |
| ATOM | 5092 | OG1 | THR | 1320 | 29.859 | -37.944 | 73.630 |
| ATOM | 5093 | CG2 | THR | 1320 | 32.191 | -38.565 | 72.987 |
| ATOM | 5094 | C | THR | 1320 | 29.459 | -36.642 | 70.954 |
| ATOM | 5095 | O | THR | 1320 | 29.368 | -35.963 | 69.910 |
| ATOM | 5096 | N | ASN | 1321 | 28.427 | -37.260 | 71.542 |
| ATOM | 5097 | CA | ASN | 1321 | 27.042 | -37.123 | 71.106 |
| ATOM | 5098 | CB | ASN | 1321 | 26.688 | -37.955 | 69.849 |
| ATOM | 5099 | CG | ASN | 1321 | 25.936 | -37.097 | 68.757 |
| ATOM | 5100 | OD1 | ASN | 1321 | 24.691 | -37.158 | 68.597 |
| ATOM | 5101 | ND2 | ASN | 1321 | 26.705 | -36.277 | 68.037 |
| ATOM | 5102 | C | ASN | 1321 | 26.125 | -37.455 | 72.290 |
| ATOM | 5103 | O | ASN | 1321 | 26.423 | -38.394 | 73.068 |
| ATOM | 5104 | N | ALA | 1322 | 25.258 | -36.455 | 72.559 |
| ATOM | 5105 | CA | ALA | 1322 | 24.187 | -36.407 | 73.584 |
| ATOM | 5106 | CB | ALA | 1322 | 24.692 | -35.920 | 74.977 |
| ATOM | 5107 | C | ALA | 1322 | 23.262 | -35.356 | 72.990 |
| ATOM | 5108 | O | ALA | 1322 | 23.738 | -34.316 | 72.524 |
| ATOM | 5109 | N | ALA | 1323 | 21.973 | -35.671 | 72.923 |
| ATOM | 5110 | CA | ALA | 1323 | 20.968 | -34.762 | 72.386 |
| ATOM | 5111 | CB | ALA | 1323 | 20.000 | -35.549 | 71.500 |
| ATOM | 5112 | C | ALA | 1323 | 20.230 | -34.031 | 73.558 |
| ATOM | 5113 | O | ALA | 1323 | 19.769 | -34.680 | 74.527 |
| ATOM | 5114 | N | TYR | 1324 | 20.180 | -32.691 | 73.490 |
| ATOM | 5115 | CA | TYR | 1324 | 19.554 | -31.841 | 74.510 |
| ATOM | 5116 | CB | TYR | 1324 | 20.496 | -31.636 | 75.704 |
| ATOM | 5117 | CG | TYR | 1324 | 21.925 | -31.260 | 75.341 |
| ATOM | 5118 | CD1 | TYR | 1324 | 22.839 | -32.242 | 74.998 |
| ATOM | 5119 | CE1 | TYR | 1324 | 24.155 | -31.937 | 74.748 |
| ATOM | 5120 | CD2 | TYR | 1324 | 22.373 | -29.949 | 75.411 |
| ATOM | 5121 | CE2 | TYR | 1324 | 23.687 | -29.629 | 75.166 |
| ATOM | 5122 | CZ | TYR | 1324 | 24.576 | -30.629 | 74.843 |
| ATOM | 5123 | OH | TYR | 1324 | 25.916 | -30.362 | 74.688 |
| ATOM | 5124 | C | TYR | 1324 | 19.305 | -30.484 | 73.912 |
| ATOM | 5125 | O | TYR | 1324 | 20.255 | -29.818 | 73.509 |
| ATOM | 5126 | N | ILE | 1325 | 18.051 | -30.058 | 73.854 |
| ATOM | 5127 | CA | ILE | 1325 | 17.736 | -28.740 | 73.303 |
| ATOM | 5128 | CB | ILE | 1325 | 16.252 | -28.496 | 73.329 |
| ATOM | 5129 | CG2 | ILE | 1325 | 15.724 | -28.711 | 74.729 |
| ATOM | 5130 | CG1 | ILE | 1325 | 15.953 | -27.089 | 72.867 |
| ATOM | 5131 | CD1 | ILE | 1325 | 14.533 | -26.909 | 72.555 |
| ATOM | 5132 | C | ILE | 1325 | 18.465 | -27.685 | 74.136 |
| ATOM | 5133 | O | ILE | 1325 | 18.545 | -27.801 | 75.360 |
| ATOM | 5134 | N | PRO | 1326 | 19.038 | -26.670 | 73.483 |

FIGURE 1DDDDD

| | Atom | | Residue AA | No. | X | Y | Z |
|---|---|---|---|---|---|---|---|
| ATOM | 5135 | CD | PRO | 1326 | 19.185 | -26.519 | 72.034 |
| ATOM | 5136 | CA | PRO | 1326 | 19.774 | -25.614 | 74.185 |
| ATOM | 5137 | CB | PRO | 1326 | 20.433 | -24.860 | 73.043 |
| ATOM | 5138 | CG | PRO | 1326 | 20.505 | -25.888 | 71.958 |
| ATOM | 5139 | C | PRO | 1326 | 19.008 | -24.666 | 75.111 |
| ATOM | 5140 | O | PRO | 1326 | 17.783 | -24.560 | 75.069 |
| ATOM | 5141 | N | TYR | 1327 | 19.759 | -23.956 | 75.936 |
| ATOM | 5142 | CA | TYR | 1327 | 19.191 | -23.011 | 76.867 |
| ATOM | 5143 | CB | TYR | 1327 | 19.848 | -23.174 | 78.227 |
| ATOM | 5144 | CG | TYR | 1327 | 19.118 | -24.029 | 79.234 |
| ATOM | 5145 | CD1 | TYR | 1327 | 19.138 | -23.700 | 80.596 |
| ATOM | 5146 | CE1 | TYR | 1327 | 18.547 | -24.521 | 81.552 |
| ATOM | 5147 | CD2 | TYR | 1327 | 18.477 | -25.196 | 78.854 |
| ATOM | 5148 | CE2 | TYR | 1327 | 17.883 | -26.028 | 79.806 |
| ATOM | 5149 | CZ | TYR | 1327 | 17.926 | -25.686 | 81.150 |
| ATOM | 5150 | OH | TYR | 1327 | 17.365 | -26.522 | 82.085 |
| ATOM | 5151 | C | TYR | 1327 | 19.599 | -21.662 | 76.365 |
| ATOM | 5152 | O | TYR | 1327 | 20.744 | -21.501 | 75.999 |
| ATOM | 5153 | N | CYS | 1328 | 18.703 | -20.684 | 76.339 |
| ATOM | 5154 | CA | CYS | 1328 | 19.112 | -19.356 | 75.897 |
| ATOM | 5155 | CB | CYS | 1328 | 18.372 | -18.902 | 74.629 |
| ATOM | 5156 | SG | CYS | 1328 | 16.696 | -18.266 | 74.798 |
| ATOM | 5157 | C | CYS | 1328 | 19.019 | -18.307 | 76.995 |
| ATOM | 5158 | O | CYS | 1328 | 18.500 | -18.570 | 78.079 |
| ATOM | 5159 | N | ILE | 1329 | 19.574 | -17.135 | 76.709 |
| ATOM | 5160 | CA | ILE | 1329 | 19.609 | -15.991 | 77.613 |
| ATOM | 5161 | CB | ILE | 1329 | 21.031 | -15.795 | 78.181 |
| ATOM | 5162 | CG2 | ILE | 1329 | 21.168 | -14.438 | 78.753 |
| ATOM | 5163 | CG1 | ILE | 1329 | 21.367 | -16.853 | 79.228 |
| ATOM | 5164 | CD1 | ILE | 1329 | 21.987 | -18.107 | 78.705 |
| ATOM | 5165 | C | ILE | 1329 | 19.284 | -14.799 | 76.718 |
| ATOM | 5166 | O | ILE | 1329 | 20.034 | -14.514 | 75.824 |
| ATOM | 5167 | N | GLU | 1330 | 18.206 | -14.079 | 76.941 |
| ATOM | 5168 | CA | GLU | 1330 | 17.954 | -13.020 | 76.028 |
| ATOM | 5169 | CB | GLU | 1330 | 16.576 | -13.172 | 75.387 |
| ATOM | 5170 | CG | GLU | 1330 | 15.379 | -12.642 | 76.157 |
| ATOM | 5171 | CD | GLU | 1330 | 14.124 | -12.570 | 75.294 |
| ATOM | 5172 | OE1 | GLU | 1330 | 13.620 | -11.466 | 75.044 |
| ATOM | 5173 | OE2 | GLU | 1330 | 13.631 | -13.619 | 74.845 |
| ATOM | 5174 | C | GLU | 1330 | 18.191 | -11.621 | 76.469 |
| ATOM | 5175 | O | GLU | 1330 | 17.347 | -11.006 | 77.065 |
| ATOM | 5176 | N | PRO | 1331 | 19.390 | -11.113 | 76.251 |
| ATOM | 5177 | CD | PRO | 1331 | 20.674 | -11.792 | 76.078 |
| ATOM | 5178 | CA | PRO | 1331 | 19.614 | -9.740 | 76.658 |
| ATOM | 5179 | CB | PRO | 1331 | 21.152 | -9.632 | 76.652 |
| ATOM | 5180 | CG | PRO | 1331 | 21.594 | -10.652 | 75.765 |
| ATOM | 5181 | C | PRO | 1331 | 18.944 | -8.724 | 75.709 |
| ATOM | 5182 | O | PRO | 1331 | 19.624 | -8.009 | 74.983 |

FIGURE 1EEEEE

| Atom | | | Residue AA | No. | X | Y | Z |
|---|---|---|---|---|---|---|---|
| ATOM | 5183 | N | SER | 1332 | 17.614 | -8.659 | 75.732 |
| ATOM | 5184 | CA | SER | 1332 | 16.823 | -7.734 | 74.893 |
| ATOM | 5185 | CB | SER | 1332 | 15.325 | -7.979 | 75.115 |
| ATOM | 5186 | OG | SER | 1332 | 14.540 | -6.824 | 74.874 |
| ATOM | 5187 | C | SER | 1332 | 17.140 | -6.257 | 75.138 |
| ATOM | 5188 | O | SER | 1332 | 17.741 | -5.927 | 76.124 |
| ATOM | 5189 | N | LEU | 1333 | 16.672 | -5.356 | 74.290 |
| ATOM | 5190 | CA | LEU | 1333 | 16.968 | -3.948 | 74.479 |
| ATOM | 5191 | CB | LEU | 1333 | 18.310 | -3.603 | 73.831 |
| ATOM | 5192 | CG | LEU | 1333 | 18.994 | -2.329 | 74.347 |
| ATOM | 5193 | CD1 | LEU | 1333 | 18.905 | -2.277 | 75.854 |
| ATOM | 5194 | CD2 | LEU | 1333 | 20.454 | -2.215 | 73.894 |
| ATOM | 5195 | C | LEU | 1333 | 15.846 | -3.069 | 73.949 |
| ATOM | 5196 | O | LEU | 1333 | 14.689 | -3.451 | 74.001 |
| ATOM | 5197 | N | GLY | 1334 | 16.169 | -1.868 | 73.500 |
| ATOM | 5198 | CA | GLY | 1334 | 15.162 | -0.970 | 72.967 |
| ATOM | 5199 | C | GLY | 1334 | 16.001 | 0.111 | 72.335 |
| ATOM | 5200 | O | GLY | 1334 | 16.610 | 0.894 | 73.056 |
| ATOM | 5201 | N | ALA | 1335 | 16.138 | 0.094 | 71.009 |
| ATOM | 5202 | CA | ALA | 1335 | 16.960 | 1.082 | 70.330 |
| ATOM | 5203 | CB | ALA | 1335 | 17.022 | 0.786 | 68.865 |
| ATOM | 5204 | C | ALA | 1335 | 16.353 | 2.440 | 70.588 |
| ATOM | 5205 | O | ALA | 1335 | 17.055 | 3.390 | 70.978 |
| ATOM | 5206 | N | ASP | 1336 | 15.035 | 2.507 | 70.433 |
| ATOM | 5207 | CA | ASP | 1336 | 14.352 | 3.748 | 70.676 |
| ATOM | 5208 | CB | ASP | 1336 | 12.833 | 3.594 | 70.454 |
| ATOM | 5209 | CG | ASP | 1336 | 12.407 | 3.743 | 68.973 |
| ATOM | 5210 | OD1 | ASP | 1336 | 11.835 | 4.793 | 68.584 |
| ATOM | 5211 | OD2 | ASP | 1336 | 12.582 | 2.779 | 68.212 |
| ATOM | 5212 | C | ASP | 1336 | 14.724 | 4.222 | 72.111 |
| ATOM | 5213 | O | ASP | 1336 | 15.316 | 5.290 | 72.244 |
| ATOM | 5214 | N | ARG | 1337 | 14.514 | 3.392 | 73.148 |
| ATOM | 5215 | CA | ARG | 1337 | 14.842 | 3.749 | 74.556 |
| ATOM | 5216 | CB | ARG | 1337 | 14.397 | 2.667 | 75.546 |
| ATOM | 5217 | CG | ARG | 1337 | 12.918 | 2.579 | 75.815 |
| ATOM | 5218 | CD | ARG | 1337 | 12.645 | 2.204 | 77.286 |
| ATOM | 5219 | NE | ARG | 1337 | 11.473 | 1.342 | 77.438 |
| ATOM | 5220 | CZ | ARG | 1337 | 11.517 | 0.012 | 77.360 |
| ATOM | 5221 | NH1 | ARG | 1337 | 12.680 | -0.613 | 77.154 |
| ATOM | 5222 | NH2 | ARG | 1337 | 10.389 | -0.693 | 77.385 |
| ATOM | 5223 | C | ARG | 1337 | 16.316 | 4.045 | 74.842 |
| ATOM | 5224 | O | ARG | 1337 | 16.654 | 5.114 | 75.327 |
| ATOM | 5225 | N | VAL | 1338 | 17.190 | 3.084 | 74.580 |
| ATOM | 5226 | CA | VAL | 1338 | 18.606 | 3.270 | 74.818 |
| ATOM | 5227 | CB | VAL | 1338 | 19.453 | 2.188 | 74.118 |
| ATOM | 5228 | CG1 | VAL | 1338 | 20.911 | 2.395 | 74.399 |
| ATOM | 5229 | CG2 | VAL | 1338 | 19.084 | 0.869 | 74.622 |
| ATOM | 5230 | C | VAL | 1338 | 19.044 | 4.651 | 74.356 |

FIGURE 1FFFFF

| Atom | | | Residue AA | No. | X | Y | Z |
|---|---|---|---|---|---|---|---|
| ATOM | 5231 | O | VAL | 1338 | 19.937 | 5.245 | 74.953 |
| ATOM | 5232 | N | THR | 1339 | 18.402 | 5.185 | 73.317 |
| ATOM | 5233 | CA | THR | 1339 | 18.789 | 6.514 | 72.836 |
| ATOM | 5234 | CB | THR | 1339 | 18.508 | 6.749 | 71.281 |
| ATOM | 5235 | OG1 | THR | 1339 | 17.125 | 6.977 | 71.014 |
| ATOM | 5236 | CG2 | THR | 1339 | 18.918 | 5.556 | 70.513 |
| ATOM | 5237 | C | THR | 1339 | 18.246 | 7.635 | 73.751 |
| ATOM | 5238 | O | THR | 1339 | 18.965 | 8.601 | 74.052 |
| ATOM | 5239 | N | LEU | 1340 | 17.037 | 7.456 | 74.287 |
| ATOM | 5240 | CA | LEU | 1340 | 16.442 | 8.466 | 75.154 |
| ATOM | 5241 | CB | LEU | 1340 | 15.052 | 8.049 | 75.588 |
| ATOM | 5242 | CG | LEU | 1340 | 14.254 | 9.105 | 76.336 |
| ATOM | 5243 | CD1 | LEU | 1340 | 14.454 | 10.426 | 75.668 |
| ATOM | 5244 | CD2 | LEU | 1340 | 12.763 | 8.737 | 76.371 |
| ATOM | 5245 | C | LEU | 1340 | 17.336 | 8.628 | 76.346 |
| ATOM | 5246 | O | LEU | 1340 | 17.590 | 9.743 | 76.787 |
| ATOM | 5247 | N | ALA | 1341 | 17.866 | 7.496 | 76.803 |
| ATOM | 5248 | CA | ALA | 1341 | 18.771 | 7.454 | 77.934 |
| ATOM | 5249 | CB | ALA | 1341 | 19.303 | 6.054 | 78.140 |
| ATOM | 5250 | C | ALA | 1341 | 19.887 | 8.382 | 77.574 |
| ATOM | 5251 | O | ALA | 1341 | 19.893 | 9.536 | 77.980 |
| ATOM | 5252 | N | PHE | 1342 | 20.743 | 7.896 | 76.688 |
| ATOM | 5253 | CA | PHE | 1342 | 21.887 | 8.636 | 76.199 |
| ATOM | 5254 | CB | PHE | 1342 | 22.430 | 7.960 | 74.949 |
| ATOM | 5255 | CG | PHE | 1342 | 23.215 | 6.701 | 75.214 |
| ATOM | 5256 | CD1 | PHE | 1342 | 22.661 | 5.455 | 74.943 |
| ATOM | 5257 | CD2 | PHE | 1342 | 24.546 | 6.772 | 75.646 |
| ATOM | 5258 | CE1 | PHE | 1342 | 23.406 | 4.307 | 75.086 |
| ATOM | 5259 | CE2 | PHE | 1342 | 25.310 | 5.621 | 75.793 |
| ATOM | 5260 | CZ | PHE | 1342 | 24.737 | 4.384 | 75.510 |
| ATOM | 5261 | C | PHE | 1342 | 21.588 | 10.112 | 75.912 |
| ATOM | 5262 | O | PHE | 1342 | 22.479 | 10.954 | 76.082 |
| ATOM | 5263 | N | LEU | 1343 | 20.357 | 10.434 | 75.493 |
| ATOM | 5264 | CA | LEU | 1343 | 19.991 | 11.837 | 75.236 |
| ATOM | 5265 | CB | LEU | 1343 | 18.655 | 11.943 | 74.474 |
| ATOM | 5266 | CG | LEU | 1343 | 18.415 | 13.071 | 73.444 |
| ATOM | 5267 | CD1 | LEU | 1343 | 16.935 | 13.188 | 73.180 |
| ATOM | 5268 | CD2 | LEU | 1343 | 18.950 | 14.414 | 73.910 |
| ATOM | 5269 | C | LEU | 1343 | 19.875 | 12.563 | 76.601 |
| ATOM | 5270 | O | LEU | 1343 | 20.593 | 13.545 | 76.882 |
| ATOM | 5271 | N | CYS | 1344 | 19.007 | 12.039 | 77.463 |
| ATOM | 5272 | CA | CYS | 1344 | 18.796 | 12.607 | 78.781 |
| ATOM | 5273 | CB | CYS | 1344 | 17.807 | 11.754 | 79.541 |
| ATOM | 5274 | SG | CYS | 1344 | 16.138 | 11.957 | 78.978 |
| ATOM | 5275 | C | CYS | 1344 | 20.070 | 12.687 | 79.583 |
| ATOM | 5276 | O | CYS | 1344 | 20.470 | 13.745 | 79.762 |
| ATOM | 5278 | CA | ASP | 1345 | 21.910 | 11.380 | 80.511 |

FIGURE 1GGGGG

| Atom | | | Residue AA | No. | X | Y | Z |
|---|---|---|---|---|---|---|---|
| ATOM | 5279 | CB | ASP | 1345 | 22.456 | 9.983 | 80.256 |
| ATOM | 5280 | CG | ASP | 1345 | 23.471 | 9.567 | 81.266 |
| ATOM | 5281 | OD1 | ASP | 1345 | 24.693 | 9.734 | 81.010 |
| ATOM | 5282 | OD2 | ASP | 1345 | 23.021 | 9.061 | 82.310 |
| ATOM | 5283 | C | ASP | 1345 | 22.955 | 12.387 | 80.078 |
| ATOM | 5284 | O | ASP | 1345 | 23.842 | 12.760 | 80.853 |
| ATOM | 5285 | N | ALA | 1346 | 22.854 | 12.807 | 78.827 |
| ATOM | 5286 | CA | ALA | 1346 | 23.804 | 13.749 | 78.270 |
| ATOM | 5287 | CB | ALA | 1346 | 24.129 | 13.365 | 76.858 |
| ATOM | 5288 | C | ALA | 1346 | 23.350 | 15.194 | 78.339 |
| ATOM | 5289 | O | ALA | 1346 | 24.184 | 16.114 | 78.255 |
| ATOM | 5290 | N | TYR | 1347 | 22.038 | 15.398 | 78.462 |
| ATOM | 5291 | CA | TYR | 1347 | 21.516 | 16.743 | 78.570 |
| ATOM | 5292 | CB | TYR | 1347 | 20.035 | 16.740 | 78.849 |
| ATOM | 5293 | CG | TYR | 1347 | 19.546 | 18.131 | 78.839 |
| ATOM | 5294 | CD1 | TYR | 1347 | 19.228 | 18.798 | 80.006 |
| ATOM | 5295 | CE1 | TYR | 1347 | 18.840 | 20.150 | 79.979 |
| ATOM | 5296 | CD2 | TYR | 1347 | 19.471 | 18.819 | 77.650 |
| ATOM | 5297 | CE2 | TYR | 1347 | 19.093 | 20.153 | 77.586 |
| ATOM | 5298 | CZ | TYR | 1347 | 18.775 | 20.827 | 78.742 |
| ATOM | 5299 | OH | TYR | 1347 | 18.387 | 22.160 | 78.617 |
| ATOM | 5300 | C | TYR | 1347 | 22.213 | 17.394 | 79.744 |
| ATOM | 5301 | O | TYR | 1347 | 22.738 | 16.700 | 80.623 |
| ATOM | 5302 | N | ASP | 1348 | 22.198 | 18.715 | 79.794 |
| ATOM | 5303 | CA | ASP | 1348 | 22.837 | 19.442 | 80.892 |
| ATOM | 5304 | CB | ASP | 1348 | 24.368 | 19.200 | 80.875 |
| ATOM | 5305 | CG | ASP | 1348 | 25.113 | 19.932 | 82.018 |
| ATOM | 5306 | OD1 | ASP | 1348 | 25.080 | 19.447 | 83.186 |
| ATOM | 5307 | OD2 | ASP | 1348 | 25.736 | 20.990 | 81.738 |
| ATOM | 5308 | C | ASP | 1348 | 22.536 | 20.924 | 80.690 |
| ATOM | 5309 | O | ASP | 1348 | 21.994 | 21.304 | 79.659 |
| ATOM | 5310 | N | GLU | 1349 | 22.819 | 21.745 | 81.694 |
| ATOM | 5311 | CA | GLU | 1349 | 22.634 | 23.188 | 81.610 |
| ATOM | 5312 | CB | GLU | 1349 | 21.337 | 23.616 | 82.303 |
| ATOM | 5313 | CG | GLU | 1349 | 20.089 | 23.055 | 81.585 |
| ATOM | 5314 | CD | GLU | 1349 | 18.739 | 23.367 | 82.250 |
| ATOM | 5315 | OE1 | GLU | 1349 | 17.858 | 24.011 | 81.609 |
| ATOM | 5316 | OE2 | GLU | 1349 | 18.546 | 22.923 | 83.404 |
| ATOM | 5317 | C | GLU | 1349 | 23.872 | 23.646 | 82.345 |
| ATOM | 5318 | O | GLU | 1349 | 24.161 | 23.172 | 83.435 |
| ATOM | 5319 | N | GLU | 1350 | 24.687 | 24.433 | 81.673 |
| ATOM | 5320 | CA | GLU | 1350 | 25.929 | 24.880 | 82.255 |
| ATOM | 5321 | CB | GLU | 1350 | 27.093 | 24.568 | 81.320 |
| ATOM | 5322 | CG | GLU | 1350 | 27.948 | 23.395 | 81.797 |
| ATOM | 5323 | CD | GLU | 1350 | 29.432 | 23.525 | 81.424 |
| ATOM | 5324 | OE1 | GLU | 1350 | 30.057 | 22.486 | 81.081 |
| ATOM | 5325 | OE2 | GLU | 1350 | 29.974 | 24.659 | 81.499 |
| ATOM | 5326 | C | GLU | 1350 | 26.044 | 26.319 | 82.685 |

FIGURE 1HHHHH

| | Atom | | Residue AA | No. | X | Y | Z |
|---|---|---|---|---|---|---|---|
| ATOM | 5327 | O | GLU | 1350 | 25.035 | 27.036 | 82.836 |
| ATOM | 5328 | N | GLY | 1351 | 27.317 | 26.656 | 82.954 |
| ATOM | 5329 | CA | GLY | 1351 | 27.797 | 27.970 | 83.371 |
| ATOM | 5330 | C | GLY | 1351 | 26.944 | 28.883 | 84.239 |
| ATOM | 5331 | O | GLY | 1351 | 27.299 | 29.131 | 85.406 |
| ATOM | 5332 | N | VAL | 1352 | 25.860 | 29.386 | 83.630 |
| ATOM | 5333 | CA | VAL | 1352 | 24.867 | 30.315 | 84.201 |
| ATOM | 5334 | CB | VAL | 1352 | 24.265 | 29.785 | 85.575 |
| ATOM | 5335 | CG1 | VAL | 1352 | 23.280 | 30.844 | 86.245 |
| ATOM | 5336 | CG2 | VAL | 1352 | 23.560 | 28.416 | 85.319 |
| ATOM | 5337 | C | VAL | 1352 | 25.311 | 31.817 | 84.229 |
| ATOM | 5338 | O | VAL | 1352 | 26.451 | 32.133 | 84.703 |
| ATOM | 5339 | OT | VAL | 1352 | 24.514 | 32.656 | 83.680 |
| ATOM | 5340 | CB | ALA | 1356 | 26.519 | 35.797 | 83.628 |
| ATOM | 5341 | C | ALA | 1356 | 26.395 | 34.681 | 81.284 |
| ATOM | 5342 | O | ALA | 1356 | 26.040 | 34.653 | 80.073 |
| ATOM | 5343 | N | ALA | 1356 | 24.298 | 35.160 | 82.580 |
| ATOM | 5344 | CA | ALA | 1356 | 25.692 | 35.645 | 82.288 |
| ATOM | 5345 | N | ALA | 1357 | 27.304 | 33.846 | 81.825 |
| ATOM | 5346 | CA | ALA | 1357 | 28.098 | 32.840 | 81.084 |
| ATOM | 5347 | CB | ALA | 1357 | 29.530 | 32.729 | 81.727 |
| ATOM | 5348 | C | ALA | 1357 | 27.414 | 31.429 | 80.990 |
| ATOM | 5349 | O | ALA | 1357 | 28.072 | 30.381 | 81.175 |
| ATOM | 5350 | N | ALA | 1358 | 26.122 | 31.421 | 80.636 |
| ATOM | 5351 | CA | ALA | 1358 | 25.349 | 30.184 | 80.512 |
| ATOM | 5352 | CB | ALA | 1358 | 23.862 | 30.496 | 80.388 |
| ATOM | 5353 | C | ALA | 1358 | 25.803 | 29.285 | 79.355 |
| ATOM | 5354 | O | ALA | 1358 | 26.817 | 29.568 | 78.704 |
| ATOM | 5355 | N | ARG | 1359 | 25.034 | 28.220 | 79.097 |
| ATOM | 5356 | CA | ARG | 1359 | 25.337 | 27.251 | 78.039 |
| ATOM | 5357 | CB | ARG | 1359 | 26.823 | 26.832 | 78.127 |
| ATOM | 5358 | CG | ARG | 1359 | 27.215 | 25.595 | 77.302 |
| ATOM | 5359 | CD | ARG | 1359 | 28.726 | 25.450 | 77.140 |
| ATOM | 5360 | NE | ARG | 1359 | 29.148 | 24.078 | 77.400 |
| ATOM | 5361 | CZ | ARG | 1359 | 30.188 | 23.473 | 76.838 |
| ATOM | 5362 | NH1 | ARG | 1359 | 30.940 | 24.134 | 75.974 |
| ATOM | 5363 | NH2 | ARG | 1359 | 30.462 | 22.198 | 77.130 |
| ATOM | 5364 | C | ARG | 1359 | 24.483 | 25.996 | 78.204 |
| ATOM | 5365 | O | ARG | 1359 | 24.199 | 25.610 | 79.336 |
| ATOM | 5366 | N | THR | 1360 | 24.003 | 25.418 | 77.096 |
| ATOM | 5367 | CA | THR | 1360 | 23.254 | 24.137 | 77.127 |
| ATOM | 5368 | CB | THR | 1360 | 21.906 | 24.102 | 76.305 |
| ATOM | 5369 | OG1 | THR | 1360 | 20.864 | 24.793 | 77.006 |
| ATOM | 5370 | CG2 | THR | 1360 | 21.452 | 22.650 | 76.105 |
| ATOM | 5371 | C | THR | 1360 | 24.215 | 23.223 | 76.391 |
| ATOM | 5372 | O | THR | 1360 | 24.685 | 23.580 | 75.309 |
| ATOM | 5373 | N | VAL | 1361 | 24.558 | 22.087 | 76.984 |
| ATOM | 5374 | CA | VAL | 1361 | 25.472 | 21.167 | 76.332 |

FIGURE 1IIIII

| | Atom | | Residue AA | No. | X | Y | Z |
|---|---|---|---|---|---|---|---|
| ATOM | 5375 | CB | VAL | 1361 | 26.789 | 20.990 | 77.107 |
| ATOM | 5376 | CG1 | VAL | 1361 | 27.929 | 20.662 | 76.167 |
| ATOM | 5377 | CG2 | VAL | 1361 | 27.085 | 22.193 | 77.882 |
| ATOM | 5378 | C | VAL | 1361 | 24.795 | 19.826 | 76.333 |
| ATOM | 5379 | O | VAL | 1361 | 23.749 | 19.651 | 76.960 |
| ATOM | 5380 | N | LEU | 1362 | 25.329 | 18.933 | 75.516 |
| ATOM | 5381 | CA | LEU | 1362 | 24.878 | 17.570 | 75.442 |
| ATOM | 5382 | CB | LEU | 1362 | 24.070 | 17.267 | 74.176 |
| ATOM | 5383 | CG | LEU | 1362 | 22.608 | 17.734 | 74.078 |
| ATOM | 5384 | CD1 | LEU | 1362 | 21.766 | 16.777 | 73.257 |
| ATOM | 5385 | CD2 | LEU | 1362 | 22.009 | 17.813 | 75.426 |
| ATOM | 5386 | C | LEU | 1362 | 26.257 | 16.996 | 75.363 |
| ATOM | 5387 | O | LEU | 1362 | 27.112 | 17.519 | 74.660 |
| ATOM | 5388 | N | HIS | 1363 | 26.535 | 16.059 | 76.244 |
| ATOM | 5389 | CA | HIS | 1363 | 27.843 | 15.448 | 76.248 |
| ATOM | 5390 | CB | HIS | 1363 | 28.445 | 15.489 | 77.668 |
| ATOM | 5391 | CG | HIS | 1363 | 28.754 | 16.871 | 78.176 |
| ATOM | 5392 | CD2 | HIS | 1363 | 29.909 | 17.580 | 78.186 |
| ATOM | 5393 | ND1 | HIS | 1363 | 27.821 | 17.663 | 78.818 |
| ATOM | 5394 | CE1 | HIS | 1363 | 28.391 | 18.793 | 79.203 |
| ATOM | 5395 | NE2 | HIS | 1363 | 29.659 | 18.767 | 78.829 |
| ATOM | 5396 | C | HIS | 1363 | 27.739 | 14.000 | 75.723 |
| ATOM | 5397 | O | HIS | 1363 | 27.637 | 13.050 | 76.527 |
| ATOM | 5398 | N | PHE | 1364 | 27.703 | 13.841 | 74.386 |
| ATOM | 5399 | CA | PHE | 1364 | 27.610 | 12.517 | 73.731 |
| ATOM | 5400 | CB | PHE | 1364 | 27.058 | 12.639 | 72.308 |
| ATOM | 5401 | CG | PHE | 1364 | 25.629 | 13.025 | 72.223 |
| ATOM | 5402 | CD1 | PHE | 1364 | 25.259 | 14.219 | 71.625 |
| ATOM | 5403 | CD2 | PHE | 1364 | 24.641 | 12.171 | 72.664 |
| ATOM | 5404 | CE1 | PHE | 1364 | 23.922 | 14.556 | 71.457 |
| ATOM | 5405 | CE2 | PHE | 1364 | 23.290 | 12.497 | 72.502 |
| ATOM | 5406 | CZ | PHE | 1364 | 22.934 | 13.691 | 71.896 |
| ATOM | 5407 | C | PHE | 1364 | 29.011 | 11.931 | 73.600 |
| ATOM | 5408 | O | PHE | 1364 | 29.954 | 12.667 | 73.337 |
| ATOM | 5409 | N | HIS | 1365 | 29.178 | 10.636 | 73.837 |
| ATOM | 5410 | CA | HIS | 1365 | 30.489 | 10.038 | 73.631 |
| ATOM | 5411 | CB | HIS | 1365 | 30.410 | 8.550 | 73.957 |
| ATOM | 5412 | CG | HIS | 1365 | 31.624 | 7.782 | 73.544 |
| ATOM | 5413 | CD2 | HIS | 1365 | 32.929 | 7.919 | 73.882 |
| ATOM | 5414 | ND1 | HIS | 1365 | 31.576 | 6.765 | 72.618 |
| ATOM | 5415 | CE1 | HIS | 1365 | 32.801 | 6.312 | 72.395 |
| ATOM | 5416 | NE2 | HIS | 1365 | 33.640 | 6.996 | 73.151 |
| ATOM | 5417 | C | HIS | 1365 | 30.703 | 10.247 | 72.116 |
| ATOM | 5418 | O | HIS | 1365 | 29.766 | 10.050 | 71.358 |
| ATOM | 5419 | N | PRO | 1366 | 31.912 | 10.633 | 71.641 |
| ATOM | 5420 | CD | PRO | 1366 | 33.200 | 10.780 | 72.331 |
| ATOM | 5421 | CA | PRO | 1366 | 32.112 | 10.837 | 70.197 |
| ATOM | 5422 | CB | PRO | 1366 | 33.630 | 10.763 | 70.060 |

FIGURE 1JJJJJ

| Atom | | | Residue AA | No. | X | Y | Z |
|---|---|---|---|---|---|---|---|
| ATOM | 5423 | CG | PRO | 1366 | 34.078 | 11.410 | 71.252 |
| ATOM | 5424 | C | PRO | 1366 | 31.419 | 9.797 | 69.306 |
| ATOM | 5425 | O | PRO | 1366 | 30.535 | 10.130 | 68.521 |
| ATOM | 5426 | N | ALA | 1367 | 31.758 | 8.529 | 69.511 |
| ATOM | 5427 | CA | ALA | 1367 | 31.190 | 7.424 | 68.755 |
| ATOM | 5428 | CB | ALA | 1367 | 31.938 | 6.145 | 69.100 |
| ATOM | 5429 | C | ALA | 1367 | 29.683 | 7.234 | 68.957 |
| ATOM | 5430 | O | ALA | 1367 | 29.164 | 6.138 | 68.795 |
| ATOM | 5431 | N | LEU | 1368 | 28.985 | 8.297 | 69.310 |
| ATOM | 5432 | CA | LEU | 1368 | 27.559 | 8.241 | 69.519 |
| ATOM | 5433 | CB | LEU | 1368 | 27.269 | 7.901 | 70.973 |
| ATOM | 5434 | CG | LEU | 1368 | 26.421 | 6.712 | 71.399 |
| ATOM | 5435 | CD1 | LEU | 1368 | 25.029 | 6.903 | 70.971 |
| ATOM | 5436 | CD2 | LEU | 1368 | 26.973 | 5.445 | 70.858 |
| ATOM | 5437 | C | LEU | 1368 | 27.011 | 9.624 | 69.195 |
| ATOM | 5438 | O | LEU | 1368 | 25.807 | 9.795 | 69.060 |
| ATOM | 5439 | N | ALA | 1369 | 27.897 | 10.611 | 69.089 |
| ATOM | 5440 | CA | ALA | 1369 | 27.509 | 11.980 | 68.785 |
| ATOM | 5441 | CB | ALA | 1369 | 28.678 | 12.888 | 68.961 |
| ATOM | 5442 | C | ALA | 1369 | 27.046 | 12.023 | 67.347 |
| ATOM | 5443 | O | ALA | 1369 | 27.663 | 11.399 | 66.488 |
| ATOM | 5444 | N | PRO | 1370 | 25.969 | 12.782 | 67.049 |
| ATOM | 5445 | CD | PRO | 1370 | 25.209 | 13.732 | 67.888 |
| ATOM | 5446 | CA | PRO | 1370 | 25.494 | 12.839 | 65.659 |
| ATOM | 5447 | CB | PRO | 1370 | 24.329 | 13.841 | 65.739 |
| ATOM | 5448 | CG | PRO | 1370 | 24.729 | 14.742 | 66.858 |
| ATOM | 5449 | C | PRO | 1370 | 26.596 | 13.261 | 64.663 |
| ATOM | 5450 | O | PRO | 1370 | 26.801 | 12.592 | 63.639 |
| ATOM | 5451 | N | TYR | 1371 | 27.278 | 14.373 | 64.959 |
| ATOM | 5452 | CA | TYR | 1371 | 28.368 | 14.869 | 64.115 |
| ATOM | 5453 | CB | TYR | 1371 | 28.232 | 16.367 | 63.834 |
| ATOM | 5454 | CG | TYR | 1371 | 27.079 | 16.743 | 62.936 |
| ATOM | 5455 | CD1 | TYR | 1371 | 27.197 | 16.696 | 61.545 |
| ATOM | 5456 | CE1 | TYR | 1371 | 26.143 | 17.065 | 60.713 |
| ATOM | 5457 | CD2 | TYR | 1371 | 25.884 | 17.165 | 63.472 |
| ATOM | 5458 | CE2 | TYR | 1371 | 24.828 | 17.533 | 62.658 |
| ATOM | 5459 | CZ | TYR | 1371 | 24.953 | 17.487 | 61.282 |
| ATOM | 5460 | OH | TYR | 1371 | 23.879 | 17.887 | 60.497 |
| ATOM | 5461 | C | TYR | 1371 | 29.659 | 14.618 | 64.861 |
| ATOM | 5462 | O | TYR | 1371 | 29.667 | 14.637 | 66.077 |
| ATOM | 5463 | N | LYS | 1372 | 30.752 | 14.408 | 64.149 |
| ATOM | 5464 | CA | LYS | 1372 | 32.000 | 14.134 | 64.820 |
| ATOM | 5465 | CB | LYS | 1372 | 32.751 | 13.018 | 64.127 |
| ATOM | 5466 | CG | LYS | 1372 | 31.986 | 11.734 | 64.116 |
| ATOM | 5467 | CD | LYS | 1372 | 31.736 | 11.246 | 65.509 |
| ATOM | 5468 | CE | LYS | 1372 | 30.296 | 10.763 | 65.660 |
| ATOM | 5469 | NZ | LYS | 1372 | 29.878 | 9.639 | 64.781 |
| ATOM | 5470 | C | LYS | 1372 | 32.873 | 15.349 | 64.924 |

FIGURE 1KKKKK

| | Atom | | Residue AA | No. | X | Y | Z |
|---|---|---|---|---|---|---|---|
| ATOM | 5471 | O | LYS | 1372 | 33.830 | 15.386 | 65.696 |
| ATOM | 5472 | N | ALA | 1373 | 32.586 | 16.351 | 64.130 |
| ATOM | 5473 | CA | ALA | 1373 | 33.368 | 17.560 | 64.204 |
| ATOM | 5474 | CB | ALA | 1373 | 34.710 | 17.385 | 63.526 |
| ATOM | 5475 | C | ALA | 1373 | 32.513 | 18.516 | 63.448 |
| ATOM | 5476 | O | ALA | 1373 | 31.374 | 18.200 | 63.108 |
| ATOM | 5477 | N | ALA | 1374 | 33.040 | 19.702 | 63.214 |
| ATOM | 5478 | CA | ALA | 1374 | 32.324 | 20.723 | 62.466 |
| ATOM | 5479 | CB | ALA | 1374 | 31.260 | 21.404 | 63.336 |
| ATOM | 5480 | C | ALA | 1374 | 33.347 | 21.737 | 61.977 |
| ATOM | 5481 | O | ALA | 1374 | 34.245 | 22.152 | 62.725 |
| ATOM | 5482 | N | ILE | 1375 | 33.274 | 22.042 | 60.687 |
| ATOM | 5483 | CA | ILE | 1375 | 34.174 | 23.016 | 60.108 |
| ATOM | 5484 | CB | ILE | 1375 | 34.696 | 22.583 | 58.744 |
| ATOM | 5485 | CG2 | ILE | 1375 | 36.129 | 23.033 | 58.614 |
| ATOM | 5486 | CG1 | ILE | 1375 | 34.664 | 21.068 | 58.626 |
| ATOM | 5487 | CD1 | ILE | 1375 | 35.715 | 20.423 | 59.437 |
| ATOM | 5488 | C | ILE | 1375 | 33.404 | 24.336 | 59.989 |
| ATOM | 5489 | O | ILE | 1375 | 32.396 | 24.445 | 59.264 |
| ATOM | 5490 | N | LEU | 1376 | 33.790 | 25.278 | 60.835 |
| ATOM | 5491 | CA | LEU | 1376 | 33.187 | 26.590 | 60.837 |
| ATOM | 5492 | CB | LEU | 1376 | 33.070 | 27.136 | 62.258 |
| ATOM | 5493 | CG | LEU | 1376 | 32.195 | 26.449 | 63.301 |
| ATOM | 5494 | CD1 | LEU | 1376 | 30.727 | 26.660 | 62.988 |
| ATOM | 5495 | CD2 | LEU | 1376 | 32.547 | 24.966 | 63.403 |
| ATOM | 5496 | C | LEU | 1376 | 34.268 | 27.355 | 60.149 |
| ATOM | 5497 | O | LEU | 1376 | 35.449 | 27.131 | 60.429 |
| ATOM | 5498 | N | PRO | 1377 | 33.918 | 28.159 | 59.145 |
| ATOM | 5499 | CD | PRO | 1377 | 32.664 | 28.421 | 58.426 |
| ATOM | 5500 | CA | PRO | 1377 | 35.029 | 28.885 | 58.533 |
| ATOM | 5501 | CB | PRO | 1377 | 34.352 | 29.600 | 57.352 |
| ATOM | 5502 | CG | PRO | 1377 | 32.931 | 29.782 | 57.830 |
| ATOM | 5503 | C | PRO | 1377 | 35.479 | 29.872 | 59.602 |
| ATOM | 5504 | O | PRO | 1377 | 36.018 | 29.485 | 60.645 |
| ATOM | 5505 | N | LEU | 1378 | 35.220 | 31.144 | 59.338 |
| ATOM | 5506 | CA | LEU | 1378 | 35.522 | 32.245 | 60.244 |
| ATOM | 5507 | CB | LEU | 1378 | 36.997 | 32.704 | 60.135 |
| ATOM | 5508 | CG | LEU | 1378 | 37.538 | 33.689 | 61.193 |
| ATOM | 5509 | CD1 | LEU | 1378 | 36.559 | 34.841 | 61.473 |
| ATOM | 5510 | CD2 | LEU | 1378 | 37.793 | 32.944 | 62.504 |
| ATOM | 5511 | C | LEU | 1378 | 34.627 | 33.305 | 59.636 |
| ATOM | 5512 | O | LEU | 1378 | 33.741 | 33.872 | 60.295 |
| ATOM | 5513 | N | SER | 1379 | 34.845 | 33.490 | 58.334 |
| ATOM | 5514 | CA | SER | 1379 | 34.130 | 34.463 | 57.539 |
| ATOM | 5515 | CB | SER | 1379 | 35.053 | 35.658 | 57.244 |
| ATOM | 5516 | OG | SER | 1379 | 34.323 | 36.800 | 56.819 |
| ATOM | 5517 | C | SER | 1379 | 33.791 | 33.763 | 56.241 |
| ATOM | 5518 | O | SER | 1379 | 34.574 | 32.894 | 55.776 |

FIGURE 1LLLLL

| Atom | | | Residue AA | No. | X | Y | Z |
|---|---|---|---|---|---|---|---|
| ATOM | 5519 | N | ALA | 1380 | 32.647 | 34.166 | 55.663 |
| ATOM | 5520 | CA | ALA | 1380 | 32.165 | 33.637 | 54.378 |
| ATOM | 5521 | CB | ALA | 1380 | 30.981 | 34.479 | 53.828 |
| ATOM | 5522 | C | ALA | 1380 | 33.330 | 33.616 | 53.371 |
| ATOM | 5523 | O | ALA | 1380 | 33.348 | 32.799 | 52.451 |
| ATOM | 5524 | N | ALA | 1381 | 34.311 | 34.499 | 53.579 |
| ATOM | 5525 | CA | ALA | 1381 | 35.505 | 34.572 | 52.737 |
| ATOM | 5526 | CB | ALA | 1381 | 36.476 | 35.635 | 53.267 |
| ATOM | 5527 | C | ALA | 1381 | 36.193 | 33.212 | 52.724 |
| ATOM | 5528 | O | ALA | 1381 | 36.327 | 32.572 | 51.653 |
| ATOM | 5529 | N | LEU | 1382 | 36.584 | 32.739 | 53.906 |
| ATOM | 5530 | CA | LEU | 1382 | 37.247 | 31.445 | 53.941 |
| ATOM | 5531 | CB | LEU | 1382 | 38.090 | 31.263 | 55.214 |
| ATOM | 5532 | CG | LEU | 1382 | 39.101 | 32.307 | 55.693 |
| ATOM | 5533 | CD1 | LEU | 1382 | 39.878 | 32.903 | 54.535 |
| ATOM | 5534 | CD2 | LEU | 1382 | 38.339 | 33.367 | 56.469 |
| ATOM | 5535 | C | LEU | 1382 | 36.279 | 30.252 | 53.752 |
| ATOM | 5536 | O | LEU | 1382 | 36.625 | 29.127 | 54.141 |
| ATOM | 5537 | N | SER | 1383 | 35.083 | 30.482 | 53.184 |
| ATOM | 5538 | CA | SER | 1383 | 34.138 | 29.388 | 52.942 |
| ATOM | 5539 | CB | SER | 1383 | 32.900 | 29.873 | 52.215 |
| ATOM | 5540 | OG | SER | 1383 | 32.065 | 30.534 | 53.130 |
| ATOM | 5541 | C | SER | 1383 | 34.860 | 28.366 | 52.090 |
| ATOM | 5542 | O | SER | 1383 | 34.927 | 27.183 | 52.445 |
| ATOM | 5543 | N | GLY | 1384 | 35.385 | 28.806 | 50.952 |
| ATOM | 5544 | CA | GLY | 1384 | 36.160 | 27.888 | 50.140 |
| ATOM | 5545 | C | GLY | 1384 | 37.421 | 27.721 | 50.986 |
| ATOM | 5546 | O | GLY | 1384 | 37.860 | 28.695 | 51.649 |
| ATOM | 5547 | N | ALA | 1385 | 37.993 | 26.510 | 50.962 |
| ATOM | 5548 | CA | ALA | 1385 | 39.202 | 26.101 | 51.741 |
| ATOM | 5549 | CB | ALA | 1385 | 40.119 | 27.313 | 52.173 |
| ATOM | 5550 | C | ALA | 1385 | 38.692 | 25.338 | 52.968 |
| ATOM | 5551 | O | ALA | 1385 | 39.183 | 24.256 | 53.298 |
| ATOM | 5552 | N | ALA | 1386 | 37.665 | 25.891 | 53.609 |
| ATOM | 5553 | CA | ALA | 1386 | 37.050 | 25.249 | 54.757 |
| ATOM | 5554 | CB | ALA | 1386 | 36.114 | 26.217 | 55.492 |
| ATOM | 5555 | C | ALA | 1386 | 36.279 | 24.063 | 54.186 |
| ATOM | 5556 | O | ALA | 1386 | 36.350 | 22.968 | 54.733 |
| ATOM | 5557 | N | ILE | 1387 | 35.608 | 24.258 | 53.048 |
| ATOM | 5558 | CA | ILE | 1387 | 34.864 | 23.169 | 52.416 |
| ATOM | 5559 | CB | ILE | 1387 | 34.167 | 23.620 | 51.149 |
| ATOM | 5560 | CG2 | ILE | 1387 | 33.291 | 22.513 | 50.635 |
| ATOM | 5561 | CG1 | ILE | 1387 | 33.295 | 24.828 | 51.449 |
| ATOM | 5562 | CD1 | ILE | 1387 | 32.855 | 25.600 | 50.219 |
| ATOM | 5563 | C | ILE | 1387 | 35.824 | 22.044 | 52.051 |
| ATOM | 5564 | O | ILE | 1387 | 35.420 | 20.882 | 51.943 |
| ATOM | 5565 | N | ALA | 1388 | 37.106 | 22.397 | 51.904 |
| ATOM | 5566 | CA | ALA | 1388 | 38.169 | 21.436 | 51.565 |

FIGURE 1MMMMMM

| | Atom | | Residue AA | No. | X | Y | Z |
|---|---|---|---|---|---|---|---|
| ATOM | 5567 | CB | ALA | 1388 | 39.442 | 22.171 | 51.151 |
| ATOM | 5568 | C | ALA | 1388 | 38.463 | 20.424 | 52.698 |
| ATOM | 5569 | O | ALA | 1388 | 38.522 | 19.204 | 52.473 |
| ATOM | 5570 | N | ILE | 1389 | 38.704 | 20.920 | 53.906 |
| ATOM | 5571 | CA | ILE | 1389 | 38.916 | 20.005 | 55.017 |
| ATOM | 5572 | CB | ILE | 1389 | 39.296 | 20.686 | 56.324 |
| ATOM | 5573 | CG2 | ILE | 1389 | 40.717 | 20.344 | 56.657 |
| ATOM | 5574 | CG1 | ILE | 1389 | 38.982 | 22.175 | 56.267 |
| ATOM | 5575 | CD1 | ILE | 1389 | 39.882 | 23.023 | 57.131 |
| ATOM | 5576 | C | ILE | 1389 | 37.605 | 19.288 | 55.255 |
| ATOM | 5577 | O | ILE | 1389 | 37.599 | 18.121 | 55.637 |
| ATOM | 5578 | N | PHE | 1390 | 36.493 | 19.976 | 55.023 |
| ATOM | 5579 | CA | PHE | 1390 | 35.206 | 19.354 | 55.207 |
| ATOM | 5580 | CB | PHE | 1390 | 34.091 | 20.212 | 54.635 |
| ATOM | 5581 | CG | PHE | 1390 | 32.824 | 19.460 | 54.464 |
| ATOM | 5582 | CD1 | PHE | 1390 | 32.625 | 18.637 | 53.355 |
| ATOM | 5583 | CD2 | PHE | 1390 | 31.883 | 19.465 | 55.459 |
| ATOM | 5584 | CE1 | PHE | 1390 | 31.524 | 17.833 | 53.255 |
| ATOM | 5585 | CE2 | PHE | 1390 | 30.769 | 18.661 | 55.370 |
| ATOM | 5586 | CZ | PHE | 1390 | 30.592 | 17.841 | 54.267 |
| ATOM | 5587 | C | PHE | 1390 | 35.209 | 18.000 | 54.511 |
| ATOM | 5588 | O | PHE | 1390 | 35.038 | 16.965 | 55.161 |
| ATOM | 5589 | N | GLU | 1391 | 35.446 | 18.009 | 53.199 |
| ATOM | 5590 | CA | GLU | 1391 | 35.456 | 16.779 | 52.398 |
| ATOM | 5591 | CB | GLU | 1391 | 35.676 | 17.108 | 50.939 |
| ATOM | 5592 | CG | GLU | 1391 | 34.535 | 17.835 | 50.312 |
| ATOM | 5593 | CD | GLU | 1391 | 34.901 | 18.397 | 48.937 |
| ATOM | 5594 | OE1 | GLU | 1391 | 36.133 | 18.491 | 48.620 |
| ATOM | 5595 | OE2 | GLU | 1391 | 33.937 | 18.745 | 48.189 |
| ATOM | 5596 | C | GLU | 1391 | 36.478 | 15.720 | 52.800 |
| ATOM | 5597 | O | GLU | 1391 | 36.141 | 14.532 | 52.930 |
| ATOM | 5598 | N | GLN | 1392 | 37.731 | 16.143 | 52.943 |
| ATOM | 5599 | CA | GLN | 1392 | 38.804 | 15.244 | 53.324 |
| ATOM | 5600 | CB | GLN | 1392 | 40.002 | 16.062 | 53.823 |
| ATOM | 5601 | CG | GLN | 1392 | 41.203 | 15.214 | 54.335 |
| ATOM | 5602 | CD | GLN | 1392 | 42.069 | 15.937 | 55.399 |
| ATOM | 5603 | OE1 | GLN | 1392 | 42.470 | 15.337 | 56.423 |
| ATOM | 5604 | NE2 | GLN | 1392 | 42.359 | 17.224 | 55.156 |
| ATOM | 5605 | C | GLN | 1392 | 38.332 | 14.300 | 54.433 |
| ATOM | 5606 | O | GLN | 1392 | 38.689 | 13.121 | 54.461 |
| ATOM | 5607 | N | LEU | 1393 | 37.495 | 14.826 | 55.318 |
| ATOM | 5608 | CA | LEU | 1393 | 37.007 | 14.071 | 56.443 |
| ATOM | 5609 | CB | LEU | 1393 | 36.937 | 14.971 | 57.674 |
| ATOM | 5610 | CG | LEU | 1393 | 38.295 | 15.633 | 57.962 |
| ATOM | 5611 | CD1 | LEU | 1393 | 38.117 | 16.725 | 58.956 |
| ATOM | 5612 | CD2 | LEU | 1393 | 39.352 | 14.646 | 58.432 |
| ATOM | 5613 | C | LEU | 1393 | 35.693 | 13.387 | 56.199 |
| ATOM | 5614 | O | LEU | 1393 | 35.477 | 12.293 | 56.727 |

FIGURE 1NNNNN

| Atom | | | Residue AA | No. | X | Y | Z |
|---|---|---|---|---|---|---|---|
| ATOM | 5615 | N | SER | 1394 | 34.832 | 13.997 | 55.384 |
| ATOM | 5616 | CA | SER | 1394 | 33.506 | 13.431 | 55.097 |
| ATOM | 5617 | CB | SER | 1394 | 32.797 | 14.200 | 53.979 |
| ATOM | 5618 | OG | SER | 1394 | 32.866 | 15.583 | 54.174 |
| ATOM | 5619 | C | SER | 1394 | 33.635 | 11.968 | 54.686 |
| ATOM | 5620 | O | SER | 1394 | 32.754 | 11.134 | 54.941 |
| ATOM | 5621 | N | SER | 1395 | 34.762 | 11.664 | 54.061 |
| ATOM | 5622 | CA | SER | 1395 | 35.084 | 10.322 | 53.590 |
| ATOM | 5623 | CB | SER | 1395 | 36.556 | 10.334 | 53.183 |
| ATOM | 5624 | OG | SER | 1395 | 37.284 | 11.169 | 54.090 |
| ATOM | 5625 | C | SER | 1395 | 34.881 | 9.255 | 54.673 |
| ATOM | 5626 | O | SER | 1395 | 34.810 | 8.052 | 54.382 |
| ATOM | 5627 | N | LYS | 1396 | 34.871 | 9.706 | 55.926 |
| ATOM | 5628 | CA | LYS | 1396 | 34.730 | 8.813 | 57.045 |
| ATOM | 5629 | CB | LYS | 1396 | 36.117 | 8.493 | 57.595 |
| ATOM | 5630 | CG | LYS | 1396 | 36.826 | 7.348 | 56.858 |
| ATOM | 5631 | CD | LYS | 1396 | 37.576 | 7.769 | 55.608 |
| ATOM | 5632 | CE | LYS | 1396 | 38.941 | 8.379 | 55.947 |
| ATOM | 5633 | NZ | LYS | 1396 | 38.812 | 9.631 | 56.743 |
| ATOM | 5634 | C | LYS | 1396 | 33.797 | 9.238 | 58.183 |
| ATOM | 5635 | O | LYS | 1396 | 33.016 | 8.399 | 58.678 |
| ATOM | 5636 | N | PHE | 1397 | 33.856 | 10.515 | 58.589 |
| ATOM | 5637 | CA | PHE | 1397 | 33.040 | 11.011 | 59.720 |
| ATOM | 5638 | CB | PHE | 1397 | 33.932 | 11.772 | 60.705 |
| ATOM | 5639 | CG | PHE | 1397 | 35.223 | 11.087 | 60.995 |
| ATOM | 5640 | CD1 | PHE | 1397 | 35.249 | 9.734 | 61.326 |
| ATOM | 5641 | CD2 | PHE | 1397 | 36.415 | 11.772 | 60.891 |
| ATOM | 5642 | CE1 | PHE | 1397 | 36.460 | 9.071 | 61.543 |
| ATOM | 5643 | CE2 | PHE | 1397 | 37.629 | 11.123 | 61.106 |
| ATOM | 5644 | CZ | PHE | 1397 | 37.655 | 9.769 | 61.432 |
| ATOM | 5645 | C | PHE | 1397 | 31.836 | 11.888 | 59.399 |
| ATOM | 5646 | O | PHE | 1397 | 31.912 | 12.772 | 58.553 |
| ATOM | 5647 | N | SER | 1398 | 30.759 | 11.709 | 60.149 |
| ATOM | 5648 | CA | SER | 1398 | 29.556 | 12.505 | 59.938 |
| ATOM | 5649 | CB | SER | 1398 | 28.376 | 11.912 | 60.732 |
| ATOM | 5650 | OG | SER | 1398 | 28.586 | 10.532 | 61.059 |
| ATOM | 5651 | C | SER | 1398 | 29.796 | 13.934 | 60.409 |
| ATOM | 5652 | O | SER | 1398 | 29.296 | 14.309 | 61.457 |
| ATOM | 5653 | N | ILE | 1399 | 30.546 | 14.736 | 59.658 |
| ATOM | 5654 | CA | ILE | 1399 | 30.801 | 16.115 | 60.083 |
| ATOM | 5655 | CB | ILE | 1399 | 32.287 | 16.474 | 59.931 |
| ATOM | 5656 | CG2 | ILE | 1399 | 33.137 | 15.271 | 60.277 |
| ATOM | 5657 | CG1 | ILE | 1399 | 32.595 | 16.925 | 58.520 |
| ATOM | 5658 | CD1 | ILE | 1399 | 34.028 | 17.276 | 58.330 |
| ATOM | 5659 | C | ILE | 1399 | 29.885 | 17.222 | 59.494 |
| ATOM | 5660 | O | ILE | 1399 | 29.275 | 17.062 | 58.441 |
| ATOM | 5661 | N | ASP | 1400 | 29.730 | 18.310 | 60.238 |
| ATOM | 5662 | CA | ASP | 1400 | 28.895 | 19.440 | 59.831 |

FIGURE 100000

| | Atom | | Residue AA | No. | X | Y | Z |
|---|---|---|---|---|---|---|---|
| ATOM | 5663 | CB | ASP | 1400 | 28.145 | 19.992 | 61.077 |
| ATOM | 5664 | CG | ASP | 1400 | 26.953 | 20.937 | 60.746 |
| ATOM | 5665 | OD1 | ASP | 1400 | 27.023 | 21.748 | 59.806 |
| ATOM | 5666 | OD2 | ASP | 1400 | 25.939 | 20.907 | 61.490 |
| ATOM | 5667 | C | ASP | 1400 | 29.877 | 20.491 | 59.315 |
| ATOM | 5668 | O | ASP | 1400 | 31.113 | 20.340 | 59.438 |
| ATOM | 5669 | N | PHE | 1401 | 29.318 | 21.510 | 58.671 |
| ATOM | 5670 | CA | PHE | 1401 | 30.064 | 22.653 | 58.159 |
| ATOM | 5671 | CB | PHE | 1401 | 30.312 | 22.515 | 56.656 |
| ATOM | 5672 | CG | PHE | 1401 | 31.106 | 23.654 | 56.061 |
| ATOM | 5673 | CD1 | PHE | 1401 | 32.500 | 23.596 | 56.003 |
| ATOM | 5674 | CD2 | PHE | 1401 | 30.460 | 24.796 | 55.569 |
| ATOM | 5675 | CE1 | PHE | 1401 | 33.238 | 24.666 | 55.463 |
| ATOM | 5676 | CE2 | PHE | 1401 | 31.189 | 25.872 | 55.028 |
| ATOM | 5677 | CZ | PHE | 1401 | 32.579 | 25.810 | 54.975 |
| ATOM | 5678 | C | PHE | 1401 | 29.124 | 23.827 | 58.419 |
| ATOM | 5679 | O | PHE | 1401 | 27.910 | 23.742 | 58.108 |
| ATOM | 5680 | N | ASP | 1402 | 29.636 | 24.885 | 59.049 |
| ATOM | 5681 | CA | ASP | 1402 | 28.783 | 26.039 | 59.317 |
| ATOM | 5682 | CB | ASP | 1402 | 28.076 | 25.947 | 60.681 |
| ATOM | 5683 | CG | ASP | 1402 | 26.811 | 26.833 | 60.764 |
| ATOM | 5684 | OD1 | ASP | 1402 | 26.045 | 26.699 | 61.748 |
| ATOM | 5685 | OD2 | ASP | 1402 | 26.570 | 27.657 | 59.849 |
| ATOM | 5686 | C | ASP | 1402 | 29.543 | 27.321 | 59.231 |
| ATOM | 5687 | O | ASP | 1402 | 30.560 | 27.517 | 59.899 |
| ATOM | 5688 | N | GLU | 1403 | 29.020 | 28.185 | 58.381 |
| ATOM | 5689 | CA | GLU | 1403 | 29.591 | 29.490 | 58.161 |
| ATOM | 5690 | CB | GLU | 1403 | 29.914 | 29.660 | 56.678 |
| ATOM | 5691 | CG | GLU | 1403 | 28.782 | 29.203 | 55.765 |
| ATOM | 5692 | CD | GLU | 1403 | 29.073 | 29.456 | 54.279 |
| ATOM | 5693 | OE1 | GLU | 1403 | 28.233 | 30.151 | 53.625 |
| ATOM | 5694 | OE2 | GLU | 1403 | 30.128 | 28.953 | 53.773 |
| ATOM | 5695 | C | GLU | 1403 | 28.601 | 30.560 | 58.624 |
| ATOM | 5696 | O | GLU | 1403 | 28.988 | 31.527 | 59.281 |
| ATOM | 5697 | N | SER | 1404 | 27.320 | 30.363 | 58.300 |
| ATOM | 5698 | CA | SER | 1404 | 26.271 | 31.319 | 58.661 |
| ATOM | 5699 | CB | SER | 1404 | 24.885 | 30.747 | 58.304 |
| ATOM | 5700 | OG | SER | 1404 | 23.889 | 31.760 | 58.190 |
| ATOM | 5701 | C | SER | 1404 | 26.348 | 31.675 | 60.153 |
| ATOM | 5702 | O | SER | 1404 | 26.531 | 30.788 | 61.002 |
| ATOM | 5703 | N | GLN | 1405 | 26.206 | 32.972 | 60.442 |
| ATOM | 5704 | CA | GLN | 1405 | 26.243 | 33.534 | 61.798 |
| ATOM | 5705 | CB | GLN | 1405 | 25.683 | 32.554 | 62.850 |
| ATOM | 5706 | CG | GLN | 1405 | 24.287 | 32.025 | 62.557 |
| ATOM | 5707 | CD | GLN | 1405 | 23.436 | 33.070 | 61.871 |
| ATOM | 5708 | OE1 | GLN | 1405 | 22.746 | 32.771 | 60.893 |
| ATOM | 5709 | NE2 | GLN | 1405 | 23.512 | 34.320 | 62.349 |
| ATOM | 5710 | C | GLN | 1405 | 27.630 | 34.035 | 62.231 |

FIGURE 1PPPPP

| Atom | | | Residue AA | No. | X | Y | Z |
|---|---|---|---|---|---|---|---|
| ATOM | 5711 | O | GLN | 1405 | 28.522 | 34.245 | 61.397 |
| ATOM | 5712 | N | SER | 1406 | 27.795 | 34.277 | 63.533 |
| ATOM | 5713 | CA | SER | 1406 | 29.064 | 34.775 | 64.056 |
| ATOM | 5714 | CB | SER | 1406 | 28.848 | 35.382 | 65.449 |
| ATOM | 5715 | OG | SER | 1406 | 28.293 | 34.427 | 66.346 |
| ATOM | 5716 | C | SER | 1406 | 30.116 | 33.673 | 64.099 |
| ATOM | 5717 | O | SER | 1406 | 30.685 | 33.310 | 63.074 |
| ATOM | 5718 | N | ILE | 1407 | 30.375 | 33.180 | 65.307 |
| ATOM | 5719 | CA | ILE | 1407 | 31.329 | 32.107 | 65.586 |
| ATOM | 5720 | CB | ILE | 1407 | 32.842 | 32.570 | 65.507 |
| ATOM | 5721 | CG2 | ILE | 1407 | 33.467 | 32.778 | 66.904 |
| ATOM | 5722 | CG1 | ILE | 1407 | 33.672 | 31.516 | 64.762 |
| ATOM | 5723 | CD1 | ILE | 1407 | 33.500 | 30.118 | 65.304 |
| ATOM | 5724 | C | ILE | 1407 | 30.964 | 31.656 | 66.998 |
| ATOM | 5725 | O | ILE | 1407 | 30.803 | 30.460 | 67.252 |
| ATOM | 5726 | N | GLY | 1408 | 30.771 | 32.632 | 67.890 |
| ATOM | 5727 | CA | GLY | 1408 | 30.387 | 32.335 | 69.256 |
| ATOM | 5728 | C | GLY | 1408 | 28.977 | 31.773 | 69.238 |
| ATOM | 5729 | O | GLY | 1408 | 28.703 | 30.753 | 69.886 |
| ATOM | 5730 | N | LYS | 1409 | 28.097 | 32.418 | 68.461 |
| ATOM | 5731 | CA | LYS | 1409 | 26.698 | 31.988 | 68.319 |
| ATOM | 5732 | CB | LYS | 1409 | 25.886 | 33.035 | 67.548 |
| ATOM | 5733 | CG | LYS | 1409 | 24.788 | 33.723 | 68.364 |
| ATOM | 5734 | CD | LYS | 1409 | 23.586 | 32.789 | 68.629 |
| ATOM | 5735 | CE | LYS | 1409 | 22.443 | 33.533 | 69.367 |
| ATOM | 5736 | NZ | LYS | 1409 | 21.202 | 32.712 | 69.624 |
| ATOM | 5737 | C | LYS | 1409 | 26.661 | 30.644 | 67.587 |
| ATOM | 5738 | O | LYS | 1409 | 25.744 | 29.817 | 67.800 |
| ATOM | 5739 | N | ARG | 1410 | 27.681 | 30.451 | 66.739 |
| ATOM | 5740 | CA | ARG | 1410 | 27.877 | 29.223 | 65.958 |
| ATOM | 5741 | CB | ARG | 1410 | 28.991 | 29.407 | 64.889 |
| ATOM | 5742 | CG | ARG | 1410 | 28.464 | 29.389 | 63.421 |
| ATOM | 5743 | CD | ARG | 1410 | 29.213 | 30.311 | 62.424 |
| ATOM | 5744 | NE | ARG | 1410 | 30.488 | 29.760 | 61.961 |
| ATOM | 5745 | CZ | ARG | 1410 | 31.351 | 30.413 | 61.180 |
| ATOM | 5746 | NH1 | ARG | 1410 | 32.489 | 29.834 | 60.821 |
| ATOM | 5747 | NH2 | ARG | 1410 | 31.081 | 31.646 | 60.756 |
| ATOM | 5748 | C | ARG | 1410 | 28.240 | 28.116 | 66.956 |
| ATOM | 5749 | O | ARG | 1410 | 27.581 | 27.063 | 66.998 |
| ATOM | 5750 | N | TYR | 1411 | 29.225 | 28.401 | 67.807 |
| ATOM | 5751 | CA | TYR | 1411 | 29.652 | 27.465 | 68.815 |
| ATOM | 5752 | CB | TYR | 1411 | 30.679 | 28.108 | 69.718 |
| ATOM | 5753 | CG | TYR | 1411 | 32.063 | 28.164 | 69.134 |
| ATOM | 5754 | CD1 | TYR | 1411 | 32.883 | 29.265 | 69.366 |
| ATOM | 5755 | CE1 | TYR | 1411 | 34.216 | 29.302 | 68.905 |
| ATOM | 5756 | CD2 | TYR | 1411 | 32.593 | 27.094 | 68.418 |
| ATOM | 5757 | CE2 | TYR | 1411 | 33.928 | 27.116 | 67.956 |
| ATOM | 5758 | CZ | TYR | 1411 | 34.736 | 28.224 | 68.207 |

FIGURE 1QQQQQ

| Atom | | | Residue AA | No. | X | Y | Z |
|---|---|---|---|---|---|---|---|
| ATOM | 5759 | OH | TYR | 1411 | 36.066 | 28.239 | 67.810 |
| ATOM | 5760 | C | TYR | 1411 | 28.454 | 27.039 | 69.640 |
| ATOM | 5761 | O | TYR | 1411 | 28.177 | 25.852 | 69.751 |
| ATOM | 5762 | N | ARG | 1412 | 27.715 | 28.004 | 70.183 |
| ATOM | 5763 | CA | ARG | 1412 | 26.533 | 27.684 | 70.998 |
| ATOM | 5764 | CB | ARG | 1412 | 25.639 | 28.922 | 71.267 |
| ATOM | 5765 | CG | ARG | 1412 | 24.282 | 28.597 | 72.016 |
| ATOM | 5766 | CD | ARG | 1412 | 22.997 | 29.418 | 71.543 |
| ATOM | 5767 | NE | ARG | 1412 | 22.447 | 29.065 | 70.204 |
| ATOM | 5768 | CZ | ARG | 1412 | 21.138 | 28.888 | 69.912 |
| ATOM | 5769 | NH1 | ARG | 1412 | 20.768 | 28.575 | 68.653 |
| ATOM | 5770 | NH2 | ARG | 1412 | 20.193 | 28.987 | 70.868 |
| ATOM | 5771 | C | ARG | 1412 | 25.666 | 26.596 | 70.366 |
| ATOM | 5772 | O | ARG | 1412 | 25.497 | 25.520 | 70.971 |
| ATOM | 5773 | N | ARG | 1413 | 25.152 | 26.863 | 69.152 |
| ATOM | 5774 | CA | ARG | 1413 | 24.264 | 25.912 | 68.458 |
| ATOM | 5775 | CB | ARG | 1413 | 23.886 | 26.402 | 67.057 |
| ATOM | 5776 | CG | ARG | 1413 | 22.892 | 25.475 | 66.360 |
| ATOM | 5777 | CD | ARG | 1413 | 23.167 | 25.336 | 64.862 |
| ATOM | 5778 | NE | ARG | 1413 | 22.619 | 24.090 | 64.302 |
| ATOM | 5779 | CZ | ARG | 1413 | 21.315 | 23.805 | 64.189 |
| ATOM | 5780 | NH1 | ARG | 1413 | 20.386 | 24.681 | 64.594 |
| ATOM | 5781 | NH2 | ARG | 1413 | 20.935 | 22.630 | 63.684 |
| ATOM | 5782 | C | ARG | 1413 | 24.797 | 24.480 | 68.363 |
| ATOM | 5783 | O | ARG | 1413 | 24.012 | 23.518 | 68.415 |
| ATOM | 5784 | N | ALA | 1414 | 26.125 | 24.356 | 68.226 |
| ATOM | 5785 | CA | ALA | 1414 | 26.814 | 23.054 | 68.130 |
| ATOM | 5786 | CB | ALA | 1414 | 28.296 | 23.261 | 67.694 |
| ATOM | 5787 | C | ALA | 1414 | 26.744 | 22.226 | 69.442 |
| ATOM | 5788 | O | ALA | 1414 | 26.478 | 21.012 | 69.436 |
| ATOM | 5789 | N | ASP | 1415 | 26.950 | 22.892 | 70.568 |
| ATOM | 5790 | CA | ASP | 1415 | 26.908 | 22.219 | 71.839 |
| ATOM | 5791 | CB | ASP | 1415 | 27.367 | 23.171 | 72.925 |
| ATOM | 5792 | CG | ASP | 1415 | 28.797 | 23.622 | 72.701 |
| ATOM | 5793 | OD1 | ASP | 1415 | 29.623 | 22.754 | 72.311 |
| ATOM | 5794 | OD2 | ASP | 1415 | 29.091 | 24.829 | 72.860 |
| ATOM | 5795 | C | ASP | 1415 | 25.529 | 21.692 | 72.090 |
| ATOM | 5796 | O | ASP | 1415 | 25.360 | 20.509 | 72.314 |
| ATOM | 5797 | N | GLU | 1416 | 24.524 | 22.528 | 71.921 |
| ATOM | 5798 | CA | GLU | 1416 | 23.173 | 22.059 | 72.164 |
| ATOM | 5799 | CB | GLU | 1416 | 22.176 | 23.201 | 72.104 |
| ATOM | 5800 | CG | GLU | 1416 | 22.410 | 24.091 | 70.933 |
| ATOM | 5801 | CD | GLU | 1416 | 21.265 | 25.027 | 70.672 |
| ATOM | 5802 | OE1 | GLU | 1416 | 20.163 | 24.849 | 71.263 |
| ATOM | 5803 | OE2 | GLU | 1416 | 21.474 | 25.930 | 69.837 |
| ATOM | 5804 | C | GLU | 1416 | 22.714 | 20.900 | 71.285 |
| ATOM | 5805 | O | GLU | 1416 | 21.651 | 20.332 | 71.543 |
| ATOM | 5806 | N | ILE | 1417 | 23.444 | 20.594 | 70.206 |

FIGURE 1RRRRR

| Atom | | | Residue AA | No. | X | Y | Z |
|---|---|---|---|---|---|---|---|
| ATOM | 5807 | CA | ILE | 1417 | 23.070 | 19.442 | 69.359 |
| ATOM | 5808 | CB | ILE | 1417 | 23.187 | 19.684 | 67.812 |
| ATOM | 5809 | CG2 | ILE | 1417 | 22.704 | 21.067 | 67.425 |
| ATOM | 5810 | CG1 | ILE | 1417 | 24.612 | 19.466 | 67.338 |
| ATOM | 5811 | CD1 | ILE | 1417 | 24.771 | 19.596 | 65.847 |
| ATOM | 5812 | C | ILE | 1417 | 24.002 | 18.311 | 69.799 |
| ATOM | 5813 | O | ILE | 1417 | 23.741 | 17.129 | 69.560 |
| ATOM | 5814 | N | GLY | 1418 | 25.119 | 18.705 | 70.401 |
| ATOM | 5815 | CA | GLY | 1418 | 26.044 | 17.744 | 70.940 |
| ATOM | 5816 | C | GLY | 1418 | 27.193 | 17.263 | 70.117 |
| ATOM | 5817 | O | GLY | 1418 | 27.389 | 16.065 | 70.021 |
| ATOM | 5818 | N | THR | 1419 | 28.008 | 18.160 | 69.590 |
| ATOM | 5819 | CA | THR | 1419 | 29.135 | 17.679 | 68.815 |
| ATOM | 5820 | CB | THR | 1419 | 29.019 | 18.064 | 67.319 |
| ATOM | 5821 | OG1 | THR | 1419 | 29.062 | 19.491 | 66.750 |
| ATOM | 5823 | C | THR | 1419 | 30.507 | 17.975 | 69.417 |
| ATOM | 5824 | O | THR | 1419 | 30.811 | 19.104 | 69.793 |
| ATOM | 5825 | N | PRO | 1420 | 31.325 | 16.925 | 69.561 |
| ATOM | 5826 | CD | PRO | 1420 | 30.837 | 15.584 | 69.185 |
| ATOM | 5827 | CA | PRO | 1420 | 32.682 | 16.827 | 70.096 |
| ATOM | 5828 | CB | PRO | 1420 | 33.098 | 15.419 | 69.673 |
| ATOM | 5829 | CG | PRO | 1420 | 31.845 | 14.662 | 69.810 |
| ATOM | 5830 | C | PRO | 1420 | 33.761 | 17.864 | 69.741 |
| ATOM | 5831 | O | PRO | 1420 | 34.659 | 18.123 | 70.562 |
| ATOM | 5832 | N | TYR | 1421 | 33.738 | 18.402 | 68.522 |
| ATOM | 5833 | CA | TYR | 1421 | 34.762 | 19.379 | 68.114 |
| ATOM | 5834 | CB | TYR | 1421 | 35.999 | 18.669 | 67.585 |
| ATOM | 5835 | CG | TYR | 1421 | 36.568 | 17.693 | 68.556 |
| ATOM | 5836 | CD1 | TYR | 1421 | 36.223 | 16.345 | 68.473 |
| ATOM | 5837 | CE1 | TYR | 1421 | 36.703 | 15.446 | 69.367 |
| ATOM | 5838 | CD2 | TYR | 1421 | 37.420 | 18.109 | 69.569 |
| ATOM | 5839 | CE2 | TYR | 1421 | 37.908 | 17.216 | 70.466 |
| ATOM | 5840 | CZ | TYR | 1421 | 37.544 | 15.883 | 70.362 |
| ATOM | 5841 | OH | TYR | 1421 | 38.002 | 14.961 | 71.259 |
| ATOM | 5842 | C | TYR | 1421 | 34.376 | 20.422 | 67.075 |
| ATOM | 5843 | O | TYR | 1421 | 33.687 | 20.112 | 66.098 |
| ATOM | 5844 | N | CYS | 1422 | 34.936 | 21.622 | 67.239 |
| ATOM | 5845 | CA | CYS | 1422 | 34.700 | 22.734 | 66.331 |
| ATOM | 5846 | CB | CYS | 1422 | 34.048 | 23.872 | 67.076 |
| ATOM | 5847 | SG | CYS | 1422 | 32.378 | 23.466 | 67.547 |
| ATOM | 5848 | C | CYS | 1422 | 35.989 | 23.215 | 65.698 |
| ATOM | 5849 | O | CYS | 1422 | 36.753 | 23.939 | 66.333 |
| ATOM | 5850 | N | VAL | 1423 | 36.236 | 22.775 | 64.463 |
| ATOM | 5851 | CA | VAL | 1423 | 37.439 | 23.149 | 63.718 |
| ATOM | 5852 | CB | VAL | 1423 | 37.876 | 22.066 | 62.693 |
| ATOM | 5853 | CG1 | VAL | 1423 | 39.181 | 22.469 | 62.036 |
| ATOM | 5854 | CG2 | VAL | 1423 | 38.019 | 20.712 | 63.373 |

FIGURE 1SSSSS

| | Atom | | Residue AA | No. | X | Y | Z |
|---|---|---|---|---|---|---|---|
| ATOM | 5855 | C | VAL | 1423 | 37.156 | 24.440 | 62.968 |
| ATOM | 5856 | O | VAL | 1423 | 36.412 | 24.470 | 61.959 |
| ATOM | 5857 | N | THR | 1424 | 37.741 | 25.511 | 63.494 |
| ATOM | 5858 | CA | THR | 1424 | 37.577 | 26.835 | 62.907 |
| ATOM | 5859 | CB | THR | 1424 | 37.392 | 27.919 | 64.005 |
| ATOM | 5860 | OG1 | THR | 1424 | 38.439 | 27.830 | 64.987 |
| ATOM | 5861 | CG2 | THR | 1424 | 36.037 | 27.714 | 64.686 |
| ATOM | 5862 | C | THR | 1424 | 38.720 | 27.183 | 61.956 |
| ATOM | 5863 | O | THR | 1424 | 39.919 | 26.988 | 62.284 |
| ATOM | 5864 | N | PHE | 1425 | 38.326 | 27.577 | 60.745 |
| ATOM | 5865 | CA | PHE | 1425 | 39.281 | 27.956 | 59.723 |
| ATOM | 5866 | CB | PHE | 1425 | 38.917 | 27.380 | 58.332 |
| ATOM | 5867 | CG | PHE | 1425 | 40.011 | 27.543 | 57.302 |
| ATOM | 5868 | CD1 | PHE | 1425 | 40.816 | 26.468 | 56.960 |
| ATOM | 5869 | CD2 | PHE | 1425 | 40.285 | 28.796 | 56.748 |
| ATOM | 5870 | CE1 | PHE | 1425 | 41.872 | 26.638 | 56.098 |
| ATOM | 5871 | CE2 | PHE | 1425 | 41.334 | 28.980 | 55.891 |
| ATOM | 5872 | CZ | PHE | 1425 | 42.135 | 27.903 | 55.562 |
| ATOM | 5873 | C | PHE | 1425 | 39.210 | 29.461 | 59.682 |
| ATOM | 5874 | O | PHE | 1425 | 38.156 | 30.051 | 59.427 |
| ATOM | 5875 | N | ASP | 1426 | 40.331 | 30.089 | 59.968 |
| ATOM | 5876 | CA | ASP | 1426 | 40.367 | 31.525 | 59.932 |
| ATOM | 5877 | CB | ASP | 1426 | 40.748 | 32.070 | 61.306 |
| ATOM | 5878 | CG | ASP | 1426 | 42.229 | 31.931 | 61.583 |
| ATOM | 5879 | OD1 | ASP | 1426 | 42.909 | 32.971 | 61.526 |
| ATOM | 5880 | OD2 | ASP | 1426 | 42.710 | 30.797 | 61.795 |
| ATOM | 5881 | C | ASP | 1426 | 41.437 | 31.905 | 58.923 |
| ATOM | 5882 | O | ASP | 1426 | 41.982 | 31.056 | 58.184 |
| ATOM | 5883 | N | PHE | 1427 | 41.807 | 33.177 | 58.995 |
| ATOM | 5884 | CA | PHE | 1427 | 42.810 | 33.746 | 58.126 |
| ATOM | 5885 | CB | PHE | 1427 | 42.824 | 35.266 | 58.306 |
| ATOM | 5886 | CG | PHE | 1427 | 41.501 | 35.911 | 57.936 |
| ATOM | 5887 | CD1 | PHE | 1427 | 41.400 | 36.765 | 56.831 |
| ATOM | 5888 | CD2 | PHE | 1427 | 40.341 | 35.633 | 58.680 |
| ATOM | 5889 | CE1 | PHE | 1427 | 40.155 | 37.341 | 56.469 |
| ATOM | 5890 | CE2 | PHE | 1427 | 39.101 | 36.197 | 58.330 |
| ATOM | 5891 | CZ | PHE | 1427 | 39.006 | 37.056 | 57.220 |
| ATOM | 5892 | C | PHE | 1427 | 44.160 | 33.089 | 58.359 |
| ATOM | 5893 | O | PHE | 1427 | 44.777 | 32.573 | 57.426 |
| ATOM | 5894 | N | ASP | 1428 | 44.610 | 33.046 | 59.598 |
| ATOM | 5895 | CA | ASP | 1428 | 45.881 | 32.389 | 59.837 |
| ATOM | 5896 | CB | ASP | 1428 | 46.346 | 32.584 | 61.276 |
| ATOM | 5897 | CG | ASP | 1428 | 46.573 | 34.051 | 61.614 |
| ATOM | 5898 | OD1 | ASP | 1428 | 45.673 | 34.879 | 61.264 |
| ATOM | 5899 | OD2 | ASP | 1428 | 47.649 | 34.368 | 62.202 |
| ATOM | 5900 | C | ASP | 1428 | 45.783 | 30.918 | 59.512 |
| ATOM | 5901 | O | ASP | 1428 | 46.783 | 30.313 | 59.165 |
| ATOM | 5902 | N | SER | 1429 | 44.577 | 30.354 | 59.590 |

FIGURE 1TTTTT

| Atom | | | Residue AA | No. | X | Y | Z |
|---|---|---|---|---|---|---|---|
| ATOM | 5903 | CA | SER | 1429 | 44.398 | 28.935 | 59.281 |
| ATOM | 5904 | CB | SER | 1429 | 42.916 | 28.529 | 59.313 |
| ATOM | 5905 | OG | SER | 1429 | 42.423 | 28.446 | 60.640 |
| ATOM | 5906 | C | SER | 1429 | 45.014 | 28.634 | 57.919 |
| ATOM | 5907 | O | SER | 1429 | 45.747 | 27.650 | 57.759 |
| ATOM | 5908 | N | LEU | 1430 | 44.716 | 29.477 | 56.935 |
| ATOM | 5909 | CA | LEU | 1430 | 45.326 | 29.256 | 55.640 |
| ATOM | 5910 | CB | LEU | 1430 | 44.641 | 30.026 | 54.484 |
| ATOM | 5911 | CG | LEU | 1430 | 44.289 | 31.512 | 54.304 |
| ATOM | 5912 | CD1 | LEU | 1430 | 43.056 | 31.881 | 55.109 |
| ATOM | 5913 | CD2 | LEU | 1430 | 45.456 | 32.424 | 54.590 |
| ATOM | 5914 | C | LEU | 1430 | 46.817 | 29.586 | 55.758 |
| ATOM | 5915 | O | LEU | 1430 | 47.666 | 28.712 | 55.554 |
| ATOM | 5916 | N | ALA | 1431 | 47.114 | 30.785 | 56.252 |
| ATOM | 5917 | CA | ALA | 1431 | 48.487 | 31.245 | 56.403 |
| ATOM | 5918 | CB | ALA | 1431 | 48.527 | 32.487 | 57.312 |
| ATOM | 5919 | C | ALA | 1431 | 49.437 | 30.162 | 56.935 |
| ATOM | 5920 | O | ALA | 1431 | 50.385 | 29.753 | 56.230 |
| ATOM | 5921 | N | ASP | 1432 | 49.178 | 29.707 | 58.169 |
| ATOM | 5922 | CA | ASP | 1432 | 50.010 | 28.688 | 58.827 |
| ATOM | 5923 | CB | ASP | 1432 | 50.000 | 28.869 | 60.354 |
| ATOM | 5924 | CG | ASP | 1432 | 48.695 | 28.402 | 61.025 |
| ATOM | 5925 | OD1 | ASP | 1432 | 47.613 | 28.404 | 60.414 |
| ATOM | 5926 | OD2 | ASP | 1432 | 48.763 | 28.031 | 62.209 |
| ATOM | 5927 | C | ASP | 1432 | 49.615 | 27.277 | 58.448 |
| ATOM | 5928 | O | ASP | 1432 | 50.356 | 26.324 | 58.711 |
| ATOM | 5929 | N | ASN | 1433 | 48.432 | 27.159 | 57.847 |
| ATOM | 5930 | CA | ASN | 1433 | 47.915 | 25.868 | 57.408 |
| ATOM | 5931 | CB | ASN | 1433 | 48.870 | 25.250 | 56.361 |
| ATOM | 5932 | CG | ASN | 1433 | 48.140 | 24.794 | 55.065 |
| ATOM | 5933 | OD1 | ASN | 1433 | 48.596 | 23.855 | 54.398 |
| ATOM | 5934 | ND2 | ASN | 1433 | 47.025 | 25.465 | 54.706 |
| ATOM | 5935 | C | ASN | 1433 | 47.617 | 24.887 | 58.576 |
| ATOM | 5936 | O | ASN | 1433 | 47.848 | 23.655 | 58.488 |
| ATOM | 5937 | N | GLN | 1434 | 47.058 | 25.449 | 59.650 |
| ATOM | 5938 | CA | GLN | 1434 | 46.661 | 24.701 | 60.846 |
| ATOM | 5939 | CB | GLN | 1434 | 47.713 | 24.805 | 61.940 |
| ATOM | 5940 | CG | GLN | 1434 | 49.042 | 24.150 | 61.569 |
| ATOM | 5941 | CD | GLN | 1434 | 50.035 | 24.079 | 62.742 |
| ATOM | 5942 | OE1 | GLN | 1434 | 51.248 | 24.257 | 62.562 |
| ATOM | 5943 | NE2 | GLN | 1434 | 49.521 | 23.808 | 63.947 |
| ATOM | 5944 | C | GLN | 1434 | 45.356 | 25.311 | 61.318 |
| ATOM | 5945 | O | GLN | 1434 | 45.022 | 26.441 | 60.958 |
| ATOM | 5946 | N | VAL | 1435 | 44.614 | 24.585 | 62.130 |
| ATOM | 5947 | CA | VAL | 1435 | 43.335 | 25.105 | 62.586 |
| ATOM | 5948 | CB | VAL | 1435 | 42.202 | 24.471 | 61.784 |
| ATOM | 5949 | CG1 | VAL | 1435 | 42.142 | 25.102 | 60.383 |
| ATOM | 5950 | CG2 | VAL | 1435 | 42.451 | 22.961 | 61.666 |

FIGURE 1UUUUU

| | Atom | | Residue AA | No. | X | Y | Z |
|---|---|---|---|---|---|---|---|
| ATOM | 5951 | C | VAL | 1435 | 43.079 | 24.951 | 64.082 |
| ATOM | 5952 | O | VAL | 1435 | 43.751 | 24.175 | 64.768 |
| ATOM | 5953 | N | THR | 1436 | 42.109 | 25.700 | 64.590 |
| ATOM | 5954 | CA | THR | 1436 | 41.786 | 25.658 | 66.020 |
| ATOM | 5955 | CB | THR | 1436 | 41.288 | 27.046 | 66.503 |
| ATOM | 5956 | OG1 | THR | 1436 | 40.778 | 27.796 | 65.377 |
| ATOM | 5957 | CG2 | THR | 1436 | 42.426 | 27.808 | 67.176 |
| ATOM | 5958 | C | THR | 1436 | 40.728 | 24.594 | 66.355 |
| ATOM | 5959 | O | THR | 1436 | 39.567 | 24.698 | 65.905 |
| ATOM | 5960 | N | VAL | 1437 | 41.156 | 23.537 | 67.060 |
| ATOM | 5961 | CA | VAL | 1437 | 40.266 | 22.430 | 67.488 |
| ATOM | 5962 | CB | VAL | 1437 | 40.969 | 21.036 | 67.421 |
| ATOM | 5963 | CG1 | VAL | 1437 | 39.999 | 19.960 | 67.849 |
| ATOM | 5964 | CG2 | VAL | 1437 | 41.472 | 20.746 | 66.015 |
| ATOM | 5965 | C | VAL | 1437 | 39.831 | 22.651 | 68.945 |
| ATOM | 5966 | O | VAL | 1437 | 40.614 | 22.405 | 69.887 |
| ATOM | 5967 | N | ARG | 1438 | 38.610 | 23.149 | 69.128 |
| ATOM | 5968 | CA | ARG | 1438 | 38.097 | 23.403 | 70.461 |
| ATOM | 5969 | CB | ARG | 1438 | 37.193 | 24.634 | 70.442 |
| ATOM | 5970 | CG | ARG | 1438 | 35.732 | 24.390 | 70.786 |
| ATOM | 5971 | CD | ARG | 1438 | 35.185 | 25.635 | 71.436 |
| ATOM | 5972 | NE | ARG | 1438 | 33.768 | 25.522 | 71.741 |
| ATOM | 5973 | CZ | ARG | 1438 | 33.119 | 26.338 | 72.571 |
| ATOM | 5974 | NH1 | ARG | 1438 | 33.770 | 27.328 | 73.188 |
| ATOM | 5975 | NH2 | ARG | 1438 | 31.809 | 26.186 | 72.761 |
| ATOM | 5976 | C | ARG | 1438 | 37.346 | 22.177 | 70.942 |
| ATOM | 5977 | O | ARG | 1438 | 36.713 | 21.480 | 70.143 |
| ATOM | 5978 | N | ASP | 1439 | 37.470 | 21.876 | 72.226 |
| ATOM | 5979 | CA | ASP | 1439 | 36.780 | 20.731 | 72.800 |
| ATOM | 5980 | CB | ASP | 1439 | 37.560 | 20.211 | 74.014 |
| ATOM | 5981 | CG | ASP | 1439 | 36.836 | 19.056 | 74.747 |
| ATOM | 5982 | OD1 | ASP | 1439 | 35.690 | 19.241 | 75.226 |
| ATOM | 5983 | OD2 | ASP | 1439 | 37.427 | 17.953 | 74.870 |
| ATOM | 5984 | C | ASP | 1439 | 35.397 | 21.212 | 73.235 |
| ATOM | 5985 | O | ASP | 1439 | 35.250 | 22.388 | 73.546 |
| ATOM | 5986 | N | ARG | 1440 | 34.399 | 20.321 | 73.266 |
| ATOM | 5987 | CA | ARG | 1440 | 33.042 | 20.702 | 73.716 |
| ATOM | 5988 | CB | ARG | 1440 | 32.000 | 19.609 | 73.411 |
| ATOM | 5989 | CG | ARG | 1440 | 30.582 | 19.909 | 73.993 |
| ATOM | 5990 | CD | ARG | 1440 | 29.766 | 18.638 | 74.127 |
| ATOM | 5991 | NE | ARG | 1440 | 30.639 | 17.493 | 74.404 |
| ATOM | 5992 | CZ | ARG | 1440 | 30.356 | 16.230 | 74.099 |
| ATOM | 5993 | NH1 | ARG | 1440 | 29.208 | 15.915 | 73.522 |
| ATOM | 5994 | NH2 | ARG | 1440 | 31.270 | 15.294 | 74.281 |
| ATOM | 5995 | C | ARG | 1440 | 32.968 | 21.038 | 75.228 |
| ATOM | 5996 | O | ARG | 1440 | 32.914 | 22.215 | 75.627 |
| ATOM | 5997 | N | ASP | 1441 | 32.923 | 20.003 | 76.070 |
| ATOM | 5998 | CA | ASP | 1441 | 32.855 | 20.216 | 77.514 |

FIGURE 1VVVVV

| Atom | | | Residue AA | No. | X | Y | Z |
|---|---|---|---|---|---|---|---|
| ATOM | 5999 | CB | ASP | 1441 | 32.984 | 18.878 | 78.309 |
| ATOM | 6000 | CG | ASP | 1441 | 33.191 | 17.610 | 77.407 |
| ATOM | 6001 | OD1 | ASP | 1441 | 34.344 | 17.122 | 77.295 |
| ATOM | 6002 | OD2 | ASP | 1441 | 32.201 | 17.053 | 76.878 |
| ATOM | 6003 | C | ASP | 1441 | 33.963 | 21.218 | 77.897 |
| ATOM | 6004 | O | ASP | 1441 | 33.673 | 22.356 | 78.249 |
| ATOM | 6005 | N | SER | 1442 | 35.209 | 20.820 | 77.624 |
| ATOM | 6006 | CA | SER | 1442 | 36.428 | 21.586 | 77.914 |
| ATOM | 6007 | CB | SER | 1442 | 37.667 | 20.867 | 77.336 |
| ATOM | 6008 | OG | SER | 1442 | 38.679 | 21.765 | 76.889 |
| ATOM | 6009 | C | SER | 1442 | 36.478 | 23.055 | 77.526 |
| ATOM | 6010 | O | SER | 1442 | 37.151 | 23.846 | 78.190 |
| ATOM | 6011 | N | MET | 1443 | 35.878 | 23.407 | 76.400 |
| ATOM | 6012 | CA | MET | 1443 | 35.883 | 24.794 | 75.933 |
| ATOM | 6013 | CB | MET | 1443 | 35.266 | 25.698 | 76.984 |
| ATOM | 6014 | CG | MET | 1443 | 33.864 | 25.328 | 77.288 |
| ATOM | 6015 | SD | MET | 1443 | 32.966 | 26.822 | 77.067 |
| ATOM | 6016 | CE | MET | 1443 | 31.494 | 26.481 | 78.064 |
| ATOM | 6017 | C | MET | 1443 | 37.263 | 25.315 | 75.557 |
| ATOM | 6018 | O | MET | 1443 | 37.394 | 26.417 | 75.029 |
| ATOM | 6019 | N | GLU | 1444 | 38.296 | 24.542 | 75.855 |
| ATOM | 6020 | CA | GLU | 1444 | 39.627 | 24.964 | 75.508 |
| ATOM | 6021 | CB | GLU | 1444 | 40.653 | 24.343 | 76.443 |
| ATOM | 6022 | CG | GLU | 1444 | 41.547 | 25.408 | 77.066 |
| ATOM | 6023 | CD | GLU | 1444 | 40.772 | 26.689 | 77.535 |
| ATOM | 6024 | OE1 | GLU | 1444 | 40.006 | 26.635 | 78.552 |
| ATOM | 6025 | OE2 | GLU | 1444 | 40.952 | 27.763 | 76.887 |
| ATOM | 6026 | C | GLU | 1444 | 39.857 | 24.562 | 74.059 |
| ATOM | 6027 | O | GLU | 1444 | 39.189 | 23.640 | 73.551 |
| ATOM | 6028 | N | GLN | 1445 | 40.747 | 25.282 | 73.373 |
| ATOM | 6029 | CA | GLN | 1445 | 41.039 | 25.006 | 71.967 |
| ATOM | 6030 | CB | GLN | 1445 | 40.197 | 25.917 | 71.059 |
| ATOM | 6031 | CG | GLN | 1445 | 40.206 | 27.404 | 71.438 |
| ATOM | 6032 | CD | GLN | 1445 | 39.254 | 28.258 | 70.567 |
| ATOM | 6033 | OE1 | GLN | 1445 | 39.671 | 29.273 | 69.979 |
| ATOM | 6034 | NE2 | GLN | 1445 | 37.976 | 27.863 | 70.501 |
| ATOM | 6035 | C | GLN | 1445 | 42.515 | 25.112 | 71.584 |
| ATOM | 6036 | O | GLN | 1445 | 43.201 | 26.068 | 71.941 |
| ATOM | 6037 | N | VAL | 1446 | 42.970 | 24.148 | 70.793 |
| ATOM | 6038 | CA | VAL | 1446 | 44.345 | 24.100 | 70.320 |
| ATOM | 6039 | CB | VAL | 1446 | 44.995 | 22.759 | 70.717 |
| ATOM | 6040 | CG1 | VAL | 1446 | 44.000 | 21.605 | 70.393 |
| ATOM | 6041 | CG2 | VAL | 1446 | 46.371 | 22.550 | 69.986 |
| ATOM | 6042 | C | VAL | 1446 | 44.397 | 24.212 | 68.793 |
| ATOM | 6043 | O | VAL | 1446 | 43.495 | 23.770 | 68.086 |
| ATOM | 6044 | N | ARG | 1447 | 45.452 | 24.839 | 68.293 |
| ATOM | 6045 | CA | ARG | 1447 | 45.632 | 24.950 | 66.853 |
| ATOM | 6046 | CB | ARG | 1447 | 46.233 | 26.312 | 66.459 |

FIGURE 1WWWWWW

| Atom | | | Residue AA | No. | X | Y | Z |
|---|---|---|---|---|---|---|---|
| ATOM | 6047 | CG | ARG | 1447 | 46.396 | 26.467 | 64.943 |
| ATOM | 6048 | CD | ARG | 1447 | 46.868 | 27.862 | 64.506 |
| ATOM | 6049 | NE | ARG | 1447 | 45.827 | 28.900 | 64.592 |
| ATOM | 6050 | CZ | ARG | 1447 | 45.295 | 29.547 | 63.553 |
| ATOM | 6051 | NH1 | ARG | 1447 | 45.685 | 29.283 | 62.310 |
| ATOM | 6052 | NH2 | ARG | 1447 | 44.370 | 30.468 | 63.774 |
| ATOM | 6053 | C | ARG | 1447 | 46.544 | 23.776 | 66.406 |
| ATOM | 6054 | O | ARG | 1447 | 47.697 | 23.625 | 66.873 |
| ATOM | 6055 | N | MET | 1448 | 45.996 | 22.917 | 65.550 |
| ATOM | 6056 | CA | MET | 1448 | 46.728 | 21.767 | 65.047 |
| ATOM | 6057 | CB | MET | 1448 | 46.081 | 20.464 | 65.533 |
| ATOM | 6058 | CG | MET | 1448 | 44.606 | 20.288 | 65.180 |
| ATOM | 6059 | SD | MET | 1448 | 43.876 | 18.775 | 65.962 |
| ATOM | 6060 | CE | MET | 1448 | 45.192 | 17.493 | 65.463 |
| ATOM | 6061 | C | MET | 1448 | 46.897 | 21.753 | 63.534 |
| ATOM | 6062 | O | MET | 1448 | 46.162 | 22.427 | 62.794 |
| ATOM | 6063 | N | PRO | 1449 | 47.932 | 21.040 | 63.063 |
| ATOM | 6064 | CD | PRO | 1449 | 48.924 | 20.314 | 63.879 |
| ATOM | 6065 | CA | PRO | 1449 | 48.246 | 20.913 | 61.635 |
| ATOM | 6066 | CB | PRO | 1449 | 49.453 | 19.970 | 61.642 |
| ATOM | 6067 | CG | PRO | 1449 | 50.116 | 20.271 | 62.969 |
| ATOM | 6068 | C | PRO | 1449 | 47.056 | 20.289 | 60.915 |
| ATOM | 6069 | O | PRO | 1449 | 46.791 | 19.087 | 61.070 |
| ATOM | 6070 | N | ILE | 1450 | 46.376 | 21.098 | 60.106 |
| ATOM | 6071 | CA | ILE | 1450 | 45.180 | 20.659 | 59.387 |
| ATOM | 6072 | CB | ILE | 1450 | 44.895 | 21.550 | 58.148 |
| ATOM | 6073 | CG2 | ILE | 1450 | 43.635 | 21.048 | 57.449 |
| ATOM | 6074 | CG1 | ILE | 1450 | 44.688 | 23.023 | 58.585 |
| ATOM | 6075 | CD1 | ILE | 1450 | 44.264 | 24.020 | 57.471 |
| ATOM | 6076 | C | ILE | 1450 | 45.208 | 19.188 | 58.982 |
| ATOM | 6077 | O | ILE | 1450 | 44.194 | 18.487 | 59.035 |
| ATOM | 6078 | N | SER | 1451 | 46.401 | 18.728 | 58.638 |
| ATOM | 6079 | CA | SER | 1451 | 46.606 | 17.356 | 58.240 |
| ATOM | 6080 | CB | SER | 1451 | 48.103 | 17.139 | 57.965 |
| ATOM | 6081 | OG | SER | 1451 | 48.591 | 15.890 | 58.478 |
| ATOM | 6082 | C | SER | 1451 | 46.120 | 16.375 | 59.297 |
| ATOM | 6083 | O | SER | 1451 | 45.236 | 15.555 | 59.049 |
| ATOM | 6084 | N | GLU | 1452 | 46.694 | 16.503 | 60.485 |
| ATOM | 6085 | CA | GLU | 1452 | 46.405 | 15.612 | 61.597 |
| ATOM | 6086 | CB | GLU | 1452 | 47.295 | 16.000 | 62.787 |
| ATOM | 6087 | CG | GLU | 1452 | 48.782 | 16.047 | 62.390 |
| ATOM | 6088 | CD | GLU | 1452 | 49.771 | 16.039 | 63.583 |
| ATOM | 6089 | OE1 | GLU | 1452 | 49.709 | 16.984 | 64.446 |
| ATOM | 6090 | OE2 | GLU | 1452 | 50.628 | 15.092 | 63.617 |
| ATOM | 6091 | C | GLU | 1452 | 44.926 | 15.424 | 62.007 |
| ATOM | 6092 | O | GLU | 1452 | 44.570 | 14.427 | 62.662 |
| ATOM | 6093 | N | LEU | 1453 | 44.064 | 16.337 | 61.574 |
| ATOM | 6094 | CA | LEU | 1453 | 42.646 | 16.261 | 61.892 |

FIGURE 1XXXXX

| Atom | | | Residue AA | No. | X | Y | Z |
|---|---|---|---|---|---|---|---|
| ATOM | 6095 | CB | LEU | 1453 | 41.869 | 17.247 | 61.007 |
| ATOM | 6096 | CG | LEU | 1453 | 41.838 | 18.749 | 61.325 |
| ATOM | 6097 | CD1 | LEU | 1453 | 40.829 | 19.054 | 62.430 |
| ATOM | 6098 | CD2 | LEU | 1453 | 43.221 | 19.238 | 61.718 |
| ATOM | 6099 | C | LEU | 1453 | 42.101 | 14.828 | 62.430 |
| ATOM | 6101 | N | GLU | 1454 | 42.675 | 14.115 | 60.716 |
| ATOM | 6102 | CA | GLU | 1454 | 42.275 | 12.747 | 60.378 |
| ATOM | 6103 | CB | GLU | 1454 | 43.030 | 12.239 | 59.142 |
| ATOM | 6104 | CG | GLU | 1454 | 42.280 | 12.426 | 57.796 |
| ATOM | 6105 | CD | GLU | 1454 | 41.782 | 11.100 | 57.169 |
| ATOM | 6106 | OE1 | GLU | 1454 | 41.474 | 11.091 | 55.938 |
| ATOM | 6107 | OE2 | GLU | 1454 | 41.697 | 10.071 | 57.903 |
| ATOM | 6108 | C | GLU | 1454 | 42.544 | 11.832 | 61.524 |
| ATOM | 6109 | O | GLU | 1454 | 41.626 | 11.265 | 62.093 |
| ATOM | 6110 | N | ALA | 1455 | 43.815 | 11.731 | 61.880 |
| ATOM | 6111 | CA | ALA | 1455 | 44.249 | 10.875 | 62.985 |
| ATOM | 6112 | CB | ALA | 1455 | 45.751 | 11.000 | 63.181 |
| ATOM | 6113 | C | ALA | 1455 | 43.526 | 11.205 | 64.296 |
| ATOM | 6114 | O | ALA | 1455 | 43.064 | 10.305 | 65.017 |
| ATOM | 6115 | N | PHE | 1456 | 43.444 | 12.500 | 64.595 |
| ATOM | 6116 | CA | PHE | 1456 | 42.784 | 12.983 | 65.795 |
| ATOM | 6117 | CB | PHE | 1456 | 42.739 | 14.525 | 65.791 |
| ATOM | 6118 | CG | PHE | 1456 | 42.128 | 15.134 | 67.045 |
| ATOM | 6119 | CD1 | PHE | 1456 | 42.835 | 16.064 | 67.783 |
| ATOM | 6120 | CD2 | PHE | 1456 | 40.846 | 14.772 | 67.490 |
| ATOM | 6121 | CE1 | PHE | 1456 | 42.274 | 16.619 | 68.940 |
| ATOM | 6122 | CE2 | PHE | 1456 | 40.281 | 15.321 | 68.637 |
| ATOM | 6123 | CZ | PHE | 1456 | 40.986 | 16.238 | 69.362 |
| ATOM | 6124 | C | PHE | 1456 | 41.373 | 12.411 | 65.900 |
| ATOM | 6125 | O | PHE | 1456 | 41.124 | 11.549 | 66.735 |
| ATOM | 6126 | N | LEU | 1457 | 40.469 | 12.886 | 65.043 |
| ATOM | 6127 | CA | LEU | 1457 | 39.080 | 12.464 | 65.071 |
| ATOM | 6128 | CB | LEU | 1457 | 38.307 | 13.128 | 63.950 |
| ATOM | 6129 | CG | LEU | 1457 | 38.107 | 14.624 | 64.106 |
| ATOM | 6130 | CD1 | LEU | 1457 | 37.332 | 15.138 | 62.925 |
| ATOM | 6131 | CD2 | LEU | 1457 | 37.338 | 14.881 | 65.373 |
| ATOM | 6132 | C | LEU | 1457 | 38.856 | 10.968 | 65.031 |
| ATOM | 6133 | O | LEU | 1457 | 37.786 | 10.489 | 65.380 |
| ATOM | 6134 | N | THR | 1458 | 39.861 | 10.235 | 64.584 |
| ATOM | 6135 | CA | THR | 1458 | 39.774 | 8.786 | 64.509 |
| ATOM | 6136 | CB | THR | 1458 | 40.864 | 8.243 | 63.636 |
| ATOM | 6137 | OG1 | THR | 1458 | 40.777 | 8.863 | 62.352 |
| ATOM | 6138 | CG2 | THR | 1458 | 40.725 | 6.752 | 63.503 |
| ATOM | 6139 | C | THR | 1458 | 39.944 | 8.145 | 65.873 |
| ATOM | 6140 | O | THR | 1458 | 39.142 | 7.281 | 66.248 |
| ATOM | 6141 | N | ALA | 1459 | 41.013 | 8.541 | 66.580 |
| ATOM | 6142 | CA | ALA | 1459 | 41.347 | 8.030 | 67.920 |

FIGURE 1YYYYY

| Atom | | | Residue AA | No. | X | Y | Z |
|---|---|---|---|---|---|---|---|
| ATOM | 6143 | CB | ALA | 1459 | 42.732 | 8.524 | 68.347 |
| ATOM | 6144 | C | ALA | 1459 | 40.317 | 8.444 | 68.962 |
| ATOM | 6145 | O | ALA | 1459 | 39.791 | 7.600 | 69.699 |
| ATOM | 6146 | N | LYS | 1460 | 39.997 | 9.739 | 68.977 |
| ATOM | 6147 | CA | LYS | 1460 | 39.041 | 10.310 | 69.924 |
| ATOM | 6148 | CB | LYS | 1460 | 39.098 | 11.839 | 69.909 |
| ATOM | 6149 | CG | LYS | 1460 | 39.123 | 12.447 | 71.298 |
| ATOM | 6150 | CD | LYS | 1460 | 40.561 | 12.592 | 71.811 |
| ATOM | 6151 | CE | LYS | 1460 | 40.707 | 12.559 | 73.366 |
| ATOM | 6152 | NZ | LYS | 1460 | 40.124 | 13.711 | 74.175 |
| ATOM | 6153 | C | LYS | 1460 | 37.629 | 9.880 | 69.620 |
| ATOM | 6154 | O | LYS | 1460 | 36.677 | 10.618 | 69.895 |
| ATOM | 6155 | N | THR | 1461 | 37.501 | 8.655 | 69.123 |
| ATOM | 6156 | CA | THR | 1461 | 36.221 | 8.087 | 68.732 |
| ATOM | 6157 | CB | THR | 1461 | 36.066 | 8.102 | 67.210 |
| ATOM | 6158 | OG1 | THR | 1461 | 36.151 | 9.448 | 66.722 |
| ATOM | 6159 | CG2 | THR | 1461 | 34.738 | 7.501 | 66.836 |
| ATOM | 6160 | C | THR | 1461 | 36.076 | 6.641 | 69.136 |
| ATOM | 6161 | O | THR | 1461 | 35.024 | 6.245 | 69.628 |
| ATOM | 6162 | N | ALA | 1462 | 37.109 | 5.873 | 68.795 |
| ATOM | 6163 | CA | ALA | 1462 | 37.258 | 4.446 | 69.038 |
| ATOM | 6164 | CB | ALA | 1462 | 38.566 | 4.179 | 69.742 |
| ATOM | 6165 | C | ALA | 1462 | 36.119 | 3.661 | 69.699 |
| ATOM | 6166 | O | ALA | 1462 | 35.898 | 2.494 | 69.338 |
| ATOM | 6167 | N | PHE | 1463 | 35.436 | 4.259 | 70.682 |
| ATOM | 6168 | CA | PHE | 1463 | 34.306 | 3.623 | 71.373 |
| ATOM | 6169 | CB | PHE | 1463 | 33.286 | 3.090 | 70.373 |
| ATOM | 6170 | CG | PHE | 1463 | 32.034 | 2.638 | 71.003 |
| ATOM | 6171 | CD1 | PHE | 1463 | 31.195 | 3.565 | 71.623 |
| ATOM | 6172 | CD2 | PHE | 1463 | 31.696 | 1.288 | 71.016 |
| ATOM | 6173 | CE1 | PHE | 1463 | 30.012 | 3.167 | 72.271 |
| ATOM | 6174 | CE2 | PHE | 1463 | 30.536 | 0.855 | 71.646 |
| ATOM | 6175 | CZ | PHE | 1463 | 29.677 | 1.811 | 72.288 |
| ATOM | 6176 | C | PHE | 1463 | 34.778 | 2.506 | 72.289 |
| ATOM | 6177 | O | PHE | 1463 | 35.824 | 2.745 | 72.915 |
| ATOM | 6178 | OT | PHE | 1463 | 34.142 | 1.434 | 72.379 |

Human Glycyl tRNA Synthetase - Monomeric Unit

METHODS USING THE *STAPHYLOCOCCUS AUREUS* GLYCYL TRNA SYNTHETASE CRYSTALLINE STRUCTURE

This is a continuation of application Ser. No. 08/792,295 filed Jan. 31, 1997.

TECHNICAL FIELD OF THE INVENTION

The invention relates to the identification of a novel enzyme active site and methods enabling the design and selection of inhibitors of that active site.

1. Background of the Invention

Transfer RNA (tRNA) synthetase enzymes are of interest as potential targets for antibacterial agents. Mupirocin, a selective inhibitor of bacterial isoleucyl tRNA synthetase, is marketed for the treatment of skin infections and the eradication of nasal carriage of MRSA (methicillin-resistant *Staphylococcus aureus*) in hospital staff and patients.

Glycyl tRNA synthetase, a class I enzyme, is unusual in that its oligomeric structure varies depending on the organism from which it was isolated. Nucleic acid and amino acid sequences for glycyl tRNA synthetases are publicly available, including those of *Thermus thermophilus, Mycoplasma genitalium, Homo sapiens,* yeast, *Boinbyx mori* and *Caenorhabditis elegans,* which are all characterized by a2 dimers, and *Coxiella burnetti, Escherichia coli, Chlamydia trachomatous, Neisseria gonorrheae,* Synechocystis sp., and *Haemophilus influezae*, which are all characterized by being a2b2 tetramers.

There is a need in the art for novel tRNA synthetase enzyme active sites and catalytic sequences to enable identification and structure-based design of synthetase inhibitors, which are useful in the treatment or prophylaxis of diseases, particularly bacterial diseases caused by bacteria of the genus Staphylococcus, as well as other bacteria which may share catalytic domains with those of the genus Staphylococcus.

2. Summart of the Invention

In one aspect, the present invention provides a novel *Staphylococcis aureus* tRNA synthetase enzyme active site crystalline form.

In still another aspect, the present invention provides a novel tRNA synthetase composition characterized by a catalytic site of 16 amino acid residues.

In yet another aspect, the invention provides a method for identifying inhibitors of the compositions described above which methods involve the steps of: providing the coordinates of the tRNA synthetase structure of the invention to a computerized modeling system; identifying compounds which will bind to the structure; and screening the compounds identified for tRNA synthetase inhibitory bioactivity.

In a further aspect, the present invention provides an inhibitor of the catalytic activity of any composition bearing the catalytic domain described above.

Another aspect of this invention includes machine readable media encoded with data representing the coordinates of the three-dimensional structure of the tRNA synthetase crystal.

Other aspects and advantages of the present invention are described further in the following detailed description of the preferred embodiments thereof.

BRIEF DESCRIPTION OF THE DRAWINGS

FIGS. 1A through 1YYYYY provide the atomic coordinates of the *Staph aureus* glycyl tRNA synthetase. The occupancy factor is 1.0 and the B factor is 19.60 for each coordinate.

DETAILED DESCRIPTION OF THE INVENTION

Figure 2:
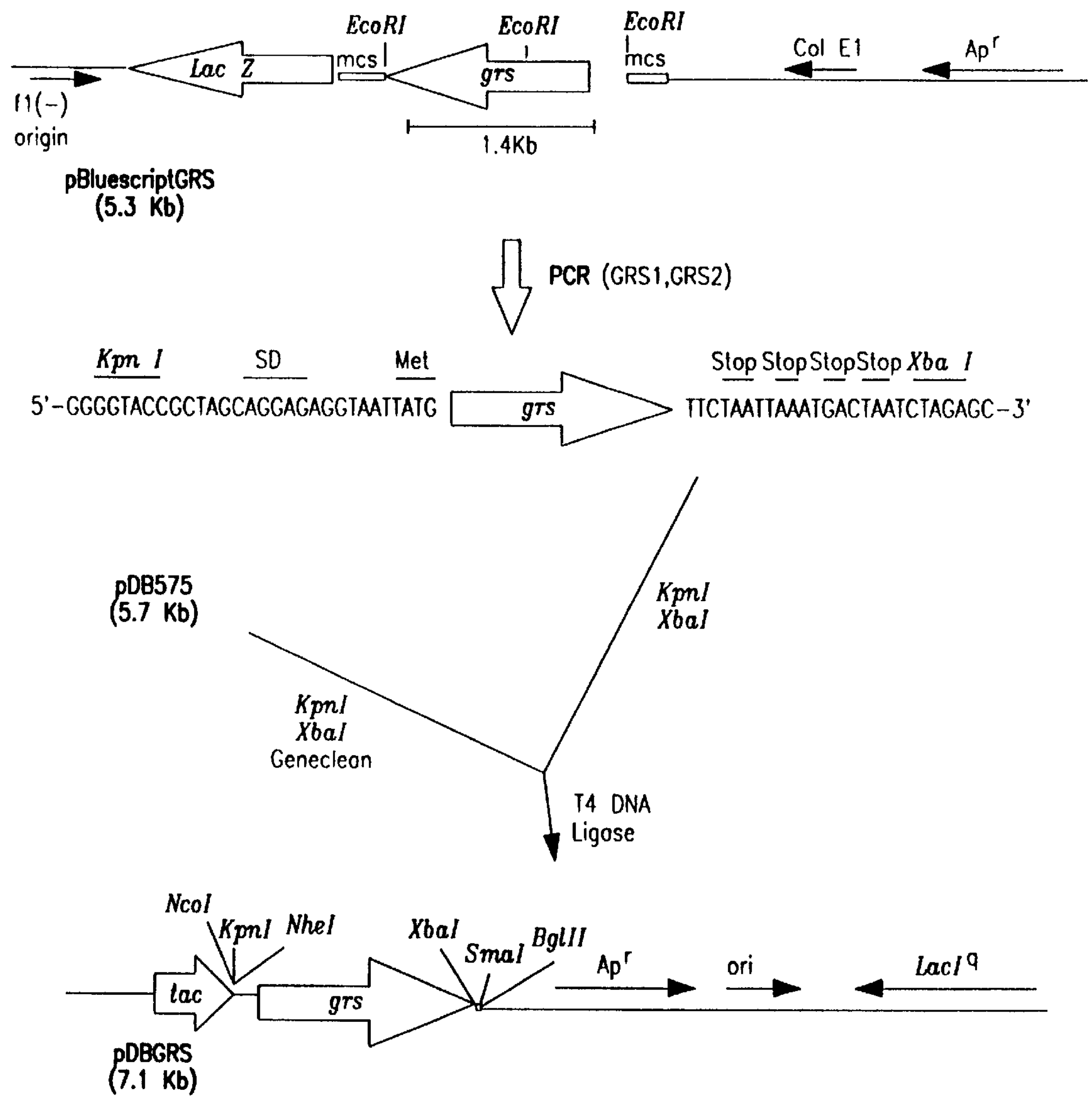
FIG. 2 illustrates the cloning of the grs gene in pDB575. Briefly, the grs gene was PCR amplified out of the pBluescript GRS vector using a GRS1 primer which provided the KpnI restriction site and the Shine-Dalgarno consensus sequence. The GRS2 primer contains the XbaI site and stop codons in the three possible reading frames.

The present invention provides a novel glycyl tRNA synthetase crystalline structure, a novel *Staph aureus* tRNA synthetase active site, and methods of use of the crystalline form and active site to identify synthetase inhibitor compounds (peptide, peptidomimetic or synthetic compositions) characterized by the ability to competitively inhibit binding to the active site of a glycyl tRNA synthetase. Also provided herein is a novel human glycyl tRNA synthetase crystalline structure. This structure can be used as described below for the Staph tRNA synthetase crystal structure.

I. The Novel Synthetase Crystalline Three-Dimensional Structure

The present invention provides a novel glycyl TRNA synthetase crystalline structure based on the *Staph aureus* tRNA synthetase. The amino acid sequences of the synthetase are provided in SEQ ID NO:1. As illustrated herein, the crystal structure is a tightly associated *S. aureus* GRS dimer. Each monomer has three structural domains: the N-terminal domain (residues 1–86 of SEQ ID NO:1), the active site domain (residues 150–340 of SEQ ID NO:1) and the C-terminal domain (residues 341–463 of SEQ ID NO:1). The N-terminal domain, having three a-helices and three b-strands, wraps around the active site domain with its second a-helix lying in the core of the dimer interface and its third b-strand adding to the central b-sheet of the active site domain to form the 7-stranded anti-parallel b sheet where the enzyme active site locates. The C-terminal domain contains mainly a 5-stranded mixed b-sheet with three flanking helices and is believed to be important to anticodon recognition. While the overall architecture of the *S. aureus* GRS is similar to that of the T thernophilus GRS, differences exit in the conformation of a number of surface loops, as well as the relative orientation of between the active site and C-terminal domains. With only 44% sequence identity, many amino acid side chains are also different, including several residues near the active site.

As described above, the *Staph aureus* synthetase is a dimer. The present invention provides both a crystalline monomer and dimer structure of *Staph aureus* synthetase. Inhibitors that perturb or interact with this dimer interface are another target for the design and selection of anti-bacterial agents.

According to the present invention, the crystal structure of *Staph aureus* tRNA synthetase has been resolved at 3.5 Å. The structure was determined using the method of molecular replacement, and refined to an R-factor of 23.4% with goal geometry.

For example, further refinement of the atomic coordinates will change the numbers in FIG. 1 and Tables I–III, refinement of the crystal structure from another crystal form will result in a new set of coordinates. However, distances and angles in FIG. 1 and Tables I–III will remain the same within experimental errors, and relative conformation of residues in the active site will remain the same within experimental error.

FIG. 1 provides the atomic coordinates of the *Staph aureus* glycyl tRNA synthetase dimer, which contains 790 amino acids; with 130 residues disordered in the crystal. The occupancy factor is 1.0 and the B factor is 19.60.

The tRNA synthetase is characterized by an active site which preferably contains a binding site for glycyl-adenylate and the receptor stem of tRNA (glycines). The crystal structure described herein was solved in the absence of glycine, ATP or tRNA. However, the region of the active site can be inferred from that of the homologous aspartyl tRNA synthetase. Particularly, the crystalline active site consists of 16 amino acid residues. These residues include Glu174, Arg206, Glu208, Phe216, Arg217, Thr218, Phe221, Gln223, Glu225, Asp279, Glu290, Leu291, Arg297, Glu330, Ser332 and Arg337 [SEQ ID NO:1]. The atomic coordinates of the active site residues are provided in Table I.

TABLE I

| NO. ATOM | X | Y | Z |
|---|---|---|---|
| 1 174N | 4.941000 | 3.175000 | 50.397999 |
| 2 174CA | 5.955000 | 4.038000 | 49.859001 |
| 3 174CB | 5.335000 | 4.880000 | 48.750000 |
| 4 174CG | 6.198000 | 6.021000 | 48.222000 |
| 5 174CD | 5.581000 | 6.686000 | 46.986000 |
| 6 174OE1 | 6.341000 | 7.002000 | 46.035999 |
| 7 174OE2 | 4.332000 | 6.862000 | 46.949001 |
| 8 174C | 6.562000 | 4.919000 | 50.930000 |
| 9 174O | 5.886000 | 5.710000 | 51.594002 |
| 10 206N | 3.716000 | −3.980000 | 50.544998 |
| 11 206CA | 2.750000 | −4.082000 | 49.455002 |
| 12 206CB | 3.479000 | −4.007000 | 48.122002 |
| 13 206CG | 3.246000 | −2.730000 | 47.368999 |
| 14 206CD | 4.122000 | −1.569000 | 47.855999 |
| 15 206NE | 5.071000 | −1.073000 | 46.834000 |
| 16 206CZ | 4.798000 | −0.830000 | 45.534000 |
| 17 206NH1 | 3.575000 | −1.030000 | 45.014999 |
| 18 206NH2 | 5.765000 | −0.360000 | 44.730999 |
| 19 206C | 1.978000 | −5.398000 | 49.502998 |
| 20 206O | 2.574000 | −6.489000 | 49.485001 |
| 21 208N | 0.743000 | −7.731000 | 47.730999 |
| 22 208CA | 0.888000 | −8.258000 | 46.355999 |
| 23 208CB | 2.298000 | −8.843000 | 46.164001 |
| 24 208CG | 2.966000 | −8.376000 | 44.889000 |
| 25 208CD | 2.847000 | −6.871000 | 44.637001 |
| 26 208OE1 | 3.887000 | −6.191000 | 44.762001 |
| 27 208OE2 | 1.741000 | −6.362000 | 44.299000 |
| 28 208C | −0.174000 | −9.223000 | 45.783001 |
| 29 208O | −1.329000 | −9.263000 | 46.256001 |

TABLE I-continued

| NO. ATOM | X | Y | Z |
|---|---|---|---|
| 30 216N | 13.129000 | −10.373000 | 44.237999 |
| 31 216CA | 12.590000 | −9.384000 | 43.311001 |
| 32 216CB | 12.766000 | −9.728000 | 41.810001 |
| 33 216CG | 12.693000 | −11.233000 | 41.452000 |
| 34 216CD1 | 11.571000 | −11.762000 | 40.764999 |
| 35 216CD2 | 13.816000 | −12.076000 | 41.622002 |
| 36 216CE1 | 11.579000 | −13.076000 | 40.243999 |
| 37 216CE2 | 13.827000 | −13.408000 | 41.095001 |
| 38 216CZ | 12.713000 | −13.890000 | 40.409000 |
| 39 216C | 11.174000 | −8.954000 | 43.654999 |
| 40 216O | 10.867000 | −7.753000 | 43.624001 |
| 41 217N | 10.311000 | −9.898000 | 44.009998 |
| 42 217CA | 8.961000 | −9.483000 | 44.380001 |
| 43 217CB | 7.932000 | −9.752000 | 43.272999 |
| 44 217CG | 7.030000 | −8.552000 | 42.960999 |
| 45 217CD | 5.864000 | −8.929000 | 42.049999 |
| 46 217NE | 4.737000 | −9.519000 | 42.785000 |
| 47 217CZ | 3.574000 | −9.900000 | 42.235001 |
| 48 217NH1 | 3.363000 | −9.770000 | 40.926998 |
| 49 217NH2 | 2.591000 | −10.372000 | 42.997002 |
| 50 217C | 8.523000 | −10.098000 | 45.709999 |
| 51 217O | 7.943000 | −11.195000 | 45.757999 |
| 52 218N | 8.772000 | −9.337000 | 46.778000 |
| 53 218CA | 8.472000 | −9.725000 | 48.148998 |
| 54 218CB | 9.711000 | −9.500000 | 49.070999 |
| 55 218OG1 | 10.388000 | −8.300000 | 48.671001 |
| 56 218CG2 | 10.689000 | −10.687000 | 49.019001 |
| 57 218C | 7.346000 | −8.848000 | 48.647999 |
| 58 218O | 7.290000 | −7.657000 | 48.326000 |
| 59 221N | 9.504000 | −5.218000 | 51.894001 |
| 60 221CA | 10.836000 | −4.815000 | 51.400002 |
| 61 221CB | 10.783000 | −4.649000 | 49.875000 |
| 62 221CG | 9.708000 | −3.696000 | 49.418999 |
| 63 221CD1 | 9.956000 | −2.330000 | 49.346001 |
| 64 221CD2 | 8.407000 | −4.164000 | 49.141998 |
| 65 221CE1 | 8.926000 | −1.445000 | 49.012001 |
| 66 221CE2 | 7.360000 | −3.282000 | 48.805000 |
| 67 221CZ | 7.619000 | −1.928000 | 48.743000 |
| 68 221C | 11.326000 | −3.494000 | 51.951000 |
| 69 221O | 10.551000 | −2.673000 | 52.439999 |
| 70 223N | 13.206000 | 0.141000 | 50.983002 |
| 71 223CA | 13.480000 | 1.112000 | 49.938000 |
| 72 223CB | 12.461000 | 2.215000 | 50.000000 |
| 73 223CG | 11.053000 | 1.686000 | 50.096001 |
| 74 223CD | 10.275000 | 1.809000 | 48.803001 |
| 75 223OE1 | 10.824000 | 1.639000 | 47.716000 |
| 76 223NE2 | 8.980000 | 2.098000 | 48.918999 |
| 77 223C | 14.863000 | 1.698000 | 50.092999 |
| 78 223O | 15.811000 | 0.967000 | 50.327999 |
| 79 225N | 15.128000 | 5.689000 | 49.512001 |
| 80 225CA | 14.827000 | 6.937000 | 48.806000 |
| 81 225CB | 13.335000 | 7.143000 | 48.845001 |
| 82 225CG | 12.636000 | 5.820000 | 48.712002 |
| 83 225CD | 11.176000 | 5.961000 | 48.533001 |
| 84 225OE1 | 10.626000 | 6.903000 | 49.126999 |
| 85 225OE2 | 10.582000 | 5.139000 | 47.798000 |
| 86 225C | 15.517000 | 8.213O00 | 49.247002 |
| 87 225O | 16.087000 | 8.285000 | 50.326000 |
| 88 279N | 14.349000 | 4.904000 | 34.318001 |
| 89 279CA | 14.639000 | 3.772000 | 35.201000 |
| 90 279CB | 13.700000 | 2.601000 | 34.933998 |
| 91 279CG | 12.310000 | 2.839000 | 35.416000 |
| 92 279OD1 | 12.056000 | 3.903000 | 36.011002 |
| 93 279OD2 | 11.468000 | 1.941000 | 35.206001 |
| 94 279C | 16.046000 | 3.310000 | 34.823002 |
| 95 279O | 16.563000 | 3.722000 | 33.782001 |
| 96 290N | 14.061000 | −3.246000 | 36.935001 |
| 97 290CA | 14.561000 | −1.978000 | 37.402000 |
| 98 290CB | 13.425000 | −0.977000 | 37.536999 |
| 99 290CG | 12.391000 | −1.284000 | 38.611000 |
| 100 290CD | 11.205000 | −0.284000 | 38.606998 |
| 101 290OE1 | 10.212000 | −0.542000 | 37.867001 |
| 102 290OE2 | 11.260000 | 0.749000 | 39.338001 |
| 103 290C | 15.324000 | −2.075000 | 38.700001 |
| 104 290O | 15.162000 | −3.026000 | 39.450001 |
| 105 291N | 16.257999 | −1.155000 | 38.882000 |
| 106 291CA | 17.030001 | −1.073000 | 40.099998 |

TABLE I-continued

| NO. ATOM | X | Y | Z |
|---|---|---|---|
| 107 291CB | 18.528000 | −0.882000 | 39.824001 |
| 108 291CG | 19.368999 | −2.096000 | 39.455002 |
| 109 291CD1 | 20.739000 | −1.973000 | 40.076000 |
| 110 291CD2 | 18.683001 | −3.342000 | 39.924999 |
| 111 291C | 16.466000 | 0.189000 | 40.699001 |
| 112 291O | 15.445000 | 0.171000 | 41.387001 |
| 113 297N | 9.206000 | 14.779000 | 39.366001 |
| 114 297CA | 7.788O00 | 14.867000 | 39.709000 |
| 115 297CB | 7.520000 | 14.064000 | 40.992001 |
| 116 297CG | 8.285O00 | 12.757000 | 41.123001 |
| 117 297CD | 8.166000 | 12.209000 | 42.539001 |
| 118 297NE | 6.771000 | 12.005000 | 42.935001 |
| 119 297CZ | 6.197000 | 10.821000 | 43.125999 |
| 120 297NH1 | 6.901000 | 9.720000 | 42.958000 |
| 121 297NH2 | 4.913000 | 10.735000 | 43.479000 |
| 122 297C | 7.342000 | 16.333000 | 39.926998 |
| 123 297O | 6.193000 | 16.584999 | 40.372002 |
| 124 330N | 12.945000 | 12.193000 | 42.535999 |
| 125 330CA | 13.135000 | 11.123000 | 43.480999 |
| 126 330CB | 11.811000 | 10.733000 | 44.127998 |
| 127 330CG | 10.940000 | 9.803000 | 43.354000 |
| 128 330CD | 9.806000 | 9.249000 | 44.179001 |
| 129 330OE1 | 9.784000 | 8.026000 | 44.432999 |
| 130 330OE2 | 8.930000 | 10.041000 | 44.563000 |
| 131 330C | 13.907000 | 9.910000 | 43.026001 |
| 132 330O | 13.355000 | 9.017000 | 42.432999 |
| 133 332N | 14.529000 | 6.954O00 | 43.724998 |
| 134 332CA | 14.141000 | 5.801000 | 44.557999 |
| 135 332CB | 12.663000 | 5.457000 | 44.334999 |
| 136 332OG | 12.375000 | 4.105000 | 44.611000 |
| 137 332C | 15.000000 | 4.581000 | 44.297001 |
| 138 332O | 15.668000 | 4.512000 | 43.289001 |
| 139 337N | 16.296000 | −5.378000 | 46.342999 |
| 140 337CA | 16.743999 | −5.561000 | 44.936001 |
| 141 337CB | 15.916000 | −4.737000 | 43.957001 |
| 142 337CG | 14.513000 | −5.233000 | 43.710999 |
| 143 337CD | 14.111000 | −5.006000 | 42.230000 |
| 144 337NE | 12.699000 | −4.631000 | 42.080002 |
| 145 337CZ | 12.236000 | −3.377000 | 42.169998 |
| 146 337NH1 | 13.073000 | −2.349000 | 42.389000 |
| 147 337NH2 | 10.919000 | −3.156000 | 42.146999 |
| 148 337C | 18.207001 | −5.259000 | 44.654999 |
| 149 337O | 18.920000 | −6.130000 | 44.188000 |

TABLE II

| Atom 1 | Atom 2 | Distance Between |
|---|---|---|
| 174N | 174CA | D = 1.436 |
| 174N | 174CB | D = 2.404 |
| 174N | 174C | D = 2.440 |
| 174N | 174O | D = 2.958 |
| 174N | 174CG | D = 3.797 |
| 174N | 223NE2 | D = 4.434 |
| 174N | 174CD | D = 4.937 |
| 174CA | 174N | D = 1.436 |
| 174CA | 174C | D = 1.514 |
| 174CA | 174CB | D = 1.524 |
| 174CA | 174O | D = 2.411 |
| 174CA | 174CG | D = 2.583 |
| 174CA | 223NE2 | D = 3.715 |
| 174CA | 174CD | D = 3.925 |
| 174CA | 174OE2 | D = 4.368 |
| 174CA | 174OE1 | D = 4.853 |
| 174CA | 223CD | D = 4.975 |
| 174CB | 174CA | D = 1.524 |
| 174CB | 174CG | D = 1.525 |
| 174CB | 174N | D = 2.404 |
| 174CB | 174C | D = 2.502 |
| 174CB | 174CD | D = 2.537 |
| 174CB | 174OE2 | D = 2.860 |
| 174CB | 174O | D = 3.013 |
| 174CB | 174OE1 | D = 3.589 |

TABLE II-continued

| Atom 1 | Atom 2 | Distance Between |
|---|---|---|
| 174CB | 223NE2 | D = 4.588 |
| 174CG | 174CB | D = 1.525 |
| 174CG | 174CD | D = 1.533 |
| 174CG | 174OE1 | D = 2.400 |
| 174CG | 174OE2 | D = 2.410 |
| 174CG | 174CA | D = 2.583 |
| 174CG | 174C | D = 2.946 |
| 174CG | 174O | D = 3.401 |
| 174CG | 174N | D = 3.797 |
| 174CG | 225OE2 | D = 4.492 |
| 174CG | 225OE1 | D = 4.605 |
| 174CG | 223NE2 | D = 4.860 |
| 174CG | 225CD | D = 4.988 |
| 174CD | 174OE1 | D = 1.257 |
| 174CD | 174OE2 | D = 1.262 |
| 174CD | 174CG | D = 1.533 |
| 174CD | 174CB | D = 2.537 |
| 174CD | 174CA | D = 3.925 |
| 174CD | 174C | D = 4.432 |
| 174CD | 174O | D = 4.720 |
| 174CD | 174N | D = 4.937 |
| 174OE1 | 174CD | D = 1.257 |
| 174OE1 | 174OE2 | D = 2.211 |
| 174OE1 | 174CG | D = 2.400 |
| 174OE1 | 174CB | D = 3.589 |
| 174OE1 | 330OE1 | D = 3.934 |
| 174OE1 | 297NH1 | D = 4.144 |
| 174OE1 | 330OE2 | D = 4.255 |
| 174OE1 | 330CD | D = 4.528 |
| 174OE1 | 297NH2 | D = 4.745 |
| 174OE1 | 297CZ | D = 4.803 |
| 174OE1 | 174CA | D = 4.853 |
| 174OE1 | 225OE2 | D = 4.956 |
| 174OE2 | 174CD | D = 1.262 |
| 174OE2 | 174OE1 | D = 2.211 |
| 174OE2 | 174CG | D = 2.410 |
| 174OE2 | 174CB | D = 2.860 |
| 174OE2 | 174CA | D = 4.368 |
| 174OE2 | 174C | D = 4.959 |
| 174C | 174O | D = 1.234 |
| 174C | 174CA | D = 1.514 |
| 174C | 174N | D = 2.440 |
| 174C | 174CB | D = 2.502 |
| 174C | 174CG | D = 2.946 |
| 174C | 223NE2 | D = 4.225 |
| 174C | 174CD | D = 4.432 |
| 174C | 225OE1 | D = 4.869 |
| 174C | 174OE2 | D = 4.959 |
| 174O | 174C | D = 1.234 |
| 174O | 174CA | D = 2.411 |
| 174O | 174N | D = 2.958 |
| 174O | 174CB | D = 3.013 |
| 174O | 174CG | D = 3.401 |
| 174O | 174CD | D = 4.720 |
| 206N | 206CA | D = 1.460 |
| 206N | 206CB | D = 2.435 |
| 206N | 206C | D = 2.473 |
| 206N | 206O | D = 2.953 |
| 206N | 206CG | D = 3.445 |
| 206N | 206CD | D = 3.634 |
| 206N | 221CE2 | D = 4.098 |
| 206N | 221CZ | D = 4.764 |
| 206N | 221CD2 | D = 4.900 |
| 206N | 206NE | D = 4.905 |
| 206CA | 206N | D = 1.460 |
| 206CA | 206CB | D = 1.521 |
| 206CA | 206C | D = 1.526 |
| 206CA | 206O | D = 2.414 |
| 206CA | 206CG | D = 2.535 |
| 206CA | 206CD | D = 3.279 |
| 206CA | 208N | D = 4.507 |
| 206CA | 206NE | D = 4.616 |
| 206CA | 221CE2 | D = 4.724 |
| 206CB | 206CG | D = 1.501 |
| 206CB | 206CA | D = 1.521 |
| 206CB | 206N | D = 2.435 |

TABLE II-continued

| Atom 1 | Atom 2 | Distance Between |
|---|---|---|
| 206CB | 206C | D = 2.469 |
| 206CB | 206CD | D = 2.535 |
| 206CB | 206O | D = 2.973 |
| 206CB | 206NE | D = 3.578 |
| 206CB | 221CE2 | D = 4.007 |
| 206CB | 208OE1 | D = 4.028 |
| 206CB | 206NH1 | D = 4.304 |
| 206CB | 206CZ | D = 4.305 |
| 206CB | 208CD | D = 4.555 |
| 206CB | 208N | D = 4.638 |
| 206CB | 221CZ | D = 4.674 |
| 206CB | 208OE2 | D = 4.815 |
| 206CG | 206CB | D = 1.501 |
| 206CG | 206CD | D = 1.534 |
| 206CG | 206NE | D = 2.522 |
| 206CG | 206CA | D = 2.535 |
| 206CG | 206NH1 | D = 2.922 |
| 206CG | 206CZ | D = 3.064 |
| 206CG | 206N | D = 3.445 |
| 206CG | 206C | D = 3.644 |
| 206CG | 206NH2 | D = 4.350 |
| 206CG | 206O | D = 4.366 |
| 206CG | 208OE1 | D = 4.380 |
| 206CG | 221CE2 | D = 4.392 |
| 206CG | 221CZ | D = 4.653 |
| 206CG | 208CD | D = 4.977 |
| 206CG | 208OE2 | D = 4.988 |
| 206CD | 206NE | D = 1.480 |
| 206CD | 206CG | D = 1.534 |
| 206CD | 206CZ | D = 2.529 |
| 206CD | 206CB | D = 2.535 |
| 206CD | 206NH1 | D = 2.943 |
| 206CD | 206CA | D = 3.279 |
| 206CD | 221CZ | D = 3.626 |
| 206CD | 206N | D = 3.634 |
| 206CD | 206NH2 | D = 3.732 |
| 206CD | 221CE2 | D = 3.784 |
| 206CD | 206C | D = 4.687 |
| 206CD | 221CE1 | D = 4.943 |
| 206NE | 206CZ | D = 1.350 |
| 206NE | 206CD | D = 1.480 |
| 206NE | 206NH2 | D = 2.327 |
| 206NE | 206NH1 | D = 2.356 |
| 206NE | 206CG | D = 2.522 |
| 206NE | 221CZ | D = 3.297 |
| 206NE | 206CB | D = 3.578 |
| 206NE | 221CE2 | D = 3.742 |
| 206NE | 221CE1 | D = 4.443 |
| 206NE | 206CA | D = 4.616 |
| 206NE | 206N | D = 4.905 |
| 206CZ | 206NH2 | D = 1.342 |
| 206CZ | 206NH1 | D = 1.344 |
| 206CZ | 206NE | D = 1.350 |
| 206CZ | 206CD | D = 2.529 |
| 206CZ | 206CG | D = 3.064 |
| 206CZ | 206CB | D = 4.305 |
| 206CZ | 221CZ | D = 4.411 |
| 206CZ | 221CE2 | D = 4.824 |
| 206NH1 | 206CZ | D = 1.344 |
| 206NH1 | 206NH2 | D = 2.308 |
| 206NH1 | 206NE | D = 2.356 |
| 206NH1 | 206CG | D = 2.922 |
| 206NH1 | 206CD | D = 2.943 |
| 206NH1 | 206CB | D = 4.304 |
| 206NH2 | 206CZ | D = 1.342 |
| 206NH2 | 206NH1 | D = 2.308 |
| 206NH2 | 206NE | D = 2.327 |
| 206NH2 | 206CD | D = 3.732 |
| 206NH2 | 206CG | D = 4.350 |
| 206NH2 | 221CZ | D = 4.690 |
| 206C | 206O | D = 1.243 |
| 206C | 206CA | D = 1.526 |
| 206C | 206CB | D = 2.469 |
| 206C | 206N | D = 2.473 |
| 206C | 208N | D = 3.179 |
| 206C | 206CG | D = 3.644 |

TABLE II-continued

| Atom 1 | Atom 2 | Distance Between |
|---|---|---|
| 206C | 208CA | D = 4.390 |
| 206C | 206CD | D = 4.687 |
| 206C | 208CB | D = 4.808 |
| 206O | 206C | D = 1.243 |
| 206O | 206CA | D = 2.414 |
| 206O | 208N | D = 2.823 |
| 206O | 206N | D = 2.953 |
| 206O | 206CB | D = 2.973 |
| 206O | 208CA | D = 3.970 |
| 206O | 208CB | D = 4.080 |
| 206O | 206CG | D = 4.366 |
| 206O | 208CD | D = 4.871 |
| 206O | 208OE1 | D = 4.911 |
| 206O | 208CG | D = 4.984 |
| 206O | 218O | D = 4.995 |
| 208N | 208CA | D = 1.480 |
| 208N | 208CB | D = 2.472 |
| 208N | 208C | D = 2.619 |
| 208N | 206O | D = 2.823 |
| 208N | 208O | D = 2.969 |
| 208N | 206C | D = 3.179 |
| 208N | 208CG | D = 3.665 |
| 208N | 208OE2 | D = 3.827 |
| 208N | 208CD | D = 3.839 |
| 208N | 206CA | D = 4.507 |
| 208N | 208OE1 | D = 4.590 |
| 208N | 206CB | D = 4.638 |
| 208CA | 208N | D = 1.480 |
| 208CA | 208CB | D = 1.539 |
| 208CA | 208C | D = 1.545 |
| 208CA | 208O | D = 2.436 |
| 208CA | 208CG | D = 2.546 |
| 208CA | 208OE2 | D = 2.925 |
| 208CA | 208CD | D = 2.952 |
| 208CA | 206O | D = 3.970 |
| 208CA | 208OE1 | D = 3.976 |
| 208CA | 217NH2 | D = 4.319 |
| 208CA | 206C | D = 4.390 |
| 208CB | 208CG | D = 1.513 |
| 208CB | 208CA | D = 1.539 |
| 208CB | 208N | D = 2.472 |
| 208CB | 208C | D = 2.530 |
| 208CB | 208CD | D = 2.554 |
| 208CB | 208OE2 | D = 3.153 |
| 208CB | 208OE1 | D = 3.395 |

TABLE III

| Atom 1 | Middle Atom | Atom 3 | Angle ° |
|---|---|---|---|
| 174N | 174CA | 223NE2 | A = 110.86 |
| 174C | 174CA | 223NE2 | A = 99.00 |
| 174CB | 174CA | 223NE2 | A = 115.83 |
| 174O | 174CA | 223NE2 | A = 124.59 |
| 174CG | 174CA | 223NE2 | A = 99.44 |
| 223NE2 | 174CA | 174CD | A = 104.16 |
| 174CD | 174OE1 | 330OE1 | A = 154.51 |
| 174OE2 | 174OE1 | 330OE1 | A = 168.53 |
| 174CG | 174OE1 | 330OE1 | A = 121.98 |
| 174CB | 174OE1 | 330OE1 | A = 135.03 |
| 206NE | 206CD | 221CZ | A = 65.40 |
| 206NE | 206CD | 221CE2 | A = 77.07 |
| 206CG | 206CD | 221CZ | A = 123.62 |
| 206CG | 206CD | 221CE2 | A = 103.04 |
| 206CZ | 206CD | 221CZ | A = 89.76 |
| 206CZ | 206CD | 221CE2 | A = 97.69 |
| 206CB | 206CD | 221CZ | A = 97.11 |
| 206CB | 206CD | 221CE2 | A = 75.84 |
| 206NH1 | 206CD | 221CZ | A = 115.70 |
| 206NH1 | 206CD | 221CE2 | A = 118.95 |
| 206CA | 206CD | 221CZ | A = 102.03 |

TABLE III-continued

| | Middle | | |
|---|---|---|---|
| Atom 1 | Atom | Atom 3 | Angle ° |
| 206CA | 206CD | 221CE2 | A = 83.62 |
| 221CZ | 206CD | 206N | A = 82.01 |
| 221CZ | 206CD | 206NH2 | A = 79.18 |
| 221CZ | 206CD | 221CE2 | A = 21.33 |
| 206N | 206CD | 221CE2 | A = 67.03 |
| 206NH2 | 206CD | 221CE2 | A = 88.85 |
| 206CZ | 206NE | 221CZ | A = 139.50 |
| 206CZ | 206NE | 221CE2 | A = 137.47 |
| 206CD | 206NE | 221CZ | A = 90.50 |
| 206CD | 206NE | 221CE2 | A = 80.25 |
| 206NH2 | 206NE | 221CZ | A = 111.86 |
| 206NH2 | 206NE | 221CE2 | A = 118.33 |
| 206NH1 | 206NE | 221CZ | A = 160.52 |
| 206NH1 | 206NE | 221CE2 | A = 143.70 |
| 206CG | 206NE | 221CZ | A = 105.43 |
| 206CG | 206NE | 221CE2 | A = 86.74 |
| 221CZ | 206NE | 206CB | A = 85.57 |
| 221CZ | 206NE | 221CE2 | A = 21.43 |
| 206CB | 206NE | 221CE2 | A = 66.33 |
| 206O | 206C | 208N | A = 62.24 |
| 206CB | 206C | 208N | A = 109.75 |
| 206N | 206C | 208N | A = 158.20 |
| 208N | 206C | 206CG | A = 110.24 |
| 206C | 206O | 208N | A = 94.83 |
| 206C | 206O | 208CA | A = 101.47 |
| 206CA | 206O | 208N | A = 118.57 |
| 206CA | 206O | 208CA | A = 117.74 |
| 208N | 206O | 206N | A = 147.93 |
| 208N | 206O | 206C | A = 106.25 |
| 208N | 206O | 208CA | A = 16.05 |
| 206N | 206O | 208CA | A = 145.65 |
| 206CB | 206O | 208CA | A = 98.04 |
| 208CG | 208CB | 217NH2 | A = 48.77 |
| 208CA | 208CB | 217NH2 | A = 110.66 |
| 208N | 208CB | 217NH2 | A = 144.69 |
| 208C | 208CB | 217NH2 | A = 83.16 |
| 208CD | 208CB | 217NH2 | A = 77.30 |
| 208OE2 | 208CB | 217NH2 | A = 79.91 |
| 208OE1 | 208CB | 217NH2 | A = 85.93 |
| 208CB | 208CG | 217NH2 | A = 107.02 |
| 208CB | 208CG | 217NE | A = 137.67 |
| 208CB | 208CG | 217CZ | A = 130.69 |
| 208CD | 208CG | 217NH2 | A = 125.76 |
| 208CD | 208CG | 217NE | A = 107.90 |
| 208CD | 208CG | 217CZ | A = 110.82 |
| 208OE1 | 208CG | 217NH2 | A = 132.66 |
| 208OE1 | 208CG | 217NE | A = 94.86 |
| 208OE1 | 208CG | 217CZ | A = 109.17 |
| 208OE2 | 208CG | 217NH2 | A = 111.25 |
| 208OE2 | 208CG | 217NE | A = 116.51 |
| 208OE2 | 208CG | 217CZ | A = 107.25 |
| 208CA | 208CG | 217NH2 | A = 108.41 |
| 208CA | 208CG | 217NE | A = 155.51 |
| 208CA | 208CG | 217CZ | A = 132.20 |
| 217NH2 | 208CG | 217NE | A = 47.37 |
| 217NH2 | 208CG | 217CZ | A = 25.22 |
| 217NH2 | 208CG | 208C | A = 82.78 |
| 217NH2 | 208CG | 208N | A = 124.97 |
| 217NE | 208CG | 217CZ | A = 25.28 |
| 217NE | 208CG | 208C | A = 130.13 |
| 217NE | 208CG | 208N | A = 167.41 |
| 217CZ | 208CG | 208C | A = 106.51 |
| 217CZ | 208CG | 208N | A = 149.73 |
| 208OE1 | 2O8CD | 217NE | A = 90.82 |
| 208OE1 | 208CD | 217NH2 | A = 126.11 |
| 208OE1 | 208CD | 217CZ | A = 109.06 |
| 208OE2 | 208CD | 217NE | A = 126.48 |
| 208OE2 | 208CD | 217NH2 | A = 101.12 |
| 208OE2 | 208CD | 217CZ | A = 107.98 |
| 208CG | 208CD | 217NE | A = 49.21 |
| 208CG | 208CD | 217NH2 | A = 35.55 |
| 208CG | 208CD | 217CZ | A = 47.86 |
| 208CB | 208CD | 217NE | A = 81.84 |
| 208CB | 208CD | 217NH2 | A = 62.69 |
| 208CB | 208CD | 217CZ | A = 79.06 |

TABLE III-continued

| | Middle | | |
|---|---|---|---|
| Atom 1 | Atom | Atom 3 | Angle ° |
| 208CA | 208CD | 217NE | A = 106.90 |
| 208CA | 208CD | 217NH2 | A = 77.18 |
| 208CA | 208CD | 217CZ | A = 96.69 |
| 217NE | 208CD | 208N | A = 121.13 |
| 217NE | 208CD | 217NH2 | A = 35.39 |
| 217NE | 208CD | 217CZ | A = 19.93 |
| 217NE | 208CD | 208C | A = 96.15 |
| 208N | 208CD | 217NH2 | A = 95.88 |
| 208N | 208CD | 217CZ | A = 114.89 |
| 217NH2 | 208CD | 217CZ | A = 19.60 |
| 217NH2 | 208CD | 208C | A = 62.59 |
| 217CZ | 208CD | 208C | A = 82.05 |
| 208CD | 208OE1 | 217NE | A = 70.82 |
| 208OE2 | 208OE1 | 217NE | A = 92.23 |
| 208CG | 208OE1 | 217NE | A = 48.48 |
| 208CB | 208OE1 | 217NE | A = 69.54 |
| 216CA | 216N | 217N | A = 58.26 |
| 216C | 216N | 217N | A = 27.55 |
| 216CB | 216N | 217N | A = 75.00 |
| 217N | 216N | 216CG | A = 80.08 |
| 217N | 216N | 216CD2 | A = 103.56 |
| 217N | 216N | 216O | A = 39.66 |
| 216N | 216CA | 217N | A = 91.16 |
| 216N | 216CA | 217CA | A = 99.04 |
| 216C | 216CA | 217N | A = 28.81 |
| 216C | 216CA | 217CA | A = 18.15 |
| 216CB | 216CA | 217N | A = 109.69 |
| 216CB | 216CA | 217CA | A = 112.13 |
| 216O | 216CA | 217N | A = 55.48 |
| 216O | 216CA | 217CA | A = 44.80 |
| 217N | 216CA | 216CG | A = 95.23 |
| 217N | 216CA | 216CD2 | A = 108.18 |
| 217N | 216CA | 216CD1 | A = 78.50 |
| 217N | 216CA | 217CA | A = 10.69 |
| 216CG | 216CA | 217CA | A = 102.67 |
| 216CD2 | 216CA | 217CA | A = 117.68 |
| 216CD1 | 216CA | 217CA | A = 84.94 |
| 216CG | 216CB | 217N | A = 93.95 |
| 216CA | 216CB | 217N | A = 44.07 |
| 216N | 216CB | 217N | A = 57.03 |
| 216C | 216CB | 217N | A = 21.81 |
| 216CD2 | 216CB | 217N | A = 107.73 |
| 216CD1 | 216CB | 217N | A = 83.39 |
| 216O | 216CB | 217N | A = 39.93 |
| 217N | 216CB | 216CE1 | A = 89.83 |
| 217N | 216CB | 216CE2 | A = 106.03 |
| 216CD2 | 216CG | 217N | A = 129.49 |
| 216CD1 | 216CG | 217N | A = 87.74 |
| 216CB | 216CG | 217N | A = 61.66 |
| 216CE1 | 216CG | 217N | A = 108.27 |
| 216CE2 | 216CG | 217N | A = 134.65 |
| 216CA | 216CG | 217N | A = 40.47 |
| 216CZ | 216CG | 217N | A = 125.90 |
| 216N | 216CG | 217N | A = 49.00 |
| 216C | 216CG | 217N | A = 20.78 |
| 216CE1 | 216CD | 217N | A = 138.03 |
| 216CG | 216CD | 217N | A = 71.23 |
| 216CD2 | 216CD1 | 217N | A = 93.79 |
| 216CZ | 216CD1 | 217N | A = 132.89 |
| 216CB | 216CD1 | 217N | A = 56.14 |
| 216CE2 | 216CD1 | 217N | A = 115.84 |
| 216CA | 216CD1 | 217N | A = 37.24 |
| 216O | 216C | 217N | A = 122.31 |
| 216O | 216C | 217CA | A = 89.58 |
| 216O | 216C | 217CB | A = 89.33 |
| 216O | 216C | 217C | A = 98.16 |
| 216O | 216C | 218N | A = 87.89 |
| 217N | 216C | 216CA | A = 117.72 |
| 217N | 216C | 217CA | A = 32.73 |
| 217N | 216C | 216N | A = 92.44 |
| 217N | 216C | 216CB | A = 112.49 |
| 217N | 216C | 217CB | A = 40.03 |
| 217N | 216C | 216CG | A = 89.28 |
| 217N | 216C | 217C | A = 29.43 |
| 217N | 216C | 218N | A = 47.60 |

TABLE III-continued

| Atom 1 | Middle Atom | Atom 3 | Angle ° |
|---|---|---|---|
| 216CA | 216C | 217CA | A = 150.43 |
| 216CA | 216C | 217CB | A = 143.72 |
| 216CA | 216C | 217C | A = 137.49 |
| 216CA | 216C | 218N | A = 135.79 |
| 217CA | 216C | 216N | A = 122.09 |
| 217CA | 216C | 216CB | A = 136.80 |
| 217CA | 216C | 217CB | A = 24.20 |
| 217CA | 216C | 216CG | A = 116.56 |
| 217CA | 216C | 217C | A = 19.82 |
| 217CA | 216C | 218N | A = 34.59 |
| 216N | 216C | 217CB | A = 130.54 |
| 216N | 216C | 217C | A = 105.55 |
| 216N | 216C | 218N | A = 103.71 |
| 216CB | 216C | 217CB | A = 116.54 |
| 216CB | 216C | 217C | A = 141.86 |
| 216CB | 216C | 218N | A = 156.61 |
| 217CB | 216C | 216CG | A = 101.05 |
| 217CB | 216C | 217C | A = 42.91 |
| 217CB | 216C | 218N | A = 58.76 |
| 216CG | 216C | 217C | A = 118.52 |
| 216CG | 216C | 218N | A = 133.95 |
| 217C | 216C | 218N | A = 19.50 |
| 216C | 216O | 217N | A = 29.92 |
| 216C | 216O | 217CA | A = 62.89 |
| 216C | 216O | 217CB | A = 70.34 |
| 216C | 216O | 217C | A = 63.58 |
| 216C | 216O | 337NE | A = 131.52 |
| 216C | 216O | 217CG | A = 92.78 |
| 217N | 216O | 216CA | A = 63.29 |
| 217N | 216O | 217CA | A = 32.97 |
| 217N | 216O | 216CB | A = 70.39 |
| 217N | 216O | 216N | A = 54.43 |
| 217N | 216O | 217CB | A = 43.89 |
| 217N | 216O | 217C | A = 35.89 |
| 217N | 216O | 337NE | A = 159.88 |
| 217N | 216O | 217CG | A = 66.32 |
| 216CA | 216O | 217CA | A = 96.25 |
| 216CA | 216O | 216N | A = 18.49 |
| 216CA | 216O | 217CB | A = 101.39 |
| 216CA | 216O | 217C | A = 95.31 |
| 216CA | 216O | 337NE | A = 98.87 |
| 216CA | 216O | 217CG | A = 122.42 |
| 217CA | 216O | 216CB | A = 100.29 |
| 217CA | 216O | 216N | A = 85.83 |
| 217CA | 216O | 217CB | A = 23.38 |
| 217CA | 216O | 217C | A = 16.01 |
| 217CA | 216O | 337NE | A = 162.34 |
| 217CA | 216O | 217CG | A = 39.79 |
| 216CB | 216O | 217CB | A = 94.84 |
| 216CB | 216O | 217C | A = 106.26 |
| 216CB | 216O | 337NE | A = 89.50 |
| 216CB | 216O | 217CG | A = 110.18 |
| 216N | 216O | 217CB | A = 97.41 |
| 216N | 216O | 217C | A = 81.13 |
| 216N | 216O | 337NE | A = 111.11 |
| 216N | 216O | 217CG | A = 120.03 |
| 217CB | 216O | 217C | A = 39.18 |
| 217CB | 216O | 337NE | A = 142.07 |
| 217CB | 216O | 217CG | A = 22.64 |
| 217C | 216O | 337NE | A = 164.24 |
| 217C | 216O | 217CG | A = 52.47 |
| 337NE | 216O | 217CG | A = 122.91 |
| 216C | 217N | 218N | A = 114.66 |
| 217CA | 217N | 218N | A = 44.76 |
| 216O | 217N | 218N | A = 95.72 |
| 216CA | 217N | 218N | A = 131.08 |
| 217C | 217N | 218N | A = 22.69 |
| 217CB | 217N | 218N | A = 77.75 |

Mutants and Derivatives

The invention further provides homologues, co-complexes, mutants and derivatives of the *Staph aureus* tRNA synthetase crystal structure of the invention.

The term "homologue" means a protein having at least 30% amino acid sequence identity with synthetase or any functional domain of glycyl tRNA synthetase.

The term "co-complex" means glycyl tRNA synthetase or a mutant or homologue of glycyl tRNA synthetase in covalent or non-covalent association with a chemical entity or compound.

The term "mutant" refers to a glycyl tRNA synthetase polypeptide, i.e., a polypeptide displaying the biological activity of wild-type glycyl tRNA synthetase activity, characterized by the replacement of at least one amino acid from the wild-type synthetase sequence. Such a mutant may be prepared, for example, by expression of *Staph aureus* synthetase cDNA previously altered in its coding sequence by oligonucleotide-directed mutagenesis.

*Staph aureus* glycyl tRNA synthetase mutants may also be generated by site-specific incorporation of unnatural amino acids into glycyl tRNA synthetase proteins using the general biosynthetic method of C. J. Noren et al, *Science,* 244:182–188 (1989). In this method, the codon encoding the amino acid of interest in wild-type glycyl tRNA synthetase is replaced by a "blank" nonsense codon, TAG, using oligonucleotide-directed mutagenesis. A suppressor tRNA directed against this codon is then chemically aminoacylated in vitro with the desired unnatural amino acid. The aminoacylated tRNA is then added to an in vitro translation system to yield a mutant glycyl tRNA synthetase enzyme with the site-specific incorporated unnatural amino acid.

Selenocysteine or selenomethionine may be incorporated into wild-type or mutant tRNA glycyl synthetase by expression of *Staph aureus* glycyl tRNA synthetase-encoding cDNAs in auxotrophic *E. coli* strains [W. A. Hendrickson et al, *EMBO J.,* 9(5):1665–1672 (1990)]. In this method, the wild-type or mutagenized tRNA synthetase cDNA may be expressed in a host organism on a growth medium depleted of either natural cysteine or methionine (or both) but enriched in selenocysteine or selenomethionine (or both).

The term "heavy atom derivative" refers to derivates of glycyl tRNA synthetase produced by chemically modifying a crystal of glycyl tRNA synthetase. In practice, a crystal is soaked in a solution containing heavy metal atom salts, or organometallic compounds, e.g., lead chloride, gold thiomalate, thimerosal or uranyl acetate, which can diffuse through the crystal and bind to the surface of the protein. The location(s) of the bound heavy metal atom(s) can be determined by X-ray diffraction analysis of the soaked crystal. This information, in turn, is used to generate the phase information used to construct three-dimensional structure of the enzyme [T. L. Blundel and N. L. Johnson, Protein Crystallography, Academic Press (1976).

II. Methods of Identifying Inhibitors of the Novel Glycyl tRNA Synthetase Crystalline Structure Another aspect of this invention involves a method for identifying inhibitors of a Staph glycyl tRNA synthetase characterized by the crystal structure and novel active site described herein, and the inhibitors themselves. The novel synthetase crystalline structure of the invention permits the identification of inhibitors of synthetase activity. Such inhibitors may be competitive, binding to all or a portion of the active site of the glycyl tRNA synthetase; or non-competitive and bind to and inhibit glycyl tRNA synthetase whether or not it is bound to another chemical entity.

One design approach is to probe the glycyl TRNA synthetase crystal of the invention with molecules composed of a variety of different chemical entities to determine optimal sites for interaction between candidate glycyl tRNA synthetase inhibitors and the enzyme. For example, high resolution X-ray diffraction data collected from crystals saturated with solvent allows the determination of where each type of solvent molecule sticks. Small molecules that bind tightly to those sites can then be designed and synthesized and tested for their glycyl tRNA synthetase inhibitor activity [J. Travis, *Science,* 262:1374 (1993)].

This invention also enables the development of compounds that can isomerize to short-lived reaction intermediates in the chemical reaction of a substrate or other compound that binds to or with glycyl tRNA synthetase. Thus, the time-dependent analysis of structural changes in glycyl tRNA synthetase during its interaction with other molecules is permitted. The reaction intermediates of glycyl tRNA synthetase can also be deduced from the reaction product in co-complex with glycyl tRNA synthetase. Such information is useful to design improved analogues of known glycyl tRNA synthetase inhibitors or to design novel classes of inhibitors based on the reaction intermediates of the glycyl tRNA synthetase enzyme and glycyl tRNA synthetase inhibitor co-complex. This provides a novel route for designing glycyl tRNA synthetase inhibitors with both high specificity and stability.

Another approach made possible by this invention, is to screen computationally small molecule data bases for chemical entities or compounds that can bind in whole, or in part, to the glycyl tRNA synthetase enzyme. In this screening, the quality of fit of such entities or compounds to the binding site may be judged either by shape complementarity or by estimated interaction energy [E. C. Meng et al, *J. Comp. Chem.,* 13:505–524 (1992)].

Because glycyl tRNA synthetase may crystallize in more than one crystal form, the structure coordinates of glycyl tRNA synthetase, or portions thereof, as provided by this invention are particularly useful to solve the structure of those other crystal forms of tRNA synthetase. They may also be used to solve the structure of glycyl tRNA synthetase mutant co-complexes, or of the crystalline form of any other protein with significant amino acid sequence homology to any functional domain of glycyl tRNA synthetase.

One method that may be employed for this purpose is molecular replacement. In this method, the unknown crystal structure, whether it is another crystal form of glycyl tRNA synthetase, a glycl tRNA synthetase mutant, or a glycyl tRNA synthetase co-complex, or the crystal of some other protein with significant amino acid sequence homology to any functional domain of glycyl tRNA synthetase, may be determined using the glycyl tRNA synthetase structure coordinates of this invention as provided in FIG. 1 and Tables I–III. This method will provide an accurate structural form for the unknown crystal more quickly and efficiently than attempting to determine such information ab initio.

Thus, the synthetase structure provided herein permits the screening of known molecules and/or the designing of new molecules which bind to the synthetase structure, particularly at the active site, via the use of computerized evaluation systems. For example, computer modelling systems are available in which the sequence of the synthetase, and the synthetase structure (i.e., the bond angles, dihedral angles, distances between atoms in the active site region, etc. as provided by FIG. 1 and Tables I–III herein) may be input. Thus, a machine readable medium may be encoded with data representing the coordinates of FIG. 1 and Tables I–III. The computer then generates structural details of the site into which a test compound should bind, thereby enabling the determination of the complementary structural details of said test compound.

More particularly, the design of compounds that bind to or inhibit glycyl tRNA synthetase according to this invention generally involves consideration of two factors. First, the compound must be capable of physically and structurally associating with glycyl tRNA synthetase. Non-covalent molecular interactions important in the association of glycyl tRNA synthetase with its substrate include hydrogen bonding, van der Waals and hydrophobic interactions.

Second, the compound must be able to assume a conformation that allows it to associate with glycyl tRNA synthetase. Although certain portions of the compound will not directly participate in this association with glycyl tRNA synthetase, those portions may still influence the overall conformation of the molecule. This, in turn, may have a significant impact on potency. Such conformational requirements include the overall three-dimensional structure and orientation of the chemical entity or compound in relation to all or a portion of the binding site, e.g., active site or accessory binding site of glycyl tRNA synthetase, or the spacing between functional groups of a compound comprising several chemical entities that directly interact with glycyl tRNA synthetase.

The potential inhibitory or binding effect of a chemical compound on glycyl tRNA synthetase may be analyzed prior to its actual synthesis and testing by the use of computer modelling techniques. If the theoretical structure of the given compound suggests insufficient interaction and association between it and glycyl tRNA synthetase, synthesis and testing of the compound is obviated. However, if computer modelling indicates a strong interaction, the molecule may then be synthesized and tested for its ability to bind to glycyl tRNA synthetase and inhibit using a suitable assay. In this manner, synthesis of inoperative compounds may be avoided.

An inhibitory or other binding compound of glycyl tRNA synthetase may be computationally evaluated and designed by means of a series of steps in which chemical entities or fragments are screened and selected for their ability to associate with the individual binding pockets or other areas of glycyl tRNA synthetase.

One skilled in the art may use one of several methods to screen chemical entities or fragments for their ability to associate with glycyl tRNA synthetase and more particularly with the individual binding pockets of the glycyl tRNA synthetase active site or accessory binding site. This process may begin by visual inspection of, for example, the active site on the computer screen based on the glycyl tRNA synthetase coordinates in FIG. 1 and Tables I–III. Selected fragments or chemical entities may then be positioned in a variety of orientations, or docked, within a binding pocket of glycyl tRNA synthetase. Docking may be accomplished using software such as Quanta and Sybyl, followed by energy minimization and molecular dynamics with standard molecular mechanics force fields, such as CHARMM and AMBER.

Specialized computer programs may also assist in the process of selecting fragments or chemical entities. These include:

1. GRID [P. J. Goodford, "A Computational Procedure for Determining Energetically Favorable Binding Sites on Biologically Important Macromolecules", *J. Med. Chem.,* 28:849–857 (1985)]. GRID is available from Oxford University, Oxford, UK.
2. MCSS [A. Miranker and M. Karplus, "Functionality Maps of Binding Sites: A Multiple Copy Simultaneous Search Method", *Proteins: Structure, Function and Genetics,* 11:29–34 (1991)]. MCSS is available from Molecular Simulations, Burlington, Mass.

3. AUTODOCK [D. S. Goodsell and A. J. Olsen, "Automated Docking of Substrates to Proteins by Simulated Annealing", *Proteins: Structure. Function, and Genetics,* 8:195–202 (1990)]. AUTODOCK is available from Scripps Research Institute, La Jolla, Calif.

4. DOCK [I. D. Kuntz et al, "A Geometric Approach to Macromolecule-Ligand Interactions", *J. Mol. Biol.,* 161:269–288 (1982)]. DOCK is available from University of California, San Francisco, Calif.

Once suitable chemical entities or fragments have been selected, they can be assembled into a single compound or inhibitor. Assembly may be proceed by visual inspection of the relationship of the fragments to each other on the three-dimensional image displayed on a computer screen in relation to the structure coordinates of glycyl tRNA synthetase. This would be followed by manual model building using software such as Quanta or Sybyl.

Useful programs to aid one of skill in the art in connecting the individual chemical entities or fragments include:

1. CAVEAT [P. A. Bartlett et al, "CAVEAT: A Program to Facilitate the Structure-Derived Design of Biologically Active Molecules", in *"Molecular Recognition in Chemical and Biological Problems"*, Special Pub., Royal Chem. Soc. 78, pp. 182–196 (1989)]. CAVEAT is available from the University of California, Berkeley, Calif.

2. 3D Database systems such as MACCS-3D (MDL Information Systems, San Leandro, Calif.). This area is reviewed in Y. C. Martin, "3D Database Searching in Drug Design", *J. Med. Chem.,* 35:2145–2154 (1992).

3. HOOK (available from Molecular Simulations, Burlington, Mass.).

Instead of proceeding to build a glycyl tRNA synthetase inhibitor in a step-wise fashion one fragment or chemical entity at a time as described above, inhibitory or other glycyl tRNA synthetase binding compounds may be designed as a whole or "de novo" using either an empty active site or optionally including some portion(s) of a known inhibitor (s). These methods include:

1. LUDI [H.-J. Bohm, "The Computer Program LUDI: A New Method for the De Novo Design of Enzyme Inhibitors", *J. Comp. Aid. Molec. Design,* 6:61–78 (1992)]. LUDI is available from Biosym Technologies, San Diego, Calif.

2. LEGEND [Y. Nishibata and A. Itai, *Tetrahedron,* 47:8985 (1991)]. LEGEND is available from Molecular Simulations, Burlington, Mass.

3. LeapFrog (available from Tripos Associates, St. Louis, Mo.).

Other molecular modelling techniques may also be employed in accordance with this invention. See, e.g., N. C. Cohen et al, "Molecular Modeling Software and Methods for Medicinal Chemistry", *J. Med. Chem.,* 33:883–894 (1990). See also, M. A. Navia and M. A. Murcko, "The Use of Structural Information in Drug Design", *Current Opinions in Structural Biology,* 2:202–210 (1992). For example, where the structures of test compounds are known, a model of the test compound may be superimposed over the model of the structure of the invention. Numerous methods and techniques are known in the art for performing this step, any of which may be used. See, e.g., P. S. Farmer, Drug Design, Ariens, E. J., ed., Vol. 10, pp 119–143 (Academic Press, New York, 1980); U.S. Pat. No. 5,331,573; U.S. Pat. No. 5,500,807; C. Verlinde, *Curr. Biol.,* 2:577–587 (1994); and I. D. Kuntz, *Science,* 257:1078–1082 (1992). The model building techniques and computer evaluation systems described herein are not a limitation on the present invention.

Thus, using these computer evaluation systems, a large number of compounds may be quickly and easily examined and expensive and lengthy testing avoided. Moreover, the need for actual synthesis of many compounds is effectively eliminated.

Once identified by the modelling techniques, the synthetase inhibitor may be tested for bioactivity using standard techniques. For example, structure of the invention may be used in binding assays using conventional formats to screen inhibitors. One particularly suitable assay format includes the enzyme-linked immunosorbent assay (ELISA). Other assay formats may be used; these assay formats are not a limitation on the present invention.

In another aspect, the synthetase structure of the invention permit the design and identification of synthetic compounds and/or other molecules which are characterized by the conformation of the synthetase of the invention. Using known computer systems, the coordinates of the synthetase structure of the invention may be provided in machine readable form, the test compounds designed and/or screened and their conformations superimposed on the structure of the synthetase of the invention. Subsequently, suitable candidates identified as above may be screened for the desired synthetase inhibitory bioactivity, stability, and the like.

Once identified and screened for biological activity, these inhibitors may be used therapeutically or prophylactically to block synthetase activity, and thus, bacterial replication.

III. Inhibitors of Glycyl tRNA Synthetase (GRS) Activity

The present invention also provides inhibitors of glycyl tRNA synthetase activity identified or designed by the methods of the invention. These inhibitors are useful as anti-bacterial agents.

One particularly desirable inhibitor is glycylsulfamoyladenosine. The structure of this compound is as follows.

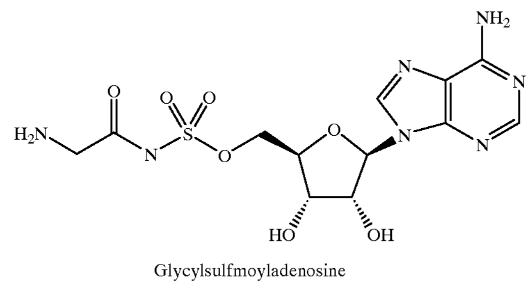

Glycylsulfmoyladenosine

Glycylsulfmoyladenosine is an analogue of the Gly-AMP reaction intermediate and inhibits GRS catalytic activity as measured by any of the techniques described in the examples below. Estimates of the potency of inhibition are obtained by performing enzyme assays in the presence of a range of inhibitor concentrations, and fitting the effect of inhibitor concentration on enzyme velocity to a four parameter logistic function that allows calculation of an $IC_{50}$ (the inhibitor concentration at which GRS activity is reduced by half). This parameter is directly related to the dissociation constant for inhibitor binding ($K_i$ or $K_d$) and has a value of around 2.4 mM for glycylsulfamoyladenosine when tested against the *S. aureus* GRS. Binding of glycylsulfamoyladenosine to GRS can also be measured directly using stopped-flow fluorescence techniques because enzyme:inhibitor binary complex has around 5% higher tryptophan fluorescence than the free enzyme. Experiments of this type yield the following elementary rate constants for inhibitor binding; $k_{on}=1.1\times10^6 s^{-1}.M^{-1}$, $k_{off}=2.9 s^{-1}$. The ratio of these yields an estimate for $K_d$ of 2.6 mM, almost identical to the result obtained in enzyme inhibition experiments.

The following examples illustrate various aspects of this invention. These examples do not limit the scope of this invention which is defined by the appended claims.

Example 1

The Expression of the Glycyl t-RNA Synthetase from *Staphylococcus aureus in Escherichia coli.*

The strategy for the expression of the glycyl t-RNA synthetase (GRS) from *Staphylococcus aureus,* using *Escherichia coli* as a host was based on the PCR amplification of the grs gene and the introduction of suitable restriction sites that allowed the cloning of the grs-containing DNA fragment in the pDB575 expression vector. After the PCR amplification the insert of the resultant recombinant plasmid, (pDBGRS hereafter), was sequenced to verify the absence of artefacts introduced by the Taq polymerase. Expression was monitored by SDS-polyacrylamide gel analysis.

A. Bacterial strains, Plasmids and Medium

The *Escherichia coli* strains used were: DH5a (supE44, DlacU169 (f 80 lacZDM15), hsdR17, recA1, endA1, gyrA96, thi-1, relA1) and HB101 (thi-1, hsdS20($r^-_B$,$m^-_B$), supE44, recA13, ara-14, leuB6, proA2, lacY1, rpsL20($str^r$), xyl-5, mtl-1). *E. coli* cells were grown at 37° C. in Luria Bertani broth (LB). These strains may all be obtained from commercial sources.

The plasmids used were pBluescript SK- [Stratagene], pUC18 [J. Sambrook et al., *Molecular Cloning: A Laboratory Manual.* Cold Spring Harbor Laboratory Press, Cold Spring Harbor, N.Y. (1989)] and pDB575. A detailed description of pDB575 is provided in A. F. Chalker et al, *Gene,* 141:103–108 (1994). Briefly, pDB575 is a expression vector of *E.coli* based on pKK223-3 [Pharmacia] with the following modifications: (i) the polylinker between EcoRI and HindIII has been replaced with a longer one (EcoRI, NcoI, KpnI, NdeI, SstI, SstII, XbaI, ClaI, SmaI, BglII, XmaIII, HindIII); (ii) it has a $lacI^q$ gene inserted; (iii) it is non-mobilizable, the pBR322 portion of pKK223-3 has been replaced by the equivalent fragment from pATIS3. pDB575 allows the selection of the recombinant clones by ampicillin resistance and the gene expression is driven by the tac promoter.

| | |
|---|---|
| Bacto-tryptone | 10 g |
| Bacto-yeast extract | 5 g |
| NaCl | 5 g |

For plasmid propagation 0.1 mg/ml of ampicillin was added to the medium.

B. DNA Manipulations

Plasmid DNA was prepared by the rapid alkaline method (Sambrook et al, 1989). Transformations of *E. coli* cells were carried out using the RbCl methods (Sambrook et al, 1989). DNA fragments were purified using the Geneclean Kit [BIO 101 Inc., La Jolla, Calif., USA]. The plasmids for sequencing were purified using QIAGEN plasmid kit [QIAGEN]. DNA sequencing was carried out on supercoiled plasmid DNA by the dideoxy chain-termination method using the Thermo Sequenase cycle sequencing kit [Amersham Life Science, Inc. USA]. DNA was also sequenced by the Automated Sequencing Service of Pharmacy Faculty in the Complutense University of Madrid. Universal or synthetic oligonucleotides [MedProbe, Norway] were used as primers. Restriction enzymes and T4 DNA ligase were obtained from Promega and Boehringer respectively and the experiments were carried out following the instructions provided by the suppliers.

The grs gene from *S. aureus* cloned in the pBluescript SK- was amplified by PCR using the primers GRS 1: (5'-GGGGTACCGCTAGCAGGAGAGGTAATTATGGCAAAAGATATG-3'; SEQ ID NO:2) and GRS2: (5'-GCTCTAGATTAGTCATTTAATTAGAATTTTGTTTTTTC AGTTAAG-3'; SEQ ID NO:3). Kpn I and Xba I restriction sites were incorporated at the 5' and 3'ends respectively of each primer to facilitate ligation of the amplified DNA into vectors. Plasmid DNA (100 ng) was amplified in 100 ml of PCR mixture containing 250 mM deoxynucleotide triphosphates (dNTPs), 0.9 mM oligonucleotide primers, the manufacturer's buffer and 2U of Taq polymerase (Promega). The following cycling parameters were used:

94° C. 5 min

94° C. 1min, 55° C. 2 min, 72° C. 2 min (35 cycles)

72° C. 10 min

Polymerase chain reaction (PCR) was performed using the DNA Thermal Cycler [Perkin Elmer Cetus]. PCR-amplified DNA fragments were purified using Wizard™ Preps DNA Purification System for Rapid Purification of DNA Fragments [Promega].

C. Cloning of the grs Gene of *S. aureus* in the Expression Vector pDB575 of *E. coli.*

The cloning strategy is shown in FIG. 2. PCR amplification of the grs gene from *S. aureus* using the primers GRS I and GRS2 resulted in a DNA fragment of 1.4 kb. This fragment was purified and ligated to the KpnI, XbaI sites of pDB575 to obtain the recombinant plasmid pDBGRS and the ligation mix was used to transform *E. coli* DH5a competent cells. The construction of pDBGRS was initially confirmed by restriction analysis of the plasmid purified from the transformants. The amplification with Taq DNA polymerase made the sequencing of the grs of pDBGRS an obligatory step to confirm that no changes were introduced due to the low fidelity of this enzyme. Sequence analysis was accomplished by using grs gene introduced in the expression plasmid pDB575 and/or in pUC 18. The sequencing of both strands showed that no artefacts had been introduced during the amplification process.

D. Small-scale Production of GRS from *S. aureus* in *E. coli*

Figure 3:
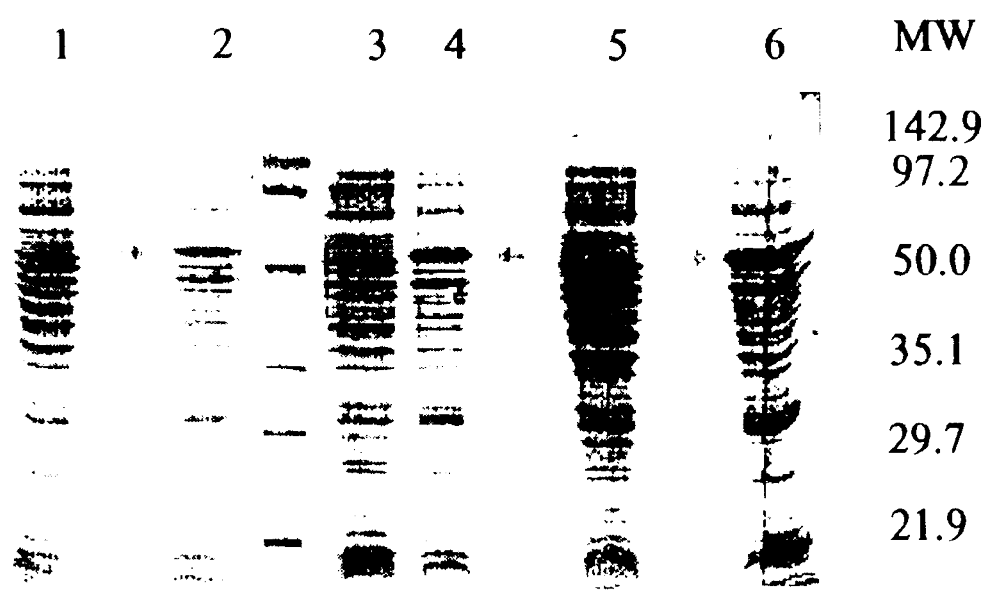
FIG. 3 illustrates the SDS-PAGE analysis of the GRS production by *E. coli. E. coli* HB101 cells, harboring either pDB575 or pDBGRS, were induced with 1 mM IPTG. Sonicated samples were electrophoresed through 0.1% SDS-15% polyacrylamide gels. The gel was stained with Coomassie brilliant blue. Lanes 1, 3 and 5 show the sonicated extracts of HB101 :pDB575 at 2, 3 and 4 hours after the induction. Lanes 2, 4 and 6 show the corresponding samples of the recombinant clone HB101 :pDBGRS.

The plasmid pDBGRS and the negative control pDB575 (vector without insert) were used to transform the *E. coli* HB101 host strain. Single clones of HB101:pDBGRS and HB101:pDB575 cells were grown overnight at 37° C. in 2 ml of LB medium in the presence of 0.1 mg/ml ampicillin. The cells were then diluted 100-fold in 30 ml LB with ampicillin. When the cultures reached a value of 0.5 at $OD_{600}$ the grs expression was induced by addition of isopropyl-thio-galactoside (IPTG) at 1 mM of final concentration. After this induction 2 ml samples were taken at different times (2, 3 and 4 hours). The cells were harvested in a microfuge for 3 min, the pellets were washed with 20 mM Tris-HCl pH 8/1 mM PMSF and resuspended in 300 ml of SDS-PAGE gel-loading buffer. The cells were broken by sonication (15 seconds). The samples were then boiled 10 minutes and after one spin, 10 ml fractions were analyzed by SDS-PAGE according to the methods of Laemmli [U. K. Laemmli, Nature 227, 680–685 (1970)]. The 12% polyacrylamide gels were stained with Coomassie blue. As shown in FIG. 3 good expression levels were detected from the early stages after induction with IPTG. The evidence was the presence of a prominent band (lanes 2, 4 and 6 in FIG. 3) that was in good agreement with the $M_r$ predicted from the primary sequence. The GRS protein has a theoretical molecular weight of about 53.7 kDa.

Example 2

Fermentation and Purification of Glycyl tRNA Synthetase

A. Fermentation

A 300 liter fermentation of *E coli HB*10:pDB575GRS was carried out in double strength Luria Bertani medium (LB), containing 50 ug/ml ampicillin. The vessel was inoculated at 2% (v/v) from a 15 hour secondary seed culture in single strength LB medium, containing 50 mg/ml ampicillin. The production vessel was incubated at 37° C., agitated at 1.5 $msec^{-1}$ and aerated at 1.0 VVM. The OD at 550 nm was monitored, and at 2.5 absorbance units, GRS expression was induced with the addition of isopropyl-thiogalactosidase to 1.0 mM and the cells harvested by centrifugation in a Westfalia CSA-19, 2 hours post induction. A total of 990 grams of cell paste was recovered.

LB Medium, per liter, contains the following components. The medium ingredients were supplied by Difco Laboratories, West Molesey, Surrey UK.

| Double strength | Single strength |
|---|---|
| Bacto Tryptone 20 g | Bacto Tryptone 10 g |
| Bacto Yeast Extract 10 g | Bacto Yeast Extract 5 g |
| Sodium Chloride 5 g | Sodium Chloride 5 g |

B. Purification

1) Lysis 125 g of cells of *E. coli* overexpressing *S. aureus* GRS obtained as described above, were resuspended in 600 ml of 20 mM Tris, 1 mM EDTA, 1 mM DTT, 5 mM $MgCl_2$ pH 7.5 (buffer A). Lysozyme (Sigma Chemicals: hen egg) was added to a final concentration of 2mg/ml. Cells were incubated at 37° C. for 20 min. The cells were then frozen in an ethanol/dry ice water bath and thawed. Dnase (Sigma; bovine pancreas type 1) was added to a final concentration of 10 Kunitz units per ml and held at 37° C. for 5 minutes. The solution was centrifuged in a Beckman JA-HS centrifuge at 14,000 g for 60 minutes using a Beckman JA-14 rotor.

2) Anion Exchange

All chromatography was performed on a Waters 650E chromatography system, fitted with a UV detector (Pharmacia S2) and conductivity monitor (Pharmacia). UV (at 280 nm) and conductivity were monitored during all operations. All operations were performed at 4° C.

The supernatant from 1) was loaded onto a Q-Sepharose high performance (Pharmacia) column of 200 ml packed into a Pharmacia XK-50 column. The column was equilibrated with buffer A prior to loading. The column is then washed with buffer A (1000 ml) at 40 ml/min, and eluted with a linear gradient of buffer A to 1M NaCl in buffer A over 140 minutes at 10 ml/min. The eluate was fractionated into 5 minute fractions using a Pharmacia Superfrac.

The eluted fractions were assayed for GRS activity by measurement of aminoacylation of $tRNA^{Gly}$, and for protein by the Bradford method. Active fractions were analyzed by reducing SDS PAGE (Pharmacia Phast System 10–15% gradient gel)

3) Hydrophobic Interaction Chromatography

Two active fractions from 2) were pooled and the ammonium sulphate concentration adjusted to 1M by addition (1 to 1) of 2 M ammonium sulphate. The material was loaded onto a 50 ml column of butyl Toyopearl 650S (Tosohaas) equilibrated with buffer A plus 1 M ammonium sulphate (column Pharmacia XK-26). The column was washed with 100 ml of the equilibration buffer and then eluted with a linear gradient of equilibration buffer to buffer A over 140 minutes at 5 ml/min.

4) Concentration/buffer Exchange

Eluted fractions are collected (1minute fraction) and assayed for GRS activity and protein. Active fractions are pooled and diafiltered against (1,000 fold buffer exchange) buffer A using an Amicon ultrafiltration cell (350 ml) under nitrogen. A final volume of 33 ml of protein was obtained containing 4.2 mg/ml of protein (by amino acid analysis). This product was greater than 95% purity by SDS PAGE and the activity showed an overall process yield of 60% from 1). N-terminal amino acid analysis confirmed identity.

C. Measurement of Glycyl tRNA Synthetase (GRS) Activity.

The enzyme catalyses the aminoacylation of $tRNA^{Gly}$, which proceeds through a two step mechanism. The first step involves the formation of a stable enzyme:glycyl adenylate complex resulting from the specific binding and reaction of ATP and L-glycine. Subsequently, the 3' terminal adenosine of enzyme-bound tRNAGly reacts with the aminoacyladenylate, leading to the esterification of the tRNA and release of AMP. These steps are summarized below.

a) L-Gly+ATP.Mg+GRS ÞGRS:Gly-AMP+PPi.Mg b) GRS:Gly-AMP+$tRNA^{Gly}$ ÞGRS+Gly-$tRNA^{Gly}$+AMP

This reaction can be assayed in order to characterize the enzyme or identify specific inhibitors of its activity in a number of ways:

(1) Measurement of the formation of Gly-$tRNA^{Gly}$ can be specifically determined using radiolabelled glycine and separating free glycine from Gly-tRNA using precipitation/filtration techniques (e.g. in cold trichloroacetic acid; see, Calender & Berg (1966) Biochemistry 5, 1681–1690; Toth MJ & Schimmel P (1990) J. Biol. Chem. 265, 1000–1004].

(2) The full acylation reaction can also be measured by analyzing production of either PPi or AMP which are produced in stoichiometric ratio to the tRNA acylation. This may be achieved in a number of ways, for example using colorimetric [Hoenig (1989) J. Biochem. Biophys. Meth. 19, 249–252]; or enzyme coupled [Webb™ (1994) Anal. Biochem. 218, 449–454] measurement of Pi after addition of excess inorganic pyrophosphatase or using enzyme coupled assays to directly measure AMP or PPi production [Sigma Chemicals Catalogue, 1986].

(3) The partial reaction (a) can be assayed through radio-label isotopic exchange between ATP and PPi, since each of the steps in this part of the reaction are freely reversible. This reaction is independent of tRNA binding, typically has a $k_{cat}$ around 20-fold higher than the full acylation reaction (a+b), and is readily measured using chromatographic principles which separate PPi from ATP (i.e. using activated charcoal; see, Calender & Berg, cited above; Toth & Schimmel, cited above).

D. Ligand Binding to GRS.

It is also possible to define ligand interactions with GRS in experiments that are not dependent upon enzyme catalyzed turnover of substrates. This type of experiment can be done in a number of ways:

(1) Effects of ligand binding upon enzyme intrinsic fluorescence (e.g. of tryptophan). Binding of either natural ligands or inhibitors may result in enzyme conformational changes which alter enzyme fluorescence. Using stopped-flow fluorescence equipment, this can be used to define the microscopic rate constants that describe binding. Alternatively, steady-state fluorescence titration methods can yield the overall dissociation constant for binding in the same way that these are accessed through enzyme inhibition experiments.

(2) Spectral effects of ligands. Where the ligands themselves are either fluorescent or possess chromophores that overlap with enzyme tryptophan fluorescence, binding can be detected either via changes in the ligand fluorescence properties (e.g. intensity, lifetime or polarization) or fluorescence resonance energy transfer with enzyme tryptophans. The ligands could either be inhibitors or variants of the natural ligands (i.e. fluorescent ATP derivatives or tRNAGly labelled with a fluorophore).

(3) Thermal analysis of the enzyme:ligand complex. Using calorimetric techniques (e.g. Isothermal Calorimetry, Differential Scanning Calorimetry) it is possible to detect thermal changes, or shifts in the stability of GRS which reports and therefore allows the characterization of ligand binding.

E. Aminoacylation Assays for GRS Activity

Assays were performed either using purified *S. aureus* GRS overexpressed in *E. coli,* or using crude cell lysate from *E. coli* overexpressing GRS. The latter contained around 10% of total protein as GRS. Enzyme was stored at −70° C. in 50 mM Tris-HCl buffer (pH 7.8), 10 mM $MgCl_2$ and 10 mM B-mercaptoethanol after flash freezing in liquid $N_2$. In experiments to determine the activity of enzyme samples, these stocks were diluted over a wide range (100 fold to 10,000 fold) in 50 mM Tris pH 7.8, 10 mM $MgCl_2$, 1 mM Dithiothreitol and stored on ice prior to assay.

The assay procedure was as follows. 50 ml of enzyme prepared and diluted as described above was mixed with reaction mixture (100 ml), comprising: 0.15 mCi L-[U-$^{14}$]-Glycine (Amersham International), 4 mg/ml *E. coli* MRE600 mixed tRNA (Boehringer Manheim), 5 mM ATP, 15 mM $MgSO_4$, 3 mM DTT, 75 mM KCl and 50 mM Tris-HCl, pH 7.8. Unless otherwise states, all reagents were obtained from Sigma Chemical Company Ltd. Concentrations are given as in the final reaction mix. After addition of the enzyme to start the reaction, assay samples were incubated at 37° C. and, at the desired time, duplicate aliquots (50 ml) were removed and quenched with 7% trichloroacetic acid (100 ml) and left on ice for 30 min. The precipitates were harvested using a Packard Filtermate 196 Cell Harvester [Packard Instruments Ltd.] onto glass fiber filters which were washed successively with 7% trichloroacetic acid and ethanol. The filters were dried at 70° C. for 1 hour and the levels of radioactivity measured by scintillation counting (Packard Topcount).

Example 3

Crystallization of *Staphylococcus aureus* Glycyl tRNA Synthetase

A. Crystallization

A large crystal (0.25×0.25×0.18 mm $^3$) was formed using the following conditions. The protein used for the crystallization was supplied @ 5.8 mg/ml in a solution of 20 mM tris, 5 mM $MgCl_2$, 1 mM DTT, 1 mM EDTA, 10% glycerol, pH 7.5). The crystal was obtained from a 1:1 mixture of the protein solution and a solution of 10% PEG 8000, 0.1M imidazole pH 8.0 and 0.2M calcium acetate using the hanging drop method, grown at room temperature.

B. X-ray Diffraction Characterization

Initially, the *Staph aureus* synthetase crystal was mounted in a sealed glass capillary with a small amount of mother liquor in each end of the capillary. The $CuK_a$ X-ray, having a wavelength of 1.54 Å, was generated by a Rigaku-RU200 rotating anode machine operating at 100 mA×50 kV electric power. The crystal was exposed to the $CuK_a$ X-ray, and the diffracted X-ray was collected by a Siemens multiwire area detector. The crystal diffracted to 3.5 Å.

By registering the position and intensity of many tens of thousands diffraction spots using the computer program XENGEN, the crystal has been determined to be an orthorhombic crystal system and P2,2,2, space group. The unit cell dimensions are a-81.5 Å, b=123.1 Å, c=127.5 Å. By established methods, an asymmetric unit was calculated to have one protein molecule. The crystal contains an estimated 60% solvent.

C. Structure Solution

It was determined that the amino acid sequences of *S. aureus* and *T. thermophilus* are 44% identical. Since the crystal structure of the *T. thermophilus* GRS has been published [D. T. Logan et al., *EMBO J.,* 14:4156–4167 (1995)], it served as a search model for structure solution using molecular replacement methods. The GRS dimer was used as the initial search model, the rotation search was carried out including all the data in 10.0–4.0 Å and the solution was evident from the 25s peak height. The subsequent translation search also yielded a pronounced solution at 15s and an R-factor of 49.4% using all the data to 3.5 Å resolution. Rigid body refinement reduced the R-factor to 47.8%. Solvent flattening and 2-fold non-crystallographic averaging was then used to improve the phases [Collaborative Computational Project, Number 4, Acta Crystallogr. D50, 760–763 (1994)], which introduced about 30° C. phase shifts and improved the averaged figure of merit from 0.4 to 0.8 and Rfree from 47% to 28%. An improved electron density map was then calculated.

D. Model Building and Refinement

Using the three-dimensional electron density map obtained from above experiments, the polypeptide chain of the *S. aureus* GRS can be traced without ambiguity. Three hundred ninety-five (395) residues (most with side chains) were built for each monomer in the 3-D computer graphics program XTALVIEW [McKee, D. E. in Practical Protein Crystallography, Academic Press, San Diego (1993)]. XTALVIEW was used in building models of the GRS structure. Using the initial model, a diffraction pattern was calculated and compared to the experimental data. The difference between the calculated and experimentally determined diffraction patterns was monitored by the value of R-factors. The refinement of the structural model was carried out by adjustments of atomic positions to minimizing the R-factor, where a value of about 20% is typical for a good quality protein structure.

The GRS model was subjected to one round of Xplor [A. Brunger et al., *Science,* 235:458–460 (1987) refinement using the standard positional, slowcool and overall B factor refining protocols. The GRS was refined as a tightly contained dimer without any solvent molecules. The R factor of the model is 23.9% with satisfactory geometry. The rms deviations are 0.017 Å for bond lengths, 2.0° for bond angles, 25.4 for dihedrals and 1.8° C. for impropers. The structure contains residues 1–86, 150–161, 164–352 and 356–463 [SEQ ID NO:1], while the other 68 residues (15%) are disordered in the crystal and not included in the model.

Example 5

The Preparation of the Glycyl tRNA Synthetase Inhibitor, 5'-O-Glycylsulfamoyladenosine A solution of 2', 3'-O-isopropylidene-5'-O-sulfamoyladenosine (J. Castro-Pichel et al, *Tetrahedron,* 1987, 43, 383) (0.50 g, 1.3 mmol) in dry tetrahydrofuran (THF) (3 ml) was added to a solution of N-t-butoxycarbonylglycine N-hydroxysuccinimide ester (Sigma Chemical Co.) in dry THF(2 ml), followed by 1,8-diazabicyclo[5.4.0]undec-7-ene (0.2 ml, 1.3 mmol), and the mixture stirred at room temperature for 1.5 h. The mixture was then partitioned between 10% aqueous citric acid (25 ml) and ethyl acetate (25 ml) and the organic phase washed with saturated $NaHCO_3$, brine, dried ($MgSO_4$) and evaporated to an oil. This was chromatographed on Kieselgel 60 eluting with 0–20% methanol in dichloromethane to afford the protected product (200 mg).

This material (100 mg) was dissolved in trifluoroacetic acid (3 ml). After stirring for 15 min at room temperature, water (3 ml) was added and the mixture stirred at room temperature for a further hour. The solution was evaporated and the residue chromatographed on reverse-phase silica gel eluting with water. The product-containing fractions were combined and freeze-dried to afford the 5'-O- glycylsulfamoyladenosine as a white solid. (10 mg); d( ppm, $D_20$) 3.78 (2H, $CH_2$), 4.49–4.52 (3H, m, 4'-H, 5'-$H_2$) 454 (1H, br.s. 3'-H), 4.63 (1H, t, J=4.84 Hz, 2'-H), 6.28 (1H, d, J=4.72 Hz, 1'-H) 8.51(1H, s, Ar-H), 8.63(1H, s, Ar-H); m/z (ESI) 404($MH^+$, 100%).

Example 6

Characterization of Inhibition by Glycylsulfamoyladenosine

The characterization of the compound as an inhibitor of the catalytic activity of GRS was performed using a procedure similar to that described in Example 2E above, except that multiple assays were performed in the presence of inhibitor concentrations ranging (in two-fold dilution steps) from 100 mM down to 0.1 mM (final concentrations). These were added from stocks prepared at 10-fold higher concentrations and added to each reaction mix. The stock of inhibitor was prepared freshly from a solid sample and dissolved in dimethylsulfoxide. The enzyme concentration used for these assays was selected so that around 50% of the tRNA available was acylated during the reaction time course. Following harvesting and counting as described above, the acylation activity (relative to controls in the absence of inhibitor) were plotted as a function of inhibitor concentration and fitted to a four-parameter logistic function (using the Grafit package; Erithacus Software Ltd.) to yield $IC_{50}$, the inhibitor concentration required to inhibit half the enzyme activity.

Example 7

Human Glycyl tRNA Synthetase

Figure 6:
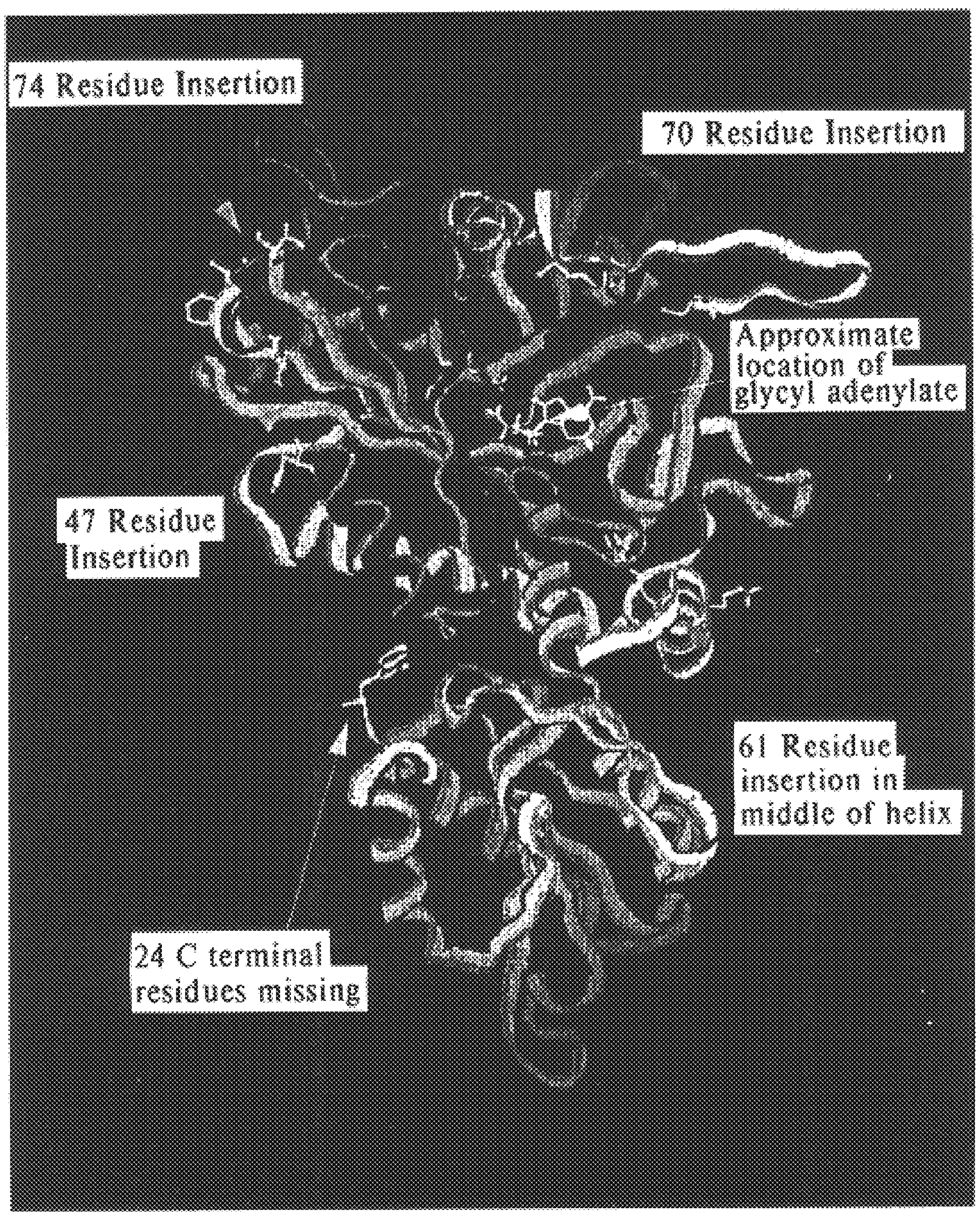
FIG. 6 provides the ribbon structure of the human glycyl tRNA synthetase monomer.
Figure 7:
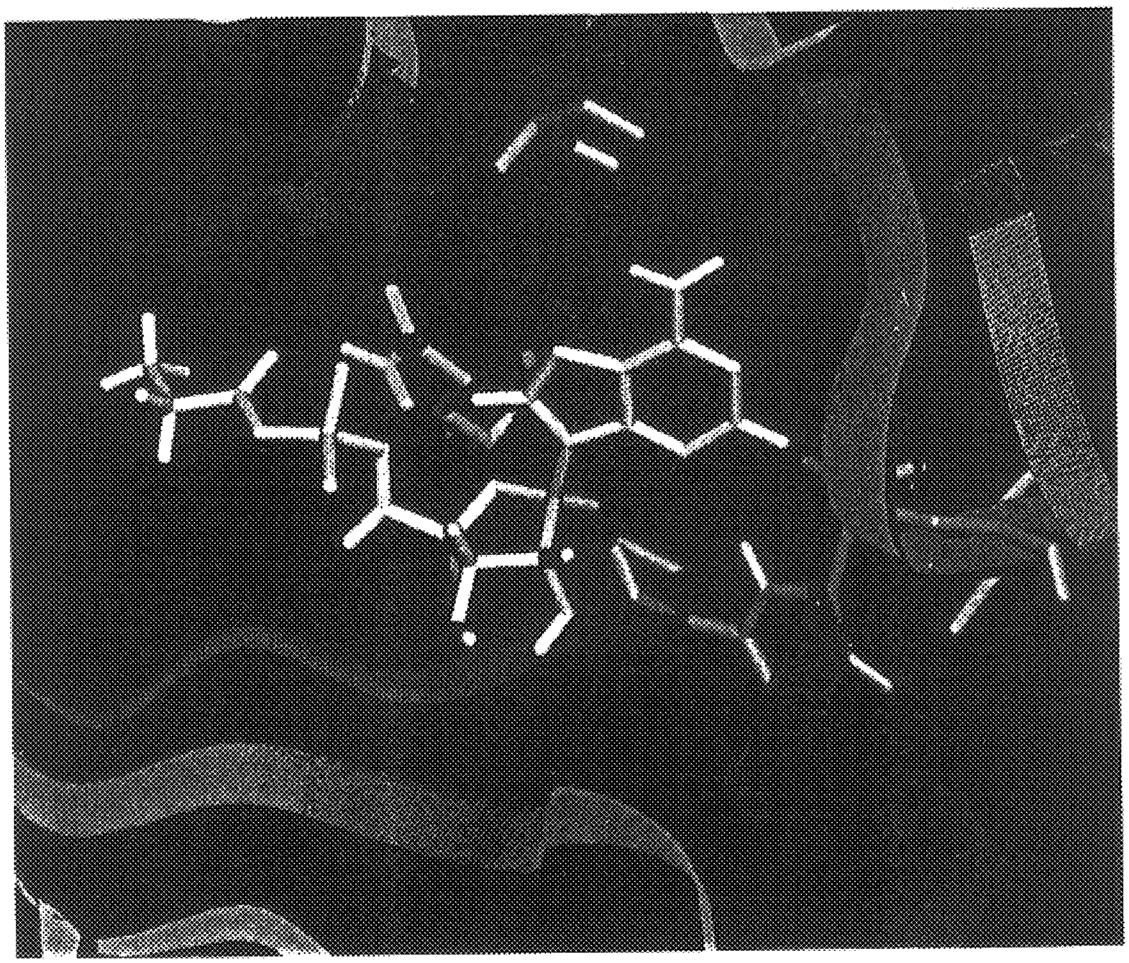
FIG. 7 provides a schematic drawing comparing the active sites of the human and *Staph aureus* glycyl tRNA synthetase enzymes.

A model of the human glycyl tRNA synthetase was constructed using Quanta version 4.1 [Molecular Simulations Inc, Burlington, MA]. The human enzyme contains a number of large surface loops (see FIG. 6). A comparison of the human and Staph enzyme aminoacylation sites is shown in FIG. 7. One of the most significant differences is that a glutamine in the prokaryotic enzyme is replaced by a methionine. The glutamine is believed to be capable of hydrogen bonding to the acyl phosphage moiety of glycyl adenylate.

This invention is not to be limited in scope by the specific embodiments described herein. Indeed, various modifications of the invention in addition to those described herein will become apparent to those skilled in the art from the foregoing description. Such modifications are intended to fall within the scope of the appended claims. The disclosures of the patents, patent applications and publications cited herein are incorporated by reference in their entireties.

---

What is claimed is:

1. A method of identifying an inhibitor compound capable of binding to, and inhibiting the enzymatic activity of a Staphylococcus glycyl tRNA synthetase, said method comprising:

introducing into a suitable computer program information defining an active site conformation of a Staphylococcus glycyl tRNA synthetase molecule comprising a conformation defined by the coordinates of FIG. 1, wherein said program displays the three-dimensional structure thereof;

creating a three dimensional structure of a test compound in said computer program;

displaying and superimposing the model of said test compound on the model of said active site;

assessing whether said test compound model fits spatially into the active site;

incorporating said test compound in a biological synthetase activity assay for a synthetase characterized by said active site; and determining whether said test compound inhibits enzymatic activity in said assay.

Figure 4:
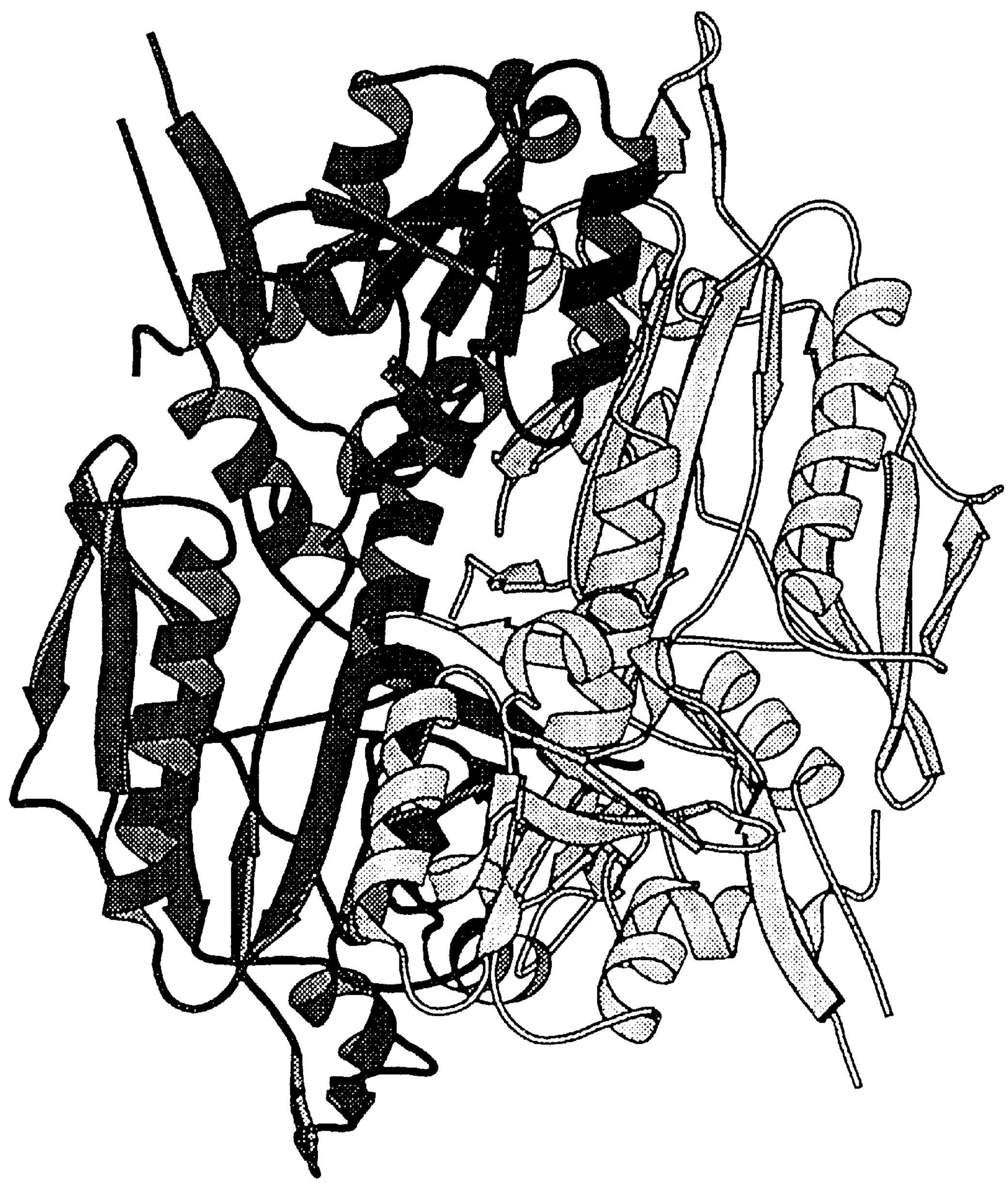
FIG. 4 provides a projection of the ribbon structure of the *Staphylococcus aureus* glycyl tRNA synthetase dimer. The two monomers are shaded in dark and light gray.
Figure 5:
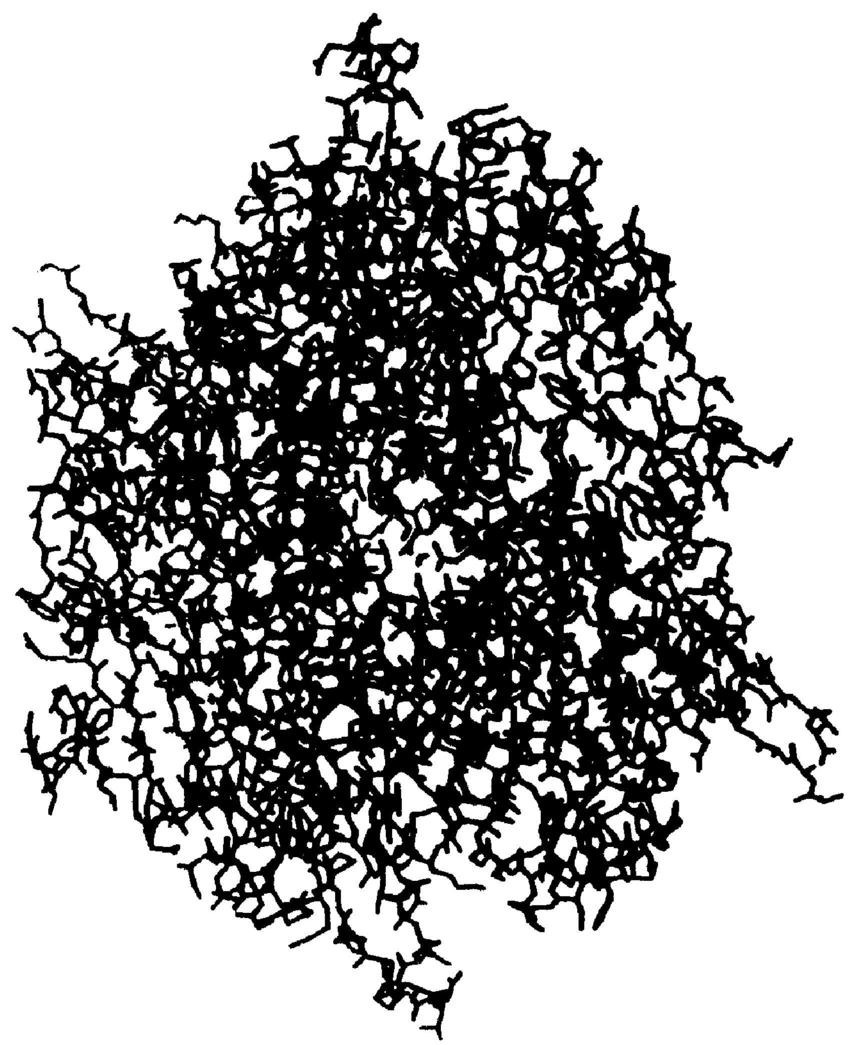
FIG. 5 provides a schematic drawing of the molecular structure of the *Staphylococcus aureus* glycyl tRNA synthetase dimer. The two monomers are shaded in dark and light gray.

2. The method according to claim 1 wherein said synthetase molecule is a dimer, wherein each monomer is characterized by an N-terminal domain having three a-helices and three b-strands, an active site domain, and a C-terminal domain containing a 5-stranded mixed b-sheet with three flanking helices, as illustrated in FIG. 4.

3. A method of identifying an inhibitor compound capable of binding to, and inhibiting the enzymatic activity of, a Staphylococcus glycyl tRNA synthetase, said method comprising:

introducing into a suitable computer program information defining an active site conformation of a glycyl tRNA synthetase molecule comprising a conformation defined by the coordinates of FIG. 1, wherein said program displays the three-dimensional structure thereof;

creating a three dimensional structure of a test compound in said computer program;

displaying and superimposing the model of said test compound on the model of said active site;

assessing whether said test compound model fits spatially into the active site;

incorporating said test compound in a biological synthetase activity assay for a synthetase characterized by said active site; and determining whether said test compound inhibits enzymatic activity in said assay.

4. The method according to claim 3 wherein said synthetase molecule is a dimer, wherein each monomer is characterized by an N-terminal domain having three a-helices and three b-strands, an active site domain, and a C-terminal domain containing a 5-stranded mixed b-sheet with three flanking helices, as illustrated in FIG. 4.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:

-continued

```
        (A) LENGTH: 463 amino acids
        (B) TYPE: amino acid
        (C) STRANDEDNESS:
        (D) TOPOLOGY: linear

    (ii) MOLECULE TYPE: protein

    (xi) SEQUENCE DESCRIPTION: SEQ ID NO:1:

Met Ala Lys Asp Met Asp Thr Ile Val Ser Leu Ala Lys His Arg Gly
1               5                   10                  15

Phe Val Phe Pro Gly Ser Asp Ile Tyr Gly Gly Leu Ser Asn Thr Trp
            20                  25                  30

Asp Tyr Gly Pro Leu Gly Val Glu Leu Lys Asn Asn Val Lys Lys Ala
        35                  40                  45

Trp Trp Gln Lys Phe Ile Thr Gln Ser Pro Phe Asn Val Gly Ile Asp
    50                  55                  60

Ala Ala Ile Leu Met Asn Pro Lys Val Trp Glu Ala Ser Gly His Leu
65                  70                  75                  80

Asn Asn Phe Asn Asp Pro Met Ile Asp Asn Lys Asp Ser Lys Ile Arg
                85                  90                  95

Tyr Arg Ala Asp Lys Leu Ile Glu Asp Tyr Met Gln Asp Val Lys Gly
            100                 105                 110

Asp Glu Asn Phe Ile Ala Asp Gly Leu Ser Phe Glu Gln Met Lys Lys
        115                 120                 125

Ile Ile Asp Asp Glu Gly Ile Val Cys Pro Val Ser Lys Thr Ala Asn
    130                 135                 140

Trp Thr Glu Ile Arg Gln Phe Asn Leu Met Phe Lys Thr Phe Gln Gly
145                 150                 155                 160

Val Thr Glu Asp Ser Thr Asn Glu Ile Phe Leu Arg Pro Glu Thr Ala
                165                 170                 175

Gln Gly Ile Phe Val Asn Tyr Lys Asn Val Gln Arg Ser Met Arg Lys
            180                 185                 190

Lys Leu Pro Phe Gly Ile Gly Gln Ile Gly Lys Ser Phe Arg Asn Glu
        195                 200                 205

Ile Thr Pro Gly Asn Phe Ile Phe Arg Thr Arg Glu Phe Glu Gln Met
    210                 215                 220

Glu Leu Glu Phe Phe Cys Lys Pro Gly Glu Glu Ile Glu Trp Gln Asn
225                 230                 235                 240

Tyr Trp Lys Thr Phe Ala Ser Asp Trp Leu Thr Ser Leu Asn Met Ser
                245                 250                 255

Ser Glu Asn Met Arg Leu Arg Asp His Asp Glu Asp Glu Leu Ser His
            260                 265                 270

Tyr Ser Asn Ala Thr Thr Asp Ile Glu Tyr Lys Phe Pro Phe Gly Trp
        275                 280                 285

Gly Glu Leu Trp Gly Ile Ala Ser Arg Thr Asp Phe Asp Leu Arg Lys
    290                 295                 300

His Ala Glu His Ser Gly Glu Asp Phe Arg Tyr His Asp Pro Glu Thr
305                 310                 315                 320

Asn Glu Lys Tyr Ile Pro Tyr Cys Ile Glu Pro Ser Leu Gly Ala Asp
                325                 330                 335

Arg Val Thr Leu Ala Phe Leu Cys Asp Ala Tyr Asp Glu Glu Gly Val
            340                 345                 350

Glu Gly Ser Lys Asp Ala Arg Thr Val Leu His Phe His Pro Ala Leu
        355                 360                 365

Ala Pro Tyr Lys Ala Ala Ile Leu Pro Leu Ser Lys Lys Leu Ser Gly
```

-continued

```
    370                 375                 380

Glu Ala Ile Lys Ile Phe Glu Gln Leu Ser Ser Lys Phe Ser Ile Asp
385                 390                 395                 400

Phe Asp Glu Ser Gln Ser Ile Gly Lys Arg Tyr Arg Arg Gln Asp Glu
                405                 410                 415

Ile Gly Thr Pro Tyr Cys Val Thr Phe Asp Phe Asp Ser Leu Glu Asp
            420                 425                 430

Asn Gln Val Thr Val Arg Asp Arg Asp Ser Met Glu Gln Val Arg Met
        435                 440                 445

Pro Ile Ser Glu Leu Glu Ala Phe Leu Thr Glu Lys Thr Lys Phe
    450                 455                 460


(2) INFORMATION FOR SEQ ID NO:2:

     (i) SEQUENCE CHARACTERISTICS:
          (A) LENGTH: 42 base pairs
          (B) TYPE: nucleic acid
          (C) STRANDEDNESS: single
          (D) TOPOLOGY: unknown

    (ii) MOLECULE TYPE: other nucleic acid
          (A) DESCRIPTION: /desc = "primer GRS1"

    (xi) SEQUENCE DESCRIPTION: SEQ ID NO:2:

GGGGTACCGC TAGCAGGAGA GGTAATTATG GCAAAAGATA TG                        42


(2) INFORMATION FOR SEQ ID NO:3:

     (i) SEQUENCE CHARACTERISTICS:
          (A) LENGTH: 45 base pairs
          (B) TYPE: nucleic acid
          (C) STRANDEDNESS: single
          (D) TOPOLOGY: unknown

    (ii) MOLECULE TYPE: other nucleic acid
          (A) DESCRIPTION: /desc = "primer GRS2"

    (xi) SEQUENCE DESCRIPTION: SEQ ID NO:3:

GCTCTAGATT AGTCATTTAA TTAGAATTTT GTTTTTTCAG TTAAG                     45
```